United States Patent
Maeba et al.

(10) Patent No.: US 10,800,784 B2
(45) Date of Patent: Oct. 13, 2020

(54) NITROGEN-CONTAINING HETEROCYCLIC AMIDE COMPOUND AND PHARMACEUTICAL USE THEREOF

(71) Applicant: Japan Tobacco Inc., Tokyo (JP)

(72) Inventors: Takaki Maeba, Osaka (JP); Koichi Suzawa, Osaka (JP); Masayuki Kotoku, Osaka (JP); Ritsuki Masuo, Osaka (JP); Dai Motoda, Osaka (JP); Nobutaka Yamaoka, Osaka (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/261,792

(22) Filed: Jan. 30, 2019

(65) Prior Publication Data
US 2020/0017505 A1 Jan. 16, 2020

(30) Foreign Application Priority Data
Feb. 1, 2018 (JP) .................................. 2018-016328

(51) Int. Cl.
*C07D 487/04* (2006.01)
*C07D 498/04* (2006.01)
*C07D 519/00* (2006.01)

(52) U.S. Cl.
CPC ......... *C07D 487/04* (2013.01); *C07D 498/04* (2013.01); *C07D 519/00* (2013.01)

(58) Field of Classification Search
CPC ... C07D 487/04; C07D 498/04; C07D 519/00
USPC ...................................................... 544/281
See application file for complete search history.

(56) References Cited

U.S. PATENT DOCUMENTS

| | | | |
|---|---|---|---|
| 8,580,956 B2 | 11/2013 | Zhu et al. | |
| 9,018,224 B2 | 4/2015 | Edmondson et al. | |
| 9,409,924 B2 | 8/2016 | Li et al. | |
| 9,751,861 B2 | 9/2017 | Buchstaller | |
| 9,944,600 B2 | 4/2018 | Lee et al. | |
| 10,414,774 B2 | 9/2019 | Cumming et al. | |
| 2010/0240634 A1* | 9/2010 | Motomura | A61K 31/045 514/210.17 |
| 2014/0296315 A1* | 10/2014 | Motomura | A61K 31/415 514/406 |
| 2015/0018403 A1* | 1/2015 | Motomura | C07D 231/12 514/406 |
| 2015/0025120 A1 | 1/2015 | Motomura et al. | |
| 2015/0166544 A1* | 6/2015 | Zhang | C07D 487/04 514/249 |
| 2016/0311798 A1* | 10/2016 | Buchstaller | C07D 401/14 |
| 2019/0010151 A1 | 1/2019 | Buchstaller | |
| 2019/0282571 A1 | 9/2019 | Kehler et al. | |

(Continued)

FOREIGN PATENT DOCUMENTS

| | | |
|---|---|---|
| CA | 2880739 A1 | 2/2014 |
| CA | 2994027 A1 | 2/2017 |
| WO | 2008/132162 A1 | 11/2007 |

(Continued)

OTHER PUBLICATIONS

Aicher; J. Med. Chem. 2000, 43, 236-249. (Year: 2000).*

(Continued)

*Primary Examiner* — Daniel R Carcanague
(74) *Attorney, Agent, or Firm* — Venable LLP

(57) ABSTRACT

The present invention provides a compound having a PDHK inhibitory activity and useful for the treatment or prophylaxis of diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease. The present invention relates to a compound of the formula [I-a] or the formula [II], or a pharmaceutically acceptable salt thereof:

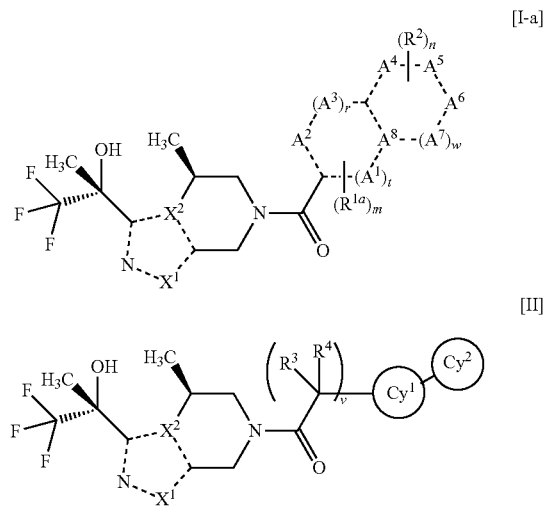

wherein each symbol means the same as that described in the specification.

37 Claims, No Drawings

Specification includes a Sequence Listing.

(56) References Cited

U.S. PATENT DOCUMENTS

| | | |
|---|---|---|
| 2019/0282572 A1 | 9/2019 | Kehler et al. |
| 2020/0062756 A1 | 2/2020 | Buchstaller |

FOREIGN PATENT DOCUMENTS

| | | | |
|---|---|---|---|
| WO | 2008/153792 A2 | 12/2008 | |
| WO | 2009/095253 A1 | 8/2009 | |
| WO | 2013/000084 A1 | 1/2013 | |
| WO | 2013/074388 A1 | 5/2013 | |
| WO | 2013/187646 A1 | 12/2013 | |
| WO | 2014/019468 A1 | 2/2014 | |
| WO | 2015/002119 A1 | 1/2015 | |
| WO | 2015/090496 A1 | 6/2015 | |
| WO | 2017/020981 A1 | 2/2017 | |
| WO | 2017/167676 A1 | 10/2017 | |
| WO | WO-2017186653 A1 * | 11/2017 | ........... C07D 401/12 |
| WO | WO-2018021508 A1 * | 2/2018 | ........... A61K 31/415 |
| WO | WO-2018034918 A1 * | 2/2018 | ........... C07D 471/04 |
| WO | 2018/078038 A1 | 5/2018 | |
| WO | 2018/078042 A1 | 5/2018 | |

OTHER PUBLICATIONS

Bebernitz; J. Med. Chem. 2000, 43, 2248-2257. (Year: 2000).*
Mayers; Biochemical Society Transactions 2003, 31, 1165-1167. (Year: 2003).*
Mayers; Biochemical Society Transactions 2005, 33, 367-370. (Year: 2005).*
Meng; J. Med. Chem. 2014, 57, 9832-9843. (Year: 2014).*
Yuan; Cancer Letters 2017, 386, 47-56. DOI: 10.1016/j.canlet.2016.11.010 (Year: 2017).*
Wu; J. Biol. Chem. 2018, 293, 9604-9613. doi: 10.1074/jbc.RA118.002838 (Year: 2018).*
International Search Report issued in PCT/JP2019/003052, dated Mar. 12, 2019 (11 pages).
STN Registry search results, dated Mar. 7, 2019 (7 pages).
Thomas D. Aicher et al., (R)-3,3,3-Trifluoro-2-hydroxy-2-methylpropionamides are orally active inhibitors of pyruvate dehydrogenase kinase; Journal of Medicinal Chemistry, vol. 42 (1999), pp. 2741-2746.
STN Registry search results, dated Jun. 16, 2019 (7 pages).
International Search Report issued in PCT/JP2019/003052, dated Mar. 12, 2019 (2 pages).

* cited by examiner

NITROGEN-CONTAINING HETEROCYCLIC AMIDE COMPOUND AND PHARMACEUTICAL USE THEREOF

TECHNICAL FIELD

The present invention relates to a nitrogen-containing heterocyclic amide compound and a pharmaceutical use thereof. More particularly, the present invention relates to a nitrogen-containing heterocyclic amide compound or a pharmaceutically acceptable salt thereof having a pyruvate dehydrogenase kinase (hereinafter to be abbreviated as PDHK) inhibitory activity, a pharmaceutical composition containing the same, a therapeutic or prophylactic agent containing the same for diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension, or Alzheimer disease, and the like.

BACKGROUND ART

In tissues, for reactions using energy such as biosynthesis, active transport, muscle contraction and the like, the energy is supplied by hydrolysis of adenosine triphosphate (ATP). ATP is produced by oxidation of metabolic fuel which yields much energy, such as glucose and free fatty acids. In oxidative tissues such as muscle, ATP is mostly produced from acetyl-CoA that enters citric acid cycle. Acetyl-CoA is produced by oxidation of glucose via glycolytic pathway or β oxidation of free fatty acid. An enzyme that plays a pivotal role in controlling acetyl-CoA production from glucose is pyruvate dehydrogenase (hereinafter to be abbreviated as PDH). PDH catalyzes reduction of nicotinamide adenine dinucleotide (NAD) to NADH, simultaneously with oxidation of pyruvic acid to acetyl-CoA and carbon dioxide (e.g., non-patent documents 1, 2).

PDH is a multienzyme complex consisting of three enzyme components (E1, E2 and E3) and some subunits localized in mitochondrial matrix. E1, E2 and E3 are responsible for decarboxylation from pyruvic acid, production of acetyl-CoA and reduction of NAD to NADH, respectively.

Two classes of enzyme having regulatory function bind to PDH. One is PDHK, which is a protein kinase having specificity to PDH. The role thereof is to inactivate E1α subunit of the PDH complex by phosphorylation. The other is PDH phosphatase, which is a specific protein phosphatase that activates PDH via dephosphorylation of E1α subunit. The proportion of PDH in its active (dephosphorylated) state is determined by the balance of kinase activity and phosphatase activity. The kinase activity is regulated by the relative concentration of metabolic substrates. For example, the kinase activity is activated by an increase in NADH/NAD, acetyl-CoA/CoA and ATP/adenosine diphosphate (ADP) ratios, and inhibited by pyruvic acid (e.g., non-patent document 3).

In the tissues of mammals, 4 kinds of PDHK isozymes are identified. Particularly, PDHK2 is expressed in a wide range of tissues including the liver, skeletal muscles and adipose tissues involved in glucose metabolism. Furthermore, since PDHK2 shows comparatively high sensitivity to activation by increased NADH/NAD or acetyl-CoA/CoA and inhibition by pyruvic acid, involvement in a short-term regulation of glucose metabolism is suggested (e.g., non-patent document 4).

In addition, PDHK1 is expressed in large amounts in cardiac muscle, skeletal muscle, pancreatic β cell and the like. Furthermore, since expression of PDHK1 is induced via activation of hypoxia inducible factor (HIF) 1 in ischemic state, its involvement in ischemic diseases and cancerous diseases is suggested (e.g., non-patent document 5).

In diseases such as insulin-dependent (type 1) diabetes, non-insulin-dependent (type 2) diabetes and the like, oxidation of lipids is promoted with simultaneous reduction in glucose utilization. This reduction in glucose utilization is one of the factors causing hyperglycemia. When the oxidative glucose metabolism decreases in type 1 and type 2 diabetes and obesity, PDH activity also decreases. It suggests involvement of reduced PDH activity in the reduced glucose utilization in type 1 and type 2 diabetes (e.g., non-patent documents 6, 7).

On the contrary, hepatic gluconeogenesis is enhanced in type 1 and type 2 diabetes, which also forms one factor causing hyperglycemia. The reduced PDH activity increases pyruvic acid concentration, which in turn increases availability of lactic acid as a substrate for hepatic gluconeogenesis. It suggests possible involvement of reduced PDH activity in the enhanced gluconeogenesis in type 1 and type 2 diabetes (e.g., non-patent documents 8, 9).

When PDH is activated by inhibition of PDHK, the rate of glucose oxidation is considered to rise. As a result, glucose utilization in the body is promoted and hepatic gluconeogenesis is suppressed, whereby hyperglycemia in type 1 and type 2 diabetes is expected to be improved (e.g., non-patent documents 10, 11, 12).

Another factor contributing to diabetes is impaired insulin secretion, which is known to be associated with reduced PDH activity in pancreatic β cells, and induction of PDHK1, 2 and 4 (e.g., non-patent documents 13, 14).

In addition, sustained hyperglycemia due to diabetes is known to cause complications such as diabetic neuropathy, diabetic retinopathy, diabetic nephropathy and the like. Thiamine and α-lipoic acid contribute to activation of PDH as coenzymes. Thiamine and α-lipoic acid, or thiamine derivatives and α-lipoic acid derivatives are shown to have a promising effect on the treatment of diabetic complications. Thus, activation of PDH is expected to improve diabetic complications (e.g., non-patent documents 15, 16).

Under ischemic conditions, limited oxygen supply reduces oxidation of both glucose and fatty acid and reduces the amount of ATP produced by oxidative phosphorylation in the tissues. In the absence of sufficient oxygen, ATP level is maintained by promoted anaerobic glycolysis. As a result, lactic acid increases and intracellular pH decreases. Even though the cells try to maintain homeostasis of ion by energy consumption, abnormally low ATP level and disrupted cellular osmolarity lead to cell death. In addition, adenosine monophosphate-activating kinase activated in an ischemic state inactivates acetyl-CoA carboxylase by phosphorylation. The levels of total malonyl-CoA in the tissue drop, carnitine palmitoyltransferase-I activity is therefore increased and fatty acid oxidation is favored over glucose oxidation by allowing the transport of acyl-CoA into mitochondria. Oxidation of glucose is capable of yielding more ATP per molecule of oxygen than is oxidation of fatty acids. Under ischemic conditions, therefore, when energy metabolism becomes glucose oxidation dominant by activation of PDH, the ability to maintain ATP level is considered to be enhanced (e.g., non-patent document 17).

In addition, since activation of PDH causes oxidation of pyruvic acid produced by glycolysis, and reducing production of lactic acid, the net proton burden is considered to be reduced in ischemic tissues. Accordingly, PDH activation by inhibition of PDHK is expected to protectively act in ischemic diseases such as cardiac muscle ischemia (e.g., non-patent documents 18, 19).

A drug that activates PDH by inhibition of PDHK is considered to decrease lactate production since it promotes pyruvate metabolism. Hence, such drug is expected to be useful for the treatment of hyperlactacidemia such as mitochondrial disease, mitochondrial encephalomyopathy and sepsis (e.g., non-patent document 20).

In cancer cells, the expression of PDHK1 or 2 increases. In cancer cells, moreover, ATP production by oxidative phosphorylation in mitochondria decreases, and ATP production via the anaerobic glycolysis in cytoplasm increases. PDH activation by inhibition of PDHK is expected to promote oxidative phosphorylation in mitochondria, and increase production of active oxygen, which will induce apoptosis of cancer cells. Therefore, the PDH activation by PDHK inhibition is useful for the treatment of cancerous diseases (e.g., non-patent document 21).

Pulmonary hypertension is characterized by high blood pressure caused by partial narrowing of the pulmonary artery due to promoted cell proliferation therein. In pulmonary hypertension, therefore, activation of PDH in the pulmonary artery cell is expected to promote oxidative phosphorylation in mitochondria, increase production of active oxygen, and induce apoptosis of the pulmonary artery cells. Therefore, the PDH activation by PDHK inhibition is considered to be useful for the treatment of pulmonary hypertension, for example, pulmonary arterial hypertension (e.g., non-patent document 22).

Energy production and glucose metabolism in the cerebrum decrease in Alzheimer disease, and also, PDH activity declines. When the PDH activity declines, production of acetyl CoA decreases. Acetyl CoA is utilized for ATP production in the electron transport system via the citric acid cycle. Acetyl CoA is also a starting material for synthesizing acetylcholine, which is one of the neurotransmitters. Therefore, reduced brain PDH activity in Alzheimer disease is considered to cause neuronal cell death due to the decreased ATP production. Moreover, it is considered that synthesis of acetylcholine, which is the transmitter for cholinergic nerve, is inhibited to induce deterioration of memory and the like. Activation of PDH in the brain is expected to enhance energy production and acetylcholine synthesis in Alzheimer disease. Therefore, activation of PDH by the inhibition of PDHK is considered to be useful for the treatment of Alzheimer disease (e.g., non-patent documents 23, 24).

It has been shown that dichloroacetic acid, which is a drug having a PDH activating action, provides promising effects for the treatment of diabetes, myocardial ischemia, myocardial infarction, angina pectoris, cardiac failure, hyperlactacidemia, brain ischemia, cerebral apoplexy, peripheral arterial disease, chronic obstructive pulmonary disease, cancerous disease, and pulmonary hypertension (e.g., non-patent documents 10, 18, 20, 22, 25, 26, 27).

From the foregoing findings, a PDHK inhibitor is considered to be useful for the treatment or prophylaxis of diseases relating to glucose utilization disorder, for example, diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.). Furthermore, a PDHK inhibitor is considered to be useful for the treatment or prophylaxis of diseases caused by limited energy substrate supply to the tissues, for example, cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia and cerebral apoplexy. Furthermore, a PDHK inhibitor is considered to be useful for the treatment or prophylaxis of mitochondrial disease, mitochondrial encephalomyopathy, cancer, pulmonary hypertension and the like.

Therefore, a PDHK inhibitor is considered to be useful for the treatment or prophylaxis of diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease.

DOCUMENT LIST

Non-Patent Documents non-patent document 1: Reed L J, Hackert M L. Structure-function relationships in dihydrolipoamide acyltransferases. J Biol Chem. 1990 Jun. 5; 265(16):8971-4.

non-patent document 2: Patel M S, Roche T E. Molecular biology and biochemistry of pyruvate dehydrogenase complexes. FASEB J. 1990 November; 4(14):3224-33.

non-patent document 3: Sugden M C, Holness M J. Recent advances in mechanisms regulating glucose oxidation at the level of the pyruvate dehydrogenase complex by PDKs. Am J Physiol Endocrinol Metab. 2003 May; 284(5):E855-62.

non-patent document 4: Bowker-Kinley M M, Davis W I, Wu P, Harris R A, Popov K M. Evidence for existence of tissue-specific regulation of the mammalian pyruvate dehydrogenase complex. Biochem J. 1998 Jan. 1; 329 (Pt 1):191-6.

non-patent document 5: Kim J W, Tchernyshyov I, Semenza G L, Dang C V. HIF-1-mediated expression of pyruvate dehydrogenase kinase: a metabolic switch required for cellular adaptation to hypoxia. Cell Metab. 2006 March; 3(3):177-85.

non-patent document 6: Morino K, Petersen K F, Dufour S, Befroy D, Frattini J, Shatzkes N, et al. Reduced mitochondrial density and increased IRS-1 serine phosphorylation in muscle of insulin-resistant offspring of type 2 diabetic parents. J Clin Invest. 2005 December; 115(12):3587-93.

non-patent document 7: Caterson I D, Fuller S J, Randle P J. Effect of the fatty acid oxidation inhibitor 2-tetradecylglycidic acid on pyruvate dehydrogenase complex activity in starved and alloxan-diabetic rats. Biochem J. 1982 Oct. 15; 208(1):53-60.

non-patent document 8: Boden G, Chen X, Stein T P. Gluconeogenesis in moderately and severely hyperglycemic patients with type 2 diabetes mellitus. Am J Physiol Endocrinol Metab. 2001 January; 280(1):E23-30.

non-patent document 9: Shangraw R E, Fisher D M. Pharmacokinetics and pharmacodynamics of dichloroacetate in patients with cirrhosis. Clin Pharmacol Ther. 1999 October; 66(4):380-90.

non-patent document 10: Stacpoole P W, Moore G W, Kornhauser D M. Metabolic effects of dichloroacetate in patients with diabetes mellitus and hyperlipoproteinemia. NEngl J Med. 1978 Mar. 9; 298 (10):526-30.

non-patent document 11: Mayers R M, Leighton B, Kilgour E. PDH kinase inhibitors: a novel therapy for Type II diabetes? Biochem Soc Trans. 2005 April; 33(Pt 2):367-70.

non-patent document 12: Jeoung N H, Rahimi Y, Wu P, Lee W N, Harris R A. Fasting induces ketoacidosis and hypothermia in PDHK2/PDHK4-double-knockout mice. Biochem J. 2012 May 1; 443(3):829-39.

non-patent document 13: Zhou Y P, Berggren P O, Grill V. A fatty acid-induced decrease in pyruvate dehydrogenase activity is an important determinant of beta-cell dysfunction in the obese diabetic db/db mouse. Diabetes. 1996 May; 45(5):580-6.

non-patent document 14: Xu J, Han J, Epstein P N, Liu Y Q. Regulation of PDK mRNA by high fatty acid and glucose in pancreatic islets. Biochem Biophys Res Commun. 2006 Jun. 9; 344(3):827-33.

non-patent document 15: Benfotiamine. Monograph. Altern Med Rev. 2006 September; 11(3):238-42.

non-patent document 16: Vallianou N, Evangelopoulos A, Koutalas P. Alpha-lipoic Acid and diabetic neuropathy. Rev Diabet Stud. 2009 Winter; 6(4):230-6.

non-patent document 17: Ussher J R, Lopaschuk G D. The malonyl CoA axis as a potential target for treating ischaemic heart disease. Cardiovasc Res. 2008 Jul. 15; 79(2): 259-68.

non-patent document 18: Wargovich T J, MacDonald R G, Hill J A, Feldman R L, StacpoolePW, Pepine C J. Myocardial metabolic and hemodynamic effects of dichloroacetate in coronary artery disease. Am J Cardiol. 1988 Jan. 1; 61(1):65-70.

non-patent document 19: Taniguchi M, Wilson C, Hunter C A, Pehowich D J, Clanachan A S, Lopaschuk G D. Dichloroacetate improves cardiac efficiency after ischemia independent of changes in mitochondrial proton leak. Am J Physiol Heart Circ Physiol. 2001 April; 280(4):H1762-9.

non-patent document 20: Stacpoole P W, Nagaraja N V, Hutson A D. Efficacy of dichloroacetate as a lactate-lowering drug. J Clin Pharmacol. 2003 July; 43(7):683-91.

non-patent document 21: Bonnet S, Archer S L, Allalunis-Turner J, Haromy A, Beaulieu C, Thompson R, et al. A mitochondria-K+ channel axis is suppressed in cancer and its normalization promotes apoptosis and inhibits cancer growth. Cancer Cell. 2007 January; 11(1):37-51.

non-patent document 22: McMurtry M S, Bonnet S, Wu X, Dyck J R, Haromy A, Hashimoto K, et al. Dichloroacetate prevents and reverses pulmonary hypertension by inducing pulmonary artery smooth muscle cell apoptosis. Circ Res. 2004 Oct. 15; 95(8):830-40.

non-patent document 23: Saxena U. Bioenergetics breakdown in Alzheimer's disease: targets for new therapies. Int J Physiol Pathophysiol Pharmacol. 2011; 3(2):133-9.

non-patent document 24: Stacpoole P W. The pyruvate dehydrogenase complex as a therapeutic target for age-related diseases. Aging Cell. 2012 June; 11(3):371-7.

non-patent document 25: Marangos P J, Turkel C C, Dziewanowska Z E, Fox A W. Dichloroacetate and cerebral ischaemia therapeutics. Expert Opin Investig Drugs. 1999 April; 8(4):373-82.

non-patent document 26: Calvert L D, Shelley R, Singh S J, Greenhaff P L, Bankart J, Morgan M D, et al. Dichloroacetate enhances performance and reduces blood lactate during maximal cycle exercise in chronic obstructive pulmonary disease. Am J Respir Crit Care Med. 2008 May 15; 177(10):1090-4.

non-patent document 27: Flavin D F. Non-Hodgkin's Lymphoma Reversal with Dichloroacetate. J Oncol. Hindawi Publishing Corporation Journal of Oncology Volume 2010, Article ID 414726, 4 pages doi:10.1155/2010/414726.

SUMMARY OF THE INVENTION

The present invention is as follow.

[1] A compound of the formula [I-a] or the formula [II], or a pharmaceutically acceptable salt thereof:

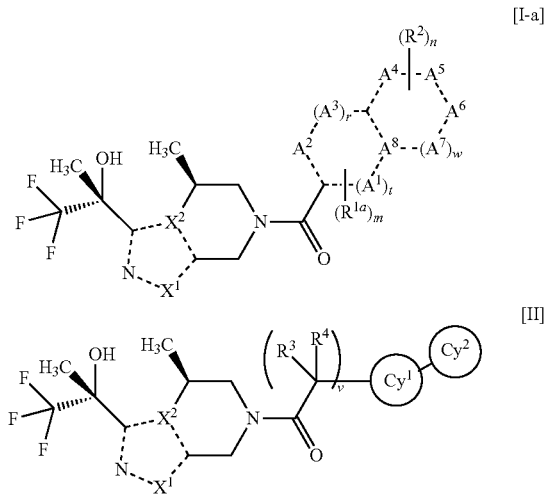

wherein
a bond in a dotted line is a single bond or a double bond,
$X^1$ is a carbon atom, a nitrogen atom or an oxygen atom,
$X^2$ is a carbon atom or a nitrogen atom,
$R^{1a}$ is $C_{1-4}$ alkyl or $C_{1-4}$ alkylcarbonyl,
$R^2$ is halogen, cyano or $C_{1-4}$ alkyl,
m is 0 or 1,
n is 0, 1 or 2, when n is 2, each $R^2$ is the same or different,
$A^1$, $A^2$, $A^3$, $A^4$, $A^5$, $A^6$ and $A^7$ are each independently selected from a carbon atom, a nitrogen atom and an oxygen atom, $A^8$ is selected from a carbon atom and a nitrogen atom, and a total number of the nitrogen atom and the oxygen atom contained in a partial structural formula:

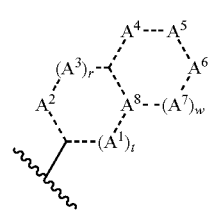

is 0, 1, 2 or 3,
t is 0 or 1,
r is 0, 1 or 2, and a total of t and r is 1 or 2,
w is 0 or 1,
$R^3$ and $R^4$ are each independently hydrogen or $C_{1-4}$ alkyl,
$Cy^1$ is
(1) (i) $C_{4-6}$ cycloalkyl or (ii) 4- to 6-membered saturated or partially saturated heterocyclyl having one nitrogen atom, the $C_{4-6}$ cycloalkyl and the saturated or partially saturated heterocyclyl is optionally substituted by one substituent independently selected from the group consisting of $C_{1-4}$ alkyl and oxo, or
(2) (i) phenyl or (ii) 5- or 6-membered heteroaryl having 1, 2 or 3 hetero atoms independently selected from the group consisting of a nitrogen atom and an oxygen atom, the phenyl and the heteroaryl are optionally substituted by 1 or 2 substituents independently selected from the group consisting of halogen, cyano, carboxy, $C_{1-4}$ alkyl, halo$C_{1-4}$ alkyl and $C_{3-6}$ cycloalkyl,
$Cy^2$ is
(1) (i) $C_{3-6}$ cycloalkyl or (ii) 4- to 6-membered saturated heterocyclyl having 1 or 2 hetero atoms independently selected from the group consisting of a nitrogen atom and an oxygen atom, and the $C_{3-6}$ cycloalkyl and the saturated heterocyclyl are optionally substituted by 1 or 2 substituents independently selected from the group consisting of halogen, hydroxy and $C_{1-4}$ alkyl, or
(2) (i) phenyl or (ii) 5- or 6-membered heteroaryl having 1, 2, 3 or 4 nitrogen atoms, and the phenyl and the heteroaryl are optionally substituted by 1 or 2 substituents independently selected from the group consisting of halogen, cyano, $C_{1-4}$ alkyl, $C_{1-4}$ alkoxy and $C_{1-4}$ alkylsulfonyl, and
v is 0 or 1.
[2] The compound of [1] wherein $X^1$ is a carbon atom, and $X^2$ is a nitrogen atom, or a pharmaceutically acceptable salt thereof.
[3] The compound of [1] or [2] wherein, in the formula [I-a], the total number of the nitrogen atom and the oxygen atom contained in the partial structural formula:

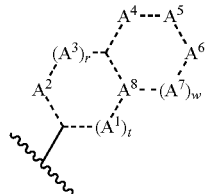

wherein each symbol is as defined in [1], is 2, or a pharmaceutically acceptable salt thereof.
[4] The compound of any one of [1] to [3], which is a compound of the formula [I-b]:

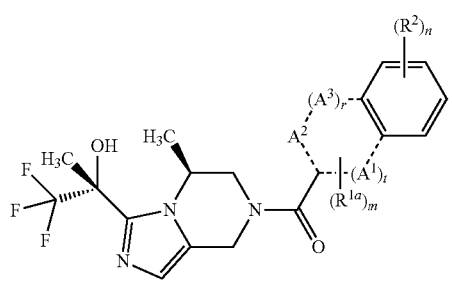

wherein each symbol is as defined in [1], or a pharmaceutically acceptable salt thereof.
[5] The compound of [1] wherein v is 0, or a pharmaceutically acceptable salt thereof.
[6] The compound of [1] or [5] wherein $Cy^1$ is 5- or 6-membered heteroaryl having 1, 2 or 3 hetero atoms independently selected from the group consisting of a nitrogen atom and an oxygen atom, and the heteroaryl is optionally substituted by 1 or 2 substituents independently selected from the group consisting of halogen, cyano, alkyl, halo$C_{1-4}$ alkyl and $C_{3-6}$ cycloalkyl, or a pharmaceutically acceptable salt thereof.
[7] The compound of any one of [1], [5] and [6] wherein $Cy^2$ is
(1) $C_{3-6}$ cycloalkyl optionally substituted by 1 or 2 substituents independently selected from the group consisting of halogen, hydroxy and $C_{1-4}$ alkyl, or
(2) phenyl optionally substituted by 1 or 2 substituents independently selected from the group consisting of halogen, cyano, $C_{1-4}$ alkyl, $C_{1-4}$ alkoxy and $C_{1-4}$ alkylsulfonyl, or a pharmaceutically acceptable salt thereof.
[8] A compound selected from the following formulas:

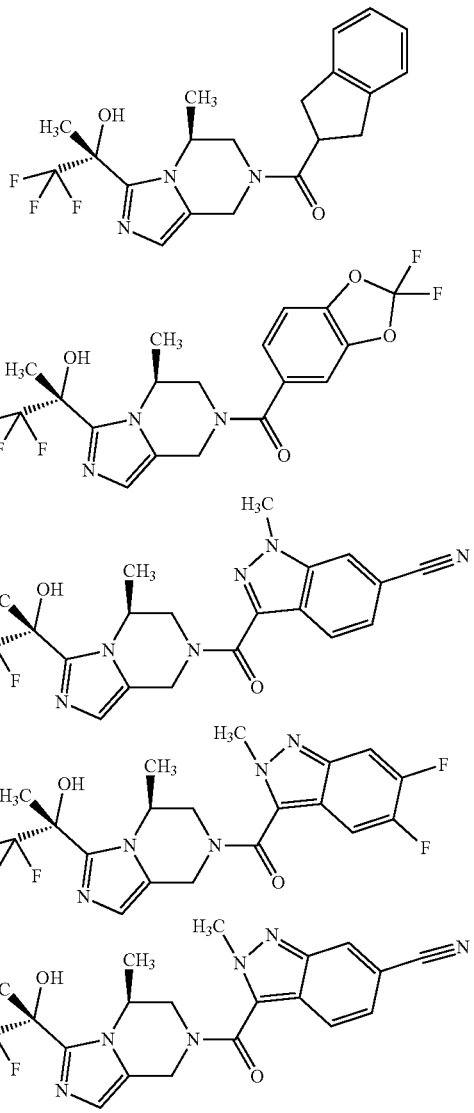

-continued

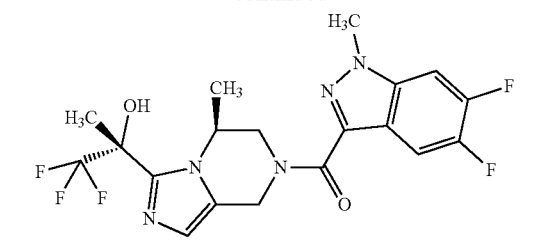

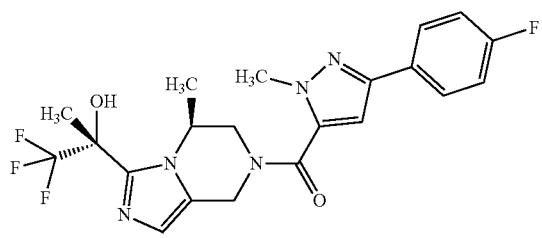

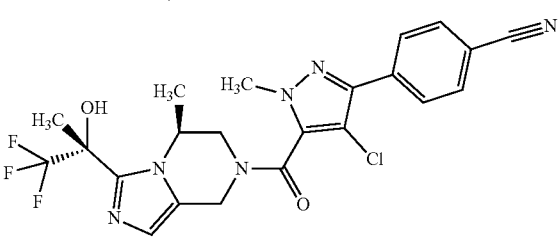

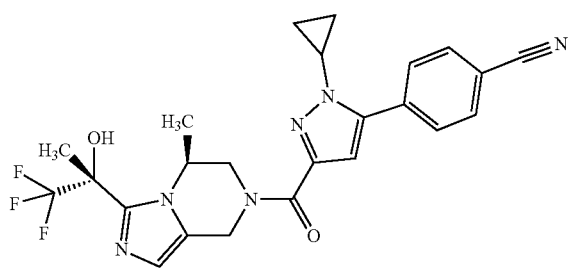

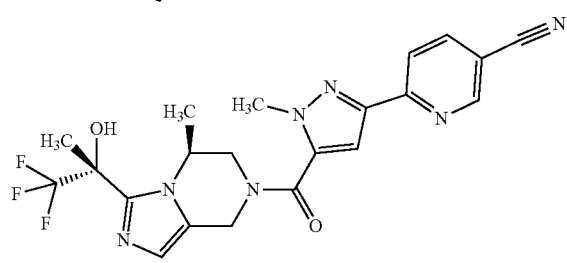

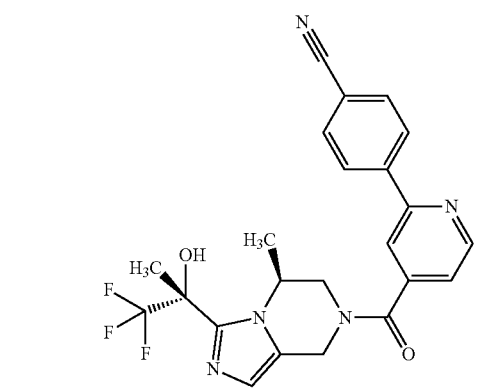

-continued

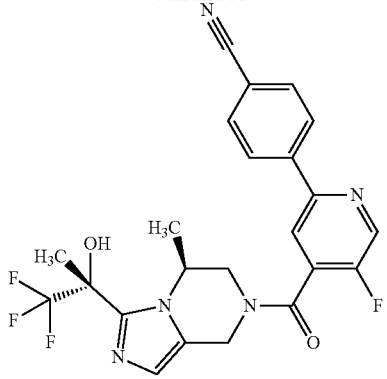

or a pharmaceutically acceptable salt thereof.

[9] A compound selected from the following formulas:

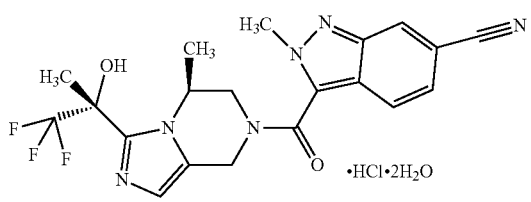

·HCl·2H₂O

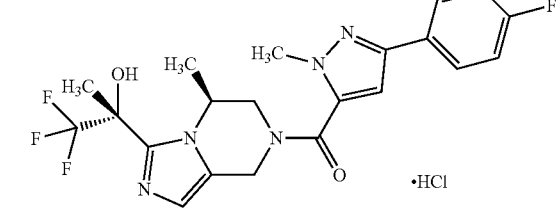

·HCl

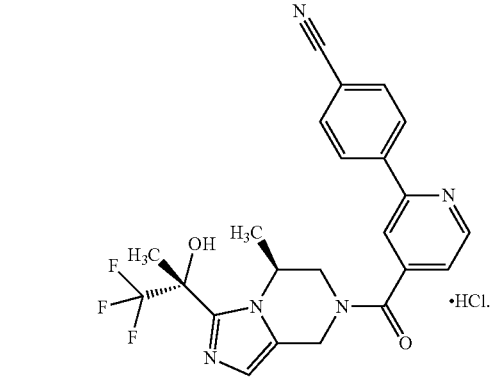

·HCl.

[10] A pharmaceutical composition comprising the compound of any one of [1] to [9], or a pharmaceutically acceptable salt thereof, and a pharmaceutically acceptable carrier.

[11] A PDHK inhibitor comprising the compound of any one of [1] to [9], or a pharmaceutically acceptable salt thereof.

[12] A PDHK1 inhibitor comprising the compound of any one of [1] to [9], or a pharmaceutically acceptable salt thereof.

[13] A PDHK2 inhibitor comprising the compound of any one of [1] to [9], or a pharmaceutically acceptable salt thereof.

[14] An agent for the treatment or prophylaxis of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer or pulmonary hypertension, the agent comprises the compound of any one of [1] to [9], or a pharmaceutically acceptable salt thereof.

[15] The agent of [14] wherein diabetes is type 1 diabetes or type 2 diabetes.

[16] The agent of [14] wherein diabetic complication is selected from the group consisting of diabetic neuropathy, diabetic retinopathy, diabetic nephropathy and cataract.

[17] The agent of [14] wherein cardiac failure is acute cardiac failure or chronic cardiac failure.

[18] The agent of [14] wherein pulmonary hypertension is pulmonary arterial hypertension.

[19] A method for inhibiting PDHK comprising administering a therapeutically effective amount of the compound of any one of [1] to [9] or a pharmaceutically acceptable salt thereof to a mammal.

[20] A method for treating or preventing a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension, the method comprising administering a therapeutically effective amount of the compound of any one of [1] to [9] or a pharmaceutically acceptable salt thereof to a mammal.

[21] The method of [20] wherein diabetes is type 1 diabetes or type 2 diabetes.

[22] The method of [20] wherein diabetic complication is selected from the group consisting of diabetic neuropathy, diabetic retinopathy, diabetic nephropathy and cataract.

[23] The method of [20] wherein cardiac failure is acute cardiac failure or chronic cardiac failure.

[24] The method of [20] wherein pulmonary hypertension is pulmonary arterial hypertension.

[25] Use of the compound of any one of [1] to [9] or a pharmaceutically acceptable salt thereof in the production of a PDHK inhibitor.

[26] Use of the compound of any one of [1] to [9] or a pharmaceutically acceptable salt thereof in the production of an agent for the treatment or prophylaxis of a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension.

[27] The use of [26] wherein diabetes is type 1 diabetes or type 2 diabetes.

[28] The use of [26] wherein diabetic complication is selected from the group consisting of diabetic neuropathy, diabetic retinopathy, diabetic nephropathy and cataract.

[29] The use of [26] wherein cardiac failure is acute cardiac failure or chronic cardiac failure.

[30] The use of [26] wherein pulmonary hypertension is pulmonary arterial hypertension.

[31] The compound of any one of [1] to [9] or a pharmaceutically acceptable salt thereof for use in the treatment or prophylaxis of a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension.

[32] The compound or a pharmaceutically acceptable salt thereof of [31] wherein diabetes is type 1 diabetes or type 2 diabetes.

[33] The compound or a pharmaceutically acceptable salt thereof of [31] wherein diabetic complication is selected from the group consisting of diabetic neuropathy, diabetic retinopathy, diabetic nephropathy and cataract.

[34] The compound or a pharmaceutically acceptable salt thereof of [31] wherein cardiac failure is acute cardiac failure or chronic cardiac failure.

[35] The compound or a pharmaceutically acceptable salt thereof of [31] wherein pulmonary hypertension is pulmonary arterial hypertension.

[36] A commercial package comprising the pharmaceutical composition of [10] and a written matter associated therewith, the written matter stating that the pharmaceutical composition can be used for the treatment or prophylaxis of a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension.

[37] A kit comprising the pharmaceutical composition of [10] and a written matter associated therewith, the written matter stating that the pharmaceutical composition can be used for the treatment or prophylaxis of a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension.

[38] A compound of the formula [I] or a pharmaceutically acceptable salt thereof:

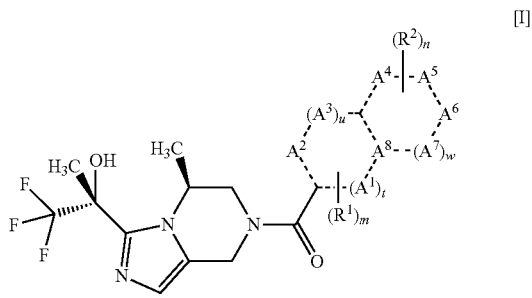

wherein
$R^1$ is $C_{1-4}$ alkyl,
$R^2$ is halogen, cyano or $C_{1-4}$ alkyl,
m is 0 or 1, n is 0, 1 or 2, when n is 2, each $R^2$ is the same or different, $A^1$, $A^2$, $A^3$, $A^4$, $A^5$, $A^6$ and $A^7$ are each independently selected from a carbon atom, a nitrogen atom and an oxygen atom, $A^6$ is selected from a carbon atom and a nitrogen atom, and a total number of the nitrogen atom and the oxygen atom contained in a partial structural formula:

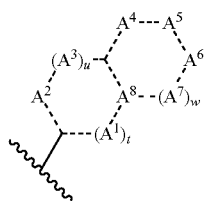

is 0, 1 or 2,
a bond in a dotted line is a single bond or a double bond,
t is 0 or 1,
u is 0 or 1, and a total of t and u is 1 or 2, and
w is 0 or 1.

[39] The compound of [38] wherein the total number of the nitrogen atom and the oxygen atom contained in the partial structural formula:

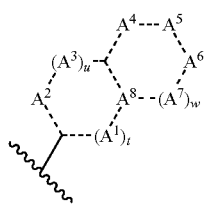

wherein each symbol is as defined in [38], is 2, or a pharmaceutically acceptable salt thereof.

[40] The compound of [38] wherein the partial structural formula:

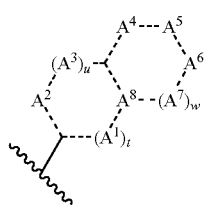

wherein each symbol is as defined in [38] is the formula:

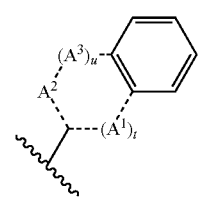

wherein each symbol is as defined in [38], or a pharmaceutically acceptable salt thereof.

[41] A compound selected from the following formulas:

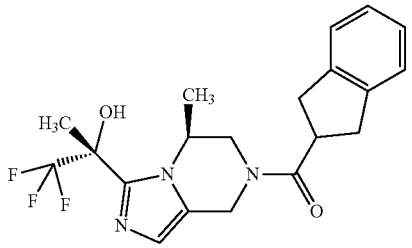

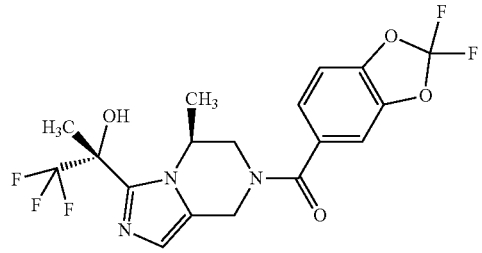

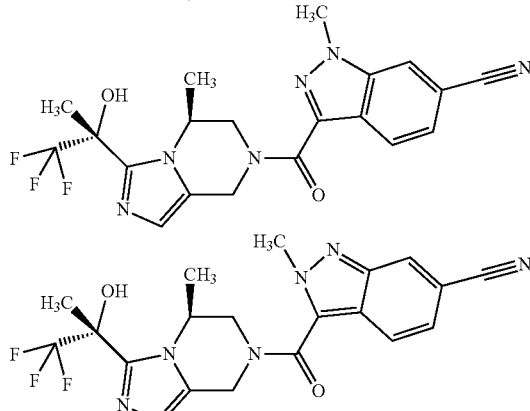

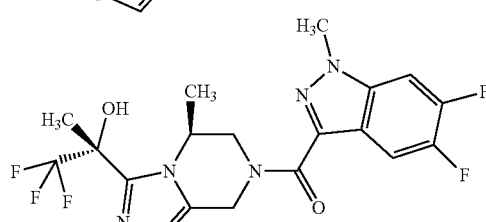

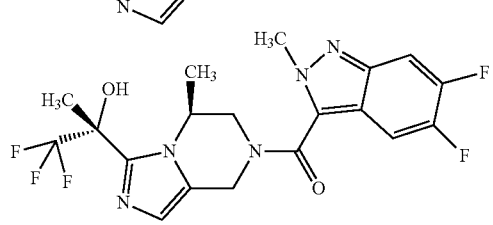

or a pharmaceutically acceptable salt thereof.

[42] A pharmaceutical composition comprising the compound of any one of [38] to [41], or a pharmaceutically acceptable salt thereof.

[43] A PDHK inhibitor comprising the compound of any one of [38] to [41], or a pharmaceutically acceptable salt thereof.

[44] A PDHK1 inhibitor comprising the compound of any one of [38] to [41], or a pharmaceutically acceptable salt thereof.

[45] A PDHK2 inhibitor comprising the compound of any one of [38] to [41], or a pharmaceutically acceptable salt thereof.

[46] A lactic acid-lowering agent comprising the compound of any one of [38] to [41], or a pharmaceutically acceptable salt thereof.
[47] An agent for the treatment or prophylaxis of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer or pulmonary hypertension, the agent comprises the compound of any one of [38] to [41], or a pharmaceutically acceptable salt thereof.
[48] The agent of [47] wherein the diabetes is type 1 diabetes or type 2 diabetes.
[49] The agent of [47] wherein the diabetic complication is selected from the group consisting of diabetic neuropathy, diabetic retinopathy, diabetic nephropathy and cataract.
[50] The agent of [47] wherein the cardiac failure is acute cardiac failure or chronic cardiac failure.
[51] The agent of [47] wherein the pulmonary hypertension is pulmonary arterial hypertension.
[52] A method for inhibiting PDHK comprising administering a therapeutically effective amount of the compound of any one of [38] to [41] or a pharmaceutically acceptable salt thereof to a mammal.
[53] A method for treating or preventing a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension, the method comprising administering a therapeutically effective amount of the compound of any one of [38] to [41] or a pharmaceutically acceptable salt thereof to a mammal.
[54] Use of the compound of any one of [38] to [41] or a pharmaceutically acceptable salt thereof in the production of a PDHK inhibitor.
[55] Use of the compound of any one of [38] to [41] or a pharmaceutically acceptable salt thereof in the production of an agent for the treatment or prophylaxis of a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension.
[56] The compound of any one of [38] to [41] or a pharmaceutically acceptable salt thereof for use in the treatment or prophylaxis of a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension.

[57] The compound or a pharmaceutically acceptable salt thereof of [56] wherein diabetes is type 1 diabetes or type 2 diabetes.
[58] The compound or a pharmaceutically acceptable salt thereof of [56] wherein diabetic complication is selected from the group consisting of diabetic neuropathy, diabetic retinopathy, diabetic nephropathy and cataract.
[59] The compound or a pharmaceutically acceptable salt thereof of [56] wherein cardiac failure is acute cardiac failure or chronic cardiac failure.
[60] The compound or a pharmaceutically acceptable salt thereof of [56] wherein pulmonary hypertension is pulmonary arterial hypertension.
[61] A commercial package comprising the pharmaceutical composition of [42] and a written matter associated therewith, the written matter stating that the pharmaceutical composition can be used for the treatment or prophylaxis of a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension.
[62] A kit comprising the pharmaceutical composition of [42] and a written matter associated therewith, the written matter stating that the pharmaceutical composition can be used for the treatment or prophylaxis of a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension.

DESCRIPTION OF EMBODIMENTS

The definitions of the terms used in the present invention are as follows.
In the following formula [I-a]:

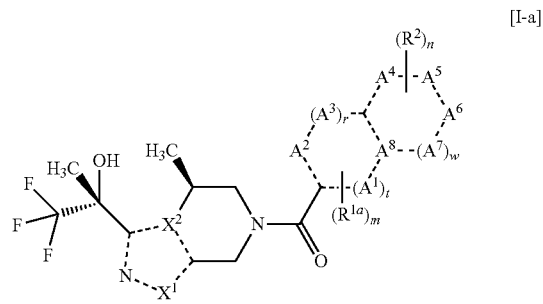

wherein each symbol is as defined for the aforementioned formula [I-a],
it means $R^{1a}$ binds to $A^1$, $A^2$ or $A^3$, and $R^2$ binds to $A^4$, $A^5$, $A^6$ or $A^7$. When n is 2, two $R^e$s may be bonded to the same atom selected from $A^4$, $A^5$, $A^6$ and $A^7$ or may be bonded to different atoms.

The following wavy line: 
in the partial structure indicates the binding point.

In the partial structural formula:

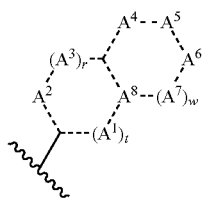

wherein each symbol is as defined for the aforementioned formula [I-a],

"a bond in a dotted line is a single bond or a double bond" means that the two rings fused in the above-mentioned formula are each a saturated ring, a partially saturated ring or an aromatic ring.

Examples of the group represented by the partial structural formula:

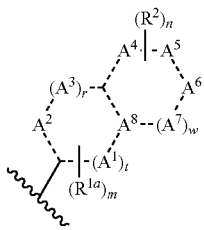

in the formula [I-a] include the following groups.

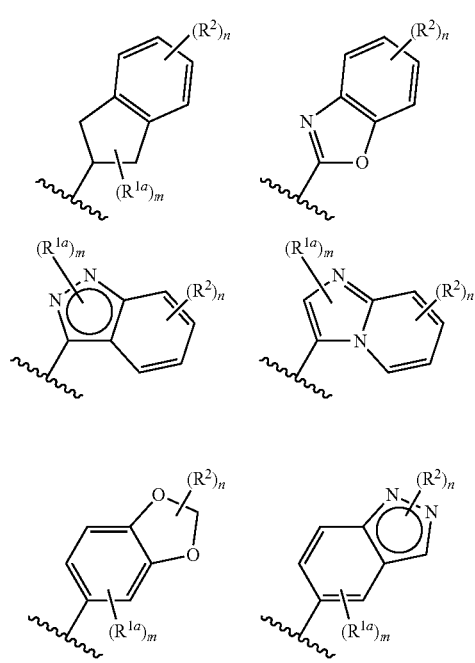

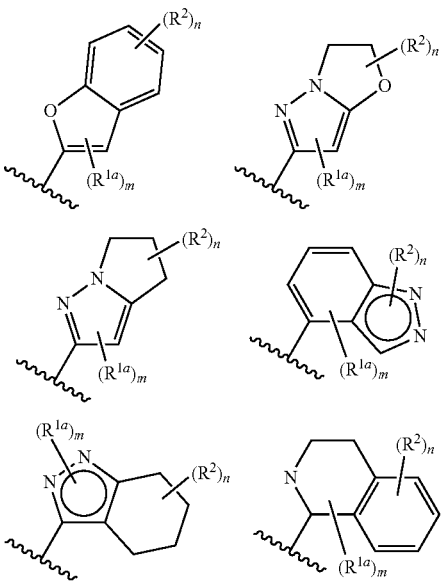

In the following formula [I]:

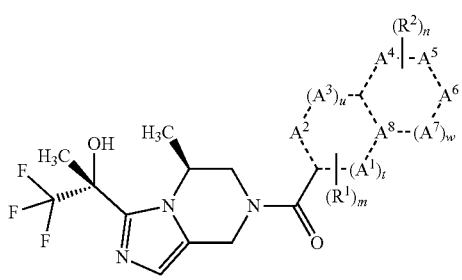

wherein each symbol is as defined for the aforementioned formula [I], it means $R^1$ binds to $A^1$, $A^2$ or $A^3$, and $R^2$ binds to $A^4$, $A^5$, $A^6$ or $A^7$. When n is 2, two $R^e$s may be bonded to the same atom selected from $A^4$, $A^5$, $A^6$ and $A^7$ or may be bonded to different atoms.

In the partial structural formula:

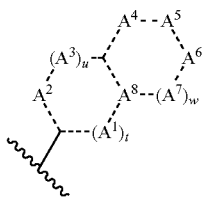

wherein each symbol is as defined for the aforementioned formula [I],

"a bond in a dotted line is a single bond or a double bond" means that the two rings fused in the above-mentioned formula are each a saturated ring, a partially saturated ring or an aromatic ring.

Examples of the group represented by partial structural formula:

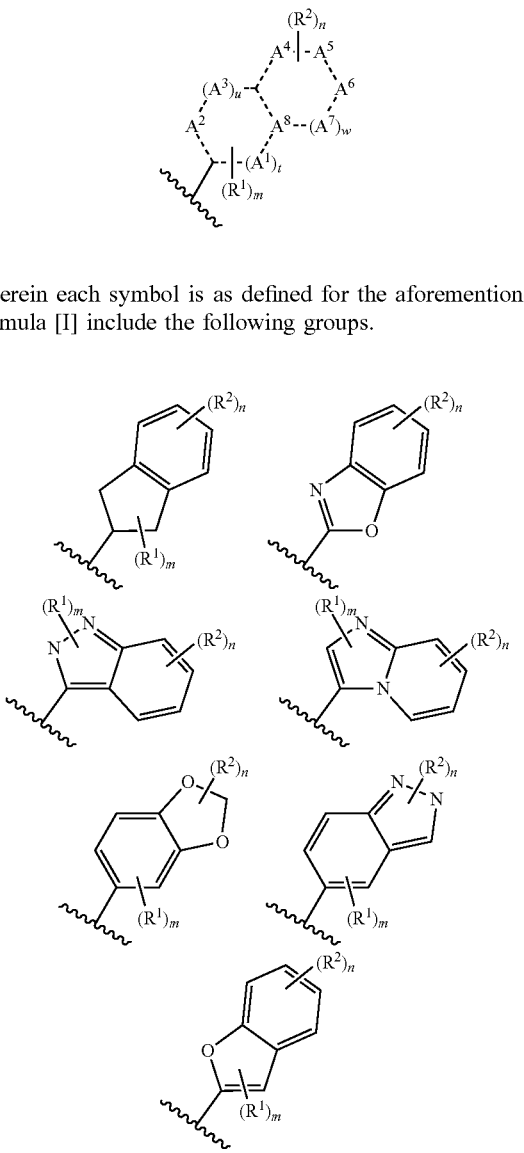

wherein each symbol is as defined for the aforementioned formula [I] include the following groups.

In the formula [II], the partial structural formula:

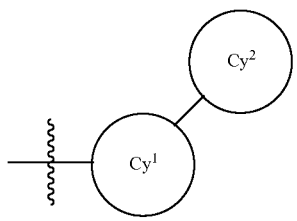

wherein each symbol is as defined for the aforementioned formula [II], indicates a group in which $Cy^1$ and $Cy^2$ are bonded to each other by a single bond. Examples of the group represented by the partial structural formula include the following groups.

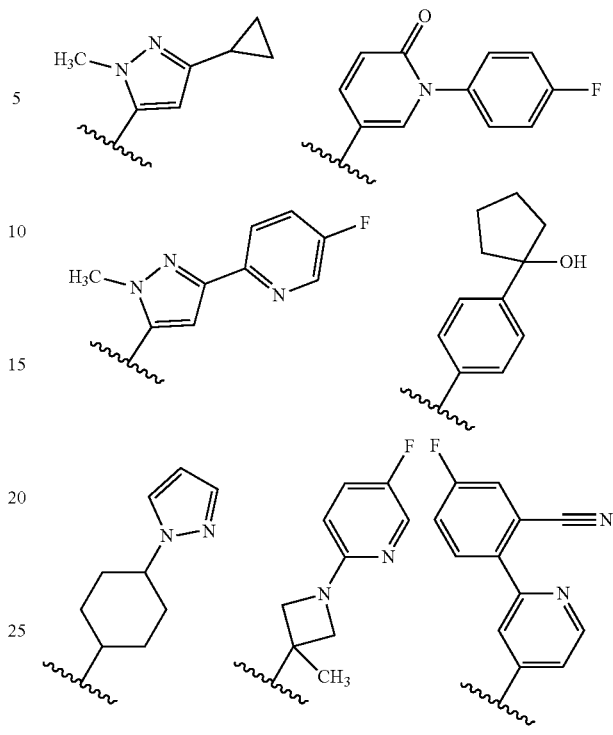

The "halogen" is fluoro, chloro, bromo or iodo. As "halogen", fluoro or chloro is preferable.

The "$C_{1-4}$ alkyl" means a straight chain or branched chain alkyl having 1 to 4 carbon atoms. Examples thereof include methyl, ethyl, propyl, isopropyl, butyl, isobutyl, sec-butyl and tert-butyl. As "$C_{1-4}$ alkyl", methyl is preferable.

The "halo$C_{1-4}$ alkyl" means straight chain or branched chain alkyl having 1 to 4 carbon atoms and substituted by 1 to "halogens" defined above. When alkyl is substituted by plural halogens, the halogens may be the same or different. Examples of the "halo$C_{1-4}$ alkyl" include fluoromethyl, trifluoromethyl and the like. As "halo$C_{1-4}$ alkyl", $C_{1-4}$ alkyl substituted by 1 to 3 fluoros is preferable.

The "$C_{1-4}$ alkoxy" means alkyl-oxy in which the alkyl moiety is "$C_{1-4}$ alkyl" defined above and includes, for example, methoxy, ethoxy, propoxy, isopropoxy, butoxy, isobutoxy, sec-butoxy and tert-butoxy. As "$C_{1-4}$ alkoxy", methoxy is preferable.

The "$C_{1-4}$ alkylcarbonyl" means alkyl-carbonyl in which the alkyl moiety is "$C_{1-4}$ alkyl" defined above and includes, for example, acetyl, propanoyl, butanoyl, 2-methylpropanoyl, pentanoyl, 3-methylbutanoyl, 2-methylbutanoyl and 2,2-dimethylpropanoyl. As "$C_{1-4}$ alkylcarbonyl", acetyl is preferable.

The "$C_{1-4}$ alkylsulfonyl" means alkyl-sulfonyl in which the alkyl moiety is "$C_{1-4}$ alkyl" defined above and includes, for example, methanesulfonyl, ethylsulfonyl, propylsulfonyl, isopropylsulfonyl, butylsulfonyl, isobutylsulfonyl, sec-butylsulfonyl and tert-butylsulfonyl. As "$C_{1-4}$ alkylsulfonyl", methanesulfonyl is preferable.

The "$C_{3-6}$ cycloalkyl" means a 3- to 6-membered monocyclic hydrocarbon ring group and includes, for example, cyclopropyl, cyclobutyl, cyclopentyl and cyclohexyl. As "$C_{3-6}$ cycloalkyl", cyclopropyl is preferable.

The "$C_{4-6}$ cycloalkyl" means a 4- to 6-membered monocyclic hydrocarbon ring group and includes, for example, cyclobutyl, cyclopentyl and cyclohexyl.

The "4- to 6-membered saturated or partially saturated heterocyclyl having one nitrogen atom" means a monocyclic heterocyclic group having one secondary or tertiary amine in the ring, wherein the heterocyclic group is saturated or partially saturated. Examples of the heterocyclyl include azetidinyl, pyrrolidinyl, piperidinyl, 1,2-dihydro-pyridyl and the like. Preferred is azetidinyl, pyrrolidinyl or 1,2-dihydro-pyridyl.

The "5- or 6-membered heteroaryl having 1, 2 or 3 hetero atoms independently selected from the group consisting of a nitrogen atom and an oxygen atom" means 5- or 6-membered monocyclic heteroaryl having, besides carbon atom, 1, 2 or 3 hetero atoms independently selected from the group consisting of a nitrogen atom and an oxygen atom. As the heteroaryl, furanyl, pyrrolyl, imidazolyl, pyrazolyl, triazolyl, oxazolyl, isoxazolyl, oxadiazolyl, pyridyl, pyrimidinyl, pyrazinyl, triazinyl and the like can be mentioned. The heteroaryl is preferably pyrazolyl, oxazolyl, isoxazolyl, oxadiazolyl, pyridyl or pyrimidinyl, more preferably pyrazolyl or pyridyl.

The "4- to 6-membered saturated heterocyclyl having 1 or 2 hetero atoms independently selected from the group consisting of a nitrogen atom and an oxygen atom" means a 4- to 6-membered monocyclic saturated heterocyclic group having, besides carbon atom, 1 or 2 hetero atoms independently selected from the group consisting of a nitrogen atom and an oxygen atom. As the heterocyclyl, oxetanyl, tetrahydrofuranyl, tetrahydropyranyl, azetidinyl, pyrrolidinyl, piperidinyl, piperazinyl, morpholinyl and the like can be mentioned. Preferred is tetrahydropyranyl, piperidinyl or piperazinyl.

The "5- or 6-membered heteroaryl having 1, 2, 3 or 4 nitrogen atoms" means 5- or 6-membered monocyclic heteroaryl having 1, 2, 3 or 4 nitrogen atoms besides carbon atom. As the heteroaryl, pyrrolyl, imidazolyl, pyrazolyl, triazolyl, tetrazolyl, pyridyl, pyrimidinyl, pyrazinyl, triazinyl and the like can be mentioned. Preferred is pyrazolyl, tetrazolyl or pyridyl.

A preferable embodiment of the compound of the formula [I-a] or the formula [II] is described below.

A preferable embodiment of $R^{1a}$ is methyl.
A preferable embodiment of $R^2$ is halogen or cyano.
A preferable embodiment of m is 0.
A preferable embodiment of n is 1.
A preferable embodiment of t is 0.
A preferable embodiment of r is 1.
A preferable embodiment of w is 1.
A preferable embodiment of a combination of $X^1$ and $X^2$ ($X^1$, $X^2$) is (carbon atom, nitrogen atom), (oxygen atom, carbon atom) or (nitrogen atom, nitrogen atom).

A preferable embodiment of the compound of the formula [I-a] is a compound having a structure of the formula [I-c]:

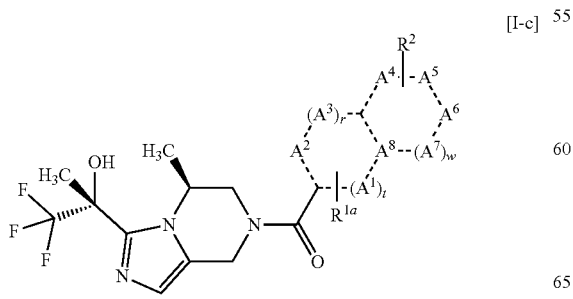

[I-c]

wherein the symbols in the formula are as defined in the definition of the aforementioned formula [I-a].

Another preferable embodiment of the compound of the formula [I-a] is a compound having a structure of the formula [I-d]:

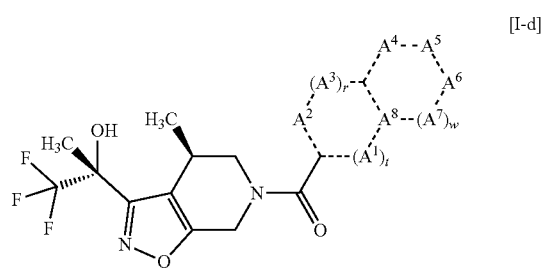

[I-d]

wherein the symbols in the formula are as defined in the definition of the aforementioned formula [I-a].

A still another preferable embodiment of the compound of the formula [I-a] is a compound having a structure of the formula [I]:

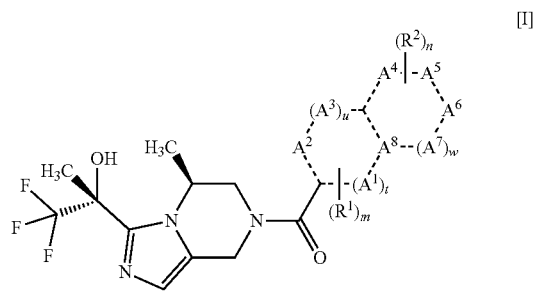

[I]

wherein the symbols in the formula are as defined in the definition of the aforementioned formula [I].

In the formula [I], $R^1$ is preferably $C_{1-4}$ alkyl, a total number of the nitrogen atom and the oxygen atom contained in the partial structural formula:

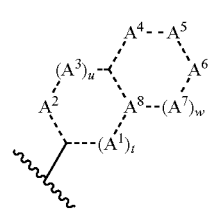

is preferably 0, 1 or 2, more preferably 2, and u is preferably 0 or 1.

In the formula [I], a preferable embodiment of the partial structural formula:

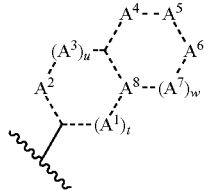

is the formula:

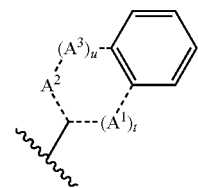

wherein $A^1$, $A^2$ and $A^3$ are each independently selected from a carbon atom, a nitrogen atom and an oxygen atom, a total number of the nitrogen atom and the oxygen atom contained in the above-mentioned formula is 0, 1 or 2, a bond in a dotted line is a single bond or a double bond, t is 0 or 1, and u is 0 or 1, and a total of t and u is 1 or 2.

A preferable embodiment of the compound of the formula [II] is a compound having a structure of the formula [II-a]:

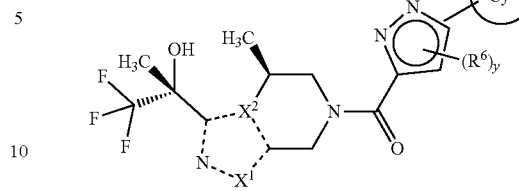

[II-a]

wherein $R^5$ is halogen or $C_{1-4}$ alkyl;

x is 0 or 1, ring $Cy^{2-a}$ is (i) phenyl or (ii) 5- or 6-membered heteroaryl having 1, 2, 3 or 4 nitrogen atoms, and the phenyl and the heteroaryl are optionally substituted by 1 or 2 substituents independently selected from the group consisting of halogen, cyano, $C_{1-4}$ alkyl, $C_{1-4}$ alkoxy and $C_{1-4}$ alkylsulfonyl; and other symbols are as defined in the definition of the aforementioned formula [II].

Another preferable embodiment of the compound of the formula [II] is a compound having a structure of the formula [II-b]:

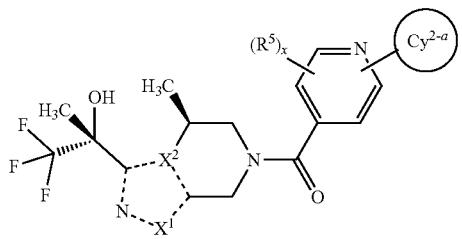

[II-b]

wherein $R^6$ is halogen, $C_{1-4}$ alkyl or cyclopropyl;

y is 0, 1 or 2, when y is 2, each $R^6$ is independently selected; and other symbols are as defined in the definition of the aforementioned formula [II].

Another preferable embodiment of the compound of the formula [II] is a compound having a structure of the formula [II-g]:

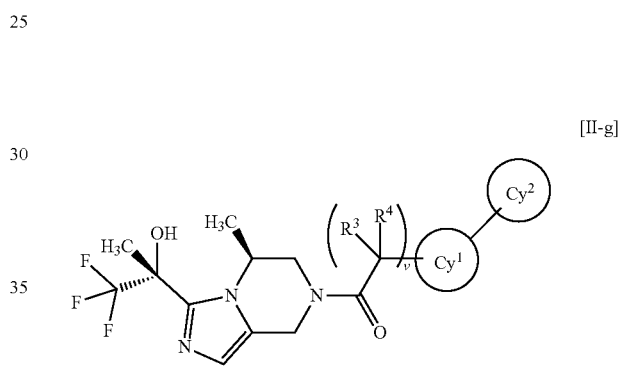

[II-g]

wherein the symbols in the formula are as defined in the definition of the aforementioned formula [II].

Another preferable embodiment of the compound of the formula [II] is a compound having a structure of the formula [II-h]:

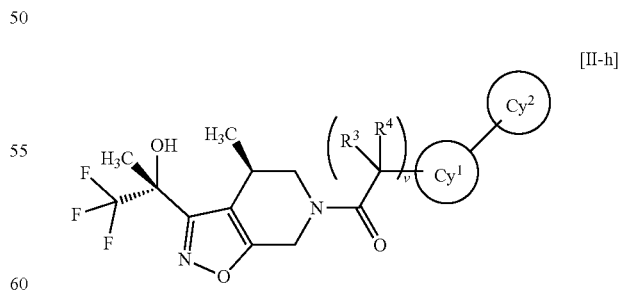

[II-h]

wherein the symbols in the formula are as defined in the definition of the aforementioned formula [II].

Another preferable embodiment of the compound of the formula [II] is a compound having a structure of the formula [II-i]:

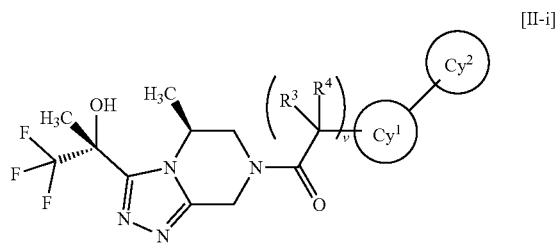

[II-i]

wherein the symbols in the formula are as defined in the definition of the aforementioned formula [II].

In the formula [II-g], the formula [II-h] and the formula [II-i], a preferable embodiment of v is 0.

The "pharmaceutically acceptable salt" may be any salt without excessive toxicity known in the art. Specifically, salts with inorganic acids, salts with organic acids, salts with inorganic bases, salts with organic bases and the like can be mentioned. Various forms of pharmaceutically acceptable salts are well known in the art and, for example, they are described in the following reference documents:
(a) Berge et al., J. Pharm. Sci., 66, p 1-19(1977),
(b) Stahl et al., "Handbook of Pharmaceutical Salts: Properties, Selection, and Use" (Wiley-VCH, Weinheim, Germany, 2002),
(c) Paulekuhn et al., J. Med. Chem., 50, p 6665-6672 (2007).

A pharmaceutically acceptable salt of a compound of the formula [I-a] or the formula [II] can be obtained by reacting the compound with an inorganic acid, organic acid, inorganic base or organic base according to a method known per se. A pharmaceutically acceptable salt of the compound of the formula [I-a] or the formula [II] may be formed with one half molecule, one molecule or two or more molecules of an acid or base per molecule of the compound of the formula [I-a] or the formula [II].

Examples of the salt with inorganic acid include salts with hydrofluoric acid, hydrochloric acid, hydrobromic acid, hydroiodic acid, nitric acid, phosphoric acid and sulfuric acid.

Examples of the salt with organic acid include salts with acetic acid, adipic acid, alginic acid, 4-aminosalicylic acid, anhydromethylenecitric acid, benzoic acid, benzenesulfonic acid, calcium edetate, camphoric acid, camphor-10-sulfonic acid, carbonic acid, citric acid, edetic acid, ethane-1,2-disulfonic acid, dodecylsulfuric acid, ethanesulfonic acid, fumaric acid, glucoheptonic acid, gluconic acid, glucuronic acid, glycolylarsanilic acid, hexylresorcylic acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclic acid, thiocyanic acid, trifluoroacetic acid, p-toluenesulfonic acid, undecanoic acid, aspartic acid and glutamic acid.

Examples of the salt with inorganic base include a salt with lithium, sodium, potassium, magnesium, calcium, barium, aluminum, zinc, bismuth or ammonium.

Examples of the salt with organic base include a salt with arecoline, betaine, choline, clemizole, ethylenediamine, N-methylglucamine, N-benzylphenethylamine, tris(hydroxymethyl)methylamine, arginine or lysine.

A preferable embodiment of the "pharmaceutically acceptable salt" is as described below.

Examples of the salt with inorganic acid include salts with hydrochloric acid, nitric acid, sulfuric acid, phosphoric acid and hydrobromic acid.

Examples of the salt with organic acid include salts with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid and 2-hydroxy-1-ethanesulfonic acid.

Examples of the salt with inorganic base include salts with sodium, potassium, calcium, magnesium and zinc.

Examples of the salt with organic base include salts with tris(hydroxymethyl)methylamine, N-methylglucamine and lysine.

The compound of the formula [I-a] or the formula [II] or a pharmaceutically acceptable salt thereof may exist as a solvate. The term "solvate" refers to the compound of the formula [I-a] or the formula [II] or a pharmaceutically acceptable salt thereof with which a solvent molecule is associated, and also includes hydrates. Such solvates are preferably pharmaceutically acceptable solvates and include, for example, hydrate, ethanol solvate, dimethyl sulfoxide-solvate and the like of the compound of the formula [I-a] or the formula [II] or a pharmaceutically acceptable salt thereof.

Specific examples include hemihydrate, monohydrate, dihydrate or mono(ethanol)solvate of the compound of the formula [I-a] or the formula [II] or a monohydrate of hydrochloride of the compound of the formula [I-a] or the formula [II], dihydrate of hydrochloride of the same and the like. Such solvates can be produced according to conventional methods.

The compound of the formula [I-a] or the formula [II] may exist as a stereoisomer that should be recognized as a cis/trans isomer. In this case, the compound of the formula [I-a] or the formula [II] may exist as a cis isomer, a trans isomer, or a mixture of a cis isomer and a trans isomer.

The compound of the formula [I-a] or the formula [II] may exist as a tautomer. In this case, the compound of the formula [I-a] or the formula [II] may exist as an individual tautomer or a mixture of tautomers.

The compound of the formula [I-a] or the formula [II] may contain one or more asymmetric carbons. In this case, the compound of the formula [I-a] or the formula [II] may exist as a single enantiomer, a single diastereomer, a mixture of enantiomers or a mixture of diastereomers.

The compound of the formula [I-a] or the formula [II] may exist as an atropisomer. In this case, the compound of the formula [I-a] or the formula [II] may exist as an individual atropisomer or a mixture of atropisomers.

The compound of the formula [I-a] or the formula [II] may simultaneously contain plural structural characteristics that produce the above-mentioned isomers. Moreover, the compound of the formula [I-a] or the formula [II] may contain the above-mentioned isomers at any ratio.

In the absence of other reference such as annotation and the like, the formulas, chemical structures and compound names indicated in the present specification without specifying the stereochemistry thereof encompass all the above-mentioned isomers that may exist.

A diastereomeric mixture can be separated into each diastereomer by conventional methods such as chromatography, crystallization and the like. In addition, each diastereomer can also be formed by using a stereochemically single starting material, or by a synthesis method using a stereoselective reaction.

An enantiomeric mixture can be separated into each single enantiomer by a method well known in the art.

For example, a mixture of enantiomers may be reacted with a substantially pure enantiomer which is known as a chiral auxiliary to form a mixture of diastereomers, which may be then isolated into a diastereomer with an enhanced isomeric ratio or a substantially pure single diastereomer by a common method such as fractionated crystallization or chromatography. The added chiral auxiliary may be removed from the isolated diastereomer by a cleavage reaction to give a desirable enantiomer.

In addition, a mixture of enantiomers of a compound can also be directly separated by a chromatography method using a chiral solid phase well known in the art. Alternatively, one of the enantiomers can also be obtained by using a substantially pure optically active starting material or stereoselective synthesis (asymmetric induction) of a prochiral intermediate using a chiral auxiliary or an asymmetric catalyst.

The absolute steric configuration can be determined based on the X-ray crystal analysis of the resultant crystalline product or intermediate. In this case, a resultant crystalline product or intermediate derivatized with a reagent having an asymmetric center with a known steric configuration may be used where necessary.

The compound of the formula [I-a] or the formula [II] may be labeled with an isotope ($2H$, $^3H$, $^{14}C$, $^{35}S$ and the like).

A compound of the formula [I-a] or the formula [II] or a pharmaceutically acceptable salt thereof is preferably a substantially purified compound of the formula [I-a] or the formula [II] or a pharmaceutically acceptable salt thereof. Further preferably, it is a compound of the formula [I-a] or the formula [II] or a pharmaceutically acceptable salt thereof that is purified to a purity of not less than 80%.

The pharmaceutical composition of the present invention may be produced by appropriately admixing a suitable amount of a compound of the formula [I-a] or the formula [II] or a pharmaceutically acceptable salt thereof with at least one kind of a pharmaceutically acceptable carrier according to a method known in the art of pharmaceutical preparations. The content of the compound of the formula [I-a] or the formula [II] or a pharmaceutically acceptable salt thereof in the pharmaceutical composition varies depending on the dosage form, the dose and the like. It is, for example, 0.1 to 100 wt % of the whole composition.

A dosage form of the compound of formula [I-a] or the formula [II] or a pharmaceutically acceptable salt thereof includes an oral preparation such as a tablet, a capsule, a granule, a powder, a lozenge, a syrup, an emulsion, and a suspension or a parenteral preparation such as an external preparation, a suppository, an injection, an eye drop, a nasal preparation, and a pulmonary preparation.

Examples of the "pharmaceutically acceptable carrier" include various organic or inorganic carrier substances conventionally used as preparation materials, and include excipient, disintegrant, binder, fluidizer, lubricant and the like for solid preparations, and solvent, solubilizing agent, suspending agent, isotonic agent, buffering agent, soothing agent and the like for liquid preparations and base, emulsifier, wetting agent, stabilizer, stabilizing agent, dispersing agent, plasticizer, pH adjuster, absorption promoter, gelation agent, preservative, filler, dissolving agent, solubilizing agents, suspending agent and the like for semisolid dosage forms. Where necessary, moreover, additives such as preservative, antioxidant, colorant, sweetening agent and the like may also be used.

Examples of the "excipient" include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic and the like.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose and the like.

Examples of the "binder" include hydroxypropylcellulose, hydroxypropylmethylcellulose, povidone, crystalline cellulose, sucrose, dextrin, starch, gelatin, carmellose sodium, gum arabic and the like.

Examples of the "fluidizer" include light anhydrous silicic acid, magnesium stearate and the like.

Examples of the "lubricant" include magnesium stearate, calcium stearate, talc and the like.

Examples of the "solvent" include purified water, ethanol, propylene glycol, macrogol, sesame oil, corn oil, olive oil and the like.

Examples of the "solubilizing agents" include propylene glycol, D-mannitol, benzyl benzoate, ethanol, triethanolamine, sodium carbonate, sodium citrate and the like.

Examples of the "suspending agent" include benzalkonium chloride, carmellose, hydroxypropylcellulose, propylene glycol, povidone, methylcellulose, glycerol monostearate and the like.

Examples of the "isotonic agent" include glucose, D-sorbitol, sodium chloride, D-mannitol and the like.

Examples of the "buffering agent" include sodium hydrogenphosphate, sodium acetate, sodium carbonate, sodium citrate and the like.

Examples of the "soothing agent" include benzyl alcohol and the like.

Examples of the "base" include water, animal and vegetable oils (olive oil, corn oil, peanut oil, sesame oil, castor oil and the like), lower alcohols (ethanol, propanol, propylene glycol, 1,3-butyleneglycol, phenol and the like), higher fatty acid and ester thereof, waxes, higher alcohol, polyhydric alcohol, hydrocarbons (white petrolatum, liquid paraffin, paraffin and the like), hydrophilic petrolatum, purified lanolin, water absorption ointment, hydrous lanolin, hydrophilic ointment, starch, pullulan, gum arabic, gum tragacanth, gelatin, dextran, cellulose derivative (methylcellulose, carboxymethylcellulose, hydroxyethylcellulose, hydroxypropylcellulose and the like), synthetic polymer (carboxyvinyl polymer, sodium polyacrylate, poly(vinyl alcohol), polyvinylpyrrolidone and the like), propylene glycol, macrogol (macrogol 200-600 and the like), and a combination of two or more kinds thereof.

Examples of the "preservative" include ethyl parahydroxybenzoate, chlorobutanol, benzyl alcohol, sodium dehydroacetate, sorbic acid and the like.

Examples of the "antioxidant" include sodium sulfite, ascorbic acid and the like.

Examples of the "colorant" include food colors (e.g., Food Color Red No. 2 or 3, Food Color yellow No. 4 or 5 etc.), β-carotene and the like.

Examples of the "sweetening agent" include saccharin sodium, dipotassium glycyrrhizinate, aspartame and the like.

The pharmaceutical composition of the present invention can be administered orally or parenterally (topical, rectal, intravenous administration, intramuscular, subcutaneous, and the like) to mammals other than human (e.g., mouse, rat, hamster, guinea pig, rabbit, cat, dog, swine, bovine, horse, sheep, monkey and the like) and human. The dose varies depending on the subject of administration, disease, symptom, dosage form, administration route and the like. For example, the daily dose for oral administration to an adult patient is generally within the range of about 0.01 mg to 1 g, based on the compound of the formula [I-a] or the formula [II] as the active ingredient. This amount can be administered in one to several portions.

The compound of the formula [I-a] or the formula [II] or a pharmaceutically acceptable salt thereof has a PDHK inhibitory action, and is useful for the treatment and/or prophylaxis of various diseases or conditions expected to be improved by controlling PDHK activity. Examples of various diseases or conditions expected to be improved by controlling PDHK activity include diseases such as diabetes (type 1 diabetes, type 2 diabetes), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer, pulmonary hypertension (pulmonary arterial hypertension), Alzheimer's disease and the like.

To "inhibit PDHK" means to eliminate or attenuate the activity of PDHK by inhibit the function thereof. For example, it means to inhibit the function as PDHK based on the conditions in the below-mentioned Experimental Example 1. To "inhibit PDHK", human PDHK is preferably inhibited. To "inhibit PDHK", preferably, "PDHK1 and PDHK2 are inhibited".

The "PDHK inhibitor" means a substance that binds to PDHK and inhibits the function of PDHK. As the "PDHK inhibitor", preferred is a "human PDHK inhibitor". As the "PDHK inhibitor", preferred is an "inhibitor of PDHK1 and 2".

In the present specification, the "treatment" also includes improvement of symptoms, prevention of severity, maintenance of remission, prevention of exacerbation, and further, prevention of recurrence.

In the present specification, the "prevention" or "prophylaxis" means to suppress the onset of symptoms.

The pharmaceutical composition of the present invention can be used in combination with one or a plurality of other medicaments (hereinafter to be also referred to as a concomitant drug) according to a method generally employed in the medical field (hereinafter to be referred to as combined use).

The administration period of a medicament containing the compound of the formula [I-a] or the formula [II] or a pharmaceutically acceptable salt thereof, and a concomitant drug is not limited, and they may be administered to an administration subject as combination preparation, or the both preparations may be administered simultaneously or at given intervals. In addition, the pharmaceutical composition of the present invention and a concomitant drug may be used as a medicament in the form of a kit. The dose of the concomitant drug is similar to the clinically-employed dose and can be appropriately selected according to the subject of administration, disease, symptom, dosage form, administration route, administration time, combination and the like. The administration form of the concomitant drug is not particularly limited, and it only needs to be combined with a medicament containing the compound of the formula [I-a] or the formula [II] or a pharmaceutically acceptable salt thereof.

Examples of the concomitant drug include therapeutic agents and/or prophylaxis agents for diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease, and the like, and one or more agents therefrom and the compound of the formula [I-a] or the formula [II] or a pharmaceutically acceptable salt thereof can be used in combination.

In the present specification, presentation of preferable embodiments and options of the compound, method, use and composition of the present invention also includes combinations of preferable embodiments and options as long as they can be combined and are free of inconsistency.

The production methods of the compound of the formula [I-a] or the formula [II] or a pharmaceutically acceptable salt thereof are explained in the following. However, the production method of the compound of the formula [I-a] or the formula [II] or a pharmaceutically acceptable salt thereof is not limited to such production methods.

The compound obtained in each step can be isolated or purified as necessary by conventional methods such as distillation, recrystallization, column chromatography and the like. In some cases, the next step may be performed without isolation or purification. When the reaction to be performed in each step is an anhydrous reaction, it is preferably performed in an inert gas atmosphere of argon, nitrogen and the like.

[Production Method 1]

(R)-1,1,1-Trifluoro-2-((S)-5-methyl-5,6,7,8-tetrahydroimidazo[1,5-a]pyrazin-3-yl)propan-2-ol dihydrochloride can be obtained by Production Method 1 shown by the following scheme.

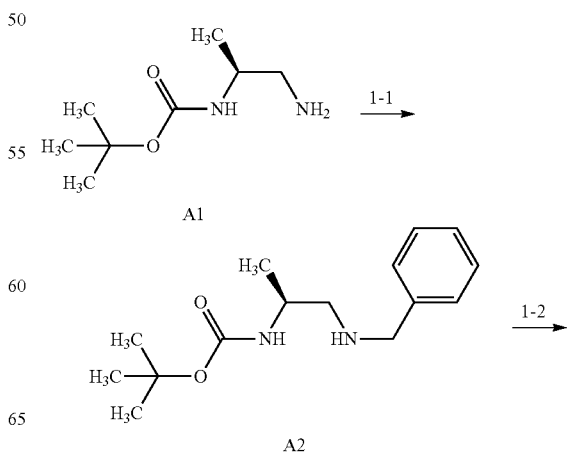

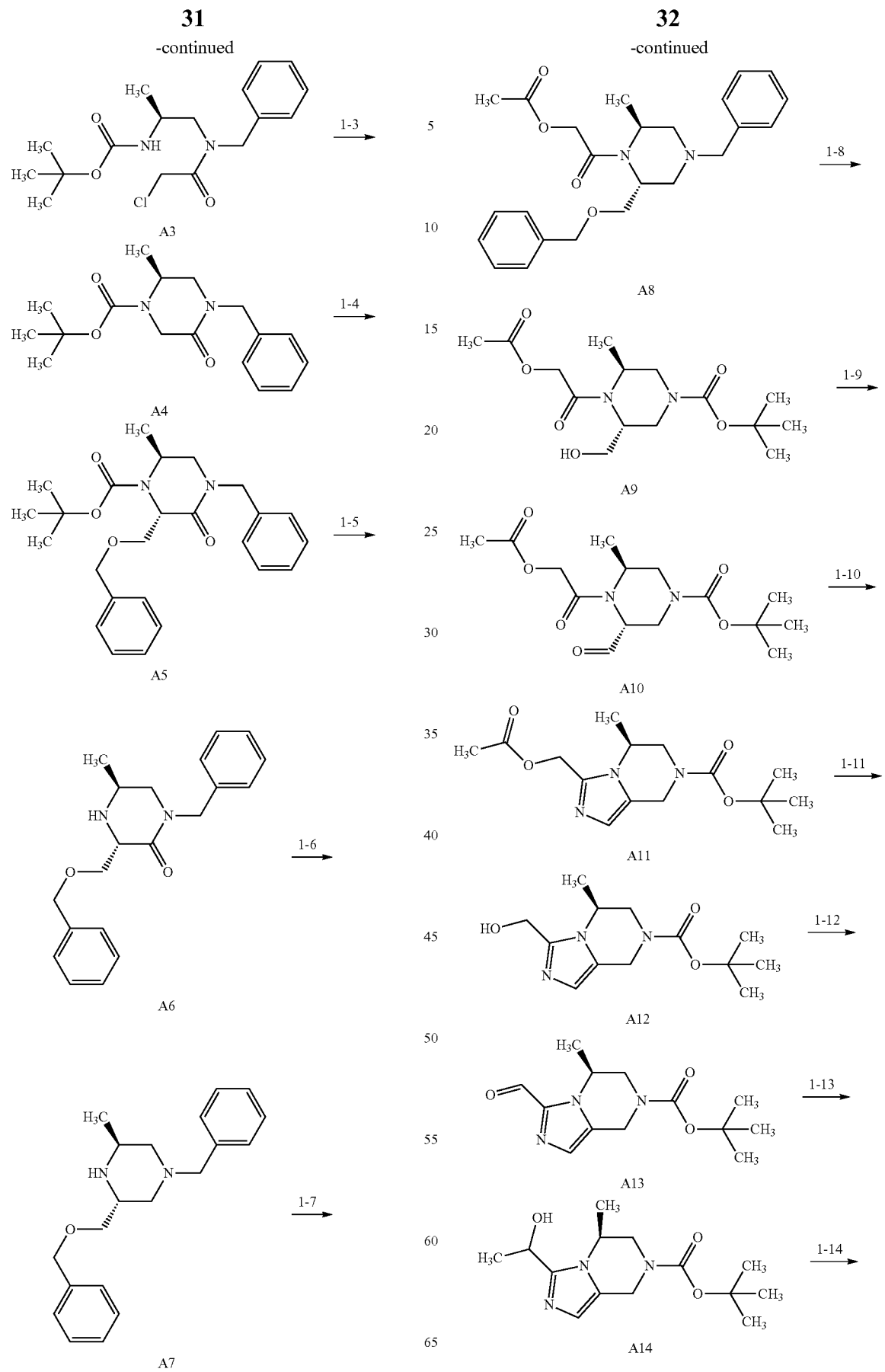

-continued

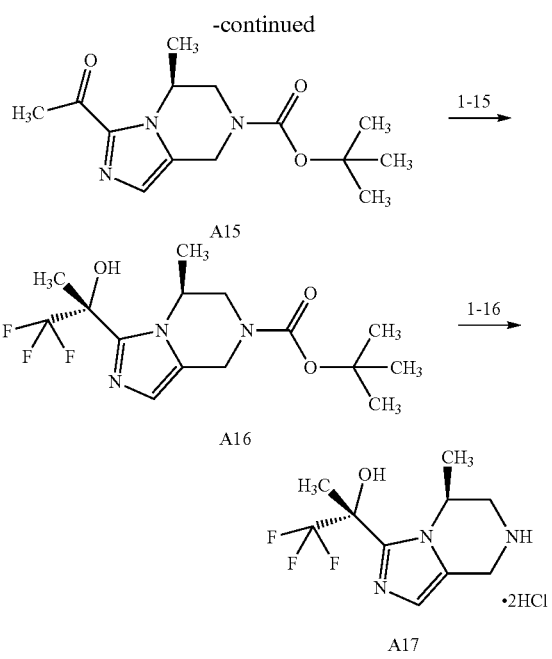

Step 1-1 tert-Butyl (S)-(1-(benzylamino)propan-2-yl)carbamate (compound A2) can be obtained by benzylation of the amino group of tert-butyl (S)-(1-aminopropan-2-yl)carbamate (compound A1). For example, compound A2 can be obtained by reacting compound A1 with benzaldehyde in a solvent at room temperature to 80° C., and then reacting with a reducing agent under ice-cooling. In addition, compound A2 can also be obtained by reacting compound A1 with benzaldehyde and then performing catalytic reduction in the presence of a platinum catalyst at room temperature under a hydrogen atmosphere.

Examples of the reducing agent include sodium borohydride.

Examples of the platinum catalyst include platinum on carbon.

Examples of the solvent include ethanol, tetrahydrofuran and toluene.

Step 1-2 tert-Butyl (S)-(1-(N-benzyl-2-chloroacetamido)propan-2-yl)carbamate (compound A3) can be obtained by reacting compound A2 with 2-chloroacetyl chloride. For example, compound A3 can be obtained by reacting compound A2 with 2-chloroacetyl chloride in a solvent in the presence of a base from ice-cooling to room temperature.

Examples of the base include sodium hydrogen carbonate and triethylamine.

Examples of the solvent include ethyl acetate, tetrahydrofuran and toluene.

Step 1-3 tert-Butyl (S)-4-benzyl-2-methyl-5-oxopiperazine-1-carboxylate (compound A4) can be obtained by an intramolecular cyclization reaction of compound A3. For example, compound A4 can be obtained by treating compound A3 with a base in a solvent from ice-cooling to room temperature.

Examples of the base include sodium hydride and potassium tert-butoxide.

Examples of the solvent include tetrahydrofuran, dimethylformamide and cyclopentyl methyl ether.

Step 1-4 tert-Butyl (2S,6S)-4-benzyl-2-((benzyloxy)methyl)-6-methyl-3-oxopiperazine-1-carboxylate (compound A5) can be obtained by alkylation of compound A4 and benzyl chloromethyl ether. For example, compound A5 can be obtained by reacting compound A4 with benzyl chloromethyl ether in a solvent in the presence of a base at −78° C. to −40° C.

Examples of the base include lithium bis(trimethylsilyl)amide, sodium bis(trimethylsilyl)amide and potassium bis(trimethylsilyl)amide.

Examples of the solvent include tetrahydrofuran and diethyl ether.

The methyl group at the 2-position of compound A4 becomes a steric hindrance and the reaction proceeds diastereoselectively. The steric configuration of compound A5 can be assumed from this reaction mechanism.

Step 1-5

(3S,5S)-1-Benzyl-3-((benzyloxy)methyl)-5-methylpiperazin-2-one (compound A6) can be obtained by removing the tert-butoxycarbonyl group of compound A5. For example, compound A6 can be obtained by reacting compound A5 with an acid in a solvent from ice-cooling to room temperature.

Examples of the acid include hydrochloric acid and trifluoroacetic acid.

Examples of the solvent include ethyl acetate, chloroform, methanol and 1,4-dioxane.

Step 1-6

(3R,5S)-1-Benzyl-3-((benzyloxy)methyl)-5-methylpiperazine (compound A7) can be obtained by removing the oxo group of compound A6 by reduction. For example, compound A7 can be obtained by reacting compound A6 with a reducing agent in a solvent at 40° C. to 70° C.

Examples of the reducing agent include lithium aluminum hydride, isobutylaluminum hydride, borane and alane.

Examples of the solvent include tetrahydrofuran and diethyl ether.

Step 1-7

2-((2R,6S)-4-Benzyl-2-((benzyloxy)methyl)-6-methylpiperazin-1-yl)-2-oxoethyl acetate (compound A8) can be obtained by acylation of compound A7 and acetoxyacetyl chloride. For example, compound A8 can be obtained by reacting compound A7 with acetoxyacetyl chloride in a solvent in the presence of a base from ice-cooling to room temperature.

Examples of the base include triethylamine and sodium hydrogen carbonate.

Examples of the solvent include tetrahydrofuran, ethyl acetate and toluene.

Step 1-8 tert-Butyl (3R,5S)-4-(2-acetoxyacetyl)-3-(hydroxymethyl)-5-methylpiperazine-1-carboxylate (compound A9)

can be obtained by removing the two benzyl groups of compound A8 and subsequently protecting nitrogen of the piperazine ring. For example, compound A9 can be obtained by subjecting compound A8 to catalytic reduction in a solvent under a hydrogen atmosphere in the presence a palladium catalyst and di-tert-butyl dicarbonate at room temperature.

Examples of the palladium catalyst include palladium hydroxide on carbon.

Examples of the solvent include ethanol, methanol and ethyl acetate.

Step 1-9 tert-Butyl (3R,5S)-4-(2-acetoxyacetyl)-3-formyl-5-methylpiperazine-1-carboxylate (compound A10) can be obtained by oxidation of the hydroxy group of compound A9. For example, compound A10 can be obtained by reacting compound A9 with an oxidizing agent in a solvent from ice-cooling to room temperature.

Examples of the oxidizing agent include a combination of 2,2,6,6-tetramethylpiperidine-1-oxyl radical (TEMPO) and diacetoxyiodobenzene, sulfur trioxide pyridine complex and Dess-Martin periodinane.

Examples of the solvent include chloroform, dichloromethane, acetonitrile and dimethyl sulfoxide.

Step 1-10 tert-Butyl (S)-3-(1-acetoxymethyl)-5-methyl-5,6-dihydroimidazo[1,5-a]pyrazine-7(8H)-carboxylate (compound A11) can be obtained by a cyclization reaction using compound A10 and an ammonia reagent. For example, compound A11 can be obtained by heating compound A10 and an ammonia reagent in a solvent at 70° C. to 110° C.

Examples of the ammonia reagent include ammonium acetate.

Examples of the solvent include acetic acid, toluene and cyclopentyl methyl ether.

Step 1-11 tert-Butyl (S)-3-(1-hydroxymethyl)-5-methyl-5,6-dihydroimidazo[1,5-a]pyrazine-7(8H)-carboxylate (compound A12) can be obtained by removing the acetyl group of compound A11. For example, compound A12 can be obtained by treating compound A11 with a base in a solvent from ice-cooling to room temperature.

Examples of the base include potassium carbonate and sodium hydroxide.

Examples of the solvent include methanol and tetrahydrofuran and a mixed solvent of these and water.

Step 1-12 tert-Butyl (S)-3-formyl-5-methyl-5,6-dihydroimidazo[1,5-a]pyrazine-7(8H)-carboxylate (compound A13) can be obtained by oxidation of the hydroxy group of compound A12. For example, compound A13 can be obtained by reacting compound A12 with an oxidizing agent in a solvent at room temperature to 80° C.

Examples of the oxidizing agent include manganese dioxide and Dess-Martin periodinane.

Examples of the solvent include tetrahydrofuran and chloroform.

Step 1-13 tert-Butyl (5S)-3-(1-hydroxyethyl)-5-methyl-5,6-dihydroimidazo[1,5-a]pyrazine-7(8H)-carboxylate (compound A14) can be obtained by reacting compound A13 with methylmagnesium halide. For example, compound A14 can be obtained by reacting compound A13 with methylmagnesium halide in a solvent under ice-cooling to room temperature.

Examples of the methylmagnesium halide include methylmagnesium bromide.

Examples of the solvent include tetrahydrofuran and diethyl ether.

Step 1-14 tert-Butyl (S)-3-acetyl-5-methyl-5,6-dihydroimidazo[1,5-a]pyrazine-7(8H)-carboxylate (compound A15) can be obtained by oxidation of the hydroxy group of compound A14. For example, compound A15 can be obtained by reacting compound A14 with an oxidizing agent in a solvent at room temperature to 90° C.

Examples of the oxidizing agent include manganese dioxide and Dess-Martin periodinane.

Examples of the solvent include tetrahydrofuran and chloroform.

Step 1-15 tert-Butyl (S)-5-methyl-3-((R)-1,1,1-trifluoro-2-hydroxypropan-2-yl)-5,6-dihydroimidazo[1,5-a]pyrazine-7 (8H)-carboxylate (compound A16) can be obtained by reacting compound A15 with (trifluoromethyl)trimethylsilane. For example, compound A16 can be obtained by reacting compound A15 with (trifluoromethyl)trimethylsilane in a solvent in the presence of an additive under ice-cooling to room temperature.

Examples of the additive include tetra-n-butylammonium fluoride, lithium acetate, potassium carbonate and cesium fluoride.

Examples of the solvent include tetrahydrofuran, dimethylformamide and methanol.

The methyl group at the 5-position of compound A15 becomes a steric hindrance and the reaction proceeds diastereoselectively. The steric configuration of compound A16 can be assumed from this reaction mechanism.

Step 1-16

(R)-1,1,1-Trifluoro-2-((S)-5-methyl-5,6,7,8-tetrahydroimidazo[1,5-a]pyrazin-3-yl)propan-2-ol can be obtained by removing the tert-butoxycarbonyl group of compound A16 with an acid. For example, (R)-1,1,1-trifluoro-2-((S)-5-methyl-5,6,7,8-tetrahydroimidazo[1,5-a]pyrazin-3-yl)propan-2-ol dihydrochloride (compound A17) can be obtained by treating compound A16 with hydrochloric acid in a solvent under ice-cooling to room temperature.

Examples of the acid include hydrochloric acid and trifluoroacetic acid.

Examples of the solvent include chloroform, 1,4-dioxane, methanol and ethyl acetate.

A free form can also be obtained by treating compound A17 with alkali.

[Production Method 2]

The compound of the formula [I] can be obtained by Production Method 2 shown by the following scheme.

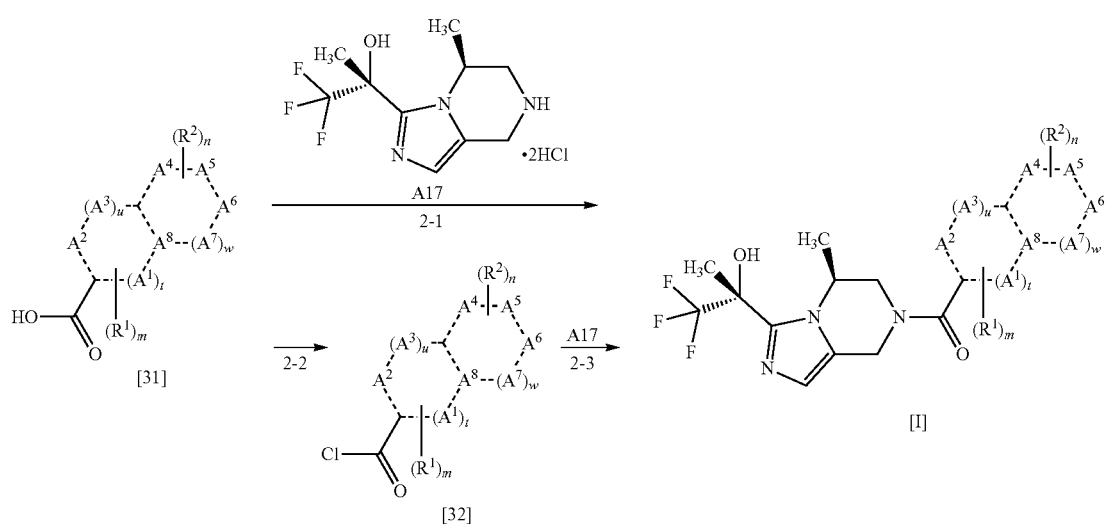

wherein each symbol is as defined for the aforementioned formula [I].

Step 2-1

Compound [I] can be obtained by an amidation reaction of compound A17 and compound [31]. For example, compound [I] can be obtained by reacting compound A17 with compound [31] in a solvent in the presence of a base and a condensing agent from ice-cooling to room temperature.

Examples of the base include diisopropylethylamine and triethylamine.

Examples of the condensing agent include a combination of 1-ethyl-3-(3-dimethylaminopropyl)carbodiimide hydrochloride (WSC.HCl) and 1-hydroxybenzotriazole (HOBt), and O-(7-azabenzotriazol-1-yl)-N,N,N',N'-tetramethyluronium hexafluorophosphate (HATU).

Examples of the solvent include dimethylformamide, acetonitrile and chloroform.

Compound [31] may be a commercially available product, or may be obtained by appropriately converting a commercially available product by a method well known to those of ordinary skill in the art.

Step 2-2

Compound [32] can be obtained by chlorination of the carboxy group of compound [31]. For example, compound [32] can be obtained by treating compound [31] with a chlorinating agent in a solvent from ice-cooling to 60° C. A catalytic amount of dimethylformamide may also be added as an additive to the reaction.

Examples of the chlorinating agent include oxalyl chloride and thionyl chloride.

Examples of the solvent include chloroform and tetrahydrofuran.

Step 2-3

Compound [I] can be obtained by an amidation reaction of compound A17 and compound [32]. For example, compound [I] can be obtained by reacting compound A17 with compound [32] in a solvent in the presence of a base from ice-cooling to room temperature.

Examples of the base include triethylamine.

Examples of the solvent include chloroform.

[Production Method 3]

The compound of the formula [I-a] or the formula [II] can be obtained by Production Method 3 shown by the following scheme.

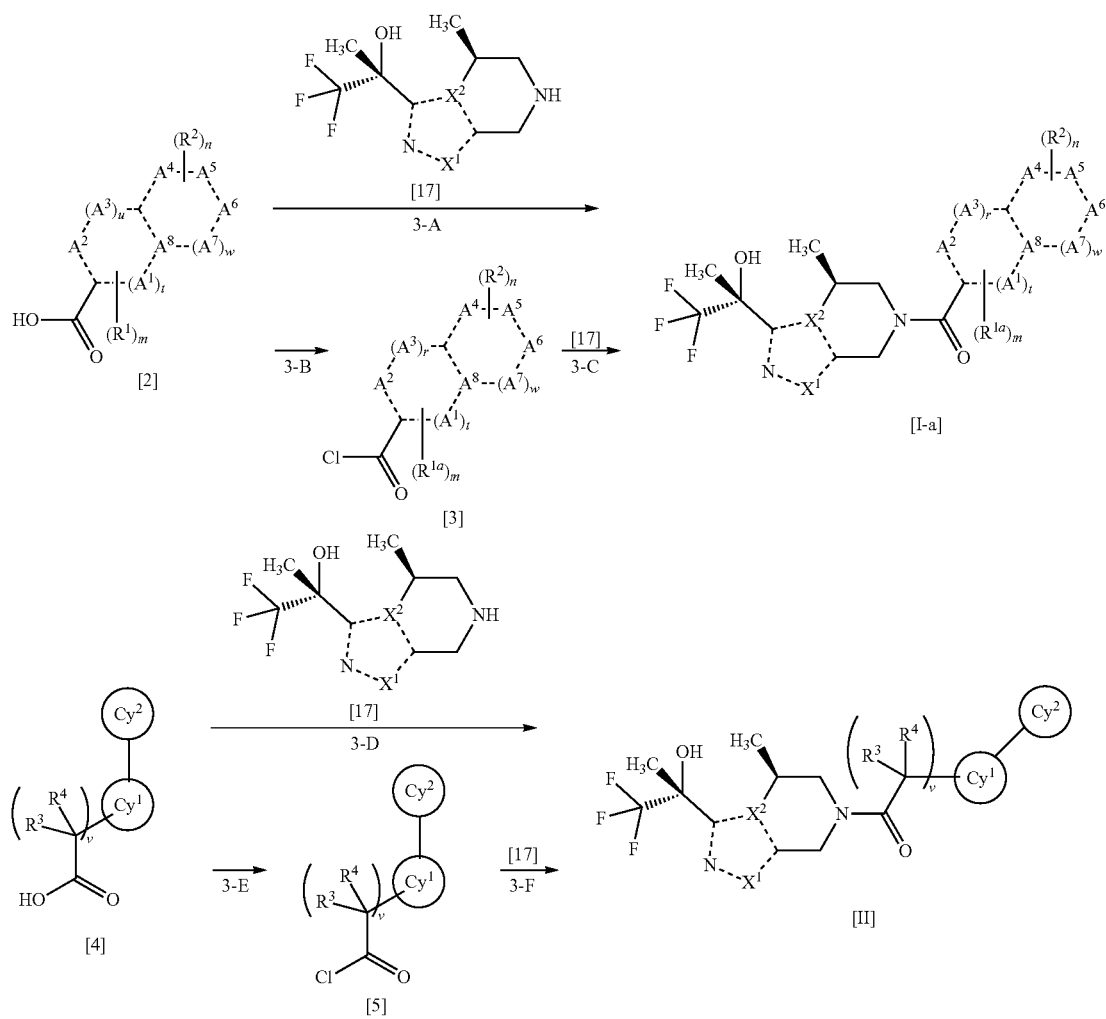

wherein each symbol is as defined for the aforementioned formula [I-a] or the formula [II].

Step 3-A

Compound [I-a] can be obtained by an amidation reaction of compound [17] and compound [2]. For example, compound [I-a] can be obtained by reacting compound [17] with compound [2] in a solvent in the presence of a base and a condensing agent from ice-cooling to room temperature.

Examples of the base include diisopropylethylamine and triethylamine.

Examples of the condensing agent include a combination of 1-ethyl-3-(3-dimethylaminopropyl)carbodiimide hydrochloride (WSC.HCl) and 1-hydroxybenzotriazole (HOBt), and O-(7-azabenzotriazol-1-yl)-N,N,N',N'-tetramethyluronium hexafluorophosphate (HATU).

Examples of the solvent include dimethylformamide, acetonitrile and chloroform.

Compound [17] may be a salt such as hydrochloride, dihydrochloride and the like. Compound [17] can be obtained according to Production Example 1, 12 or 13 described later, or a method well known to those of ordinary skill in the art.

Compound [2] may be a commercially available product, or may be obtained by appropriately converting a commercially available product by a method well known to those of ordinary skill in the art.

Step 3-B

Compound [3] can be obtained by chlorination of the carboxy group of compound [2]. For example, compound [3] can be obtained by treating compound [2] with a chlorinating agent in a solvent from ice-cooling to 60° C. A catalytic amount of dimethylformamide may also be added as an additive to the reaction.

Examples of the chlorinating agent include oxalyl chloride and thionyl chloride.

Examples of the solvent include chloroform and tetrahydrofuran.

Step 3-C

Compound [I-a] can be obtained by an amidation reaction of compound [17] and compound [3]. For example, compound [I-a] can be obtained by reacting compound [17] with compound [3] in a solvent in the presence of a base from ice-cooling to room temperature.

Examples of the base include diisopropylethylamine and triethylamine.

Examples of the solvent include dichloromethane and chloroform.

Step 3-D

Compound [II] can be obtained by an amidation reaction of compound [17] and compound [4]. For example, compound [II] can be obtained by reacting compound [17] with compound [4] according to step 3-A.

Compound [4] may be a commercially available product, or may be obtained by appropriately converting a commercially available product by a method well known to those of ordinary skill in the art.

Step 3-E

Compound [5] can be obtained by chlorination of the carboxy group of compound [4]. For example, compound [5] can be obtained by reacting compound [4] with a chlorinating agent according to step 3-B.

Step 3-F

Compound [II] can be obtained by an amidation reaction of compound [17] and compound [5]. For example, compound [II] can be obtained by reacting compound [17] with compound [5] according to step 3-C.

In Production Method 3, when compound [17] is a compound A17 represented by the formula:

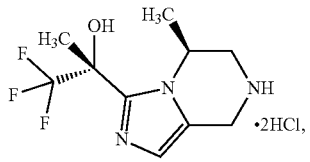

A17 compound A17 can be obtained by the aforementioned Production Method 1.

[Production Method 4]

In Production Method 3, when compound [17] is a compound B17 represented by the formula:

B17 compound B17 can be obtained by Production Method 4 shown by the following scheme.

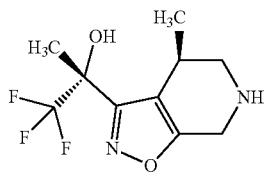

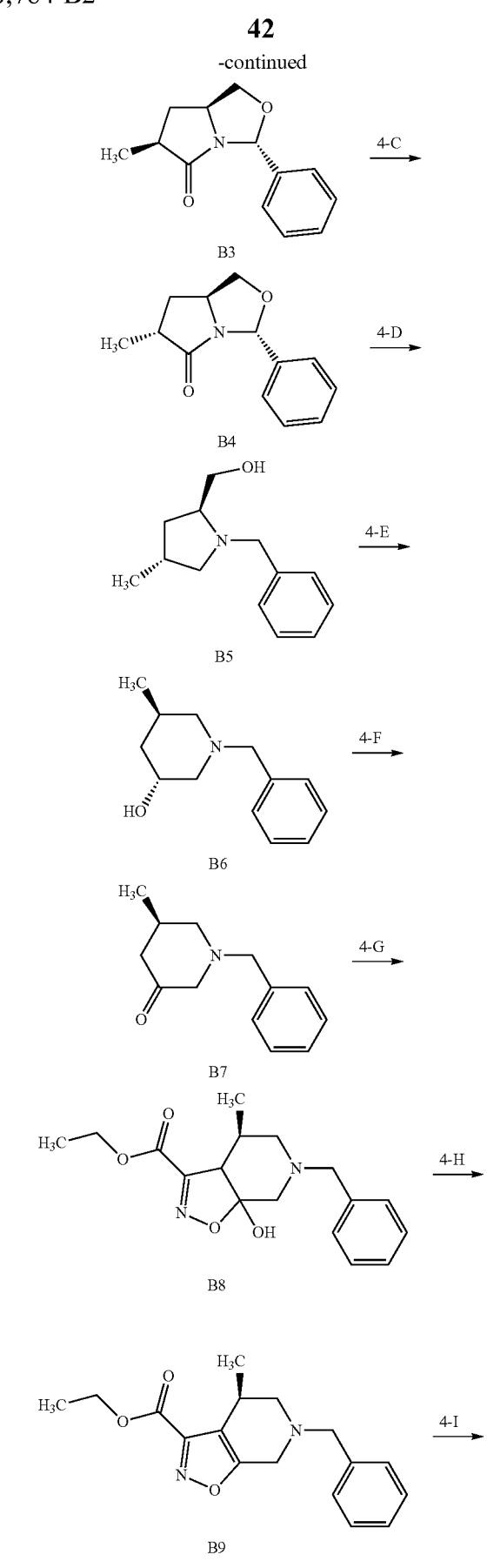

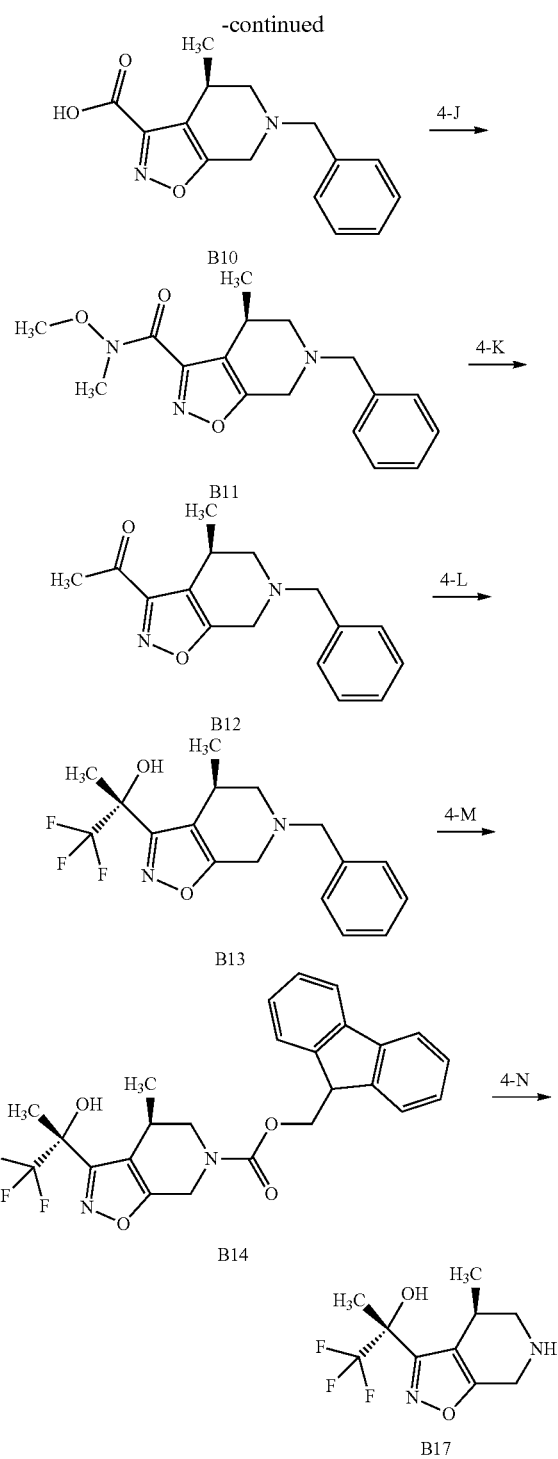

Examples of the acid include p-toluenesulfonic acid.
Examples of the solvent include toluene and benzene.

Step 4-B (3R,6S,7aS)-6-Methyl-3-phenyltetrahydro-3H,5H-pyrrolo[1,2-c]oxazol-5-one (compound B3) can be obtained by methylation of compound B2. For example, compound B3 can be obtained by reacting compound B2 with a methylating agent in a solvent in the presence of a base at −78° C. to −50° C.

Examples of the base include lithium diisopropylamide and lithium bis(trimethylsilyl)amide.
Examples of the methylating agent include methyl iodide.
Examples of the solvent include tetrahydrofuran.

Step 4-C (3R,6R,7aS)-6-Methyl-3-phenyltetrahydro-3H,5H-pyrrolo[1,2-c]oxazol-5-one (compound B4) can be obtained by isomerization of compound B3. For example, compound B4 can be obtained by reacting compound B3 with a base in a solvent at −78° C. to −50° C. and then reacting with water at −20° C. to 10° C.

Examples of the base include lithium diisopropylamide and lithium bis(trimethylsilyl)amide.
Examples of the solvent include tetrahydrofuran.

Step 4-D ((2S,4R)-1-Benzyl-4-methylpyrrolidin-2-yl)methanol (compound B5) can be obtained by reduction of compound B4. For example, compound B5 can be obtained by reacting compound B4 with a reducing agent in a solvent under ice-cooling to 80° C.

Examples of the reducing agent include lithium aluminum hydride and borane-tetrahydrofuran complex.
Examples of the solvent include tetrahydrofuran.

Step 4-E (3R,5R)-1-Benzyl-5-methylpiperidin-3-ol (compound B6) can be obtained by conversion of the hydroxy group of compound B5 to a leaving group, followed by an intramolecular cyclization and a subsequent ring opening reaction.

Conversion to a leaving group can be performed by, for example, reacting compound B5 with trifluoroacetic anhydride at −78° C. to room temperature. The intramolecular cyclization can be performed, for example, by heating the resultant product of the aforementioned reaction in a solvent in the presence of a base at 50° C. to 90° C. The ring opening reaction can be performed by, for example, reacting the resultant product from the aforementioned cyclization reaction with alkali in a solvent under ice-cooling to room temperature.

Examples of the base include triethylamine.
Examples of the alkali include sodium hydroxide.
Examples of the solvent include tetrahydrofuran and a mixed solvent of tetrahydrofuran and water.

Step 4-F (R)-1-Benzyl-5-methylpiperidin-3-one (compound B7) can be obtained by oxidation of the hydroxy group of compound B6. For example, compound B7 can be obtained by reacting compound B6 with an oxidizing agent in a solvent in the presence of a base at −78° C. to room temperature.

Step 4-A (3R,7aS)-3-Phenyltetrahydro-3H,5H-pyrrolo[1,2-c]oxazol-5-one (compound B2) can be obtained by a cyclization reaction of (S)-5-(hydroxymethyl)pyrrolidin-2-one (compound B1) and benzaldehyde. For example, compound B2 can be obtained by reacting compound B1 with benzaldehyde in a solvent in the presence of an acid at 80° C. to 150° C.

Examples of the oxidizing agent include a combination of oxalyl chloride and dimethyl sulfoxide, and a combination of sulfur trioxide pyridine complex and dimethyl sulfoxide.

Examples of the base include triethylamine.

Examples of the solvent include dichloromethane and chloroform.

Step 4-G (4R)-6-Benzyl-7a-hydroxy-4-methyl-3a,4,5,6,7,7a-hexahydroisoxazolo[5,4-c]pyridine-3-carboxylic acid ethyl ester (compound B8) can be obtained by a cyclization reaction of compound B7 and ethyl chloro(hydroxyimino)acetate. For example, compound B8 can be obtained by reacting base-treated compound B7 with base-treated ethyl chloro(hydroxyimino)acetate in a solvent at −78° C. to room temperature.

Examples of the base include lithium bis(trimethylsilyl) amide, sodium bis(trimethylsilyl)amide and potassium bis (trimethylsilyl)amide.

Examples of the solvent include tetrahydrofuran.

Step 4-H (R)-6-Benzyl-4-methyl-4,5,6,7-tetrahydroisoxazolo[5,4-c]pyridine-3-carboxylic acid ethyl ester (compound B9) can be obtained by conversion of the hydroxy group of compound B8 to a leaving group, followed by an elimination reaction. When the leaving group is a mesyloxy group, compound B9 can be obtained by reacting compound B8 with methanesulfonyl chloride in a solvent in the presence of a base under ice-cooling.

Examples of the base include triethylamine.

Examples of the solvent include tetrahydrofuran and toluene.

Step 4-I (R)-6-Benzyl-4-methyl-4,5,6,7-tetrahydroisoxazolo[5,4-c]pyridine-3-carboxylic acid (compound B10) can be obtained by hydrolysis of the ester of compound B9. For example, compound B10 can be obtained by reacting compound B9 with alkali in a solvent under ice-cooling to room temperature.

Examples of the alkali include sodium hydroxide, potassium carbonate and lithium hydroxide.

Examples of the solvent include methanol and tetrahydrofuran and a mixed solvent of these and water.

Step 4-J (R)-6-Benzyl-N-methoxy-N,4-dimethyl-4,5,6,7-tetrahydroisoxazolo[5,4-c]pyridine-3-carboxamide (compound B11) can be obtained by an amidation reaction of compound B10 and N,O-dimethylhydroxylamine. For example, compound B11 can be obtained by reacting compound B10 with N,O-dimethylhydroxylamine in a solvent in the presence of a base and a condensing agent under ice-cooling to room temperature.

Examples of the base include diisopropylethylamine and triethylamine.

Examples of the condensing agent include HATU.

Examples of the solvent include dimethylformamide.

Step 4-K (R)-1-(6-Benzyl-4-methyl-4,5,6,7-tetrahydroisoxazolo[5,4-c]pyridin-3-yl)ethan-1-one (compound B12) can be obtained by reacting compound B11 with methylmagnesium halide. For example, compound B12 can be obtained by reacting compound B11 with methylmagnesium halide in a solvent at 0° C. to room temperature.

Examples of the methylmagnesium halide include methylmagnesium bromide.

Examples of the solvent include tetrahydrofuran and diethyl ether.

Step 4-L (R)-2-((R)-6-Benzyl-4-methyl-4,5,6,7-tetrahydroisoxazolo[5,4-c]pyridin-3-yl)-1,1,1-trifluoropropan-2-ol (compound B13) can be obtained by reacting compound B12 with (trifluoromethyl)trimethylsilane. For example, compound B13 can be obtained by reacting compound B12 with (trifluoromethyl)trimethylsilane in a solvent in the presence of an additive at −78° C. to room temperature.

Examples of the additive include tetra-n-butylammonium fluoride, lithium acetate, potassium carbonate and cesium fluoride.

Examples of the solvent include tetrahydrofuran, dimethylformamide and methanol.

The methyl group at the 4-position of compound B12 becomes a steric hindrance and the reaction proceeds diastereoselectively. The steric configuration of compound B13 can be assumed from this reaction mechanism.

Step 4-M (9H-Fluoren-9-yl)methyl (R)-4-methyl-3-((R)-1,1,1-trifluoro-2-hydroxypropan-2-yl)-4,7-dihydroisoxazolo[5,4-c] pyridine-6(5H)-carboxylate (compound B14) can be obtained by reacting compound B13 with 9-fluorenylmethyl chloroformate. For example, compound B14 can be obtained by reacting compound B13 with 9-fluorenylmethyl chloroformate in a solvent under ice-cooling to room temperature.

Examples of the solvent include chloroform and toluene.

Step 4-N (R)-1,1,1-Trifluoro-2-((R)-4-methyl-4,5,6,7-tetrahydroisoxazolo[5,4-c]pyridin-3-yl)propan-2-ol (compound B17) can be obtained by deprotection of compound B14. For example, compound B17 can be obtained by reacting compound B14 with secondary amine in a solvent under ice-cooling to room temperature.

Examples of the secondary amine include diethylamine and piperidine.

Examples of the solvent include acetonitrile and dimethylformamide.

[Production Method 5]

In Production Method 3, when compound [17] is a compound C17 represented by the formula:

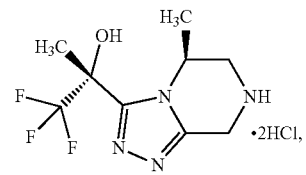

C17 compound C17 can be obtained by Production Method 5 shown by the following scheme.

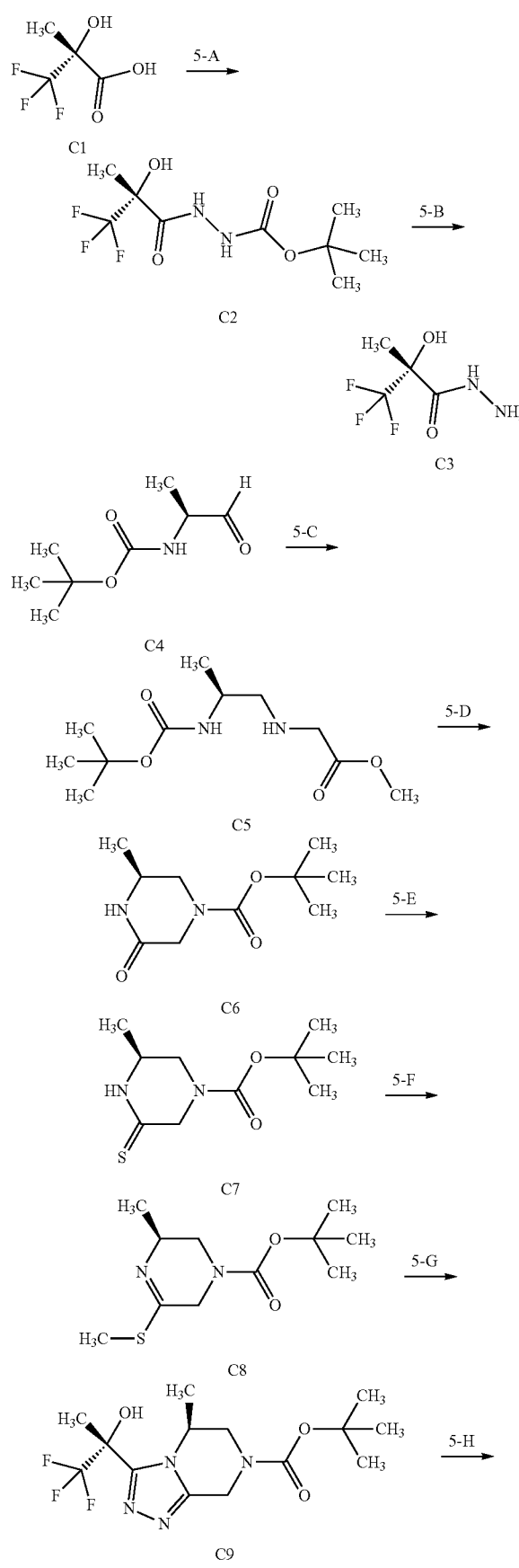

-continued

C17

Step 5-A tert-Butyl (R)-2-(3,3,3-trifluoro-2-hydroxy-2-methylpropanoyl)hydrazine-1-carboxylate (compound C2) can be obtained by reacting (R)-3,3,3-trifluoro-2-hydroxy-2-methylpropanoic acid (compound 01) with tert-butyl carbazate. For example, compound C2 can be obtained by reacting compound C1 with tert-butyl carbazate in a solvent in the presence of a condensing agent under ice-cooling to room temperature.

Examples of the condensing agent include a combination of WSC.HCl and HOBt, and HATU.

Examples of the solvent include acetonitrile and dimethylformamide.

Step 5-B (R)-3,3,3-Trifluoro-2-hydroxy-2-methylpropanehydrazide (compound C3) can be obtained by removing the tert-butoxycarbonyl group of compound C2 with an acid. For example, compound C3 can be obtained by treating compound C2 with an acid in a solvent under ice-cooling to room temperature.

Examples of the acid include hydrochloric acid and trifluoroacetic acid.

Examples of the solvent include chloroform, 1,4-dioxane, methanol and ethyl acetate.

Step 5-C (S)-(2-((tert-Butoxycarbonyl)amino)propyl)glycine methyl ester (compound C5) can be obtained by a reductive amination reaction of tert-butyl (S)-(1-oxopropan-2-yl)carbamate (compound C4) and glycine methyl ester. For example, compound C5 can be obtained by reacting compound C4 with glycine methyl ester in a solvent in the presence of a base and a reducing agent under ice-cooling to room temperature.

Examples of the base include diisopropylethylamine and sodium acetate.

Examples of the reducing agent include sodium triacetoxyborohydride.

Examples of the solvent include chloroform and dichloromethane.

Step 5-D tert-Butyl (S)-3-methyl-5-oxopiperazine-1-carboxylate (compound C6) can be obtained by removal of the tert-butoxycarbonyl group of compound C5, intramolecular cyclization and protection of amino group.

The tert-butoxycarbonyl group can be removed by, for example, reacting compound C5 with an acid in a solvent under ice-cooling to room temperature. Examples of the acid include hydrochloric acid and trifluoroacetic acid. Examples of the solvent include chloroform, 1,4-dioxane, methanol and ethyl acetate.

The intramolecular cyclization can be performed by, for example, heating the resultant product of the aforementioned deprotection in a solvent in the presence of a base at room temperature to 80° C. Examples of the base include sodium acetate. Examples of the solvent include methanol.

The protection of amino group when, for example, the protecting group is a tert-butoxycarbonyl group can be performed by reacting the resultant product of the aforementioned cyclization reaction with di-tert-butyl dicarbonate in a solvent in the presence of a base from ice-cooling to room temperature. Examples of the base include triethylamine. Examples of the solvent include chloroform.

Step 5-E tert-Butyl (S)-3-methyl-5-thioxopiperazine-1-carboxylate (compound C7) can be obtained by converting the oxo group of compound C6 to a thioxo group. For example, compound C7 can be obtained by reacting compound C6 with a sulfurizing agent in a solvent at 50° C. to 80° C.

Examples of the sulfurizing agent include Lawesson's reagent.

Examples of the solvent include tetrahydrofuran.

Step 5-F tert-Butyl (S)-3-methyl-5-(methylthio)-3,6-dihydropyrazine-1(2H)-carboxylate (compound C8) can be obtained by methylation of compound C7. For example, compound C8 can be obtained by reacting compound C7 with a methylating agent in a solvent under ice-cooling to 50° C.

Examples of the methylating agent include methyl iodide.
Examples of the solvent include acetone and acetonitrile.

Compound C8 can be obtained as a salt. For example, hydroiodide of compound C8 can be obtained by reacting compound C7 with methyl iodide.

Step 5-G tert-Butyl (S)-5-methyl-3-((R)-1,1,1-trifluoro-2-hydroxypropan-2-yl)-5,6-dihydro-[1,2,4]triazolo[4,3-a]pyrazine-7(8H)-carboxylate (compound C9) can be obtained by a cyclization reaction of compound C3 and compound C8. For example, compound C9 can be obtained by reacting compound C3 with compound C8 in a solvent in the presence of an acid.

Examples of the acid include acetic acid.
Examples of the solvent include water and isopropanol, and a mixed solvent thereof.

Step 5-H (R)-1,1,1-Trifluoro-2-((S)-5-methyl-5,6,7,8-tetrahydro[1,2,4]triazolo[4,3-a]pyrazin-3-yl)propan-2-ol dihydrochloride (compound C17) can be obtained by removing the tert-butoxycarbonyl group of compound C9 with an acid. For example, compound C17 can be obtained by treating compound C9 with an acid in a solvent under ice-cooling to 70° C.

Examples of the acid include hydrochloric acid and trifluoroacetic acid.

Examples of the solvent include chloroform, 1,4-dioxane, methanol and ethyl acetate.

A free form can also be obtained by treating compound C17 with alkali.

[Production Method 6-1]

When the compound of the formula [II] is a compound [II-d] represented by the formula:

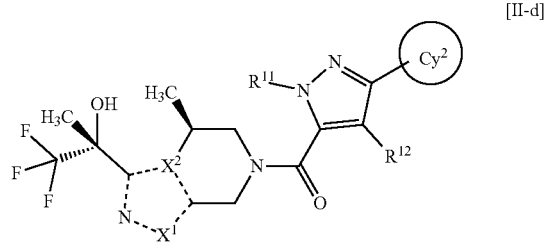

wherein $R^{11}$ is $C_{1-4}$ alkyl;
$R^{12}$ is hydrogen or $C_{1-4}$ alkyl; and
other symbols are as defined for the aforementioned formula [II],
compound [II-d] can be obtained by Production Method 6-1 shown by the following scheme.

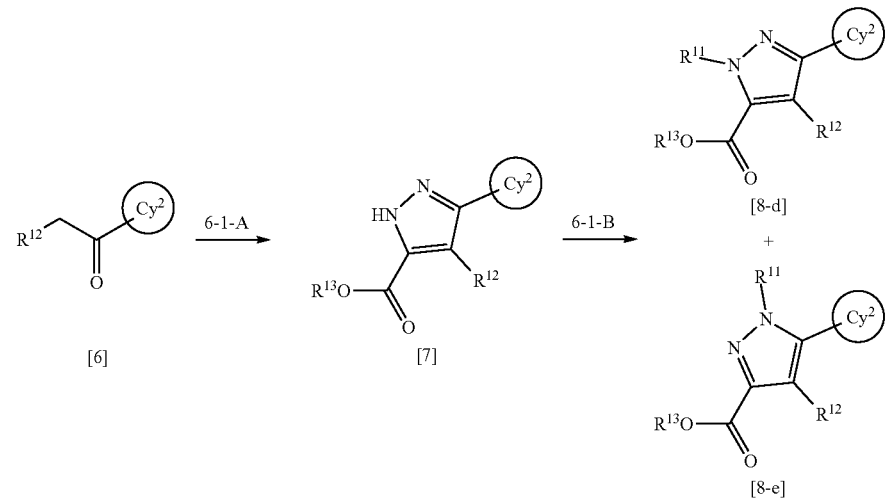

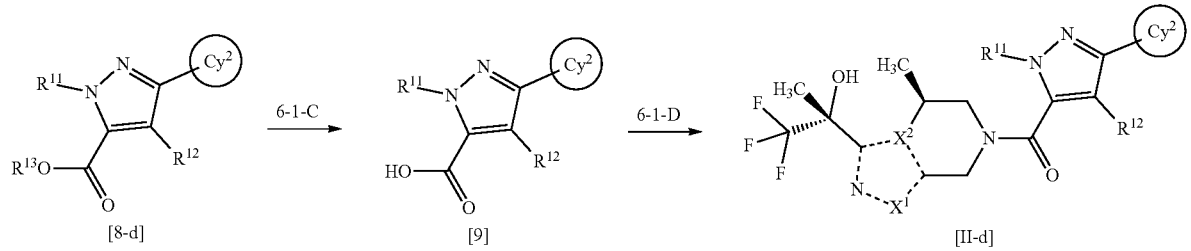

wherein $R^{13}$ is $C_{1-4}$ alkyl; and
other symbols are as defined for the aforementioned formula [II-d].

Step 6-1-A

Compound [7] can be obtained by a pyrazole cyclization reaction using compound [6]. For example, compound [7] can be obtained by reacting compound [6] with dialkyl oxalate $R^{13}O_2CCO_2R^{13}$ in a solvent in the presence of a base and alcohol from ice-cooling to 50° C. and reacting same with hydrazine in the presence of an acid from ice-cooling to 50° C. The intermediate resulting from the reaction with dialkyl oxalate may also be isolated and reacted with hydrazine.

Examples of the dialkyl oxalate include diethyl oxalate.
Examples of the base include sodium ethoxide, sodium hydride and lithium bis(trimethylsilyl)amide.
Examples of the solvent include tetrahydrofuran.
Examples of the acid include acetic acid.
Compound [6] may be a commercially available product, or may be obtained by appropriately converting a commercially available product by a method well known to those of ordinary skill in the art.

Step 6-1-B

A mixture of compounds [8-d] and [8-e] can be obtained by alkylation of the pyrazole ring of compound [7]. For example, compounds [8-d] and [8-e] can be obtained by reacting compound [7] with $C_{1-4}$ alkyl halide in a solvent in the presence of a base from ice-cooling to room temperature.
Examples of the base include sodium hydride and potassium carbonate.
Examples of the solvent include dimethylformamide.
Examples of the $C_{1-4}$ alkyl halide include methyl iodide.
The position of the alkyl group on the pyrazole ring can be assumed from the NMR data of the compound disclosed in, for example, the following literature. Schmidt, Andreas, et al. "New pyrazolium-carboxylates as structural analogues of the pseudo-cross-conjugated betainic alkaloid Nigellicine." The Journal of Organic Chemistry 68.15 (2003): 5977-5982.

Step 6-1-C

Compound [9] can be obtained by hydrolysis of the ester group of compound [8-d]. For example, compound [9] can be obtained by treating compound [8-d] with alkali in a solvent from ice-cooling to 60° C.
Examples of the alkali include sodium hydroxide, potassium carbonate and lithium hydroxide.

Examples of the solvent include methanol and tetrahydrofuran, and a mixed solvent of these and water.

Step 6-1-D

Compound [II-d] can be obtained by an amidation reaction of compound [17] in Production Method 3 and compound [9]. For example, compound [II-d] can be obtained by reacting compound [17] with compound [9] according to Production Method 3, step 3-A.

[Production Method 6-2]

Compound [II-e] in which the compound of the formula [II] has a structure shown by the formula:

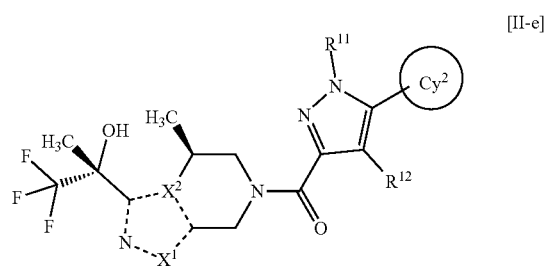

wherein each symbol is as defined in the above, can be obtained by subjecting compound [8-e] obtained by Production Method 6-1, step 6-1-B, to the reactions of step 6-1-C and step 6-1-D.

[Production Method 7]

When the compound of the formula [II] is a compound [II-f] represented by the formula:

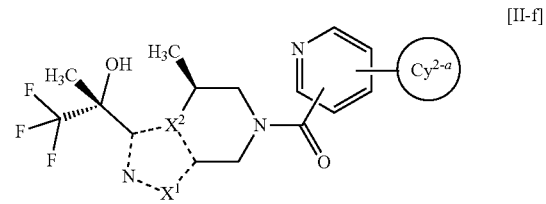

wherein ring $Cy^{2-a}$ is (i) phenyl or (ii) 5- or 6-membered heteroaryl having 1, 2, 3 or 4 nitrogen atoms, the phenyl and the heteroaryl are optionally substituted by 1 or 2 substituents independently selected from the group consisting of halogen, cyano, $C_{1-4}$ alkyl, $C_{1-4}$ alkoxy and $C_{1-4}$ alkylsulfonyl; and
other each symbol is as defined for the aforementioned formula [II],
compound [II-f] can be obtained by Production Method 7 shown by the following scheme.

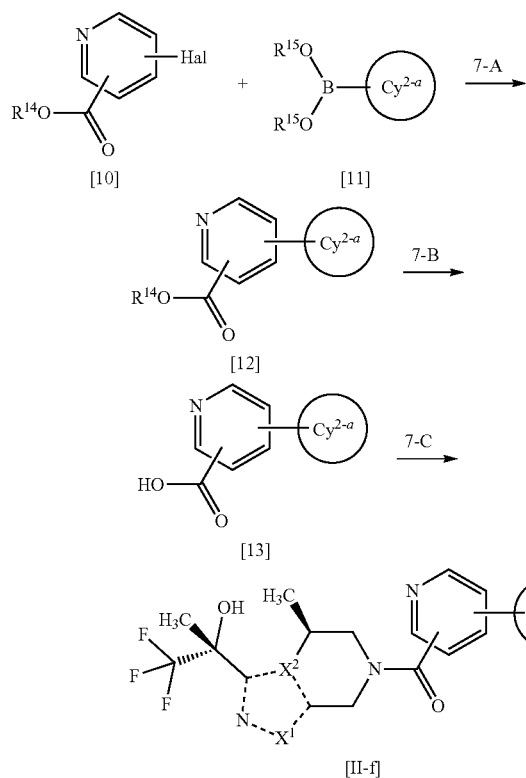

wherein Hal is chloro, bromo or iodo;
$R^{14}$ is $C_{1-4}$ alkyl;
$R^{15}$ is independently hydrogen or $C_{1-4}$ alkyl, one of $R^{15}$ may be bonded to the other $R^{15}$ to form a ring; and other symbols are as defined for the aforementioned formula [II] or [II-f].

Step 7-A

Compound [12] can be obtained by Suzuki coupling of compound [10] and compound [11]. For example, compound [12] can be obtained by reacting compound [10] with compound [11] in a solvent in the presence of a base and a palladium catalyst at room temperature to 70° C.

Examples of the base include potassium carbonate and tripotassium phosphate.

Examples of the palladium catalyst include bis(di-tert-butyl(4-dimethylaminophenyl)phosphine)dichloropalladium(II).

Examples of the solvent include dimethylacetamide, toluene and methanol.

Compound [10] may be a commercially available product, or may be obtained by appropriately converting a commercially available product by a method well known to those of ordinary skill in the art.

Compound [11] may be a commercially available product, or may be obtained by appropriately converting a commercially available product by a method well known to those of ordinary skill in the art.

Step 7-B

Compound [13] can be obtained by hydrolysis of the ester group of compound [12]. For example, compound [13] can be obtained by treating compound [12] with alkali in a solvent from ice-cooling to 60° C.

Examples of the alkali include sodium hydroxide, potassium carbonate and lithium hydroxide.

Examples of the solvent include methanol and tetrahydrofuran, and a mixed solvent of these and water.

Step 7-C

Compound [II-f] can be obtained by an amidation reaction of compound [17] in Production Method 3 and compound [13]. For example, compound [II-f] can be obtained by reacting compound [17] with compound [13] according to Production Method 3, step 3-A.

EXAMPLES

The production method of the compound of the formula [I-a] or the formula [II] or a pharmaceutically acceptable salt thereof of the present invention is specifically explained by way of the following Production Examples. However, the production method of the compound of the formula [I-a] or the formula [II] or a pharmaceutically acceptable salt thereof is not limited by the Production Examples.

Unless otherwise specified, % shows wt %. Unless otherwise specified, the ratio of a mixed solvent is a volume mixing ratio.

In the Examples, abbreviations mean the following.
DMSO: dimethyl sulfoxide
M: mol/L
N: normality
HATU: O-(7-azabenzotriazol-1-yl)-N,N,N',N'-tetramethyluronium hexafluorophosphate The measurement results of $^1$H-NMR are indicated using the following abbreviations.
s: singlet, d: doublet, dd: double doublet, dt: double triplet, t: triplet, q: quartet, dq: double quartet, m: multiplet, brs: broad singlet, brm: broad multiplet, J: coupling constant, Hz: Hertz $^1$H-NMR spectrum was measured in $CDCl_3$ or DMSO-$D_6$ using tetramethylsilane as an internal standard, and all δ values are shown in ppm.

Production Example 1

Synthesis of (R)-1,1,1-trifluoro-2-((S)-5-methyl-5,6,7,8-tetrahydroimidazo[1,5-a]pyrazin-3-yl)propan-2-ol Dihydrochloride Step 1 tert-butyl (S)-(1-(benzylamino)propan-2-yl)carbamate

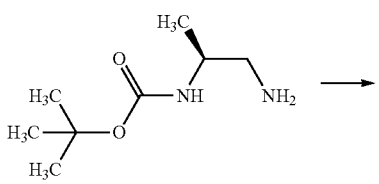

-continued

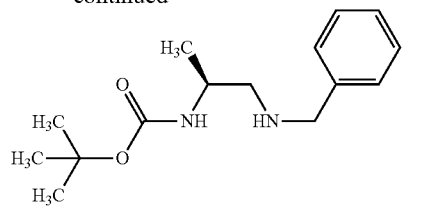

tert-Butyl (S)-(1-aminopropan-2-yl)carbamate (3.60 g) and benzaldehyde (2.64 mL) were mixed with ethanol (50 mL). This mixture was stirred at 60° C. for 1 hr. Under ice-cooling, sodium borohydride (1.51 g) was added to the reaction mixture, and the mixture was stirred at room temperature for 15 min. Under ice-cooling, saturated aqueous ammonium chloride solution and 1N hydrochloric acid were successively added to the reaction mixture until pH became 9. The reaction mixture was concentrated under reduced pressure. To the obtained residue was added saturated aqueous sodium hydrogen carbonate solution and the mixture was extracted with chloroform. The organic layer was dried over sodium sulfate. Sodium sulfate was filtered off and the filtrate was concentrated under reduced pressure. The obtained residue was purified by silica gel column chromatography (hexane:ethyl acetate=2:1 to chloroform:methanol=25:1) to give the title compound (4.47 g).

$^1$H-NMR (400 MHz, DMSO-$d_5$) δ 1.01 (d, J=6.45 Hz, 3H), 1.38 (s, 9H), 1.99 (brs, 1H), 2.36-2.48 (m, 2H), 3.54-3.57 (brm, $^1$H), 3.66 (s, 2H), 6.57 (brs, 1H), 7.19-7.30 (m, 5H)

Step 2 tert-butyl (S)-(1-(N-benzyl-2-chloroacetamido)propan-2-yl)carbamate

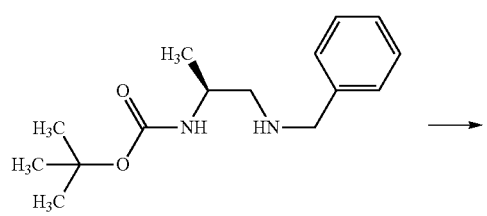

tert-Butyl (S)-(1-(benzylamino)propan-2-yl)carbamate (6.75 g) was mixed with a saturated aqueous sodium hydrogen carbonate solution (60 mL) and ethyl acetate (60 mL). Under ice-cooling, 2-chloroacetyl chloride (4.06 mL) was added to the mixture and the mixture was stirred for 50 min. The organic layer was partitioned and washed with saturated aqueous sodium chloride solution. The organic layer was dried over sodium sulfate. Sodium sulfate was filtered off and the filtrate was concentrated under reduced pressure to give the title compound (9.41 g) as a crude product.

Step 3 tert-butyl (S)-4-benzyl-2-methyl-5-oxopiperazine-1-carboxylate

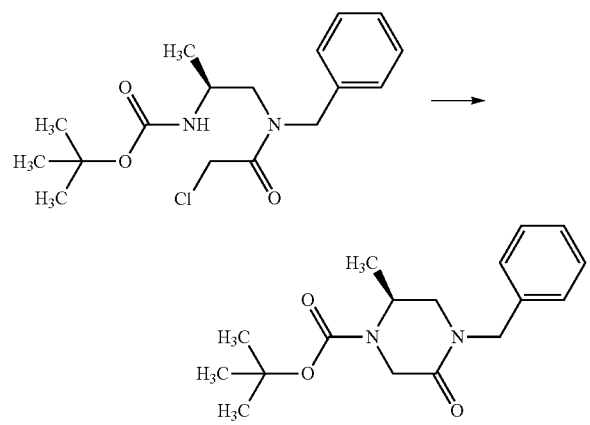

The crude product (9.4 g) of tert-butyl (S)-(1-(N-benzyl-2-chloroacetamido)propan-2-yl)carbamate obtained in the earlier step was mixed with tetrahydrofuran (45 mL) and dimethylformamide (45 mL). Under ice-cooling, 60 w/w % sodium hydride (2.6 g) was added. This mixture was stirred at room temperature for 30 min. Under ice-cooling, saturated aqueous ammonium chloride solution was added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=3:1 to 3:2) to give the title compound (7.07 g).

$^1$H-NMR (400 MHz, CDCl$_3$) δ 1.06 (d, J=6.70 Hz, 3H), 1.44 (s, 9H), 2.92 (dd, J=12.25, 1.85 Hz, 1H), 3.50 (dd, J=12.25, 4.39 Hz, 1H), 3.84 (d, J=18.50 Hz, 1H), 4.34-4.38 (m, 3H), 4.83 (d, J=14.57 Hz, 1H), 7.15-7.34 (m, 5H)

Step 4 tert-butyl (2S,6S)-4-benzyl-2-((benzyloxy)methyl)-6-methyl-3-oxopiperazine-1-carboxylate

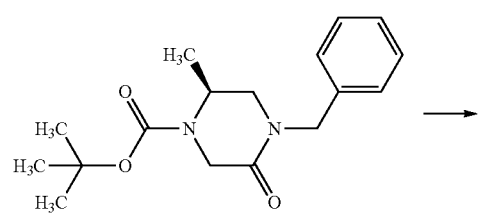

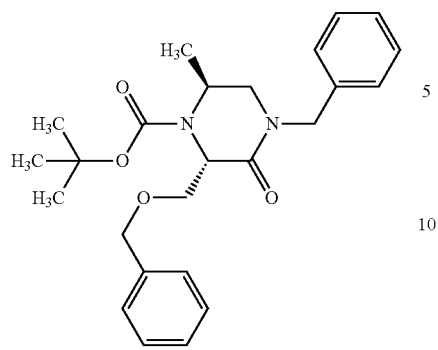

tert-Butyl (S)-4-benzyl-2-methyl-5-oxopiperazine-1-carboxylate (6.46 g) obtained in the earlier step was mixed with tetrahydrofuran (85 mL). Under an argon atmosphere, 1.1 M lithium bis(trimethylsilyl)amide/tetrahydrofuran solution (21.2 mL) was added dropwise to this mixture at −78° C. The reaction mixture was stirred at −78° C. for 1 hr, and benzyl chloromethyl ether (7.3 mL) was added dropwise. The reaction mixture was stirred at −78° C. for 1 hr. To the reaction mixture was added 1N hydrochloric acid (20 mL) at −20° C., and the mixture was extracted with ethyl acetate. The organic layer was washed successively with saturated aqueous ammonium chloride solution and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=4:1 to 3:1) to give the title compound (6.80 g).

$^1$H-NMR (400 MHz, CDCl$_3$) δ 1.01 (d, J=6.47 Hz, 3H), 1.41 (s, 9H), 1.61 (t, J=5.90 Hz, 1H), 2.77 (d, J=12.48 Hz, 1H), 3.86-3.91 (m, 2H), 4.40 (brs, 1H), 4.50-4.53 (m, 2H), 4.69 (d, J=5.78 Hz, 2H), 4.78-4.81 (m, 1H), 7.19-7.36 (m, 10H)

Step 5

(3S,5S)-1-benzyl-3-((benzyloxy)methyl)-5-methyl-piperazin-2-one

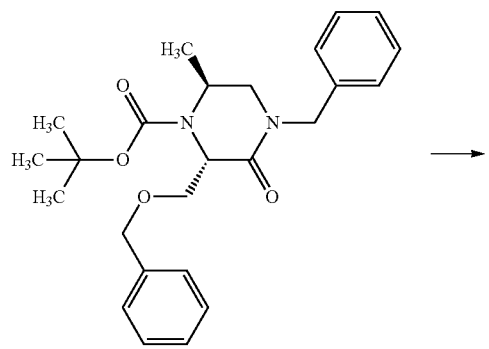

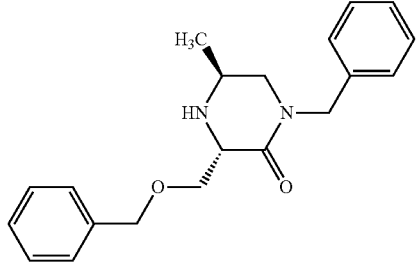

tert-Butyl (2S,6S)-4-benzyl-2-((benzyloxy)methyl)-6-methyl-3-oxopiperazine-1-carboxylate (6.80 g) obtained in the earlier step was mixed with ethyl acetate (70 mL). Under ice-cooling, 4N hydrochloric acid/ethyl acetate solution (35 mL) was added to this mixture. The reaction mixture was stirred at room temperature for 2 hr. The reaction mixture was concentrated under reduced pressure. To the obtained residue was added saturated aqueous sodium hydrogen carbonate solution, and the mixture was extracted with chloroform. The organic layer was dried over sodium sulfate. Sodium sulfate was filtered off and the filtrate was concentrated under reduced pressure. The obtained residue was purified by silica gel column chromatography (ethyl acetate to ethyl acetate:methanol=10:1) to give the title compound (4.99 g).

$^1$H-NMR (400 MHz, CDCl$_3$) δ 1.05 (d, J=6.47 Hz, 3H), 2.95 (dd, J=11.56, 8.79 Hz, 1H), 3.07 (dd, J=11.68, 3.81 Hz, 1H), 3.27-3.29 (m, 1H), 3.78-3.95 (m, 3H), 4.40 (d, J=14.80 Hz, 1H), 4.57 (q, J=11.71 Hz, 2H), 4.74 (d, J=14.57 Hz, 1H), 7.15-7.36 (m, 10H)

Step 6

(3R,5S)-1-benzyl-3-((benzyloxy)methyl)-5-methyl-piperazine

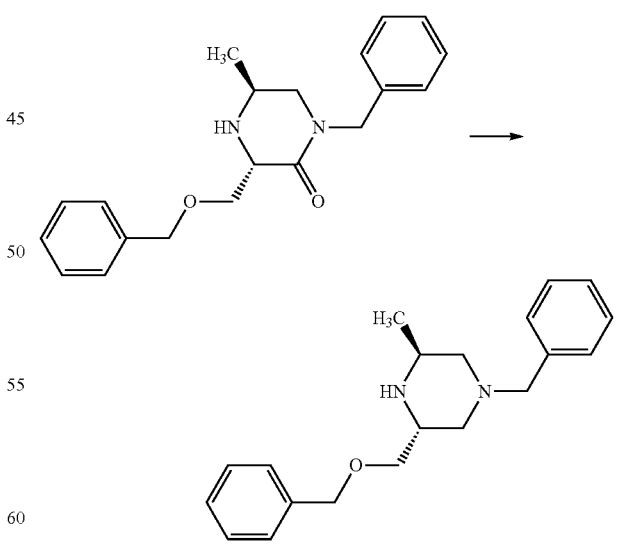

Lithium aluminum hydride (1.75 g) was mixed with tetrahydrofuran (100 mL). Under ice-cooling, a solution of (3S,5S)-1-benzyl-3-((benzyloxy)methyl)-5-methylpiperazin-2-one (4.99 g) obtained in the earlier step in tetrahydrofuran (60 mL) was added dropwise to this mixture. The reaction mixture was stirred at 70° C. for 1.5 hr. Under ice-cooling, to the reaction mixture were successively added dropwise water (1.75 mL), 4N aqueous sodium hydroxide solution (1.75 mL) and water (5.25 mL). To the reaction mixture was added sodium sulfate, and the mixture was stirred at room temperature for 1 hr. The reaction mixture was filtered through celite. The filtrate was concentrated under reduced pressure to give the title compound (6.31 g) as a crude product.

Step 7

2-((2R,6S)-4-benzyl-2-((benzyloxy)methyl)-6-methylpiperazin-1-yl)-2-oxoethyl Acetate

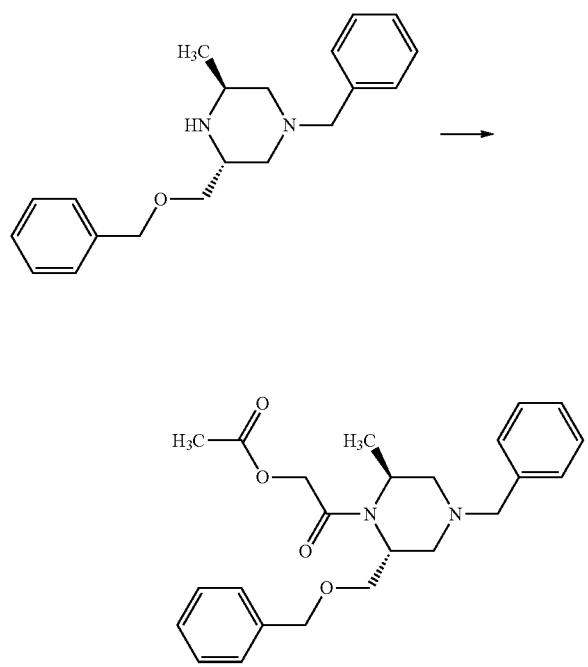 [SMILES: C[C@H]1CN(Cc2ccccc2)C[C@H](COCc2ccccc2)N1 ; CC(=O)OCC(=O)N1[C@@H](COCc2ccccc2)CN(Cc2ccccc2)C[C@@H]1C]

The crude product (6.3 g) of (3R,5S)-1-benzyl-3-((benzyloxy)methyl)-5-methylpiperazine obtained in the earlier step, tetrahydrofuran (50 mL) and triethylamine (4.3 mL) were mixed. Under ice-cooling, acetoxyacetyl chloride (1.82 mL) was added dropwise to this mixture. The reaction mixture was stirred at room temperature for 50 min. Under ice-cooling, to the reaction mixture was added dropwise a saturated aqueous ammonium chloride solution, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=3:1 to 3:2) to give the title compound (5.71 g).

¹H-NMR (400 MHz, CDCl₃) δ 1.43 (d, J=6.36 Hz, 3H), 2.16 (s, 3H), 2.19 (brs, 1H), 2.61-2.63 (m, 3H), 3.40 (d, J=13.20 Hz, 1H), 3.56 (d, J=13.20 Hz, 1H), 3.70-3.78 (m, 4H), 4.50 (dd, J=21.64, 11.86 Hz, 2H), 4.71 (d, J=14.18 Hz, 1H), 4.80 (d, J=14.43 Hz, 1H), 7.24-7.35 (m, 10H)

Step 8 tert-butyl (3R,5S)-4-(2-acetoxyacetyl)-3-(hydroxymethyl)-5-methylpiperazine-1-carboxylate

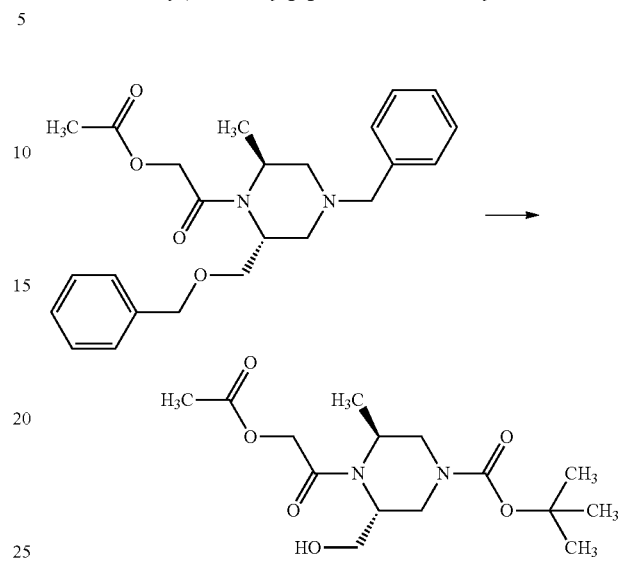

2-((2R,6S)-4-Benzyl-2-((benzyloxy)methyl)-6-methylpiperazin-1-yl)-2-oxoethyl acetate (5.71 g) obtained in the earlier step, ethanol (60 mL) and di-tert-butyl dicarbonate (3.35 g) were mixed. To this mixture was added 20 w/w % palladium hydroxide on carbon (2.9 g), and the mixture was stirred under a hydrogen atmosphere at room temperature overnight. The reaction mixture was filtered through celite and the filtrate was concentrated under reduced pressure. The obtained residue was purified by silica gel column chromatography (hexane:ethyl acetate=1:1 to hexane:acetone=1:1) to give the title compound (4.40 g).

¹H-NMR (400 MHz, CDCl₃) δ 1.35 (d, J=10.64 Hz, 3H), 1.48 (s, 9H), 2.18 (s, 3H), 2.83 (brs, 1H), 3.35-3.41 (m, 1H), 3.55 (dd, J=13.69, 3.91 Hz, 1H), 3.74-3.79 (m, 4H), 4.11-4.13 (m, 2H), 4.72-4.75 (m, 2H)

Step 9 tert-butyl (3R,5S)-4-(2-acetoxyacetyl)-3-formyl-5-methylpiperazine-1-carboxylate

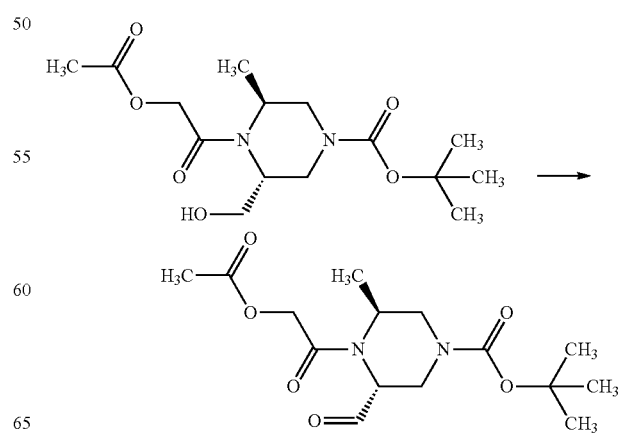

tert-Butyl (3R,5S)-4-(2-acetoxyacetyl)-3-(hydroxymethyl)-5-methylpiperazine-1-carboxylate (4.40 g) obtained in the earlier step was mixed with chloroform (44 mL). Under ice-cooling, Dess-Martin periodinane (7.4 g) was added to this mixture. The reaction mixture was stirred at room temperature for 40 min. Under ice-cooling, saturated aqueous sodium thiosulfate solution was added to the reaction mixture. The reaction mixture was concentrated under reduced pressure and extracted with ethyl acetate. The organic layer was washed successively with saturated aqueous sodium hydrogen carbonate solution and saturated aqueous sodium chloride solution. The organic layer was dried over sodium sulfate. Sodium sulfate was filtered off, and the filtrate was concentrated under reduced pressure to give the title compound (4.97 g) as a crude product.

Step 10 tert-butyl (S)-3-(1-acetoxymethyl)-5-methyl-5,6-dihydroimidazo[1,5-a]pyrazine-7(8H)-carboxylate

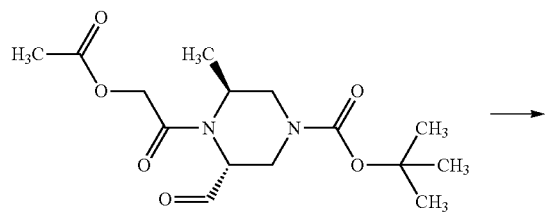

The crude product (4.97 g) of tert-butyl (3R,5S)-4-(2-acetoxyacetyl)-3-formyl-5-methylpiperazine-1-carboxylate obtained in the earlier step, acetic acid (53 mL) and ammonium acetate (4.11 g) were mixed. The reaction mixture was stirred at 90° C. for 1 hr. The reaction mixture was concentrated under reduced pressure and azeotroped with toluene. To the obtained residue was added under ice-cooling saturated aqueous sodium hydrogen carbonate solution, and the mixture was extracted with chloroform. The organic layer was dried over sodium sulfate. Sodium sulfate was filtered off and the filtrate was concentrated under reduced pressure. The obtained residue was purified by silica gel column chromatography (hexane:ethyl acetate=2:1 to hexane:acetone=1:1) to give the title compound (2.98 g).

$^1$H-NMR (400 MHz, CDCl$_3$) δ 1.38 (d, J=6.70 Hz, 3H), 1.49 (s, 9H), 2.08 (s, 3H), 3.26, (brs, 1H), 4.26-4.45 (m, 3H), 5.09-5.17 (m, 3H), 6.83 (s, 1H)

Step 11 tert-butyl (S)-3-(1-hydroxymethyl)-5-methyl-5,6-dihydroimidazo[1,5-a]pyrazine-7(8H)-carboxylate

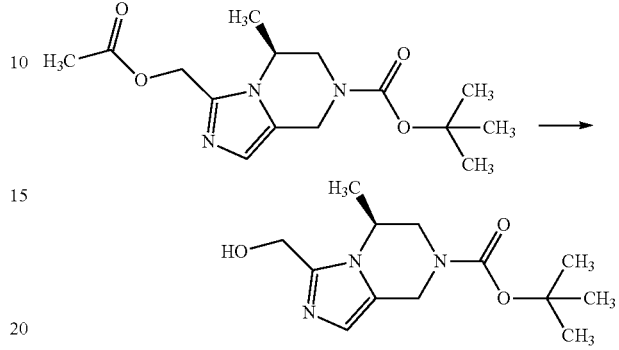

tert-Butyl (S)-3-(1-acetoxymethyl)-5-methyl-5,6-dihydroimidazo[1,5-a]pyrazine-7 (8H)-carboxylate (2.98 g) obtained in the earlier step was mixed with methanol (30 mL). Under ice-cooling, potassium carbonate (0.133 g) was added to this mixture. The reaction mixture was stirred at room temperature for 1 hr. The reaction mixture was concentrated under reduced pressure. The obtained residue was purified by silica gel column chromatography (hexane: acetone=1:2 to chloroform:methanol=15:1) to give the title compound (2.60 g).

$^1$H-NMR (400 MHz, CDCl$_3$) δ 1.43 (d, J=6.47 Hz, 3H), 1.48 (s, 9H), 3.15-3.39 (m, 1H), 4.13-4.20 (m, 2H), 4.53 (brs, 1H), 4.61 (s, 2H), 4.81-5.13 (m, 1H), 6.67 (s, 1H)

Step 12 tert-butyl (S)-3-formyl-5-methyl-5,6-dihydroimidazo[1,5-a]pyrazine-7(8H)-carboxylate

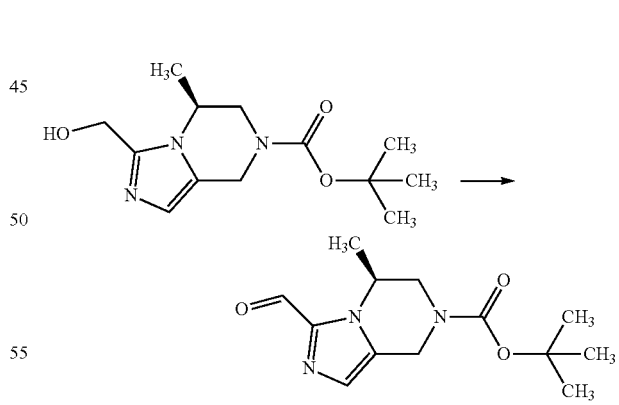

tert-Butyl (S)-3-(1-hydroxymethyl)-5-methyl-5,6-dihydroimidazo[1,5-a]pyrazine-7(8H)-carboxylate (2.40 g) obtained in the earlier step was mixed with tetrahydrofuran (40 mL). To this mixture was added at room temperature manganese dioxide (3.0 g), and the mixture was stirred at 70° C. for 2 hr and half. The reaction mixture was filtered through celite, and the filtrate was concentrated under reduced pressure to give the title compound (2.34 g) as a crude product.

Step 13 tert-butyl (5S)-3-(1-hydroxyethyl)-5-methyl-5,6-dihydroimidazo[1,5-a]pyrazine-7(8H)-carboxylate

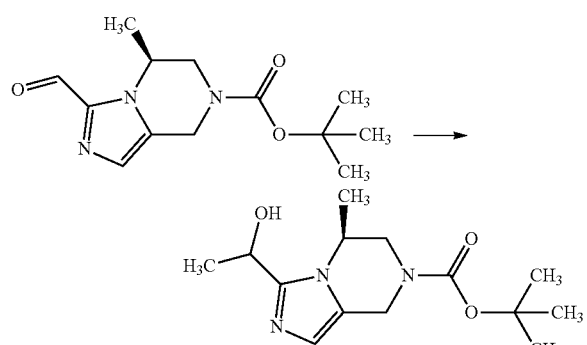

The crude product (2.34 g) of tert-butyl (S)-3-formyl-5-methyl-5,6-dihydroimidazo[1,5-a]pyrazine-7(8H)-carboxylate obtained in the earlier step was mixed with tetrahydrofuran (30 mL). Under an argon atmosphere, 3.0M methylmagnesium bromide/diethyl ether solution (4.1 mL) was added dropwise to this mixture at 0° C. The reaction mixture was stirred at room temperature for 50 min. To the reaction mixture were added under ice-cooling saturated aqueous ammonium chloride solution and saturated aqueous sodium chloride solution. The reaction mixture was extracted with chloroform:methanol=20:1. The organic layer was dried over sodium sulfate. Sodium sulfate was filtered off and the filtrate was concentrated under reduced pressure. The obtained residue was purified by silica gel column chromatography (hexane:ethyl acetate=1:1 to chloroform:methanol=15:1) to give the title compound (2.40 g).

$^1$H-NMR (400 MHz, CDCl$_3$) δ 1.44 (d, J=6.24 Hz, 3H), 1.49 (s, 9H), 1.63 (d, J=4.62 Hz, 3H), 3.12-3.36 (m, 1H), 4.02-4.73 (m, 3H), 4.77-5.07 (m, 2H), 6.74 (s, 1H)

Step 14 tert-butyl (S)-3-acetyl-5-methyl-5,6-dihydroimidazo[1,5-a]pyrazine-7(8H)-carboxylate

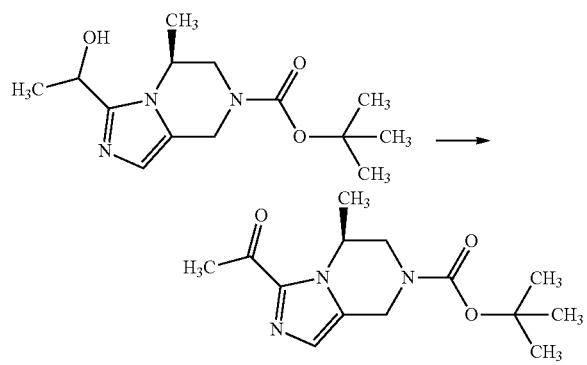

tert-Butyl (5S)-3-(1-hydroxyethyl)-5-methyl-5,6-dihydroimidazo[1,5-a]pyrazine-7(8H)-carboxylate (2.40 g) obtained in the earlier step and manganese dioxide (2.4 g) were mixed with tetrahydrofuran (35 mL). The reaction mixture was stirred at 80° C. for 3.5 hr. The reaction mixture was filtered through celite and the filtrate was concentrated under reduced pressure. The obtained residue was purified by silica gel column chromatography (hexane:ethyl acetate=1:1 to 2:3) to give the title compound (1.84 g).

$^1$H-NMR (400 MHz, CDCl$_3$) δ 1.40 (d, J=6.36 Hz, 3H), 1.53 (s, 9H), 2.65 (s, 3H), 3.25-3.27 (m, 1H), 4.10-4.30 (m, 2H), 5.05-5.21 (m, 2H), 6.99 (s, 1H)

Step 15 tert-butyl (S)-5-methyl-3-((R)-1,1,1-trifluoro-2-hydroxypropan-2-yl)-5,6-dihydroimidazo[1,5-a]pyrazine-7(8H)-carboxylate

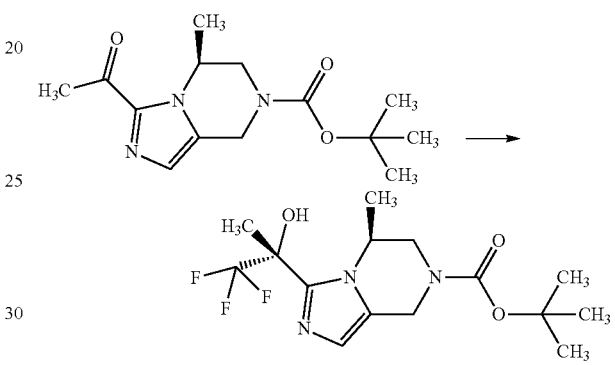

tert-Butyl (S)-3-acetyl-5-methyl-5,6-dihydroimidazo[1,5-a]pyrazine-7(8H)-carboxylate (1.84 g) obtained in the earlier step and cesium fluoride (0.15 g) were mixed with tetrahydrofuran (25 mL). Under ice-cooling, (trifluoromethyl)trimethylsilane (1.95 mL) was added to this mixture. The reaction mixture was stirred at room temperature for 1 hr. Under ice-cooling, methanol (8 mL) and 1.5 M aqueous potassium carbonate solution (13 mL) were added to the reaction mixture. The reaction mixture was stirred at 60° C. for 1 hr. The reaction mixture was partitioned by adding ethyl acetate and water. The organic layer was washed with saturated aqueous sodium chloride solution. The organic layer was dried over sodium sulfate. Sodium sulfate was filtered off and the filtrate was concentrated under reduced pressure. To the obtained residue was added ethyl acetate:hexane=1:2, and the mixture was stirred at room temperature for 1 hr. The precipitated solid was collected by filtration to give the title compound (1.65 g). The obtained compound was analyzed using a chiral column to find that the retention time of the obtained title compound was 13.4 min and the optical purity then was >99.9%. The analysis conditions using chiral column were as described below.

measurement device; HPLC system Shimadzu Corporation high-performance liquid chromatography prominence
column; Daicel CHIRALPAK IC 4.6 mmϕ×250 mm
column temperature; 40° C.
mobile phase; hexane:ethanol=19:1
flow rate; 0.5 mL/min
detection; UV (220 nm)

$^1$H-NMR (400 MHz, CDCl$_3$) δ 1.41 (d, J=6.60 Hz, 3H), 1.53 (s, 9H), 1.94 (s, 3H), 3.23 (dd, J=37.78, 13.08 Hz, 1H), 3.47 (d, J=22.99 Hz, 1H), 4.10 (dd, J=43.53, 17.06 Hz, 1H), 4.51 (d, J=16.14 Hz, 1H), 4.75 (t, J=17.85 Hz, 1H), 4.98 (brs, 1H), 6.85 (s, 1H)

Step 16

(R)-1,1,1-trifluoro-2-((S)-5-methyl-5,6,7,8-tetrahydroimidazo[1,5-a]pyrazin-3-yl)propan-2-ol Dihydrochloride

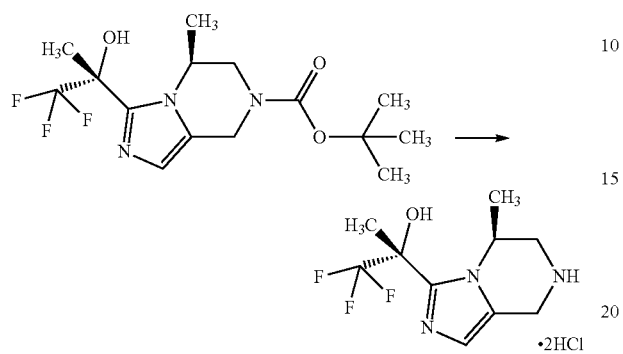

tert-Butyl (S)-5-methyl-3-((R)-1,1,1-trifluoro-2-hydroxypropan-2-yl)-5,6-dihydroimidazo[1,5-a]pyrazine-7(8H)-carboxylate (1.60 g) obtained in the earlier step was mixed with methanol (6 mL). Under ice-cooling, 4N hydrochloric acid/ethyl acetate solution (11.8 mL) was added to this mixture. The reaction mixture was stirred at room temperature for 2 hr. The reaction mixture was concentrated under reduced pressure. To the obtained residue were added ethyl acetate and diethyl ether, and the mixture was stirred at room temperature for 1 hr. The precipitated solid was collected by filtration to give the title compound (1.49 g).

$^1$H-NMR (400 MHz, DMSO-$d_6$) δ 1.56 (d, J=7.63 Hz, 3H), 1.86 (s, 3H), 3.28 (brs, 1H), 3.56 (d, J=13.18 Hz, 1H), 4.38-4.44 (m, 2H), 5.19 (brs, 1H), 7.25 (s, 1H), 7.77 (brs, 1H), 9.86 (brs, 1H), 10.49 (brs, 1H)

Production Example 2

Synthesis of (2,3-dihydro-1H-inden-2-yl)((S)-5-methyl-3-((R)-1,1,1-trifluoro-2-hydroxypropan-2-yl)-5,6-dihydroimidazo[1,5-a]pyrazin-7(8H)-yl)methanone (Compound of Example 3)

Step 1

2,3-dihydro-1H-indene-2-carbonyl Chloride

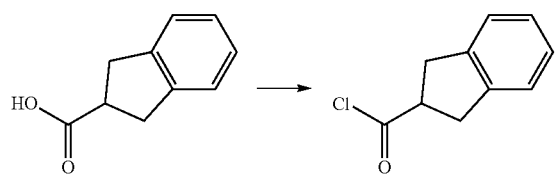 [SMILES: O=C(O)C1Cc2ccccc2C1 ; O=C(Cl)C1Cc2ccccc2C1]

2,3-Dihydro-1H-indene-2-carboxylic acid (6.4 mg) was mixed with chloroform (0.5 mL). Under ice-cooling, oxalyl chloride (15.2 μL) and a catalytic amount of dimethylformamide were added. The mixture was stirred at room temperature for 1 hr. The reaction mixture was concentrated under reduced pressure, and azeotroped with toluene to give the title compound as a crude product.

Step 2

(2,3-dihydro-1H-inden-2-yl)((S)-5-methyl-3-((R)-1,1,1-trifluoro-2-hydroxypropan-2-yl)-5,6-dihydroimidazo[1,5-a]pyrazin-7(8H)-yl)methanone

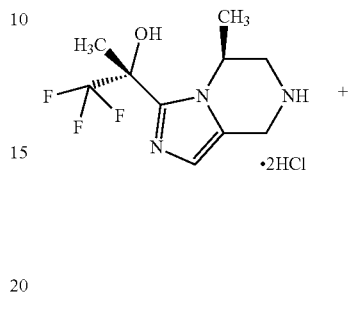

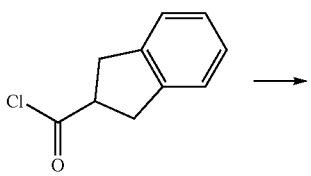

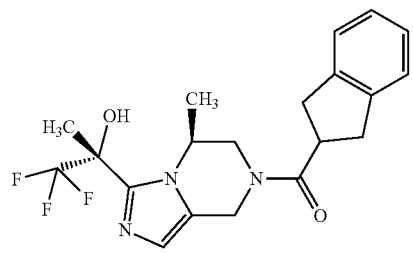

(R)-1,1,1-Trifluoro-2-((S)-5-methyl-5,6,7,8-tetrahydroimidazo[1,5-a]pyrazin-3-yl)propan-2-ol dihydrochloride (13.3 mg) and a crude product of 2,3-dihydro-1H-indene-2-carbonyl chloride obtained in the earlier step were mixed with chloroform (0.5 mL). To this mixture was added at room temperature triethylamine (15.2 μL) and the mixture was stirred for 1.5 hr. Under ice-cooling, a small amount of methanol was added to the reaction mixture to stop the reaction. The reaction mixture was purified by thin layer silica gel chromatography (hexane:ethyl acetate=1:1) to give the title compound (13.9 mg).

$^1$H-NMR (400 MHz, CDCl$_3$) δ 1.41-1.50 (m, 3H), 1.96-1.97 (m, 3H), 3.12-3.65 (m, 7H), 3.99-5.08 (m, 4H), 6.91 (s, 1H), 7.16-7.21 (m, 4H)

Production Example 3

Synthesis of 2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile (Compound of Example 4) and Salts Thereof and a Hydrate Thereof, and 1-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-1H-indazole-6-carbonitrile (Compound of Example 5)

Step 1

6-cyano-2-methyl-2H-indazole-3-carboxylic acid methyl ester and 6-cyano-1-methyl-1H-indazole-3-carboxylic acid methyl ester

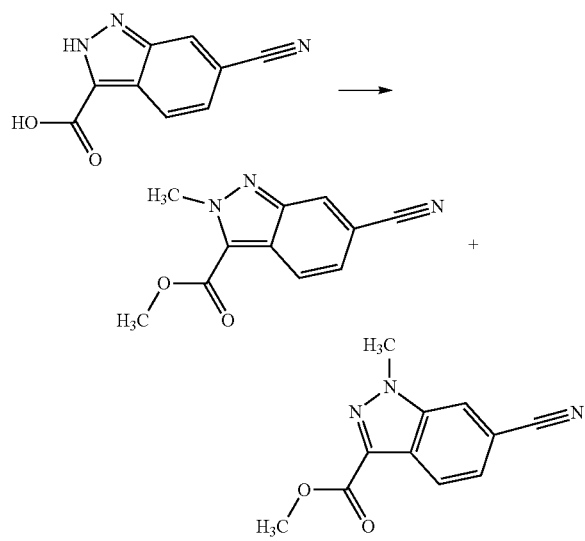

6-Cyano-2H-indazole-3-carboxylic acid (100 mg) and potassium carbonate (220 mg) were mixed with dimethylformamide (3 mL). Under ice-cooling, methyl iodide (82.5 μL) was added to this mixture. The reaction mixture was stirred at room temperature overnight. Under ice-cooling, water was added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The residue was purified by silica gel column chromatography (hexane:ethyl acetate=2:1 to 1:1) to give 6-cyano-2-methyl-2H-indazole-3-carboxylic acid methyl ester (42.9 mg) as a less polar compound.

$^1$H-NMR (400 MHz, CDCl$_3$) δ 4.05 (s, 3H), 4.55 (s, 3H), 7.41 (dd, J=8.79, 0.92 Hz, 1H), 8.11 (d, J=8.79 Hz, 1H), 8.18 (s, 1H)

In addition, 6-cyano-1-methyl-1H-indazole-3-carboxylic acid methyl ester (46.1 mg) was obtained as a more polar compound.

$^1$H-NMR (400 MHz, CDCl$_3$) δ 4.05 (s, 3H), 4.22 (s, 3H), 7.53 (d, J=8.55 Hz, 1H), 7.85 (s, 1H), 8.34 (d, J=8.32 Hz, 1H)

The structure of each isomer was determined by comparison of $^1$H-NMR spectrum of each isomer and analogs with known structure.

Step 2-1

6-cyano-2-methyl-2H-indazole-3-carboxylic Acid

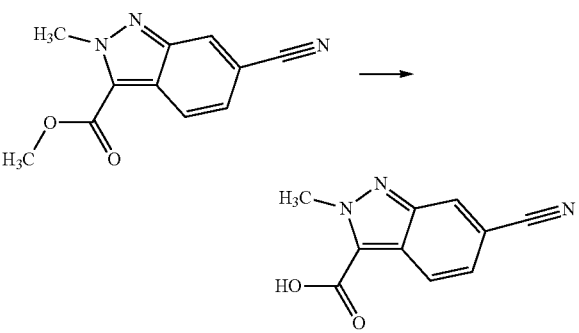

6-Cyano-2-methyl-2H-indazole-3-carboxylic acid methyl ester (42.9 mg) obtained in the earlier step was mixed with tetrahydrofuran (2 mL) and methanol (1 mL). Under ice-cooling, 2N aqueous sodium hydroxide solution (150 μL) was added to this mixture. The reaction mixture was stirred at room temperature for 3 hr. 2N Aqueous sodium hydroxide solution (50 μL) was added, and the mixture was further stirred at room temperature for 30 min. Under ice-cooling, 1N hydrochloric acid (800 μL) and water were added to the reaction mixture, and the mixture was extracted with ethyl acetate. The organic layer was washed successively with water and saturated aqueous sodium chloride solution. The organic layer was dried over sodium sulfate. Sodium sulfate was filtered off, and the filtrate was concentrated under reduced pressure to give the title compound (37.8 mg).

$^1$H-NMR (400 MHz, DMSO-dd δ 4.47 (s, 3H), 7.52 (dd, J=8.67, 1.27 Hz, 1H), 8.12 (dd, J=8.79, 0.92 Hz, 1H), 8.48 (s, 1H), 13.96 (brs, 1H)

Step 3-1

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile

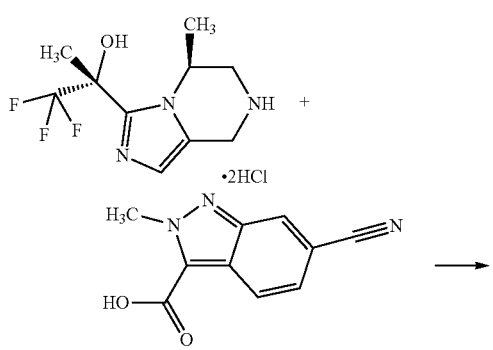

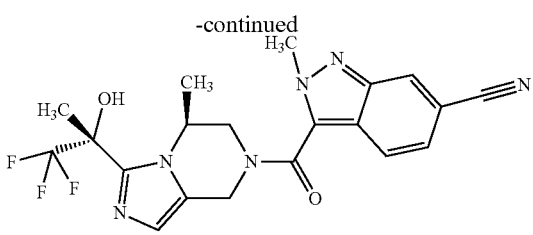

(R)-1,1,1-Trifluoro-2-((S)-5-methyl-5,6,7,8-tetrahydroimidazo[1,5-a]pyrazin-3-yl)propan-2-ol dihydrochloride (35.4 mg) and 6-cyano-2-methyl-2H-indazole-3-carboxylic acid (21.7 mg) obtained in the earlier step were mixed with dimethylformamide (1 mL). Under ice-cooling, to this mixture were added diisopropylethylamine (54.9 μL) and HATU (41.1 mg), and the mixture was stirred at room temperature overnight. Under ice-cooling, saturated aqueous sodium hydrogen carbonate solution and water were added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The obtained residue was purified by thin layer silica gel chromatography (hexane:ethyl acetate=1:1) to give the title compound (29.5 mg).

$^1$H-NMR (400 MHz, DMSO-$d_6$) δ 1.25-1.47 (m, 3H), 1.75 (s, 3H), 3.26-3.37 (m, 1H), 3.67 (brs, 1H), 4.22 (s, 3H), 4.76-5.16 (m, 3H), 6.62-6.89 (m, 1H), 7.03-7.10 (m, 1H), 7.42 (s, 1H), 7.91 (brs, 1H), 8.43 (s, 1H)

Step 4-1

Synthesis of 2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile Hydrochloride Dihydrate, Hydrochloride, Sulfate, 0.5 sulfate, p-toluenesulfonate, Methanesulfonate, Phosphate, And Tartrate 2-Methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile (50.0 mg) was mixed with tert-butyl alcohol (0.5 mL) and water (0.05 mL). To this mixture was added concentrated hydrochloric acid (0.023 mL), and the mixture was stirred at room temperature overnight. The precipitated solid was collected by filtration to give 2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile hydrochloride dihydrate (36.9 mg). The obtained compound was assumed to be monohydrochloride by measuring chloride ion by ion chromatography. In addition, the obtained compound was assumed to be dihydrate from the measurement of a decrease in weight, which corresponds to 2 equivalents of water relative to a free form, when the temperature was raised in TG-DTA (thermogravimetry-differential thermal analysis), and from the results of crystal structure analysis by powder X-ray diffraction method.

In the same manner, 2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile obtained in the earlier step was treated according to a conventional method to give hydrochloride, sulfate, 0.5 sulfate, p-toluenesulfonate, methanesulfonate, phosphate, and tartrate, respectively.

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile Hydrochloride Dihydrate $^1$H-NMR (400 MHz, DMSO-$d_6$) δ 1.34-1.55 (m, 3H), 1.91 (s, 3H), 3.51-3.79 (m, 1H), 4.24 (s, 3H), 4.68-5.29 (m, 4H), 7.30-7.45 (m, 2H), 7.89-7.91 (m, 2H), 8.45 (s, 1H)

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile Hydrochloride $^1$H-NMR (400 MHz, DMSO-$d_6$) δ 1.34-1.55 (m, 3H), 1.92 (s, 3H), 3.48-3.78 (m, 1H), 4.24 (s, 3H), 4.70-4.89 (m, 2H), 5.09-5.19 (m, 2H), 7.22-7.45 (m, 2H), 7.89-7.91 (m, 2H), 8.45 (s, 1H)

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile Sulfate $^1$H-NMR (400 MHz, DMSO-$d_6$) δ 1.33-1.55 (m, 3H), 1.89 (s, $^3$H), 3.50-3.79 (m, 2H), 4.24 (s, 3H), 4.85-4.89 (m, 1H), 5.10-5.20 (m, 2H), 7.26-7.68 (m, 2H), 7.88-7.91 (m, 2H), 8.46 (s, 1H)

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile 0.5 Sulfate (400 MHz, DMSO-$d_6$) 1.29-1.51 (m, 3H), 1.84 (s, 3H), 3.47-3.75 (m, 1H), 4.23 (s, 3H), 4.88-5.15 (m, 4H), 7.04-7.34 (m, 1H), 7.43-7.46 (m, 1H), 7.60 (brs, 1H), 7.87-7.89 (m, 1H), 8.45 (s, 1H)

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile p-toluenesulfonate (400 MHz, DMSO-$d_6$) 1.33-1.54 (m, 3H), 1.88 (s, 3H), 2.27 (s, 3H), 3.50-3.80 (m, 1H), 4.24 (s, 3H), 4.90-5.18 (m, 4H), 7.10 (dd, J=8.44, 0.58 Hz, 2H), 7.45-7.47 (m, 4H), 8.03-8.31 (m, 3H)

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile Methanesulfonate $^1$H-NMR (400 MHz, DMSO-$d_6$) δ 1.33-1.54 (m, 3H), 1.88 (s, 3H), 2.32 (s, 3H), 3.50-3.78 (m, 1H), 4.24 (s, 3H), 4.70-4.88 (m, 2H), 5.05-5.26 (m, 2H), 7.20-7.54 (m, 2H), 7.83-7.91 (m, 2H), 8.45 (s, 1H)

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile Phosphate $^1$H-NMR (400 MHz, DMSO-$d_6$) δ 1.26-1.48 (m, 3H), 1.76 (s, 3H), 3.36-3.65 (m, 1H), 4.22 (s, 3H), 4.63-4.77 (m, 2H), 4.88-5.16 (m, 2H), 6.62-6.89 (m, 1H), 7.06 (brs, 1H), 7.42 (s, 1H), 7.89 (s, 1H), 8.43 (s, 1H)

2-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-2H-indazole-6-carbonitrile Tartrate ¹H-NMR (400 MHz, DMSO-d₆) 1.26-1.48 (m, 3H), 1.76 (s, 3H), 3.40-3.69 (m, 1H), 4.22 (s, 3H), 4.29 (s, 2H), 4.76-5.16 (m, 5H), 6.62-6.89 (m, 1H), 7.03-7.10 (m, 1H), 7.42 (s, 1H), 7.89 (s, 1H), 8.43 (s, 1H), 12.64 (brs, 2H)

Step 2-2

6-cyano-1-methyl-1H-indazole-3-carboxylic Acid

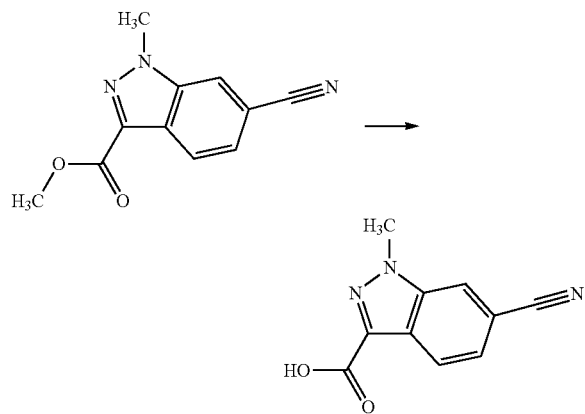

6-Cyano-1-methyl-1H-indazole-3-carboxylic acid methyl ester (46.1 mg) obtained in Step 1 was mixed with tetrahydrofuran (5 mL) and methanol (2 mL). Under ice-cooling, 2N aqueous sodium hydroxide solution (160 μL) was added to this mixture. The reaction mixture was stirred at room temperature for 3 hr. 2N Aqueous sodium hydroxide solution (160 μL) was added, and the mixture was further stirred at room temperature for 30 min. Under ice-cooling, 1N hydrochloric acid (1.3 mL) and water were added to the reaction mixture, and the mixture was extracted with ethyl acetate. The organic layer was washed successively with water and saturated aqueous sodium chloride solution. The organic layer was dried over sodium sulfate. Sodium sulfate was filtered off, and the filtrate was concentrated under reduced pressure to give the title compound (41.8 mg).

¹H-NMR (400 MHz, DMSO-dd δ 4.21 (s, 3H), 7.63 (dd, J=8.44, 1.27 Hz, 1H), 8.21 (d, J=8.55 Hz, 1H), 8.52 (s, 1H), 13.29 (s, 1H)

Step 3-2

1-methyl-3-((S)-5-methyl-3-((R)-1,1,1-trifluoro-2-hydroxypropan-2-yl)-5,6,7,8-tetrahydroimidazo[1,5-a]pyrazine-7-carbonyl)-1H-indazole-6-carbonitrile

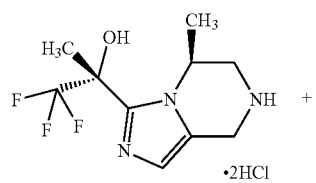

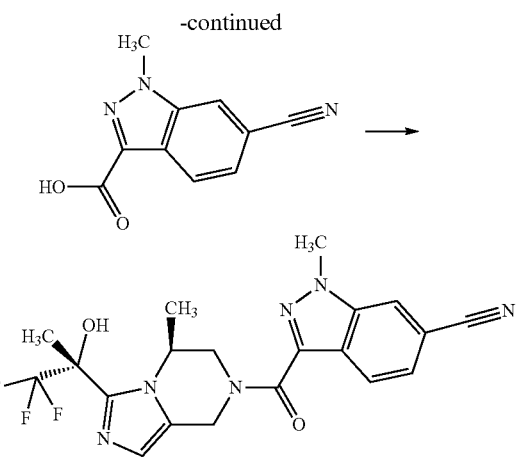

(R)-1,1,1-Trifluoro-2-((S)-5-methyl-5,6,7,8-tetrahydroimidazo[1,5-a]pyrazin-3-yl)propan-2-ol dihydrochloride (35.4 mg) and 6-cyano-1-methyl-1H-indazole-3-carboxylic acid (21.7 mg) obtained in the earlier step were mixed with dimethylformamide (1 mL). Under ice-cooling, to this mixture were added diisopropylethylamine (54.9 μL) and HATU (41.1 mg), and the mixture was stirred at room temperature overnight. Under ice-cooling, saturated aqueous sodium hydrogen carbonate solution and water were added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The obtained residue was purified by thin layer silica gel chromatography (hexane:ethyl acetate=1:1) to give the title compound (32.3 mg).

¹H-NMR (400 MHz, DMSO-d₅) δ 1.37-1.42 (m, 3H), 1.78 (s, 3H), 3.26-3.63 (m, 1H), 4.21-4.24 (m, 3H), 4.84-5.39 (m, 4H), 6.77-6.87 (m, 1H), 7.08-7.09 (m, 1H), 7.60 (d, J=8.52 Hz, 1H), 8.22 (d, J=8.37 Hz, 1H), 8.52-8.54 (m, 1H)

Production Example 4

Synthesis of (5,6-difluoro-2-methyl-2H-indazol-3-yl) ((S)-5-methyl-3-((R)-1,1,1-trifluoro-2-hydroxypropan-2-yl)-5,6-dihydroimidazo[1,5-a]pyrazin-7(8H)-yl)methanone and (5,6-difluoro-1-methyl-1H-indazol-3-yl)((S)-5-methyl-3-((R)-1,1,1-trifluoro-2-hydroxypropan-2-yl)-5,6-dihydroimidazo[1,5-a]pyrazin-7(8H)-yl)methanone (Compounds of Examples 9 and 10)

Step 1

5,6-difluoro-2-methyl-2H-indazole-3-carboxylic acid methyl ester and 5,6-difluoro-1-methyl-1H-indazole-3-carboxylic Acid Methyl Ester

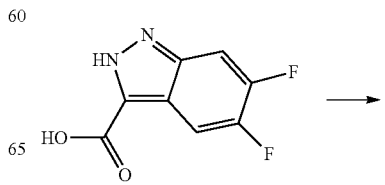

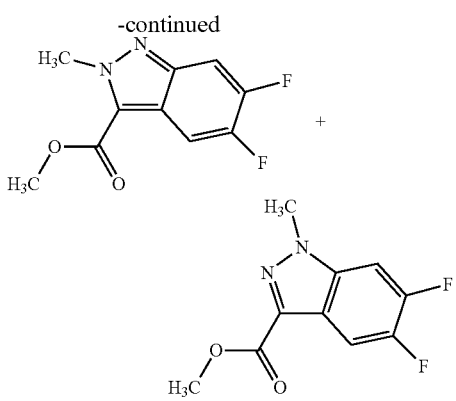

5,6-Difluoro-2H-indazole-3-carboxylic acid (500 mg) and potassium carbonate (1046 mg) were mixed with dimethylformamide (5 mL). Under ice-cooling, methyl iodide (394 μL) was added to this mixture. The reaction mixture was stirred at room temperature overnight. Under ice-cooling, saturated aqueous ammonium chloride solution was added to the reaction mixture, and the mixture was extracted with ethyl acetate. The organic layer was washed with saturated aqueous sodium chloride solution, and dried over sodium sulfate. Sodium sulfate was filtered off and the filtrate was concentrated under reduced pressure. The residue was purified by silica gel column chromatography (hexane:ethyl acetate=20:1 to 3:2) to give 5,6-difluoro-2-methyl-2H-indazole-3-carboxylic acid methyl ester (202 mg) as a less polar compound.

$^1$H-NMR (400 MHz, CDCl$_3$) δ 4.04 (s, 3H), 4.48 (s, 3H), 7.48 (dd, J=10.02, 7.03 Hz, 1H), 7.73 (dd, J=10.16, 7.77 Hz, 1H)

In addition, 5,6-difluoro-1-methyl-1H-indazole-3-carboxylic acid methyl ester (259 mg) was obtained as a more polar compound.

$^1$H-NMR (400 MHz, CDCl$_3$) δ 4.03 (s, 3H), 4.14 (s, 3H), 7.24 (dd, J=9.42, 6.13 Hz, 1H), 7.98 (dd, J=9.72, 7.62 Hz, 1H)

The structure of each isomer was determined by comparison of $^1$H-NMR spectrum of each isomer and analogs with known structure.

Step 2-1

5,6-difluoro-2-methyl-2H-indazole-3-carboxylic Acid

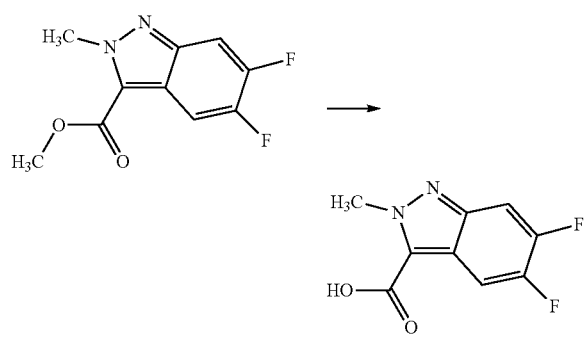

5,6-Difluoro-2-methyl-2H-indazole-3-carboxylic acid methyl ester (202 mg) obtained in the earlier step was mixed with tetrahydrofuran (2 mL) and methanol (2 mL). To this mixture was added 2N aqueous sodium hydroxide solution (671 μL) at room temperature. The reaction mixture was stirred at room temperature for 3 hr. Under ice-cooling, 1N hydrochloric acid (1.8 mL) and water were added to the reaction mixture. The mixture was stirred at room temperature for 30 min, and the precipitated solid was collected by filtration to give the title compound (171 mg).

$^1$H-NMR (400 MHz, DMSO-d$_6$) δ 4.39 (s, 3H), 7.79-7.84 (m, 2H), 13.88 (brs, 1H)

(5,6-difluoro-2-methyl-2H-indazol-3-yl) ((S)-5-methyl-3-((R)-1,1,1-trifluoro-2-hydroxypropan-2-yl)-5,6-dihydroimidazo[1,5-a]pyrazin-7(8H)-yl) methanone

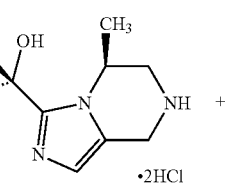

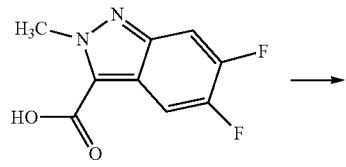

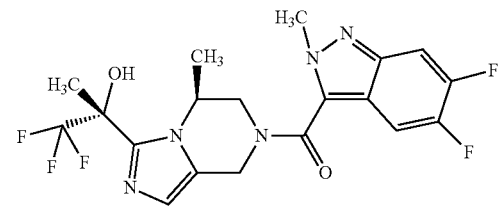

(R)-1,1,1-Trifluoro-2-((S)-5-methyl-5,6,7,8-tetrahydroimidazo[1,5-a]pyrazin-3-yl)propan-2-ol dihydrochloride (70.0 mg) and 5,6-difluoro-2-methyl-2H-indazole-3-carboxylic acid (53.3 mg) obtained in the earlier step were mixed with dimethylformamide (675 μL). Under ice-cooling, to this mixture were added diisopropylethylamine (146 μL) and HATU (96 mg), and the mixture was stirred at room temperature overnight. Under ice-cooling, saturated aqueous sodium hydrogen carbonate solution was added to the reaction mixture, and the mixture was extracted with ethyl acetate. The organic layer was purified by SCX column chromatography (methanol to 1N ammonia/methanol solution). The obtained crude product was purified by silica gel column chromatography (hexane:acetone=5:1 to 1:4) to give the title compound (69.0 mg).

$^1$H-NMR (400 MHz, DMSO-d$_6$) δ 1.24-1.45 (m, 3H), 1.75 (s, 3H-), 3.29-3.35 (m, 1H), 3.70 (brs, 1H), 4.13 (s, 3H), 4.72-5.16 (m, 3H), 6.64-6.88 (m, 1H), 7.03-7.08 (m, 1H), 7.75-7.78 (m, 2H)

Step 2-2

5,6-difluoro-1-methyl-1H-indazole-3-carboxylic Acid

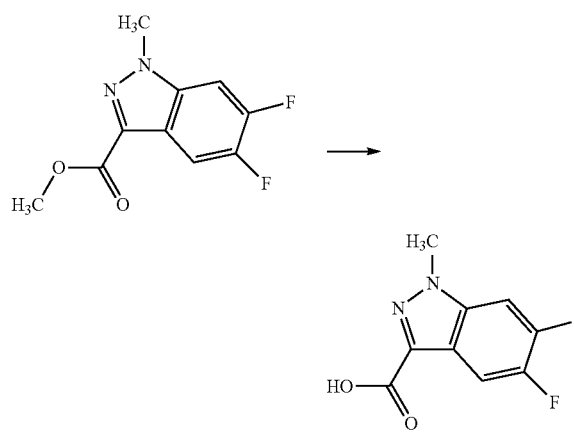

5,6-Difluoro-1-methyl-1H-indazole-3-carboxylic acid methyl ester (259 mg) obtained in Step 1 was mixed with tetrahydrofuran (4 mL) and methanol (4 mL). To this mixture was added 2N aqueous sodium hydroxide solution (857 μL) at room temperature. The reaction mixture was stirred at room temperature for 4 hr. Under ice-cooling, 1N hydrochloric acid (2.3 mL) and water were added to the reaction mixture. The mixture was stirred at room temperature for 30 min, and the precipitated solid was collected by filtration to give the title compound (238 mg).

$^1$H-NMR (400 MHz, DMSO-$d_6$) δ 4.12 (d, J=6.47 Hz, 3H), 7.89 (dd, J=10.06, 7.74 Hz, 1H), 8.00 (dd, J=10.63, 6.70 Hz, 1H), 13.18 (s, 1H)

Step 3-2

(5,6-difluoro-1-methyl-1H-indazol-3-yl)((S)-5-methyl-3-((R)-1,1,1-trifluoro-2-hydroxypropan-2-yl)-5,6-dihydroimidazo[1,5-a]pyrazin-7(8H)-yl)methanone

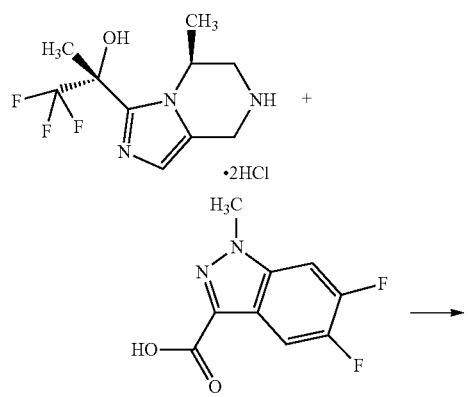

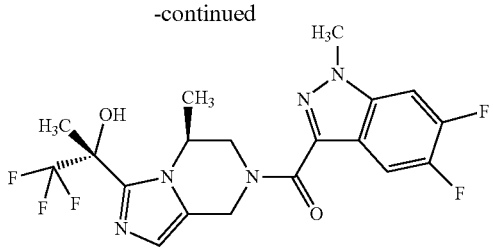

(R)-1,1,1-Trifluoro-2-((S)-5-methyl-5,6,7,8-tetrahydroimidazo[1,5-a]pyrazin-3-yl)propan-2-ol dihydrochloride (70.0 mg) and 5,6-difluoro-1-methyl-1H-indazole-3-carboxylic acid (53.3 mg) obtained in the earlier step were mixed with dimethylformamide (675 μL). Under ice-cooling, to this mixture were added diisopropylethylamine (146 μL) and HATU (96 mg), and the mixture was stirred at room temperature overnight. Under ice-cooling, saturated aqueous sodium hydrogen carbonate solution was added to the reaction mixture, and the mixture was extracted with ethyl acetate. The organic layer was purified by SCX column chromatography (methanol to 1N ammonia/methanol solution). The obtained crude product was purified by silica gel column chromatography (hexane:acetone=5:1 to 1:4) to give the title compound (78.2 mg).

$^1$H-NMR (400 MHz, DMSO-$d_6$) δ 1.35-1.39 (m, 3H), 1.77 (s, 3H), 3.25-3.57 (m, 1H), 4.11-4.14 (m, 3H), 4.90-5.35 (m, 4H), 6.77-6.84 (m, 1H), 7.06-7.07 (m, 1H), 7.95-7.99 (m, 2H)

Production Example 5

Synthesis of (2,2-difluorobenzo[d][1,3]dioxol-5-yl)((S)-5-methyl-3-((R)-1,1,1-trifluoro-2-hydroxypropan-2-yl)-5,6-dihydroimidazo[1,5-a]pyrazin-7(8H)-yl)methanone (Compound of Example 11)

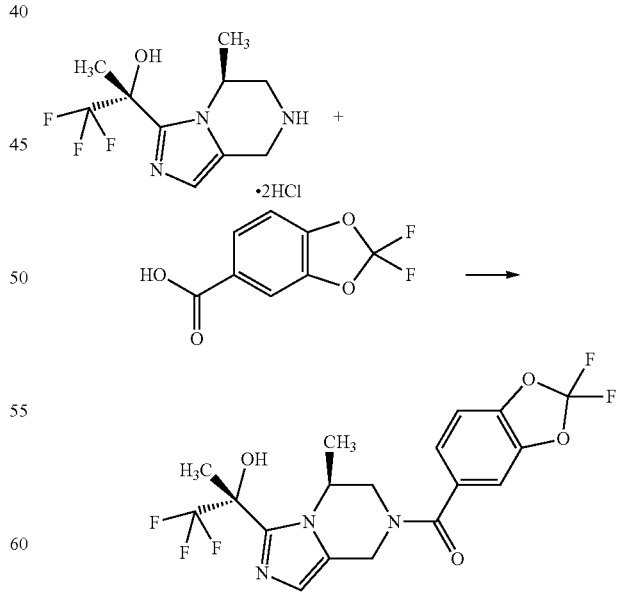

2,2-Difluorobenzo[d][1,3]dioxole-5-carboxylic acid (55.0 mg), diisopropylethylamine (146 μL) and HATU (96.0 mg) were mixed with dimethylformamide (1 mL). Under ice-cooling, (R)-1,1,1-trifluoro-2-((S)-5-methyl-5,6,7,8-tetrahydroimidazo[1,5-a]pyrazin-3-yl)propan-2-ol dihydrochloride (70.0 mg) was added to this mixture, and the mixture was stirred at room temperature overnight. Under ice-cooling, saturated aqueous sodium hydrogen carbonate solution and water were added to the reaction mixture, and the mixture was extracted with ethyl acetate. The organic layer was washed successively with aqueous sodium hydrogen carbonate solution and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:acetone=9:1 to 1:4) to give the title compound (80.7 mg).

$^1$H-NMR (400 MHz, DMSO-$d_6$) δ 1.26-1.40 (m, 3H), 1.75 (s, 3H), 3.15-5.04 (m, 5H), 6.65-6.84 (m, 1H), 7.05 (s, 1H), 7.33-7.35 (m, 1H), 7.50 (d, J=8.09 Hz, 1H), 7.57 (brs, 1H)

Production Example 6

Synthesis of 6-(1-methyl-5-((S)-5-methyl-3-((R)-1,1,1-trifluoro-2-hydroxypropan-2-yl)-5,6,7,8-tetrahydroimidazo[1,5-a]pyrazine-7-carbonyl)-1H-pyrazol-3-yl)nicotinonitrile (Compound of Example 73)

Step 1

6-acetylnicotinonitrile

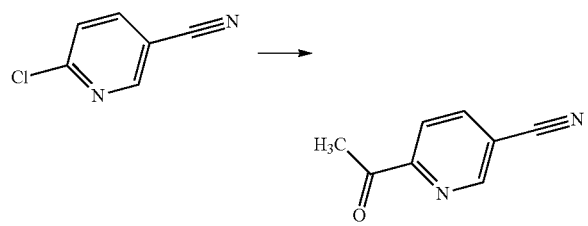

2-Chloro-5-cyanopyridine (1.5 g) and dichlorobis(triphenylphosphine)palladium(II) (760 mg) were mixed with toluene (15 mL). Under an argon atmosphere, tributyl(1-ethoxyvinyl)tin (4.4 mL) was added to this mixture at room temperature. The reaction mixture was stirred at 130° C. for 2 hr. Under ice-cooling, 6N hydrochloric acid (4 mL) was added to the reaction mixture, and the mixture was stirred at room temperature for 1 hr. Under ice-cooling, 4N aqueous sodium hydroxide solution (4 mL), and successively, saturated aqueous sodium hydrogen carbonate solution were added to the reaction mixture to adjust the pH to 9. Under ice-cooling, aqueous potassium fluoride solution was added to the reaction mixture, and the mixture was stirred at room temperature for 30 min. The reaction mixture was filtered through celite, and the filtrate was extracted with ethyl acetate. The organic layer was washed successively with aqueous potassium fluoride solution and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=20:1 to 3:2) to give the title compound (1.3 g).

$^1$H-NMR (400 MHz, CDCl$_3$) δ 2.73 (s, 3H), 8.09-8.14 (m, 2H), 8.94 (s, 1H)

Step 2 ethyl 3-(5-cyanopyridin-2-yl)-1H-pyrazole-5-carboxylate

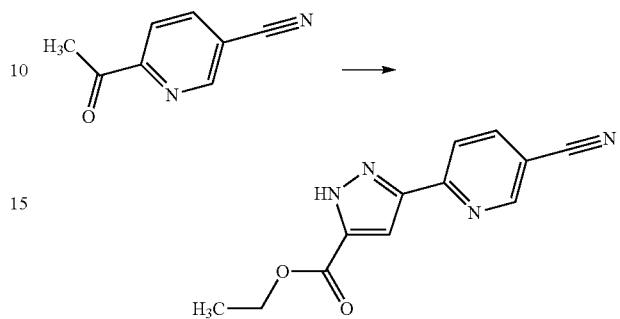

6-Acetylnicotinonitrile (731 mg) obtained in the earlier step was mixed with tetrahydrofuran (7 mL). Under ice-cooling, to this mixture were added diethyl oxalate (812 μL), ethanol (29.2 μL) and 60 w/w % sodium hydride (220 mg). The reaction mixture was stirred at room temperature for 2 hr. Under ice-cooling, hydrazine monohydrate (267 μL) and acetic acid (630 μL) were added to the reaction mixture, and the mixture was stirred at room temperature for 5 hr. Under ice-cooling, saturated aqueous sodium hydrogen carbonate solution was added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=1:1) to give the title compound (182 mg).

$^1$H-NMR (400 MHz, CDCl$_3$) δ 1.43 (t, J=7.17 Hz, 3H), 4.44 (q, J=7.08 Hz, 2H), 7.45 (s, 1H), 7.98-8.03 (m, 2H), 8.88 (d, J=1.49 Hz, 1H)

Step 3

3-(5-cyanopyridin-2-yl)-1-methyl-1H-pyrazole-5-carboxylic Acid Ethyl Ester

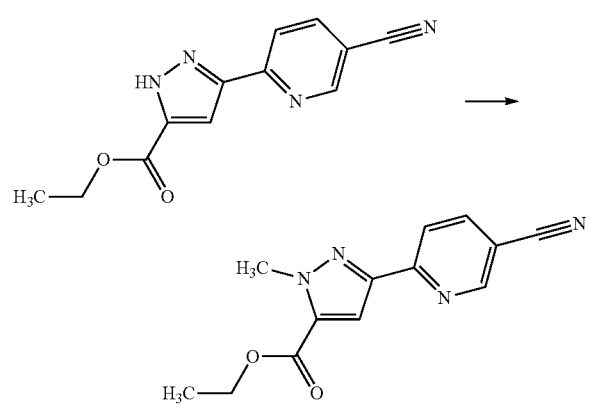

Ethyl 3-(5-cyanopyridin-2-yl)-1H-pyrazole-5-carboxylate (182 mg) obtained in the earlier step was mixed with dimethylformamide (2 mL). Under ice-cooling, to this mixture were added 60 w/w % sodium hydride (36 mg) and methyl iodide (140 μL). The reaction mixture was stirred at room temperature for 1 hr. Under ice-cooling, acetic acid (51.5 μL) was added to the reaction mixture. The reaction mixture was purified by silica gel column chromatography (hexane:ethyl acetate=4:1 to 3:2) to give the title compound (86.2 mg).

$^1$H-NMR (400 MHz, CDCl$_3$) δ 1.39 (t, J=7.17 Hz, 3H), 4.26 (s, 3H), 4.37 (q, J=7.17 Hz, 2H), 7.50 (s, 1H), 7.95-8.07 (m, 2H), 8.86 (d, J=2.08 Hz, 1H)

Step 4

3-(5-cyanopyridin-2-yl)-1-methyl-1H-pyrazole-5-carboxylic Acid

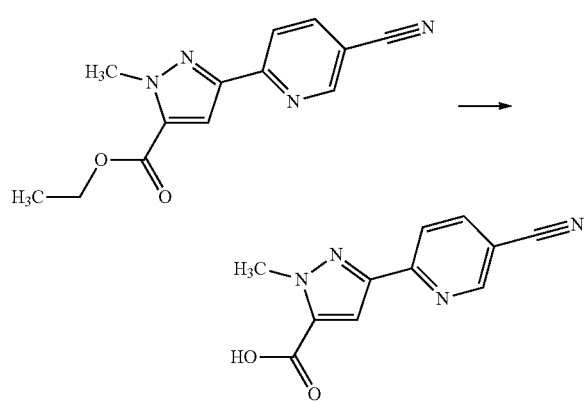

3-(5-Cyanopyridin-2-yl)-1-methyl-1H-pyrazole-5-carboxylic acid ethyl ester (86.2 mg) obtained in the earlier step was mixed with tetrahydrofuran (1.6 mL) and water (0.4 mL). Under ice-cooling, lithium hydroxide monohydrate (16.9 mg) was added to this mixture. The reaction mixture was stirred at room temperature for 30 min. Under ice-cooling, 1N hydrochloric acid (403 μL) and water (10 mL) were added to the reaction mixture, and the mixture was stirred at room temperature for 1 hr. The precipitated solid was collected by filtration to give the title compound (70.5 mg).

$^1$H-NMR (400 MHz, DMSO-d$_6$) δ 4.19 (d, J=0.60 Hz, 3H), 7.39 (s, 1H), 8.09 (d, J=8.37 Hz, 1H), 8.34 (dd, J=8.37, 2.09 Hz, 1H), 9.04-9.54 (m, 1H), 13.64 (brs, 1H)

Step 5

6-(1-methyl-5-((S)-5-methyl-3-((R)-1,1,1-trifluoro-2-hydroxypropan-2-yl)-5,6,7,8-tetrahydroimidazo[1,5-a]pyrazine-7-carbonyl)-1H-pyrazol-3-yl)nicotinonitrile

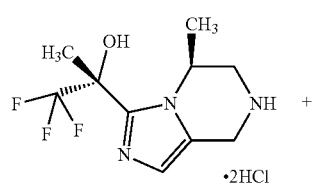

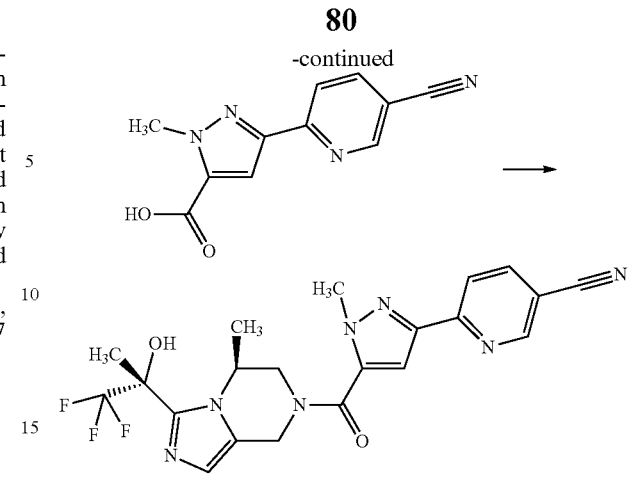

(R)-1,1,1-Trifluoro-2-((S)-5-methyl-5,6,7,8-tetrahydroimidazo[1,5-a]pyrazin-3-yl)propan-2-ol dihydrochloride (60.0 mg) and 3-(5-cyanopyridin-2-yl)-1-methyl-1H-pyrazole-5-carboxylic acid (41.1 mg) obtained in the earlier step were mixed with dimethylformamide (0.5 mL). Under ice-cooling, to this mixture were added diisopropylethylamine (91.4 μL) and HATU (68.4 mg) and the mixture was stirred at room temperature overnight. Under ice-cooling, saturated aqueous sodium hydrogen carbonate solution and water were added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. To the obtained residue was added ethyl acetate:hexane=1:1, and the mixture was stirred at room temperature for 1 hr. The precipitated solid was collected by filtration to give the title compound (70.9 mg).

$^1$H-NMR (400 MHz, DMSO-d$_5$) δ 1.32, 1.42 (d, J=6.47, 3H), 1.76 (s, 3H), 3.21-3.68 (m, 1H), 3.97-5.09 (m, 7H), 6.72-7.36 (m, 3H), 8.09 (d, J=8.20 Hz, 1H), 8.33 (dd, J=8.20, 1.85 Hz, 1H), 9.02 (s, 1H)

Production Example 7

Synthesis of (3-(4-fluorophenyl)-1-methyl-1H-pyrazol-5-yl) ((S)-5-methyl-3-((R)-1,1,1-trifluoro-2-hydroxypropan-2-yl)-5,6-dihydroimidazo[1,5-a]pyrazin-7(8H)-yl)methanone (Compound of Example 16) and Hydrochloride Thereof

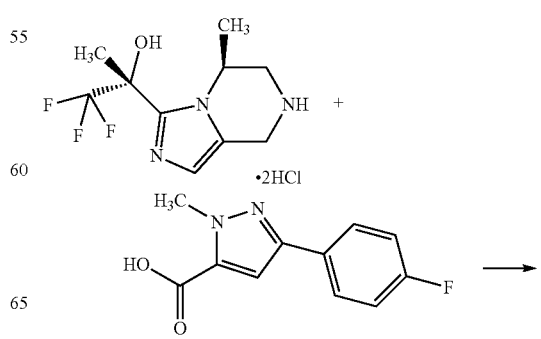

-continued

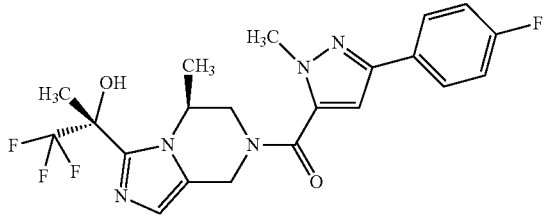

(R)-1,1,1-Trifluoro-2-((S)-5-methyl-5,6,7,8-tetrahydroimidazo[1,5-a]pyrazin-3-yl)propan-2-ol dihydrochloride (60 mg) and 3-(4-fluorophenyl)-1-methyl-1H-pyrazole-5-carboxylic acid (46.5 mg) were mixed with dimethylformamide (0.4 mL). Under ice-cooling, to this mixture were added diisopropylethylamine (107 μL) and HATU (80.2 mg). The reaction mixture was stirred at room temperature overnight. Ethyl acetate was added to the reaction mixture at room temperature. The reaction mixture was washed successively with saturated aqueous sodium hydrogen carbonate solution and saturated aqueous sodium chloride solution. The organic layer was dried over sodium sulfate. Sodium sulfate was filtered off and the filtrate was concentrated under reduced pressure. The obtained residue was purified by thin layer silica gel chromatography (ethyl acetate) to give the title compound (76.2 mg).
$^1$H-NMR (400 MHz, DMSO-$d_6$) δ 1.31-1.47 (m, 3H), 1.78 (s, 3H), 3.19-3.69 (m, 1H), 3.92 (s, 3H), 4.03-4.56 (m, 1H), 4.68-5.16 (m, 3H), 6.74, 6.87 (s, 1H), 7.01-7.31 (m, 4H), 7.82-7.91 (m, 2H)

(3-(4-fluorophenyl)-1-methyl-1H-pyrazol-5-yl)((S)-5-methyl-3-((R)-1,1,1-trifluoro-2-hydroxypropan-2-yl)-5,6-dihydroimidazo[1,5-a]pyrazin-7(8H)-yl) methanone Hydrochloride

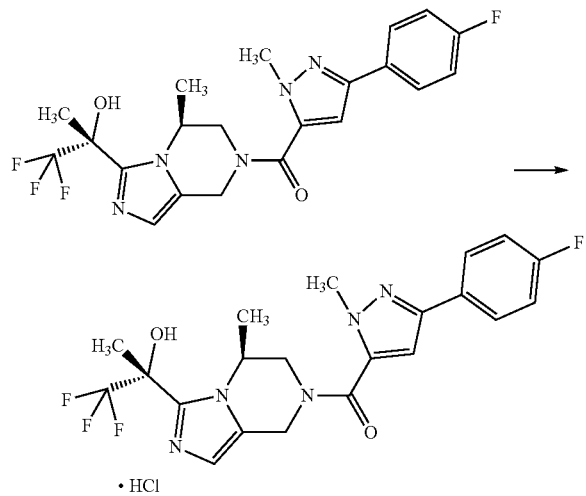

(3-(4-Fluorophenyl)-1-methyl-1H-pyrazol-5-yl)((S)-5-methyl-3-((R)-1,1,1-trifluoro-2-hydroxypropan-2-yl)-5,6-dihydroimidazo[1,5-a]pyrazin-7(8H)-yl)methanone obtained in the earlier step was treated according to a conventional method to give hydrochloride.
$^1$H-NMR (400 MHz, DMSO-$d_6$) δ 1.43-1.50 (m, 3H), 1.93 (s, 3H), 3.37-3.74 (m, 1H), 3.90 (s, 3H), 4.13-5.30 (m, 4H), 7.00-7.54 (m, 4H), 7.84-8.00 (m, 3H)

Production Example 8

Synthesis of 4-(1-cyclopropyl-3-((S)-5-methyl-3-((R)-1,1,1-trifluoro-2-hydroxypropan-2-yl)-5,6,7,8-tetrahydroimidazo[1,5-a]pyrazine-7-carbonyl)-1H-pyrazol-5-yl)benzonitrile (Compound of Example 53)

Step 1

(Z)-4-(4-cyanophenyl)-2-hydroxy-4-oxobut-2-enoic Acid Ethyl Ester

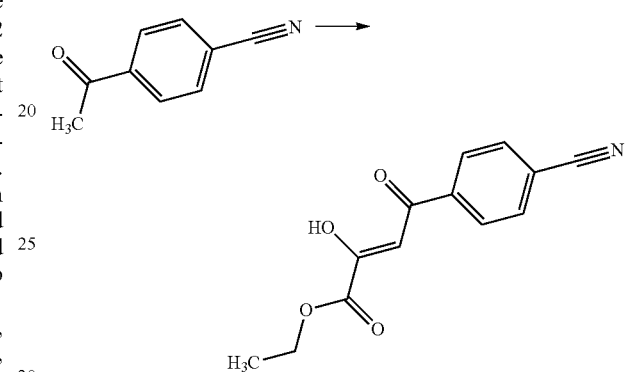

4-Acetylbenzonitrile (1.00 g) and diethyl oxalate (1.21 mL) were mixed with acetonitrile (8 mL). Under ice-cooling, sodium tert-butoxide (1.32 g) was added to this mixture. The reaction mixture was stirred at room temperature overnight. Under ice-cooling, water was added to the reaction mixture, and the mixture was washed twice with diethyl ether. Under ice-cooling, 1N hydrochloric acid was added to the aqueous layer until the pH became about 4. The aqueous layer was extracted with ethyl acetate. The organic layer was washed with saturated aqueous sodium chloride solution. The organic layer was dried over sodium sulfate. Sodium sulfate was filtered off, and the filtrate was concentrated under reduced pressure to give the title compound (1.02 g) as a crude product.
$^1$H-NMR (400 MHz, CDCl$_3$) δ 1.41 (t, J=7.17 Hz, 4H), 4.40 (q, J=7.17 Hz, 2H), 7.05 (s, 1H), 7.78-7.80 (m, 2H), 8.06-8.08 (m, 2H)

Step 2

5-(4-cyanophenyl)-1-cyclopropyl-1H-pyrazole-3-carboxylic Acid Ethyl Ester

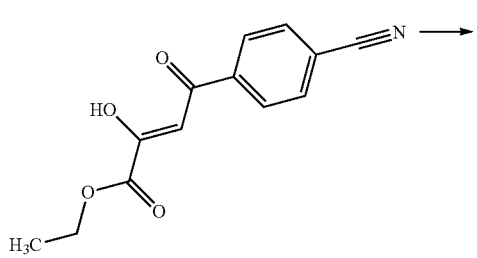

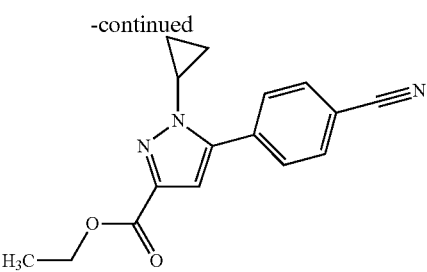

(Z)-4-(4-Cyanophenyl)-2-hydroxy-4-oxobut-2-enoic acid ethyl ester (400 mg) obtained in the earlier step and cyclopropylhydrazine hydrochloride (177 mg) were mixed with ethanol (8 mL). The reaction mixture was stirred at room temperature for 1.5 hr and at 60° C. for 6 hr. Under ice-cooling, cyclopropylhydrazine hydrochloride (177 mg) was added to the reaction mixture, and the mixture was stirred at 60° C. for 1 hr. The reaction mixture was concentrated under reduced pressure, and ethyl acetate was added to the obtained residue. The reaction mixture was washed successively with saturated aqueous sodium hydrogen carbonate solution and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=1:1) and thin layer silica gel chromatography (chloroform:methanol=20:1) to give the title compound (213 mg).

$^1$H-NMR (400 MHz, CDCl$_3$) δ 1.04-1.05 (m, 2H), 1.20-1.20 (m, 2H), 1.38 (t, J=7.05 Hz, 3H), 3.60-3.64 (m, 1H), 4.40 (q, J=7.17 Hz, 3H), 6.91 (s, 1H), 7.70-7.71 (m, 2H), 7.76-7.77 (m, 2H)

Step 3

5-(4-cyanophenyl)-1-cyclopropyl-1H-pyrazole-3-carboxylic Acid

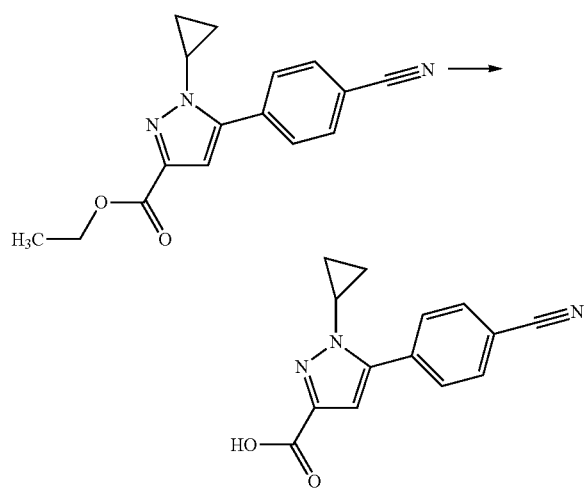

5-(4-Cyanophenyl)-1-cyclopropyl-1H-pyrazole-3-carboxylic acid ethyl ester (38.5 mg) obtained in the earlier step was mixed with tetrahydrofuran (400 μL) and methanol (400 μL). Under ice-cooling, 2N aqueous sodium hydroxide solution (137 μL) was added to this mixture. The reaction mixture was stirred at room temperature for 2 hr. Under ice-cooling, 6N hydrochloric acid (46 μL) was added to the reaction mixture. The reaction mixture was concentrated under reduced pressure, and azeotroped with toluene to give the title compound (43.9 mg) as a crude product.

Step 4

4-(1-cyclopropyl-3-((S)-5-methyl-3-((R)-1,1,1-trifluoro-2-hydroxypropan-2-yl)-5,6,7,8-tetrahydroimidazo[1,5-a]pyrazine-7-carbonyl)-1H-pyrazol-5-yl) benzonitrile

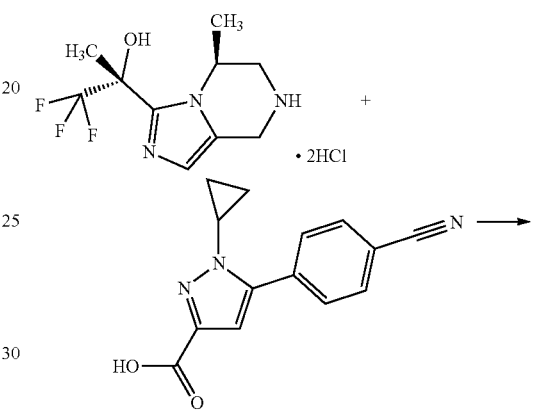

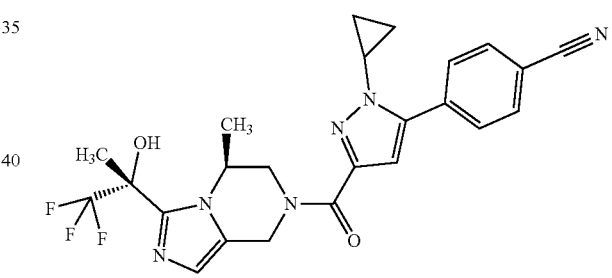

5-(4-Cyanophenyl)-1-cyclopropyl-1H-pyrazole-3-carboxylic acid (43.9 mg) obtained in the earlier step was mixed with dimethylformamide (0.4 mL). Under ice-cooling, to this mixture were added diisopropylethylamine (88.4 μL), HATU (51.9 mg) and (R)-1,1,1-trifluoro-2-((S)-5-methyl-5,6,7,8-tetrahydroimidazo[1,5-a]pyrazin-3-yl)propan-2-ol dihydrochloride (48.8 mg), and the mixture was stirred at room temperature overnight. Under ice-cooling, saturated aqueous sodium hydrogen carbonate solution was added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The obtained residue was purified by thin layer silica gel chromatography (chloroform:methanol=10:1) to give the title compound (55.9 mg).

$^1$H-NMR (400 MHz, CDCl$_3$) δ 0.98-1.24 (m, 4H), 1.46-1.47 (m, 3H), 1.95 (s, 3H), 3.26-3.66 (m, 2H), 3.98-5.61 (m, 5H), 6.81-6.90 (m, 1H), 7.67-7.80 (m, 4H)

Production Example 9

Synthesis of 4-(4-chloro-1-methyl-5-((S)-5-methyl-3-((R)-1,1,1-trifluoro-2-hydroxypropan-2-yl)-5,6,7,8-tetrahydroimidazo[1,5-a]pyrazine-7-carbonyl)-1H-pyrazol-3-yl)benzonitrile (Compound of Example 40)

Step 1

3-(4-cyanophenyl)-1H-pyrazole-5-carboxylic Acid Ethyl Ester

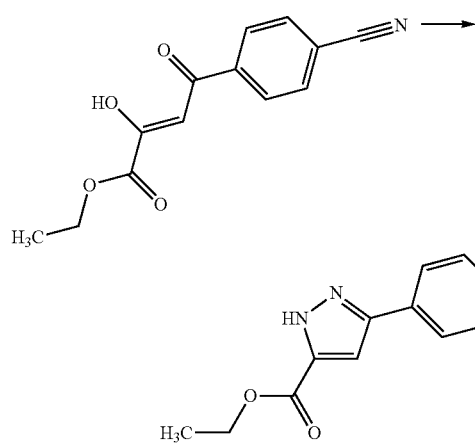

(Z)-4-(4-Cyanophenyl)-2-hydroxy-4-oxobut-2-enoic acid ethyl ester (600 mg) and hydrazine monohydrate (119 μL) were mixed with ethanol (9 mL). Under ice-cooling, acetic acid (140 μL) was added to this mixture. The reaction mixture was stirred at room temperature overnight and at 50° C. for 4.5 hr. The reaction mixture was concentrated under reduced pressure, ethanol and hexane were added to the obtained residue, and the mixture was stirred at room temperature for 1 hr. The precipitated solid was collected by filtration to give the title compound (462 mg).

Step 2

3-(4-cyanophenyl)-1-methyl-1H-pyrazole-5-carboxylic Acid Ethyl Ester

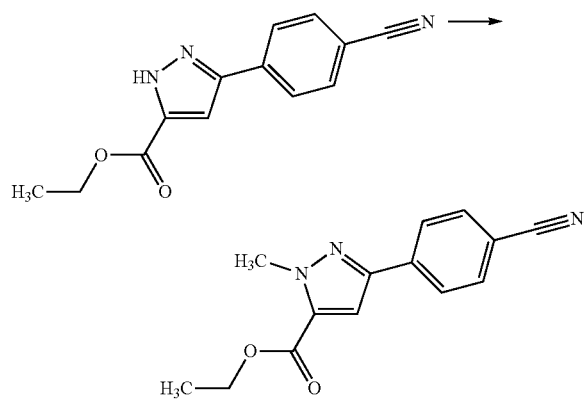

3-(4-Cyanophenyl)-1H-pyrazole-5-carboxylic acid ethyl ester (241 mg) obtained in the earlier step was mixed with dimethylformamide (2.5 mL). Under ice-cooling, to this mixture were added 60 w/w % sodium hydride (44 mg) and methyl iodide (187 μL). The reaction mixture was stirred at room temperature for 1 hr. Under ice-cooling, saturated aqueous ammonium chloride solution was added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=3:7) to give the title compound (201 mg).

Step 3

4-chloro-3-(4-cyanophenyl)-1-methyl-1H-pyrazole-5-carboxylic Acid Ethyl Ester

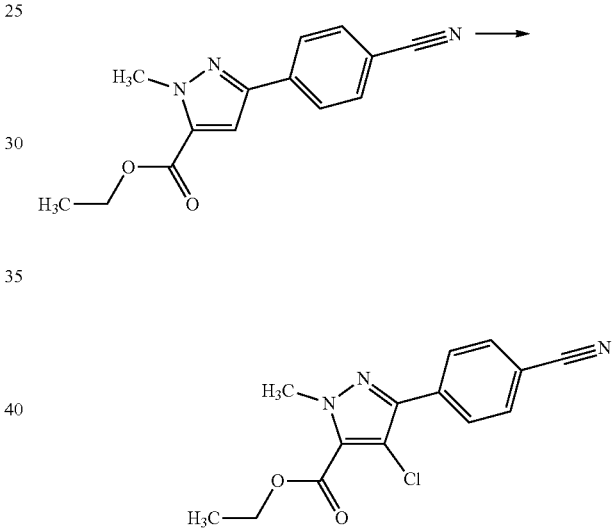

3-(4-Cyanophenyl)-1-methyl-1H-pyrazole-5-carboxylic acid ethyl ester (50.0 mg) obtained in the earlier step was mixed with acetonitrile (750 μL). Under ice-cooling, to this mixture were added N-chlorosuccinimide (52.3 mg) and trifluoroacetic acid (33.0 μL). The reaction mixture was stirred at room temperature overnight. Chloroform (750 μL) was added to the reaction mixture at room temperature, and the mixture was stirred at room temperature overnight and at 70° C. for 6 hr. The reaction mixture was concentrated under reduced pressure, and ethyl acetate was added to the obtained residue. The reaction mixture was washed successively with saturated aqueous sodium sulfite solution, saturated aqueous sodium hydrogen carbonate solution and saturated aqueous sodium chloride solution. The organic layer was dried over sodium sulfate. Sodium sulfate was filtered off, and the filtrate was concentrated under reduced pressure to give the title compound (61.8 mg).

$^1$H-NMR (400 MHz, CDCl$_3$) δ 1.45 (t, J=7.03 Hz, 3H), 4.21 (s, 3H), 4.45 (q, J=7.17 Hz, 2H), 7.72 (d, J=8.67 Hz, 2H), 8.05 (d, J=8.97 Hz, 2H)

Step 4

4-chloro-3-(4-cyanophenyl)-1-methyl-1H-pyrazole-5-carboxylic Acid

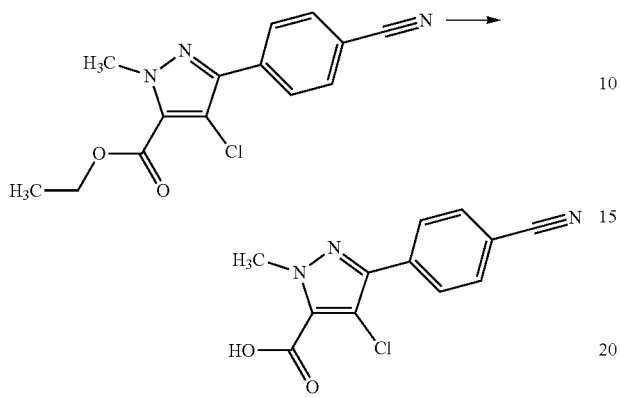

4-Chloro-3-(4-cyanophenyl)-1-methyl-1H-pyrazole-5-carboxylic acid ethyl ester (38.5 mg) obtained in the earlier step was mixed with tetrahydrofuran (400 μL) and methanol (400 μL). Under ice-cooling, 2N aqueous sodium hydroxide solution (137 μL) was added to this mixture. The reaction mixture was stirred at room temperature for 6 hr. Under ice-cooling, 6N hydrochloric acid (46 μL) was added to the reaction mixture. The reaction mixture was concentrated under reduced pressure, and azeotroped with toluene to give the title compound (49.3 mg) as a crude product.

Step 5

4-(4-chloro-1-methyl-5-((S)-5-methyl-3-((R)-1,1,1-trifluoro-2-hydroxypropan-2-yl)-5,6,7,8-tetrahydroimidazo[1,5-a]pyrazine-7-carbonyl)-1H-pyrazol-3-yl)benzonitrile

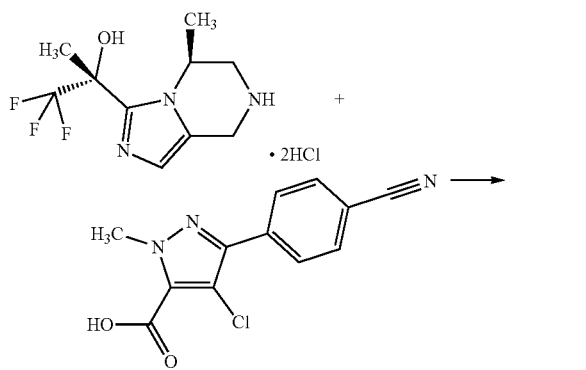

The crude product (42.1 mg) of 4-chloro-3-(4-cyanophenyl)-1-methyl-1H-pyrazole-5-carboxylic acid obtained in the earlier step was mixed with dimethylformamide (400 μL). Under ice-cooling, to this mixture were added diisopropylethylamine (86.5 μL), HATU (51.9 mg) and (R)-1,1,1-trifluoro-2-((S)-5-methyl-5,6,7,8-tetrahydroimidazo[1,5-a]pyrazin-3-yl)propan-2-ol dihydrochloride (48.8 mg), and the mixture was stirred at room temperature overnight. Under ice-cooling, saturated aqueous sodium hydrogen carbonate solution was added to the reaction mixture, and the mixture was extracted with ethyl acetate. The organic layer was washed successively with water and saturated aqueous sodium chloride solution. The organic layer was dried over sodium sulfate. Sodium sulfate was filtered off and the filtrate was concentrated under reduced pressure. The obtained residue was purified by thin layer silica gel chromatography (chloroform:methanol=12:1) to give the title compound (46.4 mg).

$^1$H-NMR (400 MHz, CDCl$_3$) δ 1.33-1.57 (m, 3H), 1.94 (s, 3H), 3.38-3.96 (m, 6H), 4.61-5.29 (m, 3H), 6.80, 6.94 (s, 1H), 7.71 (d, J=8.55 Hz, 2H), 8.03 (d, J=8.32 Hz, 2H)

Production Example 10

Synthesis of (2-(4-fluorophenyl)pyridin-4-yl)((S)-5-methyl-3-((R)-1,1,1-trifluoro-2-hydroxypropan-2-yl)-5,6-dihydroimidazo[1,5-a]pyrazin-7(8H)-yl)methanone (Compound of Example 48) and Hydrochloride Thereof

Step 1

2-(4-fluorophenyl)isonicotinoyl Chloride

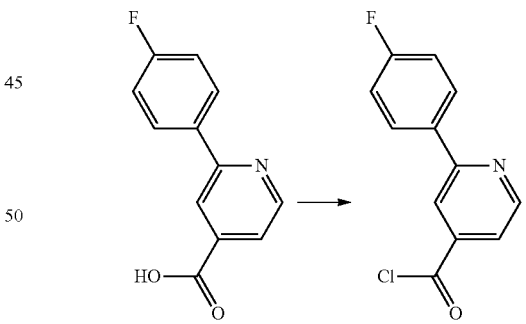

2-(4-Fluorophenyl)isonicotinic acid (34 mg) was mixed with chloroform (1.2 mL). Under ice-cooling, oxalyl chloride (26 μL) and a catalytic amount of dimethylformamide were added. To the reaction mixture was added tetrahydrofuran (1 mL), and the mixture was stirred at 50° C. for 1 hr. The reaction mixture was concentrated under reduced pressure, and azeotroped with toluene to give the title compound as a crude product.

Step 2

(2-(4-fluorophenyl)pyridin-4-yl)((S)-5-methyl-3-((R)-1,1,1-trifluoro-2-hydroxypropan-2-yl)-5,6-dihydroimidazo[1,5-a]pyrazin-7(8H)-yl)methanone

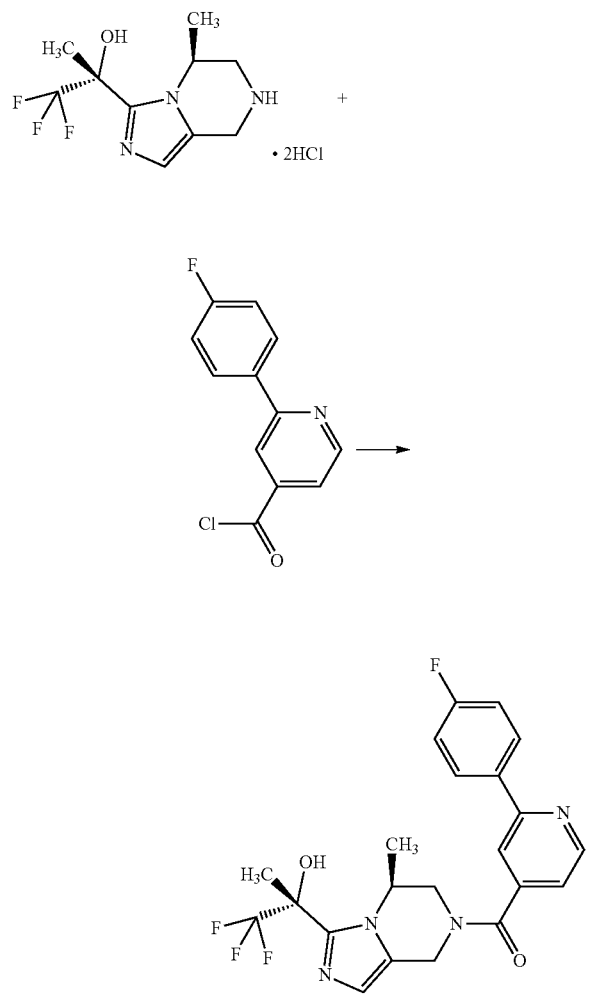

The crude product of 2-(4-fluorophenyl)isonicotinoyl chloride obtained in the earlier step was mixed with chloroform (1.0 mL). Under ice-cooling, to this mixture were added (R)-1,1,1-trifluoro-2-((S)-5-methyl-5,6,7,8-tetrahydroimidazo[1,5-a]pyrazin-3-yl)propan-2-ol dihydrochloride (39 mg) and triethylamine (67 μL). The reaction mixture was stirred at room temperature for 1 hr. To the reaction mixture was added ethyl acetate, and the mixture was washed successively with saturated aqueous ammonium chloride solution, water and saturated aqueous sodium chloride solution. The organic layer was dried over sodium sulfate. Sodium sulfate was filtered off and the filtrate was concentrated under reduced pressure. The obtained residue was purified by thin layer silica gel chromatography (chloroform:methanol-10:1) to give the title compound (14.3 mg).

$^1$H-NMR (400 MHz, DMSO-d$_6$) δ 1.28-1.46 (m, 3H), 1.75 (s, 3H), 3.19-5.11 (m, 5H), 6.65-6.87 (m, 1H), 7.03-7.09 (m, 1H), 7.29-7.35 (m, 2H), 7.37-7.43 (m, 1H), 8.01-8.02 (m, 1H), 8.18-8.21 (m, 2H), 8.75-8.76 (m, 1H)

Step 3

(2-(4-fluorophenyl)pyridin-4-yl) ((S)-5-methyl-3-((R)-1,1,1-trifluoro-2-hydroxypropan-2-yl)-5,6-dihydroimidazo[1,5-a]pyrazin-7(8H)-yl)methanone Hydrochloride

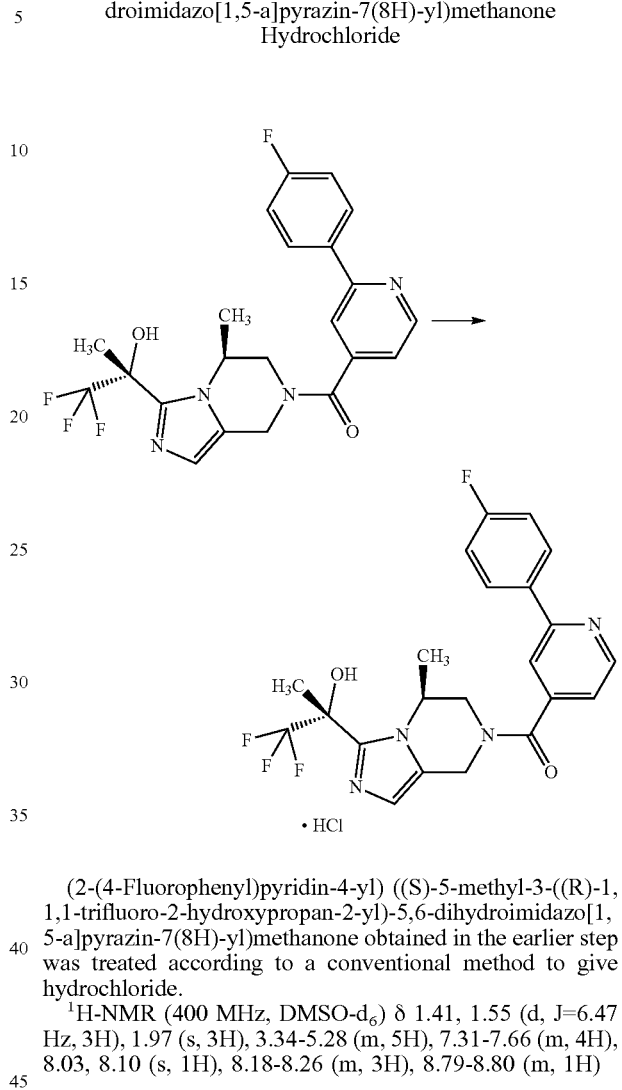

(2-(4-Fluorophenyl)pyridin-4-yl) ((S)-5-methyl-3-((R)-1,1,1-trifluoro-2-hydroxypropan-2-yl)-5,6-dihydroimidazo[1,5-a]pyrazin-7(8H)-yl)methanone obtained in the earlier step was treated according to a conventional method to give hydrochloride.

$^1$H-NMR (400 MHz, DMSO-d$_6$) δ 1.41, 1.55 (d, J=6.47 Hz, 3H), 1.97 (s, 3H), 3.34-5.28 (m, 5H), 7.31-7.66 (m, 4H), 8.03, 8.10 (s, 1H), 8.18-8.26 (m, 3H), 8.79-8.80 (m, 1H)

Production Example 11

Synthesis of 4-(5-fluoro-4-((S)-5-methyl-3-((R)-1,1,1-trifluoro-2-hydroxypropan-2-yl)-5,6,7,8-tetrahydroimidazo[1,5-a]pyrazine-7-carbonyl)pyridin-2-yl)benzonitrile (Compound of Example 68)

Step 1

2-bromo-5-fluoroisonicotinic Acid Methyl Ester

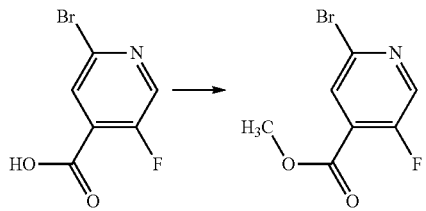

2-Bromo-5-fluoroisonicotinic acid (1.1 g) was mixed with toluene (15 mL) and methanol (5 mL). To this mixture was added 2M trimethylsilyldiazomethane/hexane solution at room temperature. The reaction mixture was stirred at room temperature for 1 hr. The reaction mixture was concentrated under reduced pressure to give the title compound (1.17 g) as a crude product.

Step 2

2-(4-cyanophenyl)-5-fluoroisonicotinic Acid Methyl Ester

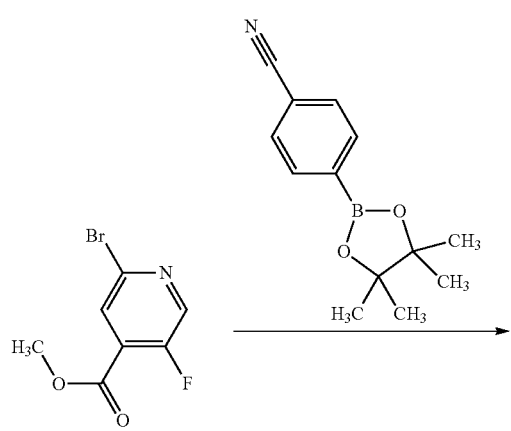

The crude product of 2-bromo-5-fluoroisonicotinic acid methyl ester (234 mg) obtained in the earlier step, 4-(4,4,5,5-tetramethyl-1,3,2-dioxaborolan-2-yl)benzonitrile (229 mg), bis(di-tert-butyl(4-dimethylaminophenyl)phosphine)dichloropalladium(II) (14 mg) and potassium carbonate (415 mg) were mixed with toluene (3 mL) and methanol (2 mL). The reaction mixture was stirred at 65° C. for 2 hr. Under ice-cooling, 1N hydrochloric acid was added to the reaction mixture to adjust the pH to 7. To the reaction mixture was added ethyl acetate, and the mixture was washed successively with water and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=10:1 to 5:1). The eluate was concentrated and hexane was added to the obtained residue. The precipitated solid was collected by filtration to give the title compound (152 mg).

Step 3

2-(4-cyanophenyl)-5-fluoroisonicotinic Acid

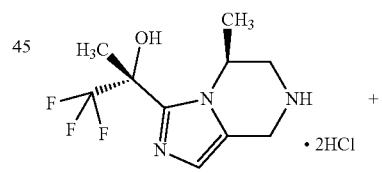

2-(4-Cyanophenyl)-5-fluoroisonicotinic acid methyl ester (43 mg) obtained in the earlier step was mixed with tetrahydrofuran (1 mL) and methanol (0.3 mL). To this mixture was added 2N aqueous sodium hydroxide solution (140 µL) at room temperature. The reaction mixture was stirred at room temperature overnight. Under ice-cooling, 6N hydrochloric acid (47 µL) was added to the reaction mixture. The reaction mixture was concentrated under reduced pressure, and azeotroped with toluene to give the title compound as a crude product.

Step 4

4-(5-fluoro-4-((S)-5-methyl-3-((R)-1,1,1-trifluoro-2-hydroxypropan-2-yl)-5,6,7,8-tetrahydroimidazo[1,5-a]pyrazine-7-carbonyl)pyridin-2-yl)benzonitrile

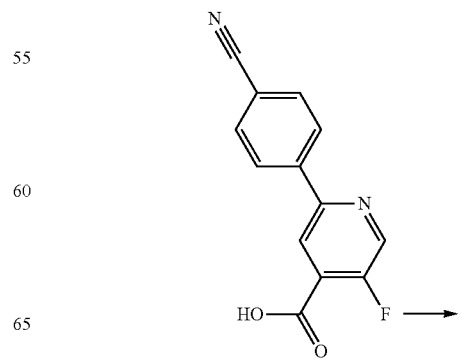

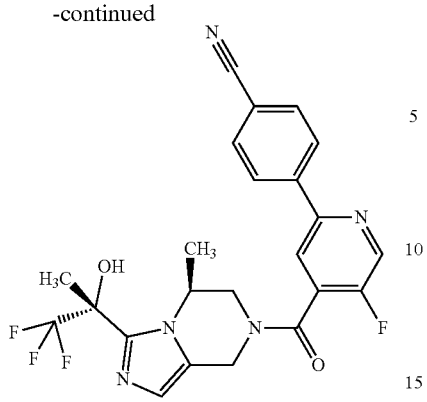

(R)-1,1,1-Trifluoro-2-((S)-5-methyl-5,6,7,8-tetrahydroimidazo[1,5-a]pyrazin-3-yl)propan-2-ol dihydrochloride (45 mg) and a crude product of 2-(4-cyanophenyl)-5-fluoroisonicotinic acid obtained in the earlier step were mixed with dimethylformamide (1 mL). Under ice-cooling, to this mixture were added diisopropylethylamine (96 μL) and HATU (64 mg). The reaction mixture was stirred at room temperature overnight. Ethyl acetate was added to the reaction mixture at room temperature. The reaction mixture was washed successively with saturated aqueous sodium hydrogen carbonate solution, water and saturated aqueous sodium chloride solution. The organic layer was dried over sodium sulfate. Sodium sulfate was filtered off and the filtrate was concentrated under reduced pressure. The obtained residue was purified by thin layer silica gel chromatography (chloroform:methanol=9:1) to give the title compound (59.4 mg).

$^1$H-NMR (400 MHz, DMSO-d$_6$) δ 1.29-1.44 (m, 3H), 1.75 (s, 3H), 3.23-5.12 (m, 5H), 6.64-6.88 (m, 1H), 7.06-7.11 (m, 1H), 7.96-7.99 (m, 2H), 8.25-8.32 (m, 3H), 8.85-8.86 (m, 1H)

Production Example 12

Synthesis of (3-cyclopropyl-1H-pyrazol-5-yl)((R)-4-methyl-3-((R)-1,1,1-trifluoro-2-hydroxypropan-2-yl)-4,7-dihydroisoxazolo[5,4-c]pyridin-6(5H)-yl)methanone (Compound of Example 111)

Step 1

(3R,7aS)-3-phenyltetrahydro-3H,5H-pyrrolo[1,2-c]oxazol-5-one

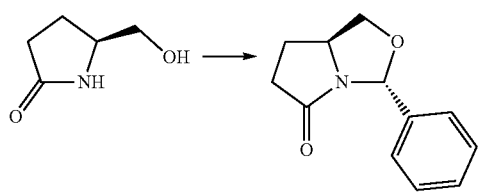 [SMILES: O=C1CC[C@@H](CO)N1 ; O=C1CC[C@H]2CO[C@H](c3ccccc3)N12]

(S)-5-(Hydroxymethyl)pyrrolidin-2-one (50 g), benzaldehyde (69.1 g) and p-toluenesulfonic acid hydrate were mixed with toluene (300 mL). The reaction mixture was stirred overnight at 130° C. while removing water by a Dean-Stark apparatus. The reaction mixture was concentrated under reduced pressure. The obtained residue was purified by silica gel column chromatography (hexane:ethyl acetate=10:1 to 1:1) to give the title compound (45.8 g).

$^1$H-NMR (400 MHz, CDCl$_3$) δ 1.92-1.95 (m, 1H), 2.33-2.41 (m, 1H), 2.52-2.57 (m, 1H), 2.80 (dt, J=18.34, 8.67 Hz, 1H), 3.48 (t, J=7.98 Hz, 1H), 4.10-4.17 (m, 1H), 4.22 (dd, J=7.86, 6.24 Hz, 1H), 6.32 (s, 1H), 7.30-7.35 (m, 3H), 7.42-7.44 (m, 2H)

Step 2

(3R,6S,7aS)-6-methyl-3-phenyltetrahydro-3H,5H-pyrrolo[1,2-c]oxazol-5-one

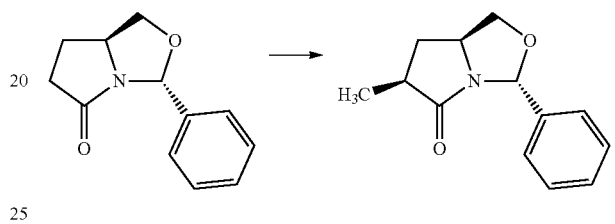

Diisopropylamine (13.2 mL) was mixed with tetrahydrofuran (50 mL). To this solution was added dropwise 1.6 M normal butyllithium/hexane solution (57.8 mL) under ice-cooling. The reaction mixture was cooled to −78° C., and a solution of (3R,7aS)-3-phenyltetrahydro-3H,5H-pyrrolo[1,2-c]oxazol-5-one (17.4 g) obtained in the earlier step in tetrahydrofuran (50 mL) was added dropwise. The reaction mixture was stirred at −78° C. for 30 min, and methyl iodide (5.86 mL) was added dropwise at −78° C. The reaction mixture was stirred at −78° C. for 1 hr, and saturated aqueous ammonium chloride solution and water were added dropwise. The reaction mixture was extracted twice with ethyl acetate and the combined organic layer was washed with saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=3:1) to give the title compound (11.3 g).

$^1$H-NMR (400 MHz, CDCl$_3$) 1.23 (d, J=6.01 Hz, 3H), 1.50-1.53 (m, 1H), 2.58-2.62 (m, 1H), 2.90-2.97 (m, 1H), 3.51 (d, J=7.74 Hz, 1H), 4.08 (s, 1H), 4.22 (dd, J=8.21, 6.36 Hz, 1H), 6.32 (s, 1H), 7.31-7.35 (m, 3H), 7.42-7.44 (m, 2H)

Step 3

(3R,6R,7aS)-6-methyl-3-phenyltetrahydro-3H,5H-pyrrolo[1,2-c]oxazol-5-one

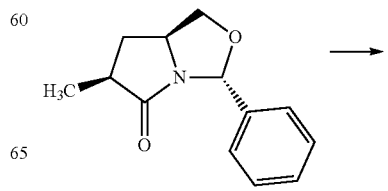

-continued

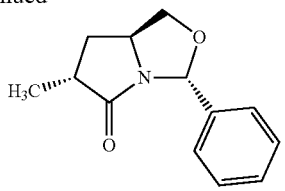

A 2.0M lithium diisopropylamide/tetrahydrofuran/heptane/ethylbenzene solution (97.9 mL) was mixed with tetrahydrofuran (180 mL). To this mixture was added dropwise a solution of (3R,6S,7aS)-6-methyl-3-phenyltetrahydro-3H,5H-pyrrolo[1,2-c]oxazol-5-one (30.4 g) in tetrahydrofuran (120 mL) at −78° C. The mixture was stirred at −78° C. for 30 min and tetrahydrofuran/water (60 mL/30 mL) was added. Water (200 mL) was added to the reaction mixture at 0° C. and the mixture was extracted twice with ethyl acetate. The combined organic layer was washed successively with saturated aqueous ammonium chloride solution and saturated aqueous sodium chloride solution. The organic layer was dried over sodium sulfate. Sodium sulfate was filtered off and the filtrate was concentrated under reduced pressure to give the title compound (34.8 g) as a crude product.

$^1$H-NMR (400 MHz, CDCl$_3$) δ 1.34 (d, J=7.40 Hz, 3H), 1.94-2.01 (m, 1H), 2.15-2.22 (m, 1H), 2.70-2.74 (m, 1H), 3.41 (t, J=8.32 Hz, 1H), 4.08 (s, 1H), 4.21 (t, J=7.17 Hz, 1H), 6.30 (s, 1H), 7.30-7.37 (m, 3H), 7.43-7.44 (m, 2H)

Step 4

((2S,4R)-1-benzyl-4-methylpyrrolidin-2-yl)methanol

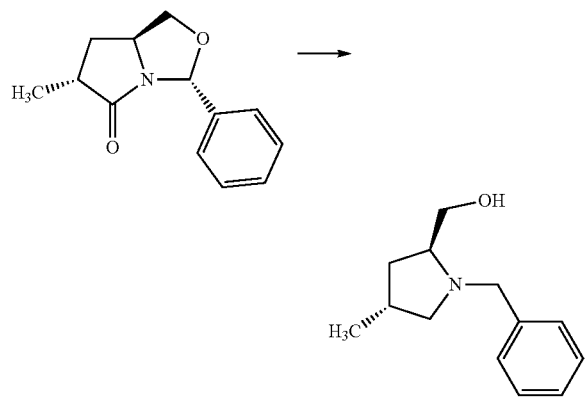

To 2.5M lithium aluminum hydride/tetrahydrofuran solution (73.6 mL) was added dropwise under ice-cooling a solution of a crude product (30.8 g) of (3R,6R,7aS)-6-methyl-3-phenyltetrahydro-3H,5H-pyrrolo[1,2-c]oxazol-5-one obtained in the earlier step in tetrahydrofuran (110 mL). This reaction mixture was stirred at 80° C. for 2 hr. To the reaction mixture were slowly added dropwise under ice-cooling water (7 mL), 4N aqueous sodium hydroxide solution (7 mL) and water (21 mL). The reaction mixture was stirred at room temperature for 1 hr, sodium sulfate was added, and the mixture was stood at room temperature overnight. This mixture was filtered through celite and the solid was washed successively with ethyl acetate (100 mL) and tetrahydrofuran (400 mL). The filtrate was concentrated under reduced pressure, and azeotroped with toluene to give the title compound (32.5 g) as a crude product.

$^1$H-NMR (400 MHz, CDCl$_3$) 0.94 (d, J=6.47 Hz, 3H), 1.50-1.55 (m, 1H), 1.94-1.98 (m, 2H), 2.10-2.12 (m, 1H), 2.80 (s, 1H), 3.01 (dd, J=7.51, 3.76 Hz, 1H), 3.34-3.37 (m, 2H), 3.61 (dd, J=10.75, 3.35 Hz, 1H), 3.92 (d, J=12.95 Hz, 1H), 7.15-7.32 (m, 5H)

Step 5

(3R,5R)-1-benzyl-5-methylpiperidin-3-ol

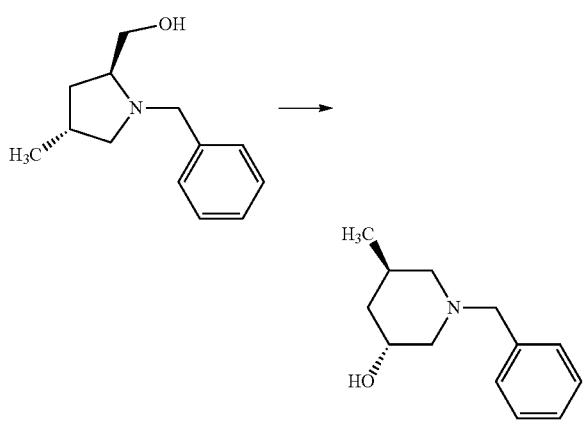

The crude product (32.5 g) of ((2S,4R)-1-benzyl-4-methylpyrrolidin-2-yl)methanol obtained in the earlier step was mixed with tetrahydrofuran (200 mL). To this mixture was added trifluoroacetic anhydride (23.6 mL) at −78° C. The reaction mixture was stirred at room temperature for 1 hr. To the reaction mixture was added triethylamine (78.9 mL) at −78° C. The reaction mixture was stirred at 80° C. for 6 hr. To the reaction mixture was added 2N aqueous sodium hydroxide solution (234 mL) at room temperature, and the mixture was stirred at room temperature for 2 hr. Water was added to the reaction mixture and the mixture was extracted three times with ethyl acetate. The combined organic layer was washed with saturated aqueous sodium chloride solution and dried over sodium sulfate. Sodium sulfate was filtered off and the filtrate was concentrated under reduced pressure. The obtained residue was purified by silica gel column chromatography (hexane:ethyl acetate=1:1) to give the title compound (25.4 g).

$^1$H-NMR (400 MHz, CDCl$_3$) δ 0.82 (d, J=6.70 Hz, 3H), 0.99-1.06 (m, 1H), 1.81-1.84 (m, 1H), 1.96-2.00 (m, 1H), 2.09 (dd, J=11.21, 1.50 Hz, 1H), 2.77 (dt, J=11.02, 2.02 Hz, 1H), 2.83-2.85 (m, 2H), 3.49 (s, 2H), 3.85 (brs, 1H), 7.22-7.32 (m, 5H)

Step 6

(R)-1-benzyl-5-methylpiperidin-3-one

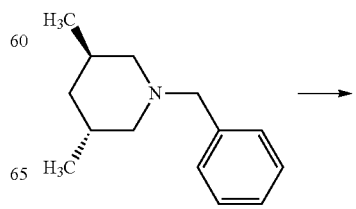

-continued

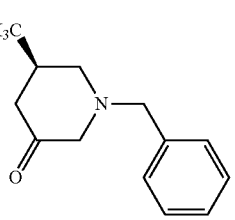

(3R,5R)-1-Benzyl-5-methylpiperidin-3-ol (25.2 g) obtained in the earlier step, triethylamine (49.8 g) and dimethyl sulfoxide (48.0 g) were mixed with chloroform (180 mL). To the reaction mixture was added sulfur trioxide pyridine complex (43.1 g) under ice-cooling. The reaction mixture was stirred at room temperature for 1 hr. Under ice-cooling, water (150 mL) was added to the reaction mixture, and the mixture was extracted with chloroform. A saturated aqueous sodium hydrogen carbonate solution was added to the aqueous layer and the mixture was extracted 4 times with ethyl acetate. The combined organic layer was washed with saturated brine. The organic layer was dried over sodium sulfate. Sodium sulfate was filtered off and the filtrate was concentrated under reduced pressure. The obtained residue was purified by silica gel column chromatography (hexane:ethyl acetate=6:1) to give the title compound (20.6 g).

$^1$H-NMR (400 MHz, CDCl$_3$) δ 0.97 (d, J=6.24 Hz, 3H), 1.95 (dd, J=15.14, 9.83 Hz, 1H), 2.08-2.16 (m, 2H), 2.44-2.49 (m, 1H), 2.76 (d, J=14.33 Hz, 1H), 2.85-2.86 (m, 1H), 3.15 (dt, J=14.33, 1.50 Hz, 1H), 3.57 (d, J=5.45 Hz, 2H), 7.23-7.33 (m, 5H)

Step 7

(4R)-6-benzyl-7a-hydroxy-4-methyl-3a,4,5,6,7,7a-hexahydroisoxazolo[5,4-c]pyridine-3-carboxylic Acid Ethyl Ester

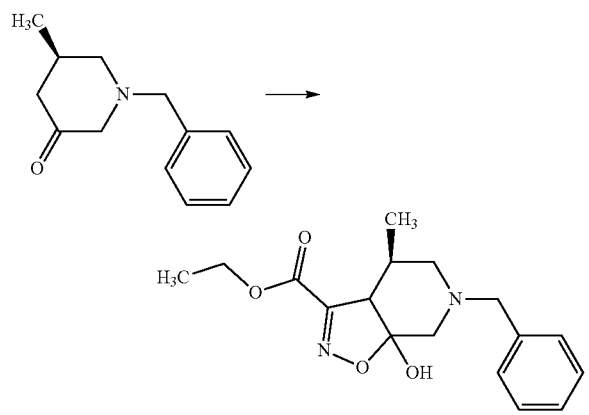

Ethyl 2-chloro-2-(hydroxyimino)acetate (16.4 g) was mixed with tetrahydrofuran (150 mL). A 1.1M lithium bis(trimethylsilyl)amide/tetrahydrofuran solution (108 mL) was added dropwise to this solution at −78° C. to prepare a nitrile oxide solution. In another reaction vessel, 1.1 M lithium bis(trimethylsilyl)amide/tetrahydrofuran solution (90.0 mL) was added. To this solution was added at −78° C. a solution of (R)-1-benzyl-5-methylpiperidin-3-one (18.3 g) obtained in the earlier step in tetrahydrofuran (140 mL). This reaction mixture was added dropwise through a cannula to the aforementioned nitrile oxide solution cooled to −78° C. This reaction mixture was stirred at −78° C. for 30 min and allowed to warm to 10° C. over 1 hour and half. To the reaction mixture was added dropwise 2N hydrochloric acid (150 mL) at −20° C. Under ice-cooling, saturated aqueous sodium hydrogen carbonate solution and water were added to the reaction mixture to adjust the pH to about 8. This mixture was extracted with ethyl acetate. The organic layer was washed successively with water and saturated aqueous sodium chloride solution and dried over sodium sulfate. Sodium sulfate was filtered off and the filtrate was concentrated under reduced pressure. The obtained residue was purified by silica gel column chromatography (hexane:ethyl acetate=3:1) to give the title compound (22.4 g).

$^1$H-NMR (400 MHz, CDCl$_3$) δ 1.09 (d, J=6.70 Hz, 3H), 1.37 (t, J=7.17 Hz, 3H), 1.59-1.66 (m, 1H), 1.79 (t, J=11.44 Hz, 1H), 2.37-2.40 (brm, 1H), 2.71-2.76 (m, 3H), 3.33 (dd, J=12.60, 1.50 Hz, 1H), 3.58-3.63 (m, 2H), 4.36 (ddd, J=14.28, 7.11, 1.10 Hz, 2H), 7.23-7.31 (m, 5H)

Step 8

(R)-6-benzyl-4-methyl-4,5,6,7-tetrahydroisoxazolo[5,4-c]pyridine-3-carboxylic Acid Ethyl Ester

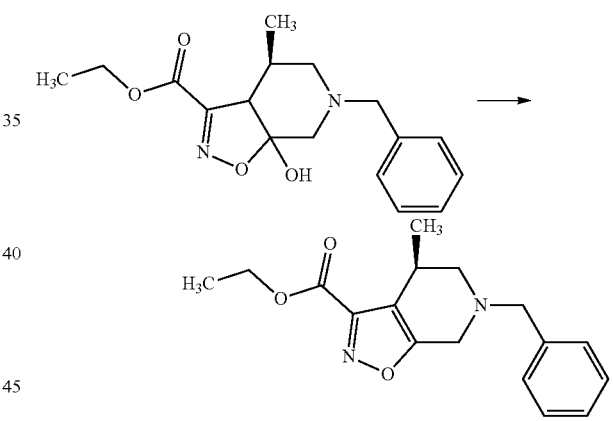

(4R)-6-Benzyl-7a-hydroxy-4-methyl-3a,4,5,6,7,7a-hexahydroisoxazolo[5,4-c]pyridine-3-carboxylic acid ethyl ester (22.4 g) obtained in the earlier step and triethylamine (39.2 mL) were mixed with tetrahydrofuran (200 mL). Under ice-cooling, methanesulfonyl chloride (10.9 mL) was added dropwise to this mixture and the mixture was stirred for 1 hr. Under ice-cooling, saturated aqueous sodium hydrogen carbonate solution and water were added to the reaction mixture. The reaction mixture was extracted with ethyl acetate. The organic layer was washed with saturated aqueous sodium chloride solution and dried over sodium sulfate. Sodium sulfate was filtered off and the filtrate was concentrated under reduced pressure. The obtained residue was purified by silica gel column chromatography (hexane:ethyl acetate=2:1) to give the title compound (19.0 g).

$^1$H-NMR (400 MHz, CDCl$_3$) δ 1.26 (d, J=6.70 Hz, 3H), 1.40 (t, J=7.17 Hz, 3H), 2.61 (m, 2H), 3.03 (brs, 1H), 3.40 (d, J=15.72 Hz, 1H), 3.71-3.77 (m, 3H), 4.42 (q, J=7.09 Hz, 2H), 7.27-7.34 (m, 5H)

Step 9

(R)-6-benzyl-4-methyl-4,5,6,7-tetrahydroisoxazolo[5,4-c]pyridine-3-carboxylic Acid

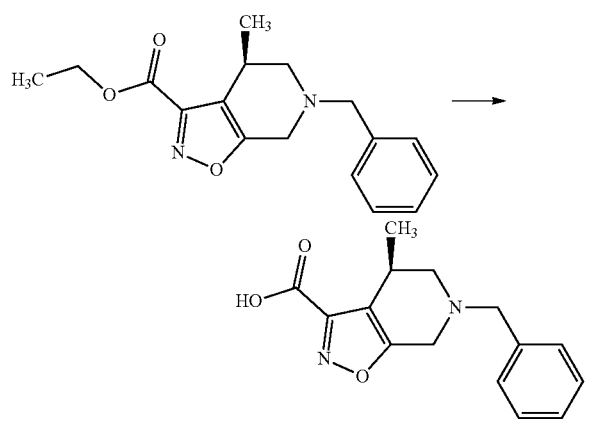

(R)-6-Benzyl-4-methyl-4,5,6,7-tetrahydroisoxazolo[5,4-c]pyridine-3-carboxylic acid ethyl ester (19.0 g) obtained in the earlier step was mixed with tetrahydrofuran (95 mL) and methanol (95 mL). Under ice-cooling, 2N aqueous sodium hydroxide solution (44.9 mL) was added dropwise to this mixture. The reaction mixture was stirred at room temperature for 2 hr. Under ice-cooling, 6N hydrochloric acid (15.0 mL) was added dropwise to the reaction mixture. This reaction mixture was concentrated under reduced pressure to give the title compound as a crude product.

Step 10

(R)-6-benzyl-N-methoxy-N,4-dimethyl-4,5,6,7-tetrahydroisoxazolo[5,4-c]pyridine-3-carboxamide

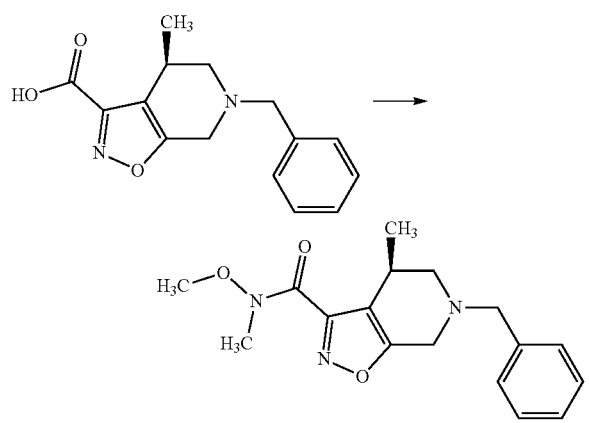

The crude product of (R)-6-benzyl-4-methyl-4,5,6,7-tetrahydroisoxazolo[5,4-c]pyridine-3-carboxylic acid obtained in the earlier step and N,O-dimethylhydroxylamine hydrochloride (9.39 g) were mixed with dimethylformamide (190 mL). Under ice-cooling, to this mixture were added diisopropylethylamine (33.5 mL) and HATU (29.3 g), and the mixture was stirred at room temperature overnight. Under ice-cooling, saturated aqueous sodium hydrogen carbonate solution and water were added to the reaction mixture, and the mixture was extracted with ethyl acetate. The organic layer was washed successively with saturated aqueous sodium hydrogen carbonate solution, water and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=2:1) to give the title compound (19.3 g).

$^1$H-NMR (400 MHz, CDCl$_3$) δ 1.14 (d, J=6.70 Hz, 3H), 2.39 (dd, J=11.56, 6.01 Hz, 1H), 2.78 (dd, J=11.79, 4.62 Hz, 1H), 2.99 (brs, 1H), 3.37 (brs, 3H), 3.55-3.63 (m, 2H), 3.70-3.73 (m, 5H), 7.29-7.32 (m, 5H)

Step 11

(R)-1-(6-benzyl-4-methyl-4,5,6,7-tetrahydroisoxazolo[5,4-c]pyridin-3-yl)ethan-1-one

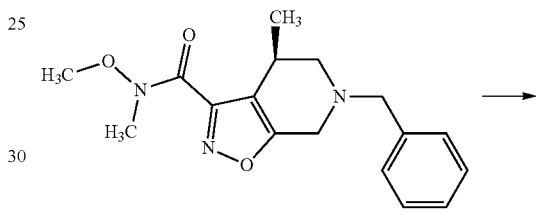

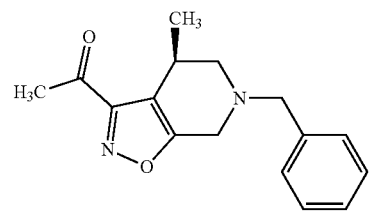

(R)-6-Benzyl-N-methoxy-N,4-dimethyl-4,5,6,7-tetrahydroisoxazolo[5,4-c]pyridine-3-carboxamide (19.3 g) obtained in the earlier step was mixed with tetrahydrofuran (100 mL). Under ice-cooling, 3.0M methylmagnesium bromide/diethyl ether solution (30.6 mL) was added dropwise to this mixture. The reaction mixture was stirred at room temperature for 1 hr. Under ice-cooling, saturated aqueous ammonium chloride solution (100 mL) was slowly added to the reaction mixture. Water (100 mL) was added to the reaction mixture, and the mixture was extracted with ethyl acetate. The organic layer was washed with saturated aqueous sodium chloride solution and dried over sodium sulfate. Sodium sulfate was filtered off and the filtrate was concentrated under reduced pressure. The obtained residue was purified by silica gel column chromatography (hexane:ethyl acetate=4:1) to give the title compound (15.7 g).

$^1$H-NMR (400 MHz, CDCl$_3$) δ 1.23 (d, J=5.66 Hz, 3H), 2.54-2.65 (m, 2H), 2.54 (s, 3H), 3.03 (d, J=6.47 Hz, 1H), 3.39 (d, J=15.26 Hz, 1H), 3.68-3.77 (m, 3H), 7.26-7.39 (m, 5H)

Step 12

(R)-2-((R)-6-benzyl-4-methyl-4,5,6,7-tetrahydroisoxazolo[5,4-c]pyridin-3-yl)-1,1,1-trifluoropropan-2-ol

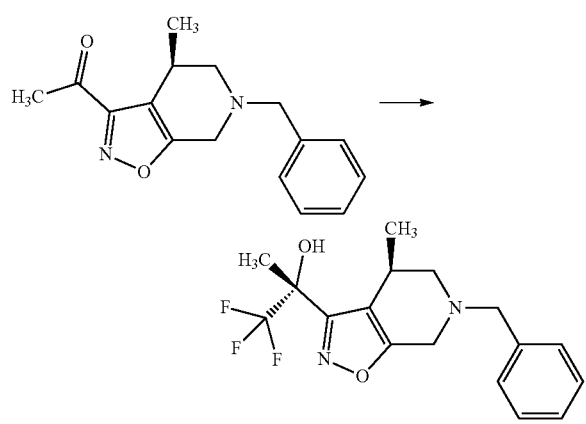

(R)-1-(6-Benzyl-4-methyl-4,5,6,7-tetrahydroisoxazolo[5,4-c]pyridin-3-yl)ethan-1-one (15.5 g) obtained in the earlier step was mixed with tetrahydrofuran (150 mL). Under ice-cooling, cesium fluoride (1.71 g) was added to this mixture, and (trifluoromethyl)trimethylsilane (12.5 mL) was added dropwise. This reaction mixture was stirred under ice-cooling for 1 hr. Under ice-cooling, methanol (150 mL) and potassium carbonate (11.7 g) were added to the reaction mixture, and the mixture was stirred at room temperature for 1 hr. This reaction mixture was concentrated under reduced pressure. To the obtained residue was added water, and the mixture was extracted with ethyl acetate. The organic layer was washed with saturated aqueous sodium chloride solution and dried over sodium sulfate. Sodium sulfate was filtered off and the filtrate was concentrated under reduced pressure. The obtained residue was purified by silica gel column chromatography (hexane:ethyl acetate=6:1) to give the title compound (10.3 g).

$^1$H-NMR (400 MHz, CDCl$_3$) δ 1.30 (d, J=6.94 Hz, 3H), 1.83 (s, 3H), 2.52 (dd, J=11.56, 3.70 Hz, 1H), 2.67 (dd, J=11.68, 2.66 Hz, $^1$H), 2.84 (s, 1H), 2.89 (brs, 1H), 3.28 (d, J=15.72 Hz, 1H), 3.72 (dd, J=15.95, 13.18 Hz, 2H), 3.83 (d, J=15.49 Hz, 1H), 7.25-7.37 (m, 5H)

Step 13

(9H-fluoren-9-yl)methyl (R)-4-methyl-3-((R)-1,1,1-trifluoro-2-hydroxypropan-2-yl)-4,7-dihydroisoxazolo[5,4-c]pyridine-6 (5H)-carboxylate

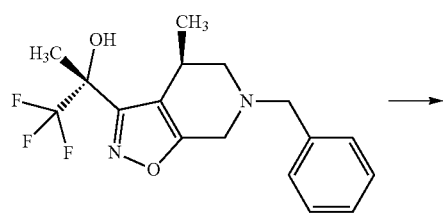

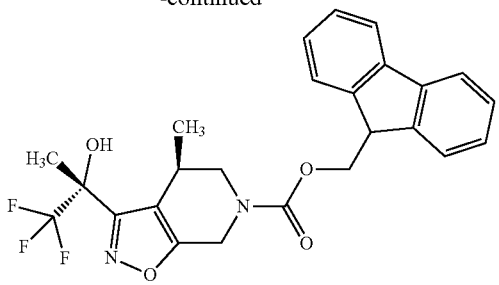

(R)-2-((R)-6-Benzyl-4-methyl-4,5,6,7-tetrahydroisoxazolo[5,4-c]pyridin-3-yl)-1,1,1-trifluoropropan-2-ol (10.3 g) obtained in the earlier step was mixed with chloroform (150 mL). Under ice-cooling, 9-fluorenylmethyl chloroformate (9.3 g) was added to this mixture, and the mixture was stirred at room temperature for 5 hr. This reaction mixture was concentrated under reduced pressure. The obtained residue was purified by silica gel column chromatography (hexane:ethyl acetate=4:1) to give the title compound (9.9 g).

$^1$H-NMR (400 MHz, CDCl$_3$) δ 0.96, 1.12 (m, 3H), 1.84 (s, 3H), 2.80-2.98 (m, 3H), 3.84-4.15 (m, 3H), 4.55-4.58 (m, 2H), 4.81-5.05 (m, 1H), 7.33-7.37 (m, 4H), 7.56 (d, J=7.40 Hz, 2H), 7.76 (d, J=7.40 Hz, 2H)

Step 14

(R)-1,1,1-trifluoro-2-((R)-4-methyl-4,5,6,7-tetrahydroisoxazolo[5,4-c]pyridin-3-yl)propan-2-ol

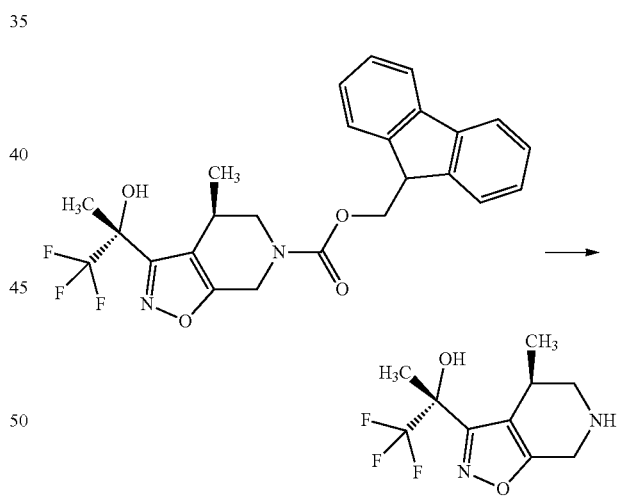

(9H-Fluoren-9-yl)methyl (R)-4-methyl-3-((R)-1,1,1-trifluoro-2-hydroxypropan-2-yl)-4,7-dihydroisoxazolo[5,4-c]pyridine-6(5H)-carboxylate (9.9 g) obtained in the earlier step was mixed with acetonitrile (200 mL). Under ice-cooling, diethylamine (32.3 mL) was added to this mixture, and the mixture was stirred at room temperature overnight. The reaction mixture was concentrated under reduced pressure and azeotroped with methanol. The obtained residue was purified by SCX column chromatography (methanol to 1N ammonia/methanol solution) and further purified by silica gel column chromatography (hexane:ethyl acetate=1:2). Ethyl acetate (10 mL) and hexane (10 mL) were added to the obtained solid, and the mixture was stirred at room temperature for 1 hr. The precipitated solid was collected by filtration to give the title compound (3.91 g).

¹H-NMR (400 MHz, CDCl₃) δ 1.27 (d, J=6.88 Hz, 3H), 1.86 (s, 3H), 2.91-2.93 (m, 3H), 3.93-4.01 (m, 2H)

Step 15

(3-cyclopropyl-1H-pyrazol-5-yl)((R)-4-methyl-3-((R)-1,1,1-trifluoro-2-hydroxypropan-2-yl)-4,7-dihydroisoxazolo[5,4-c]pyridin-6(5H)-yl)methanone

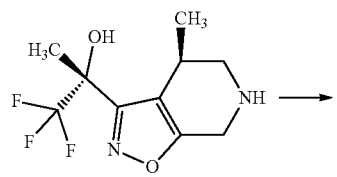

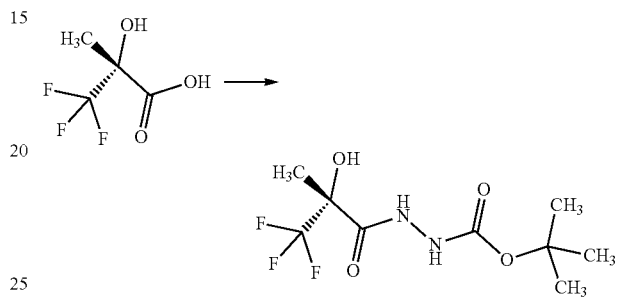

(R)-1,1,1-Trifluoro-2-((R)-4-methyl-4,5,6,7-tetrahydroisoxazolo[5,4-c]pyridin-3-yl)propan-2-ol (90 mg) obtained in the earlier step and 3-cyclopropyl-1H-pyrazole-5-carboxylic acid (61 mg) were mixed with dimethylformamide (675 μL). Under ice-cooling, to this mixture were added diisopropylethylamine (87 μL) and HATU (151 mg), and the mixture was stirred at room temperature overnight. Under ice-cooling, saturated aqueous sodium hydrogen carbonate solution was added to the reaction mixture, and the mixture was extracted with ethyl acetate. The organic layer was washed successively with water and saturated aqueous sodium chloride solution and dried over sodium sulfate. Sodium sulfate was filtered off and the filtrate was concentrated under reduced pressure. To the obtained residue were added chloroform and diethyl ether, and the mixture was stirred at room temperature for 1 hr. The precipitated solid was collected by filtration to give the title compound (119 mg).

¹H-NMR (400 MHz, DMSO-d₆) δ 0.68-0.72 (m, 2H), 0.90-0.97 (m, 2H), 1.11-1.17 (m, 3H), 1.71 (s, 3H), 1.88-1.95 (m, 1H), 2.95-3.10 (m, 1.5H), 3.34-3.46 (m, 0.5H), 4.24-4.54 (m, 1H), 4.61-4.97 (m, 1H), 5.18-5.30 (m, 0.5H), 5.76-5.91 (m, 0.5H), 6.22-6.35 (m, 1H), 7.09 (s, 1H), 13.01 (s, 1H)

Production Example 13

Synthesis of ((S)-5-methyl-3-((R)-1,1,1-trifluoro-2-hydroxypropan-2-yl)-5,6-dihydro-[1,2,4]triazolo[4,3-a]pyrazin-7 (8H)-yl) (1-methyl-3-phenyl-1H-pyrazol-5-yl)methanone (Compound of Example 122)

Step 1 tert-butyl (R)-2-(3,3,3-trifluoro-2-hydroxy-2-methylpropanoyl)hydrazine-1-carboxylate

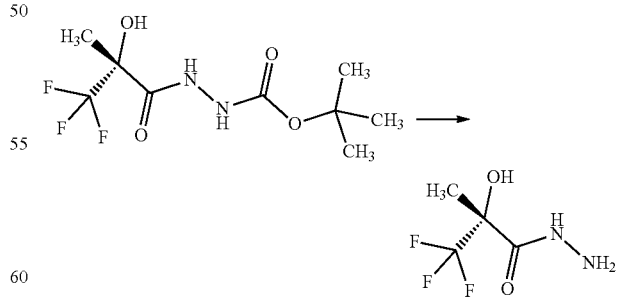

(R)-3,3,3-Trifluoro-2-hydroxy-2-methylpropanoic acid (4.74 g), tert-butyl carbazate (5.55 g) and 1-hydroxybenzotriazole monohydrate were mixed with acetonitrile (50 mL). Under ice-cooling, 1-ethyl-3-(3-dimethylaminopropyl)carbodiimide hydrochloride (2.75 g) was added and the mixture was stirred at room temperature overnight. This mixture was concentrated under reduced pressure. Ethyl acetate and 0.5N hydrochloric acid were added and the layers were separated. The organic layer was washed successively with water, saturated aqueous sodium hydrogen carbonate solution and saturated aqueous sodium chloride solution. The organic layer was dried over sodium sulfate. Sodium sulfate was filtered off, and the filtrate was concentrated under reduced pressure to give the title compound (9.18 g) as a crude product.

Step 2

(R)-3,3,3-trifluoro-2-hydroxy-2-methylpropanehydrazide

The crude product (4.74 g) of tert-butyl (R)-2-(3,3,3-trifluoro-2-hydroxy-2-methylpropanoyl)hydrazine-1-carboxylate obtained in the earlier step was mixed with ethyl acetate (40 mL). Under ice-cooling, 4N hydrochloric acid/ethyl acetate solution (40 mL) was added to this mixture, and the mixture was stirred at room temperature overnight. This mixture was concentrated under reduced pressure. To the obtained residue was added saturated aqueous sodium hydrogen carbonate solution, and the mixture was extracted with ethyl acetate. The organic layer was washed with saturated aqueous sodium chloride solution, and dried over sodium sulfate. Sodium sulfate was filtered off and the filtrate was concentrated under reduced pressure. The obtained residue was purified by silica gel column chromatography (chloroform:methanol=20:1 to 9:1) to give the title compound (4.10 g).

$^1$H-NMR (400 MHz, DMSO-d$_6$) δ 1.45 (s, 3H), 4.34 (brs, 2H), 6.85 (brs, 1H), 9.30 (brs, 1H)

Step 3

(S)-(2-((tert-butoxycarbonyl)amino)propyl)glycine Methyl Ester

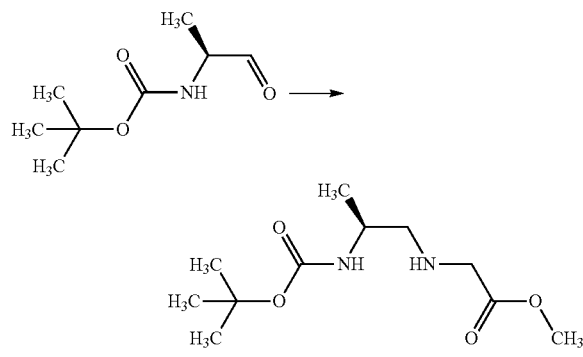

tert-Butyl (S)-(1-oxopropan-2-yl)carbamate (5.2 g) and glycine methyl ester hydrochloride (7.53 g) were mixed with chloroform (100 mL). Under ice-cooling, diisopropylethylamine (7.75 mL) and sodium triacetoxyborohydride (9.93 g) were added. This mixture was stirred at room temperature overnight. Under ice-cooling, saturated aqueous sodium hydrogen carbonate solution was added to the reaction mixture, and the layers were separated. The organic layer was dried over sodium sulfate. Sodium sulfate was filtered off and the filtrate was concentrated under reduced pressure. The obtained residue was purified by silica gel column chromatography (hexane:ethyl acetate=1:1 to chloroform:methanol=20:1) to give the title compound (8.44 g).

$^1$H-NMR (400 MHz, DMSO-d$_6$) δ 0.99 (d, J=6.60 Hz, 3H), 1.37 (s. 9H), 1.95 (brs, 1H), 2.39-2.48 (m, 2H), 3.48 (brs, 1H), 3.61-3.62 (m, 4H), 6.56 (brs, 1H)

Step 4 tert-butyl (S)-3-methyl-5-oxopiperazine-1-carboxylate

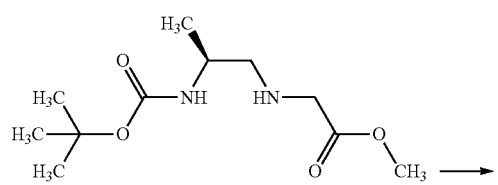

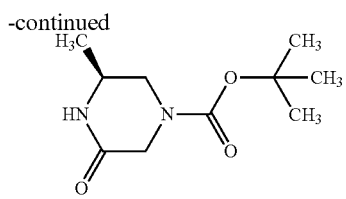

(S)-(2-((tert-Butoxycarbonyl)amino)propyl)glycine methyl ester (8.4 g) obtained in the earlier step was mixed with methanol (80 mL). To this mixture was added 4N hydrochloric acid/1,4-dioxane solution (23 mL) at room temperature, and the mixture was stirred at room temperature overnight. The reaction mixture was concentrated under reduced pressure. To the obtained residue were added methanol (90 mL) and sodium acetate (7.4 g), and the mixture was stirred at 70° C. for 4 hr. The reaction mixture was filtered at room temperature, and the filtrate was concentrated under reduced pressure and azeotroped with toluene. Chloroform (100 mL), triethylamine (5.0 mL) and di-tert-butyl dicarbonate were added to the obtained residue, and the mixture was stirred at room temperature overnight. The reaction mixture was filtered at room temperature and the filtrate was concentrated under reduced pressure. The obtained residue was purified by silica gel column chromatography (hexane:ethyl acetate=1:1 to ethyl acetate:methanol=20:1). Ethyl acetate (8 mL) and hexane (35 mL) were added to the obtained solid, and the mixture was stirred at room temperature for 1 hr. This mixture was collected by filtration to give the title compound (3.13 g).

$^1$H-NMR (400 MHz, DMSO-d$_6$) δ 1.04 (d, J=6.47 Hz, 3H), 1.39 (s, 9H), 3.00 (brs, 1H), 3.43 (brs, 1H), 3.61 (brs, 1H), 3.75-3.83 (m, 2H), 8.03 (brs, 1H)

Step 5 tert-butyl (S)-3-methyl-5-thioxopiperazine-1-carboxylate

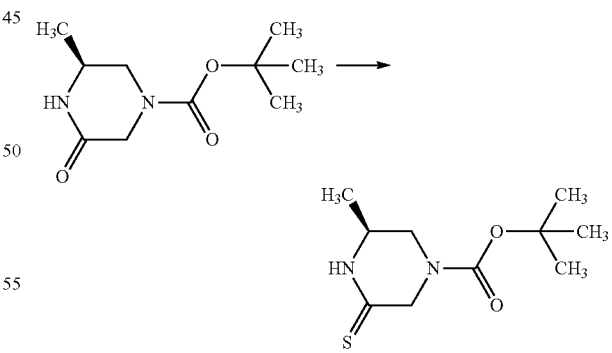

tert-Butyl (S)-3-methyl-5-oxopiperazine-1-carboxylate (3.1 g) obtained in the earlier step and Lawesson's reagent (4.14 g) were mixed with tetrahydrofuran (50 mL). This mixture was stirred at 75° C. for 4 hr. The reaction mixture was concentrated under reduced pressure. The obtained residue was purified by silica gel column chromatography (hexane:ethyl acetate=3:1 to 3:2) to give the title compound (2.69 g).

$^1$H-NMR (400 MHz, DMSO-d$_6$) δ 1.26 (d, J=6.47 Hz, 3H), 1.46 (s, 9H), 2.98 (brs, 1H), 3.65 (brs, 1H), 3.99 (brs, 1H), 4.34 (d, J=19.88 Hz, 1H), 4.67 (d, J=20.11 Hz, 1H), 8.25 (brs, 1H)

Step 6 tert-butyl (S)-3-methyl-5-(methylthio)-3,6-dihydropyrazine-1(2H)-carboxylate Hydroiodide

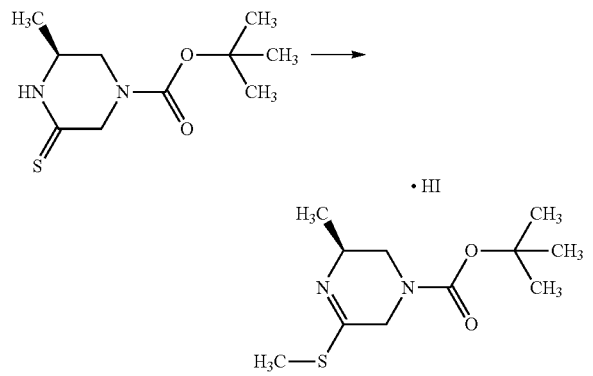

tert-Butyl (S)-3-methyl-5-thioxopiperazine-1-carboxylate (2.68 g) obtained in the earlier step was mixed with acetone (50 mL). To this mixture was added iodomethane (3.63 mL) and the mixture was stirred at 45° C. for 1 hr. The reaction mixture was concentrated under reduced pressure to give the title compound as a crude product.

$^1$H-NMR (400 MHz, DMSO-d$_6$) δ 1.23 (d, J=6.47 Hz, 3H), 1.42 (s, 9H), 2.62 (s, 3H), 3.26 (brs, 1H), 3.67 (dd, J=13.41, 4.16 Hz, 1H), 3.87-3.89 (m, 1H), 4.52 (brs, 2H)

Step 7 tert-butyl (S)-5-methyl-3-((R)-1,1,1-trifluoro-2-hydroxypropan-2-yl)-5,6-dihydro-[1,2,4]triazolo[4,3-a]pyrazine-7(8H)-carboxylate

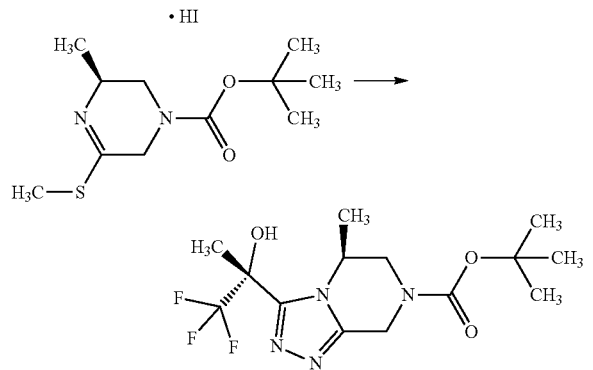

The crude product of tert-butyl (S)-3-methyl-5-(methylthio)-3,6-dihydropyrazine-1(2H)-carboxylate hydroiodide obtained in the earlier step and (R)-3,3,3-trifluoro-2-hydroxy-2-methylpropanehydrazide (2.01 g) obtained in Step 2 were mixed with 2-propanol (80 mL) and water (15 mL). To this mixture was added acetic acid (1.33 mL), and the mixture was stirred at 100° C. overnight. Under ice-cooling, saturated aqueous sodium hydrogen carbonate solution was added to the reaction mixture, and the mixture was extracted with chloroform. The organic layer was washed with saturated aqueous sodium chloride solution and dried over sodium sulfate. Sodium sulfate was filtered off and the filtrate was concentrated under reduced pressure. The obtained residue was purified by silica gel column chromatography (hexane:ethyl acetate=1:9 to ethyl acetate). Diethyl ether and hexane were added to the obtained solid, and the mixture was stirred at room temperature for 1 hr. The solid was collected by filtration to give the title compound (1.30 g).

$^1$H-NMR (400 MHz, DMSO-d$_6$) δ 1.32 (d, J=5.78 Hz, 3H), 1.43 (s, 9H), 1.82 (s, 3H), 3.12-3.30 (m, 1H), 4.05 (d, J=38.15 Hz, 1H), 4.44 (dd, J=43.70, 17.11 Hz, 1H), 4.80 (s, 1H), 4.96 (d, J=16.88 Hz, 1H), 7.42 (s, 1H)

Step 8

(R)-1,1,1-trifluoro-2-((S)-5-methyl-5,6,7,8-tetrahydro[1,2,4]triazolo[4,3-a]pyrazin-3-yl)propan-2-ol Dihydrochloride

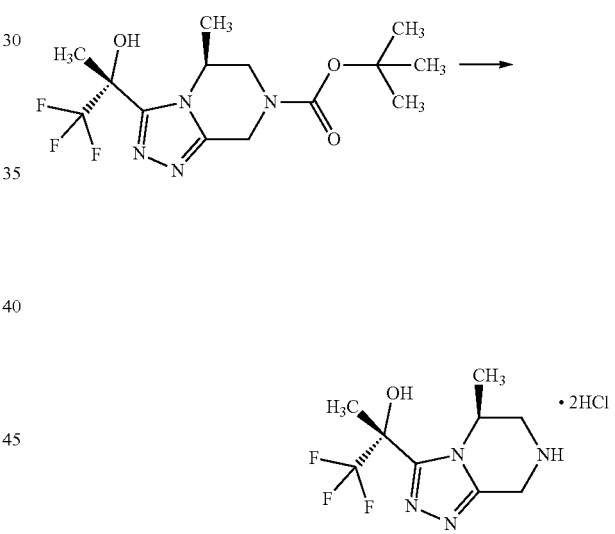

tert-Butyl (S)-5-methyl-3-((R)-1,1,1-trifluoro-2-hydroxypropan-2-yl)-5,6-dihydro-[1,2,4]triazolo[4,3-a]pyrazine-7 (8H)-carboxylate (1.3 g) obtained in the earlier step was mixed with methanol (2 mL) and ethyl acetate (2 mL). Under ice-cooling, 4N hydrochloric acid/ethyl acetate solution (5.0 mL) was added to this mixture, and the mixture was stirred at room temperature for 1 hr and further at 60° C. for 1 hr. The reaction mixture was concentrated under reduced pressure. To the obtained residue were added methanol, ethyl acetate and diethyl ether. The precipitated solid was collected by filtration to give the title compound (1.08 g).

$^1$H-NMR (400 MHz, DMSO-d$_6$) δ 1.60 (d, J=6.70 Hz, 3H), 1.84 (s, 3H), 3.42 (dd, J=14.10, 6.94 Hz, 1H), 3.57 (d, J=12.48 Hz, 1H), 4.45 (d, J=16.18 Hz, 1H), 4.58 (d, J=15.95 Hz, 1H), 4.97-4.98 (m, 1H), 7.64 (brs, 2H), 9.93 (brs, 1H), 10.81 (brs, 1H)

Step 9

((S)-5-methyl-3-((R)-1,1,1-trifluoro-2-hydroxypropan-2-yl)-5,6-dihydro-[1,2,4]triazolo[4,3-a]pyrazin-7(8H)-yl)(1-methyl-3-phenyl-1H-pyrazol-5-yl)methanone

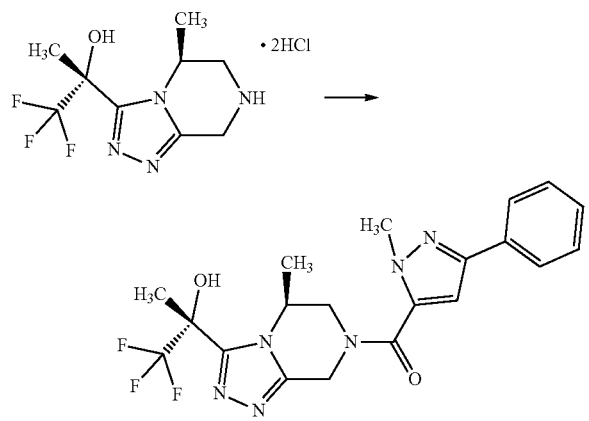

(R)-1,1,1-Trifluoro-2-((S)-5-methyl-5,6,7,8-tetrahydro[1,2,4]triazolo[4,3-a]pyrazin-3-yl)propan-2-ol dihydrochloride (39 mg) obtained in the earlier step and 1-methyl-3-phenyl-1H-pyrazole-5-carboxylic acid (29.1 mg) were mixed with dimethylformamide (0.6 mL). Under ice-cooling, to this mixture were added diisopropylethylamine (83 μL) and HATU (55 mg), and the mixture was stirred at room temperature overnight. Under ice-cooling, saturated aqueous sodium hydrogen carbonate solution and water were added to the reaction mixture, and the mixture was extracted with ethyl acetate. The organic layer was washed successively with saturated aqueous sodium hydrogen carbonate solution, water and saturated aqueous sodium chloride solution. The organic layer was dried over sodium sulfate. Sodium sulfate was filtered off and the filtrate was concentrated under reduced pressure. The obtained residue was purified by silica gel column chromatography (hexane:ethyl acetate=2:1 to chloroform:methanol=20:1). Ethyl acetate and hexane were added to the obtained solid, and the mixture was stirred at room temperature for 1 hr. The solid was collected by filtration to give the title compound (41.7 mg).

$^1$H-NMR (400 MHz, DMSO-$d_6$) δ 1.34-1.46 (m, 3H), 1.83 (s, 3H), 3.26-3.38 (m, 0.5H), 3.64-3.77 (m, 0.5H), 3.91 (s, 3H), 4.10-4.22 (m, 0.5H), 4.60-4.75 (m, 1H), 4.85-5.06 (m, 1.5H), 5.18-5.32 (m, 1H), 6.93-7.02 (m, 0.5H), 7.19-7.27 (m, 0.5H), 7.32 (tt, J=7.40, 1.46 Hz, 1H), 7.42 (t, J=7.63 Hz, 2H), 7.48 (s, 1H), 7.80-7.86 (m, 2H)

The compounds of Examples 1 to 123 were obtained according to methods similar to the above-mentioned Production Method 1 to Production Method 6 and Production Examples 1 to 13, or other known methods as necessary. The structural formulas and property data of the Example compounds are shown in the following Tables.

TABLE 1-1

| Example | Structure | $^1$H-NMR | Mass M + 1 | Mass M − 1 |
|---|---|---|---|---|
| 1 | 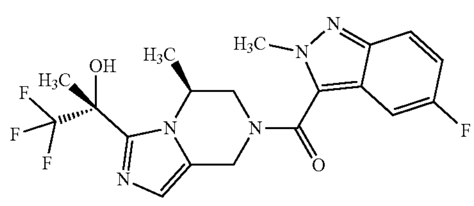 [SMILES: C[C@H]1CN(C(=O)c2c3cc(F)ccc3nn2C)Cc2cnc([C@@](C)(O)C(F)(F)F)n21] | (400 MHz, DMSO-$d_6$) δ: 1.25-1.47 (m, 3H), 1.77 (s, 3H), 3.26-3.40 (m, 1H), 3.74 (brs, 1H), 4.17 (s, 3H), 4.77-4.91 (m, 2H), 5.14-5.17 (m, 1H), 6.67-6.89 (m, 1H), 7.05 (s, 1H), 7.23-7.25 (m, 1H), 7.48 (brs, 1H), 7.80 (brs, 1H) | 426 | 424 |
| 2 | 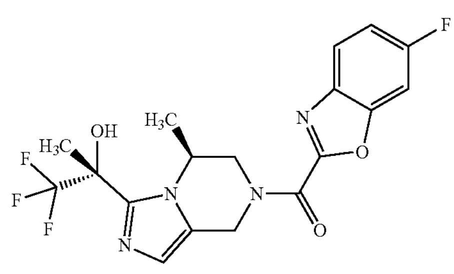 [SMILES: C[C@H]1CN(C(=O)c2nc3ccc(F)cc3o2)Cc2cnc([C@@](C)(O)C(F)(F)F)n21] | (400 MHz, CDCl$_3$) δ: 1.49-1.51 (m, 3H), 1.96 (s, 3H), 3.39-3.76 (m, 1H), 3.63 (brs, 1H), 4.76-4.84 (m, 1H), 5.24-5.53 (m, 3H), 6.92-6.94 (m, 1H), 7.22-7.28 (m, 1H), 7.48-7.54 (m, 1H), 7.60-7.62 (m, 1H) | 413 | 411 |
| 3 | 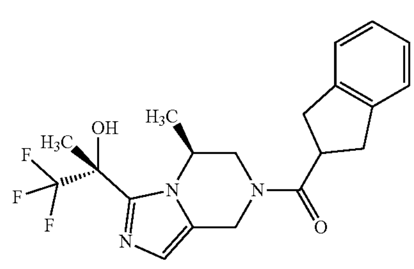 [SMILES: C[C@H]1CN(C(=O)C2Cc3ccccc3C2)Cc2cnc([C@@](C)(O)C(F)(F)F)n21] | (400 MHz, CDCl$_3$) δ: 1.41-1.50 (m, 3H), 1.96-1.97 (m, 3H), 3.12-3.65 (m, 7H), 3.99-5.08 (m, 4H), 6.91 (s, 1H), 7.16-7.21 (m, 4H) | 394 | 392 |

TABLE 1-1-continued

| Example | Structure | ¹H-NMR | Mass M + 1 | Mass M − 1 |
|---|---|---|---|---|
| 4 | 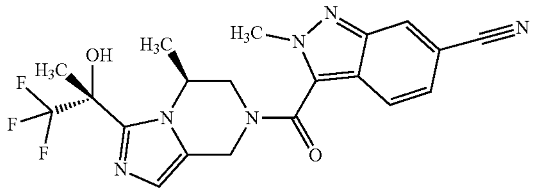 [SMILES: C[C@H]1CN(C(=O)c2c3ccc(C#N)cc3nn2C)Cc2cnc([C@@](C)(O)C(F)(F)F)n21] | (400 MHz, DMSO-d₆) δ: 1.25-1.47 (m, 3H), 1.75 (s, 3H), 3.26-3.37 (m, 1H), 3.67 (brs, 1H), 4.22 (s, 3H), 4.76-5.16 (m, 3H), 6.62-6.89 (m, 1H), 7.03-7.10 (m, 1H), 7.42 (s, 1H), 7.91 (brs, 1H), 8.43 (s, 1H) | 433 | 431 |
| 5 | 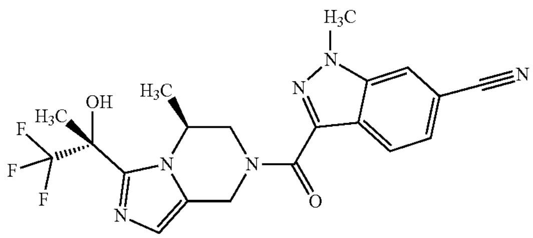 [SMILES: C[C@H]1CN(C(=O)c2nn(C)c3cc(C#N)ccc23)Cc2cnc([C@@](C)(O)C(F)(F)F)n21] | (400 MHz, DMSO-d₆) δ: 1.37-1.42 (m, 3H), 1.78 (s, 3H), 3.26-3.63 (m, 1H), 4.21-4.24 (m, 3H), 4.84-5.39 (m, 4H), 6.77-6.87 (m, 1H), 7.08-7.09 (m, 1H), 7.60 (d, J = 8.52 Hz, 1H), 8.22 (d, J = 8.37 Hz, 1H), 8.52-8.54 (m, 1H) | 433 | 431 |
| 6 | 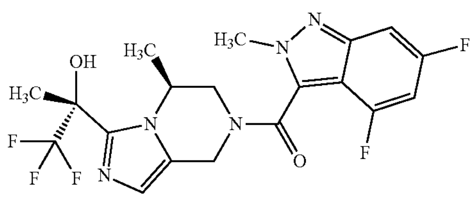 [SMILES: C[C@H]1CN(C(=O)c2c3c(F)cc(F)cc3nn2C)Cc2cnc([C@@](C)(O)C(F)(F)F)n21] | (400 MHz, DMSO-d₆) δ: 1.26-1.41 (m, 3H), 1.75-1.76 (m, 3H), 3.33-5.15 (m, 5H), 4.08-4.11 (m, 3H), 6.69-6.81 (m, 1H), 7.01-7.09 (m, 1H), 7.33-7.36 (m, 1H) | 444 | 442 |

TABLE 1-2

| Example | Structure | ¹H-NMR | Mass M + 1 | Mass M − 1 |
|---|---|---|---|---|
| 7 | 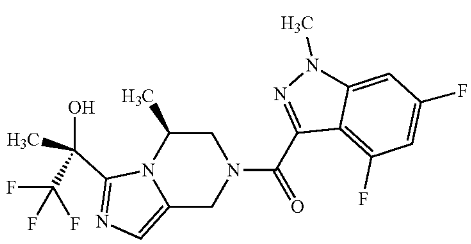 [SMILES: C[C@H]1CN(C(=O)c2nn(C)c3cc(F)cc(F)c23)Cc2cnc([C@@](C)(O)C(F)(F)F)n21] | (400 MHz, DMSO-d₆) δ: 1.29-1.41 (m, 3H), 1.76 (s, 3H), 3.30-5.10 (m, 5H), 4.06-4.16 (m, 3H), 6.64-6.84 (m, 1H), 7.05-7.10 (m, 1H), 7.55-7.56 (m, 1H) | 444 | 488 (M − 1 + 46) |
| 8 | 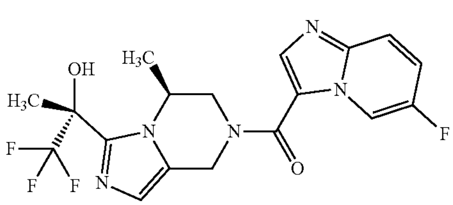 [SMILES: C[C@H]1CN(C(=O)c2cnc3ccc(F)cn23)Cc2cnc([C@@](C)(O)C(F)(F)F)n21] | (400 MHz, DMSO-d₆) δ: 1.38 (d, J = 6.47 Hz, 3H), 1.77 (s, 3H), 3.55 (brs, 1H), 4.42 (d, J = 12.72 Hz, 1H), 4.97-5.07 (m, 3H), 6.82 (s, 1H), 7.09 (s, 1H), 7.56-7.61 (m, 1H), 7.82 (dd, J = 9.94, 5.32 Hz, 1H), 8.26 (s, 1H), 9.11-9.12 (m, 1H) | 412 | 410 |
| 9 | 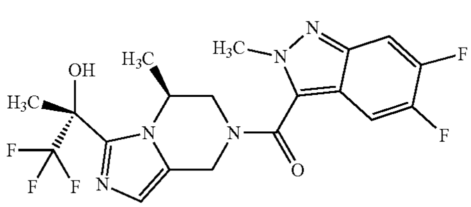 [SMILES: C[C@H]1CN(C(=O)c2c3cc(F)c(F)cc3nn2C)Cc2cnc([C@@](C)(O)C(F)(F)F)n21] | (400 MHz, DMSO-d₆) δ: 1.24-1.45 (m, 3H), 1.75 (s, 3H), 3.29-3.35 (m, 1H), 3.70 (brs, 1H), 4.13 (s, 3H), 4.72-5.16 (m, 3H), 6.64-6.88 (m, 1H), 7.03-7.08 (m, 1H), 7.75-7.78 (m, 2H) | 444 | 442 |

TABLE 1-2-continued

| Example | Structure | ¹H-NMR | Mass M + 1 | Mass M − 1 |
|---|---|---|---|---|
| 10 | 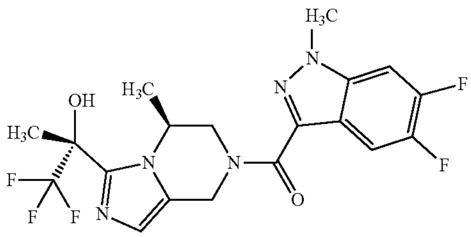 [SMILES: C[C@H]1CN(C(=O)c2nn(C)c3cc(F)c(F)cc23)Cc2cnc([C@@](C)(O)C(F)(F)F)n21] | (400 MHz, DMSO-d₆) δ: 1.35-1.39 (m, 3H), 1.77 (s, 3H), 3.25-3.57 (m, 1H), 4.11-4.14 (m, 3H), 4.90-5.35 (m, 4H), 6.77-6.84 (m, 1H), 7.06-7.07 (m, 1H), 7.95-7.99 (m, 2H) | 444 | 442 |
| 11 | 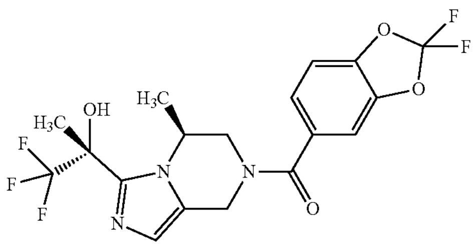 [SMILES: C[C@H]1CN(C(=O)c2ccc3c(c2)OC(F)(F)O3)Cc2cnc([C@@](C)(O)C(F)(F)F)n21] | (400 MHz, DMSO-d₆) δ: 1.26-1.40 (m, 3H), 1.75 (s, 3H), 3.15-5.04 (m, 5H), 6.65-6.84 (m, 1H), 7.05 (s, 1H), 7.33-7.35 (m, 1H), 7.50 (d, J = 8.09 Hz, 1H), 7.57 (brs, 1H) | 434 | 432 |
| 12 | 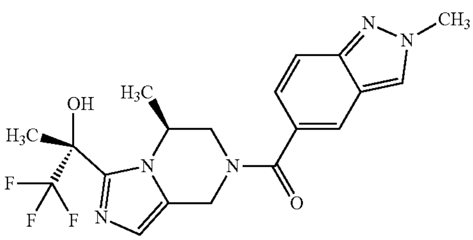 [SMILES: C[C@H]1CN(C(=O)c2ccc3nn(C)cc3c2)Cc2cnc([C@@](C)(O)C(F)(F)F)n21] | (400 MHz, DMSO-d₆) δ: 1.24-1.31 (m, 3H), 1.77 (s, 3H), 3.44-3.69 (m, 2H), 4.20 (s, 3H), 4.71-4.87 (m, 3H), 6.79 (brs, 1H), 7.05 (s, 1H), 7.30 (d, J = 8.80 Hz, 1H), 7.65 (d, J = 8.80 Hz, 1H), 7.88 (s, 1H), 8.45 (s, 1H) | 408 | 406 |

TABLE 1-3

| Example | Structure | ¹H-NMR | Mass M + 1 | Mass M − 1 |
|---|---|---|---|---|
| 13 | 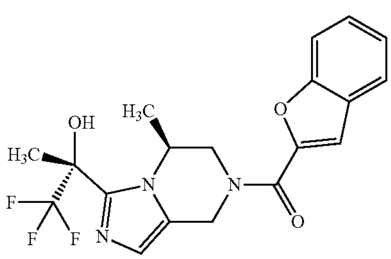 [SMILES: C[C@H]1CN(C(=O)c2cc3ccccc3o2)Cc2cnc([C@@](C)(O)C(F)(F)F)n21] | (400 MHz, DMSO-d₆) δ: 1.39 (d, J = 6.47 Hz, 3H), 1.77 (s, 3H), 3.69 (brs, 1H), 4.55-5.01 (m, 4H), 6.83 (brs, 1H), 7.09 (s, 1H), 7.34 (t, J = 7.17 Hz, 1H), 7.44-7.49 (m, 1H), 7.51 (brs, 1H), 7.69 (d, J = 8.32 Hz, 1H), 7.77 (d, J = 7.63 Hz, 1H) | 394 | 392 |
| 14 | 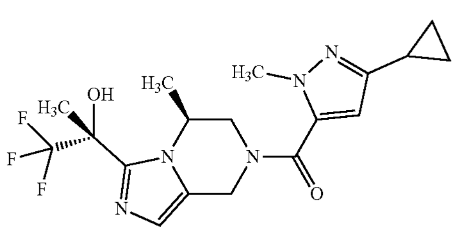 [SMILES: C[C@H]1CN(C(=O)c2cc(C3CC3)nn2C)Cc2cnc([C@@](C)(O)C(F)(F)F)n21] | (400 MHz, CDCl₃) δ: 0.68-0.78 (m, 2H), 0.90-0.97 (m, 2H), 1.35-1.49 (m, 3H), 1.86-1.98 (m, 1H), 1.96 (s, 3H), 2.93-3.39 (m, 0.7H), 3.54-3.65 (m, 0.4H), 3.91 (s, 3H), 4.02-4.17 (m, 0.6H), 4.54-4.76 (m, 0.3H), 4.72 (d, J = 17.73 Hz, 1H), 4.94-5.14 (m, 2H), 5.95-6.16 (m, 1H), 6.77-6.99 (m, 1H) | 398 | 396 |

TABLE 1-3-continued

| Example | Structure | ¹H-NMR | Mass M + 1 | Mass M − 1 |
|---|---|---|---|---|
| 15 | 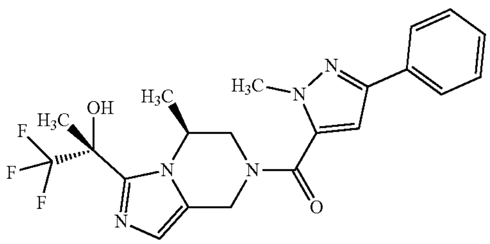 [SMILES: C[C@H]1CN(C(=O)c2cc(-c3ccccc3)nn2C)Cc2cnc([C@@](C)(O)C(F)(F)F)n21] | (400 MHz, DMSO-d₆) δ: 1.35-1.39 (m, 3H), 1.77 (s, 3H), 3.21-3.25 (m, 1H), 3.62-5.09 (m, 5H), 3.92 (s, 3H), 6.72-6.86 (m, 1H), 7.07-7.15 (m, 2H), 7.31 (t, J = 7.40 Hz, 1H), 7.41 (t, J = 7.40 Hz, 2H), 7.81 (d, J = 7.17 Hz, 2H) | 434 | 432 |
| 16 | 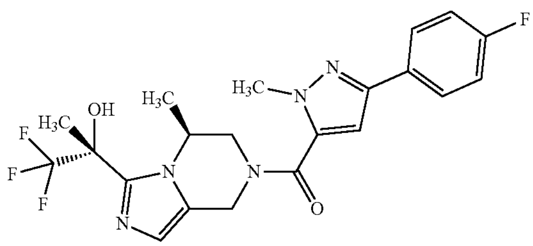 [SMILES: C[C@H]1CN(C(=O)c2cc(-c3ccc(F)cc3)nn2C)Cc2cnc([C@@](C)(O)C(F)(F)F)n21] | (400 MHz, DMSO-d₆) δ: 1.31-1.47 (m, 3H), 1.78 (s, 3H), 3.19-3.69 (m, 1H), 3.92 (s, 3H), 4.03-4.56 (m, 1H), 4.68-5.16 (m, 3H), 6.74, 6.87 (s, 1H), 7.01-7.31 (m, 4H), 7.82-7.91 (m, 2H) | 452 | 450 |
| 17 | 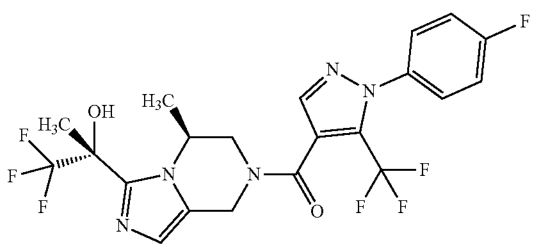 [SMILES: C[C@H]1CN(C(=O)c2cnn(-c3ccc(F)cc3)c2C(F)(F)F)Cc2cnc([C@@](C)(O)C(F)(F)F)n21] | (400 MHz, DMSO-d₆) δ: 1.29-1.41 (m, 3H), 1.78 (s, 3H), 3.16-3.93 (m, 2H), 4.55-5.13 (m, 3H), 6.71-6.89 (m, 1H), 7.11 (s, 1H), 7.41-7.52 (m, 2H), 7.59-7.72 (m, 2H), 8.05-8.18 (m, 1H) | 506 | 504 |
| 18 | 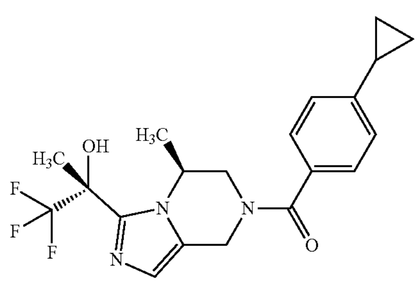 [SMILES: C[C@H]1CN(C(=O)c2ccc(C3CC3)cc2)Cc2cnc([C@@](C)(O)C(F)(F)F)n21] | (400 MHz, DMSO-d₆) δ: 0.68-0.74 (m, 2H), 0.95-1.02 (m, 2H), 1.20-1.43 (m, 3H), 1.75 (s, 3H), 1.92-1.99 (m, 1H), 3.10-3.31 (m, 0.5H), 3.43-3.58 (m, 0.6H), 3.65-3.78 (m, 0.6H), 4.39-5.06 (m, 3.3H), 6.58-6.86 (m, 1H), 7.03 (s, 1H), 7.14 (d, J = 8.09 Hz, 2H), 7.33 (d, J = 7.40 Hz, 2H) | 394 | 392 |

TABLE 1-4

| Example | Structure | ¹H-NMR | Mass M + 1 | Mass M − 1 |
|---|---|---|---|---|
| 19 | 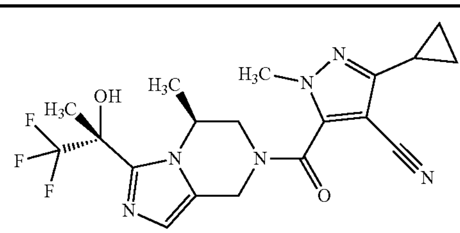 | (400 MHz, CDCl₃) δ: 1.00-1.01 (m, 4H), 1.37, 1.50 (d, J = 6.47 Hz, 3H), 1.93 (s, 3H), 1.97-1.98 (m, 1H), 3.42-3.77 (m, 2H), 3.83 (s, 3H), 4.03-5.20 (m, 4H), 6.81, 6.92 (s, 1H) | 423 | 421 |

TABLE 1-4-continued

| Example | Structure | ¹H-NMR | Mass M + 1 | Mass M − 1 |
|---|---|---|---|---|
| 20 | 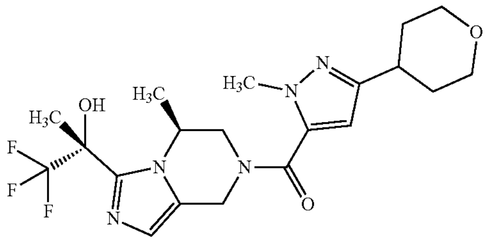 [SMILES: C[C@H]1CN(C(=O)c2cc(C3CCOCC3)nn2C)Cc2cnc([C@@](C)(O)C(F)(F)F)n21] | (400 MHz, DMSO-d₆) δ: 1.27-1.42 (m, 3H), 1.57-1.68 (m, 2H), 1.73-1.83 (m, 2H), 1.76 (s, 3H), 2.75-2.85 (m, 1H), 3.13-3.24 (m, 0.4H), 3.40 (t, J = 10.87 Hz, 2H), 3.51-3.61 (m, 0.6H), 3.79 (s, 3H), 3.84-3.92 (m, 2H), 3.93-4.01 (m, 0.6H), 4.39-4.52 (m, 0.4H), 4.60-4.94 (m, 2H), 4.96-5.10 (m, 1H), 6.36-6.58 (m, 1H), 6.70-6.85 (na 1H), 7.07 (s, 1H) | 442 | 440 |
| 21 | 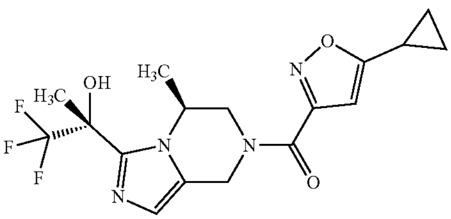 [SMILES: C[C@H]1CN(C(=O)c2cc(C3CC3)on2)Cc2cnc([C@@](C)(O)C(F)(F)F)n21] | (400 MHz, CDCl₃) δ: 0.99-1.02 (m, 2H), 1.09-1.13 (m, 2H), 1.43-1.45 (m, 3H), 1.93 (s, 3H), 2.05-2.10 (m, 1H), 3.28-3.63 (m, 1H), 3.66-5.33 (m, 5H), 6.28 (s, 1H), 6.83, 6.90 (s, 1H) | 385 | 383 |
| 22 | 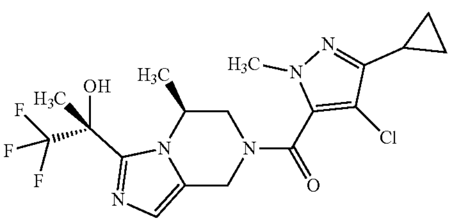 [SMILES: C[C@H]1CN(C(=O)c2c(Cl)c(C3CC3)nn2C)Cc2cnc([C@@](C)(O)C(F)(F)F)n21] | (400 MHz, DMSO-d₆) δ: 0.73-0.94 (m, 4H), 1.23-1.43 (m, 3H), 1.75 (s, 3H), 1.78-1.87 (m, 1H), 3.22-3.33 (m, 0.6H), 3.49-3.80 (m, 4.1H), 4.44-4.78 (m, 1.8H), 4.88-5.10 (m, 1.5H), 6.74 (s, 0.4H), 6.84 (s, 0.6H), 7.06-7.10 (m, 1H) | 432 | 430 |
| 23 | 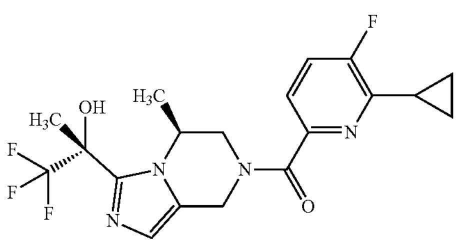 [SMILES: C[C@H]1CN(C(=O)c2ccc(F)c(C3CC3)n2)Cc2cnc([C@@](C)(O)C(F)(F)F)n21] | (400 MHz, DMSO-d₆) δ: 0.96-1.09 (m, 4H), 1.31 (d, J = 6.85 Hz, 1.8H), 1.39 (d, J = 6.36 Hz, 1.2H), 1.77 (s, 3H), 2.32-2.38 (m, 1H), 3.20-3.25 (m, 0.4H), 3.38-3.44 (m, 0.6H), 3.98-4.03 (m, 0.6H), 4.51-4.55 (m, 0.4H), 4.62-4.68 (m, 1H), 4.82-4.99 (m, 1.6H), 5.03-5.09 (m, 0.4H), 6.68 (s, 0.4H), 6.84 (s, 0.6H), 7.06-7.09 (m, 1H), 7.47-7.53 (m, 1H), 7.73-7.80 (m, 1H) | 413 | 411 |
| 24 | 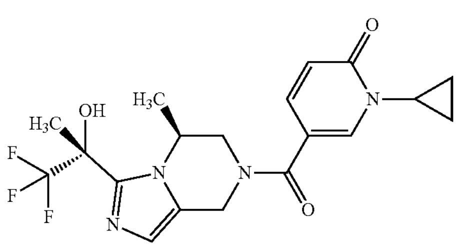 [SMILES: C[C@H]1CN(C(=O)c2ccc(=O)n(C3CC3)c2)Cc2cnc([C@@](C)(O)C(F)(F)F)n21] | (400 MHz, DMSO-d₆) δ: 0.87-1.01 (m, 4H), 1.32 (d, J = 6.58 Hz, 3H), 1.77 (s, 3H), 2.45-2.60 (m, 1H), 3.27-3.39 (m, 3H), 4.56-5.07 (m, 3H), 6.41 (d, J = 9.27 Hz, 1H), 6.79 (s, 1H), 7.07 (s, 1H), 7.49-7.58 (m, 1H), 7.80 (s, 1H) | 411 | 455 (M − 1 + 46) |

TABLE 1-5

| Example | Structure | ¹H-NMR | Mass M + 1 | Mass M − 1 |
|---|---|---|---|---|
| 25 | 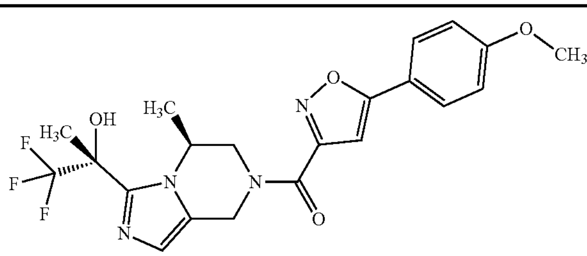 | (400 MHz, CDCl₃) δ: 1.46-1.48 (m, 3H), 1.95 (s, 3H), 3.35-3.66 (m, 1H), 3.78 (brs, 1H), 3.86 (s, 3H), 4.67-5.42 (m, 4H), 6.78-6.92 (m, 2H), 6.97-7.01 (m, 2H), 7.72-7.74 (m, 2H) | 451 | 495 (M − 1 + 46) |

TABLE 1-5-continued

| Example | Structure | ¹H-NMR | Mass M + 1 | Mass M − 1 |
|---|---|---|---|---|
| 26 | 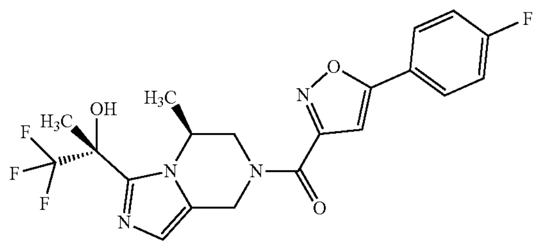 [SMILES: C[C@H]1CN(C(=O)c2cc(-c3ccc(F)cc3)on2)Cc2cnc([C@@](C)(O)C(F)(F)F)n21] | (400 MHz, CDCl₃) δ: 1.47-1.49 (m, 3H), 1.95 (s, 3H), 3.35-3.69 (m, 1H), 3.82 (brs, 1H), 4.68-5.42 (m, 4H), 6.87-6.91 (m, 2H), 7.18-7.20 (m, 2H), 7.77-7.82 (m, 2H) | 439 | 437 |
| 27 | 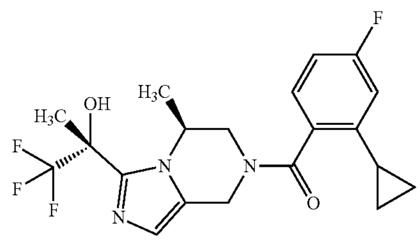 [SMILES: C[C@H]1CN(C(=O)c2ccc(F)cc2C2CC2)Cc2cnc([C@@](C)(O)C(F)(F)F)n21] | (400 MHz, DMSO-d₆) δ: 0.59-1.02 (m, 4H), 1.26-1.32 (m, 2H), 1.36-1.46 (m, 1H), 1.70-1.99 (m, 1H), 1.76 (s, 3H), 3.15-3.26 (m, 0.4H), 3.39-3.49 (m, 1.2H), 4.31-5.10 (m, 3.4H), 6.67-6.87 (m, 2H), 6.98-7.11 (m, 2H), 7.19-7.32 (m, 1H) | 412 | 410 |
| 28 | 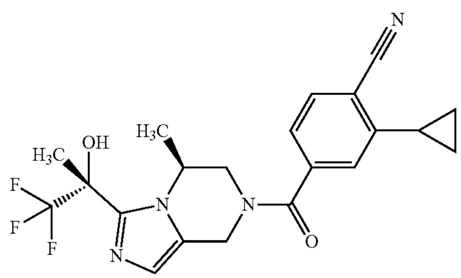 [SMILES: C[C@H]1CN(C(=O)c2ccc(C#N)c(C3CC3)c2)Cc2cnc([C@@](C)(O)C(F)(F)F)n21] | (400 MHz, DMSO-d₆) δ: 0.83-0.94 (m, 2H), 1.12-1.17 (m, 2H), 1.26 (d, J = 6.11 Hz, 2H), 1.42 (d, J = 7.09 Hz, 1H), 1.76 (s, 3H), 2.17-2.26 (m, 1H), 3.15-3.22 (m, 0.4H), 3.46-3.56 (m, 1.3H), 4.48-4.65 (m, 1.7H), 4.86-4.95 (m, 1.3H), 5.03-5.10 (m, 0.3H), 6.66 (s, 0.4H), 6.85 (s, 0.6H), 7.04-7.16 (m, 2H), 7.36-7.43 (m, 1H), 7.86 (d, J = 7.58 Hz, 1H) | 419 | 417 |
| 29 | 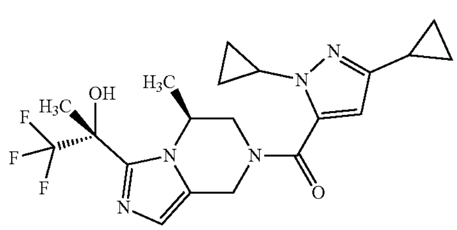 [SMILES: C[C@H]1CN(C(=O)c2cc(C3CC3)nn2C2CC2)Cc2cnc([C@@](C)(O)C(F)(F)F)n21] | (400 MHz, DMSO-d₆) δ: 0.57-1.13 (m, 8H), 1.26-1.43 (m, 3H), 1.77 (s, 3H), 1.81-1.91 (m, 1H), 3.14-3.90 (m, 3H), 4.49-5.13 (m, 3H), 6.14-6.33 (m, 1H), 6.70-6.87 (m, 1H), 7.08 (s, 1H) | 424 | 422 |
| 30 | 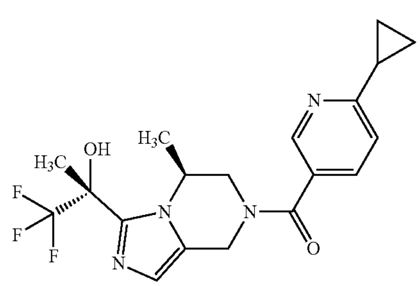 [SMILES: C[C@H]1CN(C(=O)c2ccc(C3CC3)nc2)Cc2cnc([C@@](C)(O)C(F)(F)F)n21] | (400 MHz, DMSO-d₆) δ: 0.92-1.02 (m, 4H), 1.21-1.44 (m, 3H), 1.75 (s, 3H), 2.11-2.18 (m, 1H), 3.12-3.25 (m 0.4H), 3.52-3.76 (m, 1.2H), 4.43-5.09 (m, 3.4H), 6.63-6.86 (m, 1H), 7.05 (s, 1H), 7.38 (d, J = 8.09 Hz, 1H), 7.70-7.80 (m, 1H), 8.48 (brs, 1H) | 395 | 393 |

TABLE 1-6

| Example | Structure | ¹H-NMR | Mass M + 1 | Mass M − 1 |
|---|---|---|---|---|
| 31 | 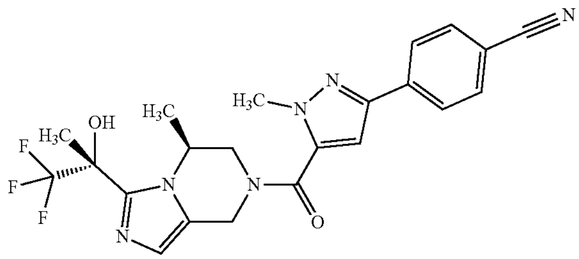 [SMILES: C[C@H]1CN(C(=O)c2cc(-c3ccc(C#N)cc3)nn2C)Cc2cnc([C@@](C)(O)C(F)(F)F)n21] | (400 MHz, CDCl₃) δ: 1.43 (brs, 3H), 1.95 (s, 3H), 3.49-3.67 (m, 2H), 4.07 (s, 3H), 4.10-5.06 (m, 4H), 6.95 (s, 2H), 7.68 (d, J = 8.55 Hz, 2H), 7.88 (d, J = 7.63 Hz, 2H) | 459 | 457 |
| 32 | 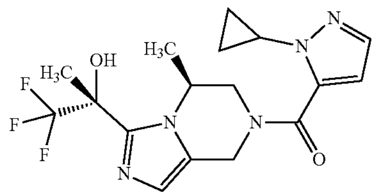 [SMILES: C[C@H]1CN(C(=O)c2ccnn2C2CC2)Cc2cnc([C@@](C)(O)C(F)(F)F)n21] | (400 MHz, DMSO-d₆) δ: 0.84-1.17 (m, 4H), 1.27-1.46 (m, 3H), 1.77 (s, 3H), 3.20-3.61 (m, 1H), 3.75-5.12 (m, 5H), 6.48-6.89 (m, 2H), 7.09 (s, 1H), 7.44-7.51 (m, 1H). | 384 | 382 |
| 33 | 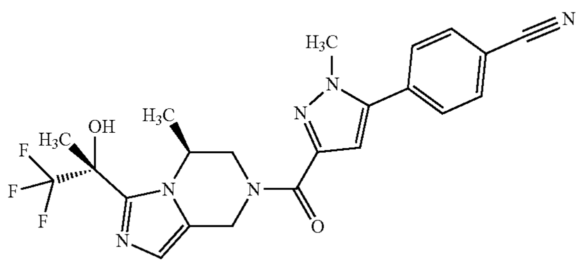 [SMILES: C[C@H]1CN(C(=O)c2cc(-c3ccc(C#N)cc3)n(C)n2)Cc2cnc([C@@](C)(O)C(F)(F)F)n21] | (400 MHz, CDCl₃) δ: 1.43-1.51 (m, 3H), 1.95 (s, 3H), 3.24-4.37 (m, 5H), 4.66-5.67 (m, 4H), 6.83-6.95 (m, 2H), 7.56 (d, J = 8.09 Hz, 2H), 7.78 (d, J = 8.09 Hz, 2H) | 459 | 457 |
| 34 | 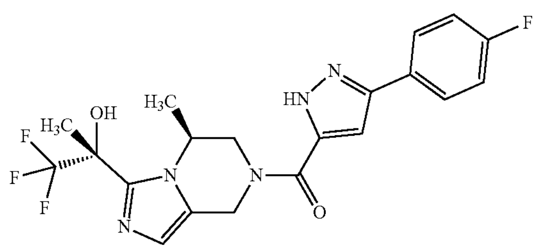 [SMILES: C[C@H]1CN(C(=O)c2cc(-c3ccc(F)cc3)n[nH]2)Cc2cnc([C@@](C)(O)C(F)(F)F)n21] | (400 MHz, DMSO-d6) δ: 1.34-1.41 (m, 3H), 1.78 (s, 3H), 3.14-3.24 (m, 1H), 3.56-4.11 (m, 1H), 4.55-5.12 (m, 3H), 6.75-6.87 (m, 1H), 7.05-7.23 (m, 2H), 7.27-7.35 (m, 2H), 7.64-7.65 (m, 2H), 13.72 (brs, 1H) | 438 | 436 |
| 35 | 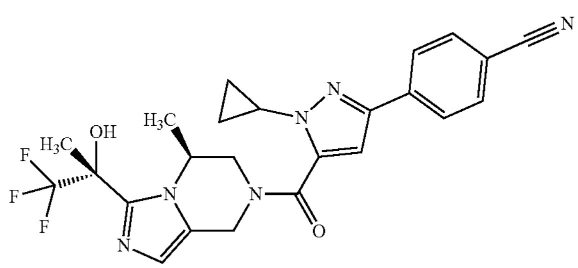 [SMILES: C[C@H]1CN(C(=O)c2cc(-c3ccc(C#N)cc3)nn2C2CC2)Cc2cnc([C@@](C)(O)C(F)(F)F)n21] | (400 MHz, CDCl₃) δ: 1.17-1.38 (m, 7H), 1.95 (s, 3H), 3.27-4.03 (m, 4H), 4.85-5.01 (m, 3H), 6.70-6.90 (m, 2H), 7.66 (d, J = 8.32 Hz, 2H), 7.86 (d, J = 7.63 Hz, 2H) | 485 | 464 |
| 36 | 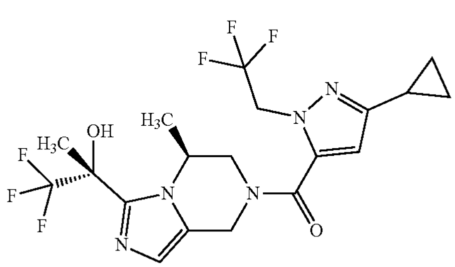 [SMILES: C[C@H]1CN(C(=O)c2cc(C3CC3)nn2CC(F)(F)F)Cc2cnc([C@@](C)(O)C(F)(F)F)n21] | (400 MHz, DMSO-d₆) δ: 0.64-0.98 (m, 4H), 1.24-1.38 (m, 3H), 1.77 (s, 3H), 1.87-2.00 (m, 1H), 3.18-5.35 (m, 7H), 6.51-6.88 (m, 2H), 7.09 (s, 1H) | 466 | 464 |

TABLE 1-7

| Example | Structure | ¹H-NMR | Mass M + 1 | Mass M − 1 |
|---|---|---|---|---|
| 37 | 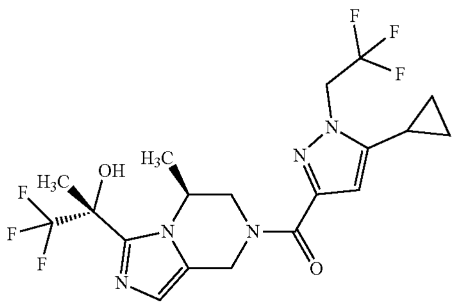 [SMILES: C[C@H]1CN(C(=O)c2cc(C3CC3)n(CC(F)(F)F)n2)Cc2cnc([C@@](C)(O)C(F)(F)F)n21] | (400 MHz, DMSO-d₆) δ: 0.70-0.76 (m, 2H), 0.98-1.05 (m, 2H), 1.34 (d, J = 6.60 Hz, 3H), 1.77 (s, 3H), 1.99-2.07 (m, 1H), 3.13-3.52 (m, 1H), 4.49-5.41 (m, 6H), 6.33-6.37 (m, 1H), 6.70-6.82 (m 1H), 7.07 (s, 1H) | 466 | 464 |
| 38 | 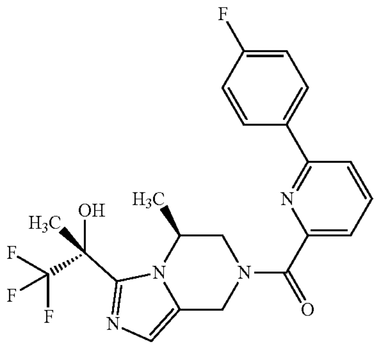 [SMILES: C[C@H]1CN(C(=O)c2cccc(-c3ccc(F)cc3)n2)Cc2cnc([C@@](C)(O)C(F)(F)F)n21] | (400 MHz, DMSO-d₆) δ: 1.34 (d, J = 6.01 Hz, 2H), 1.44 (d, J = 6.01 Hz, 1H), 1.76 (s, 3H), 3.24-3.32 (m, 0.3H), 3.50-3.55 (m, 0.6H), 4.08-4.13 (m, 0.6H), 4.56-4.61 (m, 0.4H), 4.69 (d, J = 17.80 Hz, 0.6H), 4.78 (d, J = 16.41 Hz, 0.4H), 4.91-5.03 (m, 1.7H), 5.07-5.13 (m, 0.4H), 6.67 (s, 0.4H), 6.85 (s, 0.6H), 7.01-7.10 (m, 1H), 7.30-7.36 (m, 2H), 7.57-7.63 (m, 1H), 8.00-8.19 (m, 4H) | 449 | 447 |
| 39 | 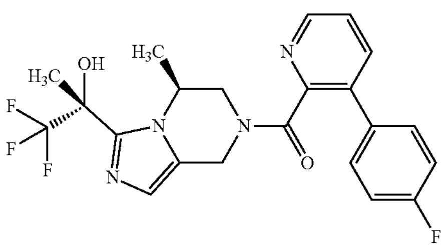 [SMILES: C[C@H]1CN(C(=O)c2ncccc2-c2ccc(F)cc2)Cc2cnc([C@@](C)(O)C(F)(F)F)n21] | (400 MHz, DMSO-d₆) δ:1.02 (d, J = 6.01 Hz, 1.5H), 1.10 (d, J = 6.01 Hz, 1.5H), 1.72 (s, 3H), 3.02-3.13 (m, 1H), 3.41-3.45 (m, 0.5H), 4.27-4.43 (m, 1.5H), 4.52 (d, J = 17.34 Hz, 0.5H), 4.70-4.76 (m, 0.5H), 4.81-4.87 (m, 0.5H), 4.92-4.99 (m, 0.5H), 6.61 (s, 0 5H), 6.79 (s, 0.5H), 7.00 (d, J = 8.55 Hz, 1H), 7.20-7.30 (m, 2H), 7.44-7.51 (m, 2H), 7.56-7.62 (m, 1H), 7.92-7.96 (m, 1H), 8.60-8.66 (m, 1H) | 449 | 447 |
| 40 | 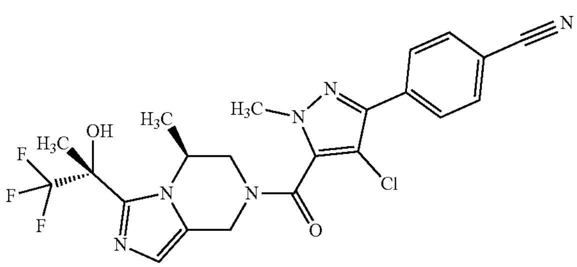 [SMILES: C[C@H]1CN(C(=O)c2c(Cl)c(-c3ccc(C#N)cc3)nn2C)Cc2cnc([C@@](C)(O)C(F)(F)F)n21] | (400 MHz, CDCl₃) δ: 1.33-1.57 (m, 3H), 1.94 (s, 3H), 3.38-3.96 (m, 6H), 4.61-5.29 (m, 3H), 6.80, 6.94 (s, 1H), 7.71 (d, J = 8.55 Hz, 2H), 8.03 (d, J = 8.32 Hz, 2H) | 493 | 491 |
| 41 | 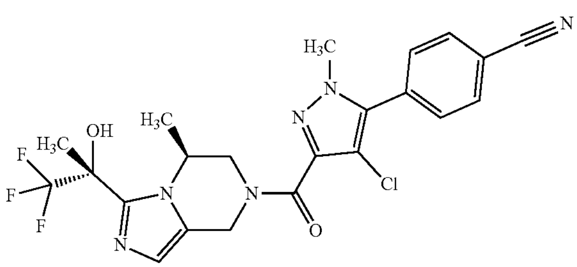 [SMILES: C[C@H]1CN(C(=O)c2nn(C)c(-c3ccc(C#N)cc3)c2Cl)Cc2cnc([C@@](C)(O)C(F)(F)F)n21] | (400 MHz, CDCl₃) δ: 1.45, 1.52 (d, J = 6.47 Hz, 3H), 1.94 (s, 3H), 3.31, 3.67 (d, J = 10.40 Hz, 1H), 3.82, 3.88 (s, 3H), 4.32-5.15 (m, 5H), 6.79, 6.92 (s, 1H), 7.58 (d, J = 8.44 Hz, 2H), 7.83 (d, J = 8.44 Hz, 2H) | 493 | 537 (M − 1 + 46) |

TABLE 1-8

| Example | Structure | ¹H-NMR | Mass M + 1 | Mass M − 1 |
|---|---|---|---|---|
| 42 | 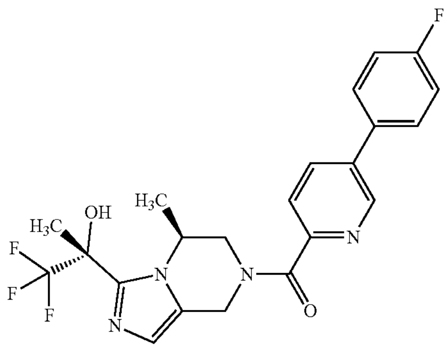 [SMILES: C[C@H]1CN(C(=O)c2ccc(-c3ccc(F)cc3)cn2)Cc2cnc([C@@](C)(O)C(F)(F)F)n21] | (400 MHz, DMSO-d$_6$) δ: 1.33 (d, J = 6.01 Hz, 1.8H), 1.42 (d, J = 6.47 Hz, 1.2H), 1.76 (s, 3H), 3.20-3.29 (m, 0.4H), 3.49-3.55 (m, 0.6H), 4.09-4.15 (m, 0.6H), 4.56-4.78 (m, 1.4H), 4.92-5.03 (m, 1.6H), 5.05-5.11 (m, 0.4H), 6.67 (s, 0.4H), 6.85 (s, 0.6H), 7.02-7.09 (m, 1H), 7.33-7.40 (m, 2H), 7.75 (t, J = 7.74 Hz, 1H), 7.82-7.89 (m, 2H), 8.21-8.26 (m, 1H), 8.92-8.95 (m, 1H) | 449 | 447 |
| 43 | 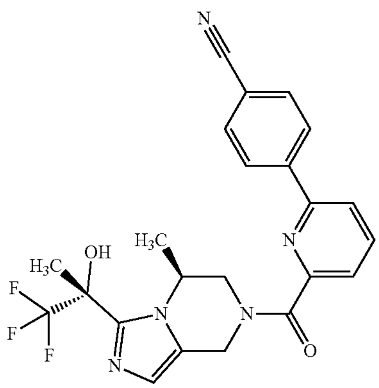 [SMILES: C[C@H]1CN(C(=O)c2cccc(-c3ccc(C#N)cc3)n2)Cc2cnc([C@@](C)(O)C(F)(F)F)n21] | (400 MHz, DMSO-d$_6$) δ: 1.35 (d, J = 6.36 Hz, 1.8H), 1.46 (d, J = 6.60 Hz, 1.2H), 1.78 (s, 3H), 3.26-3.32 (m, 0.4H), 3.52-3.58 (m, 0.6H), 4.08-4.13 (m, 0.6H), 4.58-4.83 (m, 1.4H), 4.93-5.05 (m, 1.6H), 5.08-5.15 (m, 0.4H), 6.68 (s, 0.4H), 6.87 (s, 0.6H), 7.05 (s, 0.6H), 7.10 (s, 0.4H), 7.68-7.74 (m, 1H), 7.97-8.01 (m, 2H), 8.10-8.15 (m, 1H), 8.20-8.34 (m, 3H) | 456 | 454 |
| 44 | 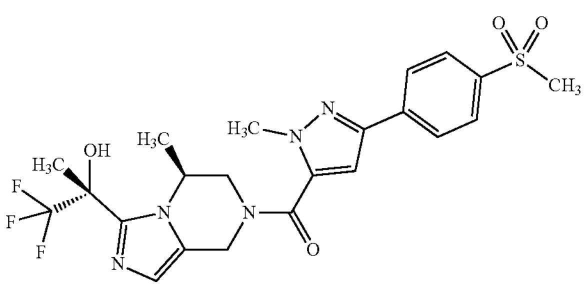 [SMILES: C[C@H]1CN(C(=O)c2cc(-c3ccc(S(C)(=O)=O)cc3)nn2C)Cc2cnc([C@@](C)(O)C(F)(F)F)n21] | (400 MHz, DMSO-d$_6$) δ: 1.33-1.47 (m, 3H), 1.78 (s, 3H), 3.24 (s, 3H), 3.25-3.69 (m, 1H), 3.97 (s, 3H), 4.05-4.55 (m, 1H), 4.70-5.16 (m, 3H), 6.72-6.90 (m, 1H), 7.08-7.42 (m, 2H), 7.94-8.00 (m, 2H), 8.07-8.13 (m, 2H) | 512 | 510 |
| 45 | 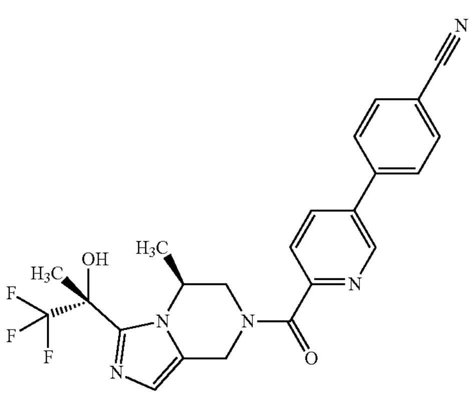 [SMILES: C[C@H]1CN(C(=O)c2ccc(-c3ccc(C#N)cc3)cn2)Cc2cnc([C@@](C)(O)C(F)(F)F)n21] | (400 MHz, DMSO-d$_6$) δ: 1.35 (d, J = 5.87 Hz, 1.8H), 1.44 (d, J = 6.60 Hz, 1.2H), 1.78 (s, 3H), 3.24-3.30 (m, 0.4H), 3.51-3.56 (m, 0.6H), 4.07-4.12 (m, 0.6H), 4.57-4.79 (m, 1.4H), 4.93-5.04 (m, 1.6H), 5.07-5.13 (m, 0.4H), 6.68 (s, 0.4H), 6.87 (s, 0.6H), 7.05-7.10 (m, 1H), 7.81 (t, J = 8.19 Hz, 1H), 7.99-8.06 (m, 4H), 8.34-8.38 (m, 1H), 9.02-9.06 (m, 1H) | 456 | 454 |

TABLE 1-8-continued
| Example | Structure | ¹H-NMR | Mass M + 1 | Mass M − 1 |
|---|---|---|---|---|
| 46 | 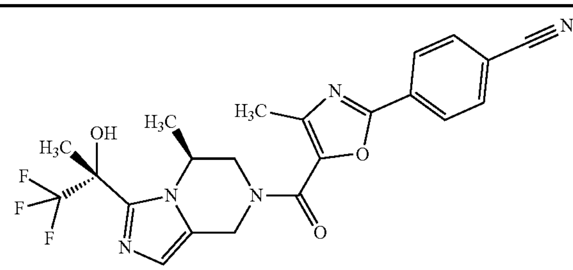 | (400 MHz, DMSO-d₆) δ: 1.41 (d, J = 6.36 Hz, 3H), 1.79 (s, 3H), 2.40-2.43 (m, 3H), 3.61-4.70 (m, 3H), 4.91-5.33 (m, 2H), 6.85 (br s, 1H), 7.11 (s, 1H), 8.01-8.27 (m, 4H). | 460 | 458 |
TABLE 1-9
| Example | Structure | ¹H-NMR | Mass M + 1 | Mass M − 1 |
|---|---|---|---|---|
| 47 | 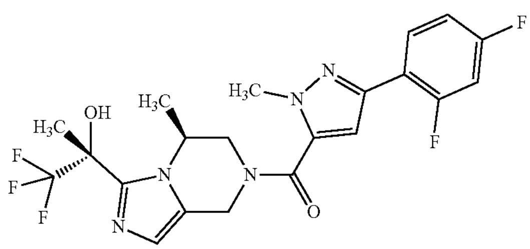 [SMILES: C[C@H]1CN(C(=O)c2cc(-c3ccc(F)cc3F)nn2C)Cc2cnc([C@@](C)(O)C(F)(F)F)n21] | (400 MHz, DMSO-d₆) δ: 1.30-1.48 (m, 3H), 1.78 (s, 3H), 3.21-3.68 (m, 1H), 3.94 (s, 3H), 3.99-4.56 (m, 1H), 4.66-5.16 (m, 3H), 6.71-7.11 (m, 3H), 7.15-7.22 (m, 1H), 7.31-7.41 (m, 1H), 7.93-8.01 (m, 1H) | 470 | 468 |
| 48 | 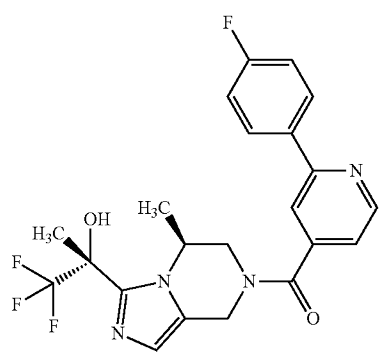 [SMILES: C[C@H]1CN(C(=O)c2ccnc(-c3ccc(F)cc3)c2)Cc2cnc([C@@](C)(O)C(F)(F)F)n21] | (400 MHz, DMSO-d₆) δ: 1.28-1.46 (m, 3H), 1.75 (s, 3H), 3.19-5.11 (m, 5H), 6.65-6.87 (m, 1H), 7.03-7.09 (m, 1H), 7.29-7.35 (m, 2H), 7.37-7.43 (m, 1H), 8.01-8.02 (m, 1H), 8.18-8.21 (m, 2H), 8.75-8.76 (m, 1H) | 449 | 447 |
| 49 | 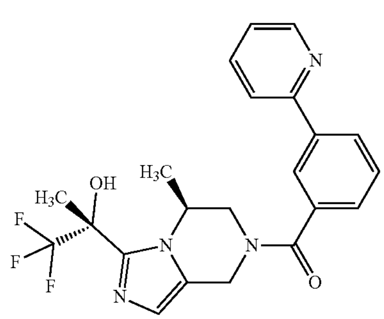 [SMILES: C[C@H]1CN(C(=O)c2cccc(-c3ccccn3)c2)Cc2cnc([C@@](C)(O)C(F)(F)F)n21] | (400 MHz, DMSO-d₆) δ: 1.26-1.47 (m, 3H), 1.75 (s, 3H), 3.19-3.29 (m, 0.4H), 3.52-3.62 (m, 0.6H), 3.71-3.79 (m, 0.6H), 4.52-4.72 (m, 1.7H), 4.91-5.10 (m, 1.7H), 6.65 (brs, 0.4H), 6.85 (brs, 0.6H), 7.00-7.08 (m, 1H), 7.38 (dd, J = 7.28, 4.97 Hz, 1H), 7.49-7.54 (m, 1H), 7.59 (t, J = 7.51 Hz, 1H), 7.89 (td, J = 7.74, 1.77 Hz, 1H), 8.02 (d, J = 7.63 Hz, 1H), 8.15 (s, 1H), 8.19 (d, J = 8.32 Hz, 1H), 8.67 (d, J = 4.86 Hz, 1H) | 431 | 429 |

TABLE 1-9-continued

| Example | Structure | ¹H-NMR | Mass M + 1 | Mass M − 1 |
|---|---|---|---|---|
| 50 | 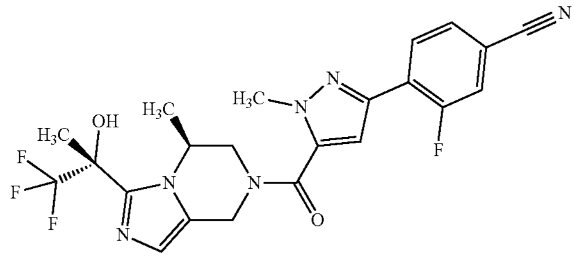 [SMILES: C[C@H]1CN(C(=O)c2cc(-c3ccc(C#N)cc3F)nn2C)Cc2cnc([C@@](C)(O)C(F)(F)F)n21] | (400 MHz, CDCl₃) δ: 1.30-1.51 (m, 3H), 1.94 (s, 3H), 3.25-3.78 (m, 1H), 4.08 (s, 3H), 4.48-5.29 (m, 5H), 6.73-7.00 (m, 2H), 7.36-7.54 (m, 2H), 8.18 (t, J = 7.74 Hz, 1H) | 477 | 475 |
| 51 | 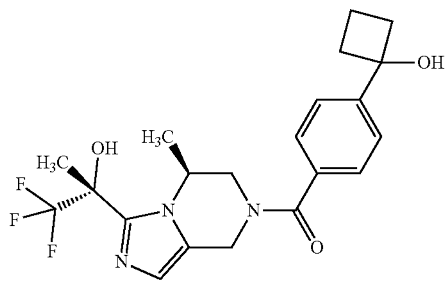 [SMILES: C[C@H]1CN(C(=O)c2ccc(C3(O)CCC3)cc2)Cc2cnc([C@@](C)(O)C(F)(F)F)n21] | (400 MHz, DMSO-d₆) δ: 1.24-1.45 (m, 3H), 1.63-1.74 (m, 1H), 1.77 (s, 3H), 1.90-2.00 (m, 1H), 2.24-2.44 (m, 4H), 3.15-3.78 (m, 2H), 4.55-5.08 (m, 3H), 5.59 (s, 1H), 6.64-6.87 (m, 1H), 7.05 (s, 1H), 7.44 (d, J = 7.63 Hz, 2H), 7.57 (d, J = 8.09 Hz, 2H). | 424 | 468 (M − 1 + 46) |

TABLE 1-10

| Example | Structure | ¹H-NMR | Mass M + 1 | Mass M − 1 |
|---|---|---|---|---|
| 52 | 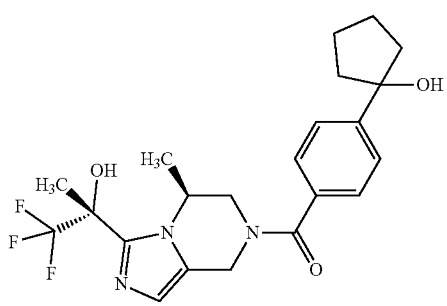 [SMILES: C[C@H]1CN(C(=O)c2ccc(C3(O)CCCC3)cc2)Cc2cnc([C@@](C)(O)C(F)(F)F)n21] | (400 MHz, DMSO-d₆) δ: 1.23-1.47 (m, 3H), 1.71-1.93 (m, 11H), 3.49-3.80 (m, 1H), 4.46-5.08 (m, 4H), 6.63-6.89 (m, 1H), 7.05 (br s, 1H), 7.41 (d, J = 7.58 Hz, 2H), 7.55 (d, J = 8.07 Hz, 2H). | 438 | 436 |
| 53 | 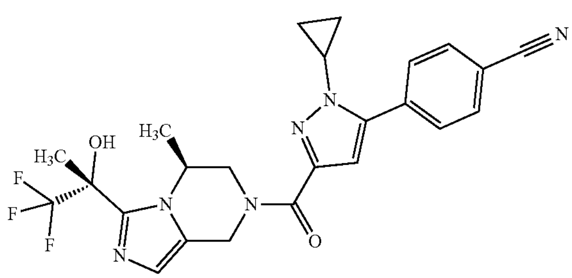 [SMILES: C[C@H]1CN(C(=O)c2cc(-c3ccc(C#N)cc3)n(C3CC3)n2)Cc2cnc([C@@](C)(O)C(F)(F)F)n21] | (400 MHz, CDCl₃) δ: 0.98-1.24 (m, 4H), 1.46-1.47 (m, 3H), 1.95 (s, 3H), 3.26-3.66 (m, 2H), 3.98-5.61 (m, 5H), 6.81-6.90 (m, 1H), 7.67-7.80 (m, 4H) | 485 | 529 (M − 1 + 46) |

TABLE 1-10-continued

| Example | Structure | ¹H-NMR | Mass M + 1 | Mass M − 1 |
|---|---|---|---|---|
| 54 | 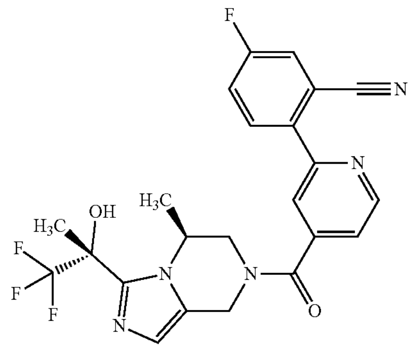 [SMILES: C[C@H]1CN(C(=O)c2ccnc(-c3ccc(F)cc3C#N)c2)Cc2cnc([C@@](C)(O)C(F)(F)F)n21] | (400 MHz, DMSO-d$_6$) δ: 1.30-1.45 (m, 3H), 1.75 (s, 3H), 3.19-5.11 (m, 5H), 6.65-6.87 (m, 1H), 7.04-7.09 (m, 1H), 7.54-7.59 (m, 1H), 7.70-7.75 (m, 1H), 7.91-8.04 (m, 3H), 8.83-8.86 (m, 1H) | 474 | 472 |
| 55 | 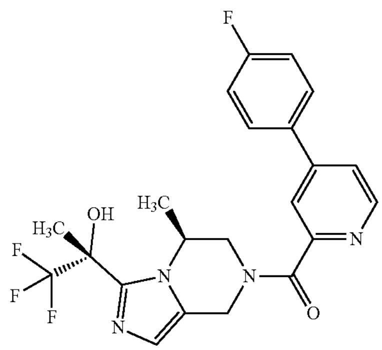 [SMILES: C[C@H]1CN(C(=O)c2cc(-c3ccc(F)cc3)ccn2)Cc2cnc([C@@](C)(O)C(F)(F)F)n21] | (400 MHz, DMSO-d$_6$) δ: 1.33 (d, J = 6.47 Hz, 1.8H), 1.43 (d, J = 6.47 Hz, 1.2H), 1.76 (s, 3H), 3.22-3.28 (m, 0.4H), 3.48-3.53 (m, 0.6H), 3.98-4.04 (m, 0.6H), 4.56-4.61 (m, 0.4H), 4.66-4.73 (m, 1H), 4.84-5.01 (m, 1.6H), 5.05-5.11 (m, 0.4H), 6.66 (s, 0.4H), 6.85 (s, 0.6H), 7.02-7.08 (m, 1H), 7.33-7.39 (m, 2H), 7.82-7.86 (m, 1H), 7.90-7.96 (m, 3H), 8.65-8.69 (m, 1H) | 449 | 447 |
| 56 | 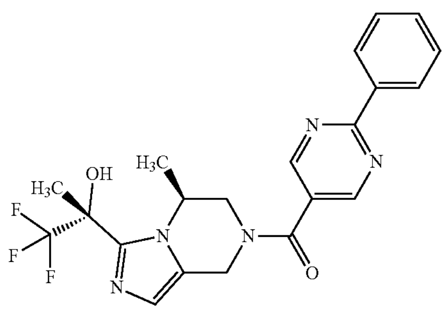 [SMILES: C[C@H]1CN(C(=O)c2cnc(-c3ccccc3)nc2)Cc2cnc([C@@](C)(O)C(F)(F)F)n21] | (400 MHz, DMSO-d$_6$) δ: 1.31 (d, J = 4.86 Hz, 1.8H), 1.45 (d, J = 6.01 Hz, 1.2H), 1.76 (s, 3H), 3.19-3.28 (m, 0.4H), 3.63-3.71 (m, 0.6H), 3.85-3.92 (m, 0.6H), 4.48-4.55 (m, 0.4H), 4.68-5.00 (m, 2.6H), 5.07-5.15 (m, 0.4H), 6.66 (s, 0.4H), 6.87 (s, 0.6H), 7.07 (s, 1H), 7.53-7.60 (m, 3H), 8.41-8.46 (m, 2H), 9.02-9.08 (m, 2H) | 432 | 430 |

TABLE 1-11

| Example | Structure | ¹H-NMR | Mass M + 1 | Mass M − 1 |
|---|---|---|---|---|
| 57 | 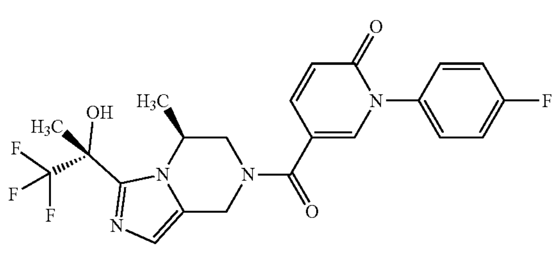 [SMILES: C[C@H]1CN(C(=O)c2ccc(=O)n(-c3ccc(F)cc3)c2)Cc2cnc([C@@](C)(O)C(F)(F)F)n21] | (400 MHz, DMSO-d$_6$) δ: 1.33 (d, J = 7.09 Hz, 3H), 1.77 (s, 3H), 4.11-4.28 (m, 1H), 4.57-4.76 (m, 1H), 4.86-4.94 (m, 1H), 4.98-5.05 (m, 1H), 6.55 (d, J = 9.29 Hz, 1H), 6.78 (s, 1H), 7.08 (s, 1H), 7.08 (s, 1H), 7.34-7.40 (m, 2H), 7.51-7.57 (m, 2H), 7.66 (dd, J = 9.66, 2.81 Hz, 1H), 7.97 (s, 1H) | 465 | 463 |

TABLE 1-11-continued

| Example | Structure | ¹H-NMR | Mass M + 1 | Mass M − 1 |
|---|---|---|---|---|
| 58 | 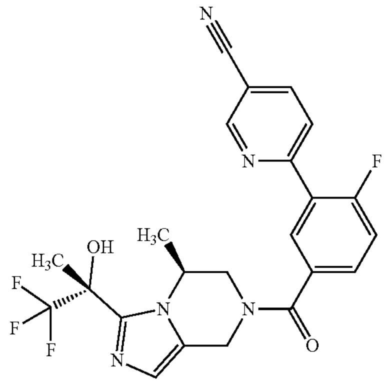 [SMILES: C[C@H]1CN(C(=O)c2ccc(F)c(-c3ccc(C#N)cn3)c2)Cc2cnc([C@@](C)(O)C(F)(F)F)n21] | (400 MHz, DMSO-d$_6$) δ: 1.26-1.46 (m, 3H), 1.77 (s, 3H), 3.19-3.31 (m, 0.4H), 3.54-3.64 (m, 0.6H), 3.73-3.85 (m, 0.6H), 4.51-4.77 (m, 1.8H), 4.89-5.11 (m, 1.6H), 6.67 (s, 0.4H), 6.85 (s, 0.6H), 7.06 (s, 1H), 7.52 (dd, J = 10.88, 8.44 Hz, 1H), 7.66-7.75 (m, 1H), 8.06 (d, J = 8.07 Hz, 1H), 8.10 (dd, J = 7.46, 2.08 Hz, 1H), 8.46 (dd, J = 8.31, 2.20 Hz, 1H), 9.17-9.18 (m, 1H) | 474 | 472 |
| 59 | 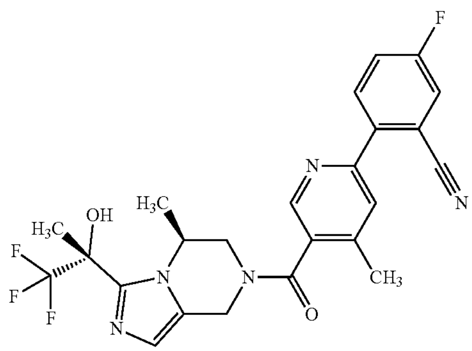 [SMILES: Cc1cc(-c2ccc(F)cc2C#N)ncc1C(=O)N1Cc2cnc([C@@](C)(O)C(F)(F)F)n2[C@@H](C)C1] | (400 MHz, DMSO-d$_6$) δ: 1.34 (d, J = 6.36 Hz, 2H), 1.46 (d, J = 6.36 Hz, 1H), 1.77 (s, 3H), 2.37 (d, J = 5.38 Hz, 3H), 3.23-3.30 (m, 0.4H), 3.53-3.56 (m, 1.2H), 4.50-4.79 (m, 1.8H), 4.92-5.03 (m, 1.2H), 5.08-5.14 (m, 0.4H), 6.70 (s, 0.4H), 6.88 (s, 0.6H), 7.05-7.13 (m, 1H), 7.72-7.78 (m, 1H), 7.87 (d, J = 6.11 Hz, 1H), 7.96-8.03 (m, 2H), 8.58 (s, 0.6H), 8.65 (s, 0.4H) | 488 | 486 |
| 60 | 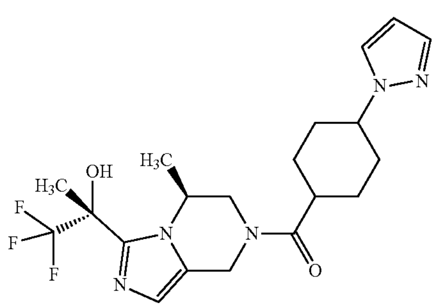 [SMILES: C[C@H]1CN(C(=O)C2CCC(n3cccn3)CC2)Cc2cnc([C@@](C)(O)C(F)(F)F)n21] | (400 MHz, CDCl$_3$) δ: 1.36, 1.43 (d, J = 6.30 Hz, 3H), 1.81-1.95 (m, 9H), 2.21-2.25 (m, 2H), 2.58-2.66 (m, 1H), 3.07 (d, J = 10.63 Hz, 0.5H), 3.58-3.89 (m, 1H), 4.17-4.19 (m, 1H), 4.64 (d, J = 17.11 Hz, 1H), 4.75 (t, J = 15.72 Hz, 1H), 4.90 (d, J = 15.26 Hz, 0.5H), 5.13-5.19 (m, 1H), 5.37-5.59 (m, 1H), 6.24 (s, 1H), 6.85 (s, 1H), 7.41 (s, 1H), 7.49 (s, 1H) | 426 | 424 |
| 61 | 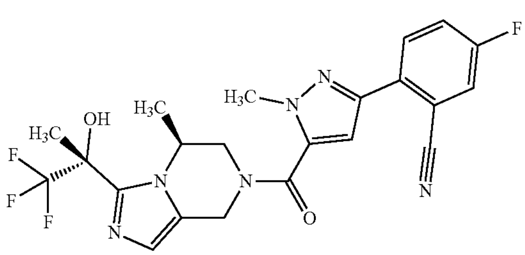 [SMILES: C[C@H]1CN(C(=O)c2cc(-c3ccc(F)cc3C#N)nn2C)Cc2cnc([C@@](C)(O)C(F)(F)F)n21] | (400 MHz, DMSO-d$_6$) δ: 1.35-1.43 (m, 3H), 1.76 (s, 3H), 3.22-5.11 (m, 5H), 3.95 (s, 3H), 6.69-6.86 (m, 1H), 7.08-7.23 (m, 2H), 7.65-7.70 (m, 1H), 7.91-7.98 (m, 2H) | 477 | 521 (M − 1 + 46) |

TABLE 1-12

| Example | Structure | ¹H-NMR | Mass M + 1 | Mass M − 1 |
|---|---|---|---|---|
| 62 | 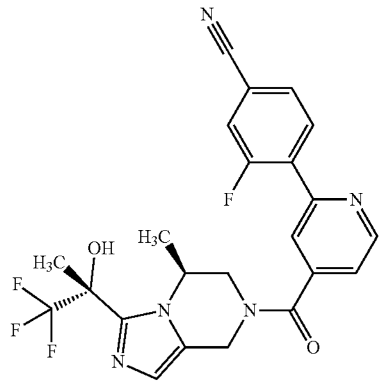 [SMILES: C[C@H]1CN(C(=O)c2ccnc(-c3ccc(C#N)cc3F)c2)Cc2cnc([C@@](C)(O)C(F)(F)F)n21] | (400 MHz, DMSO-d₆) δ: 1.29-1.43 (m, 3H), 1.75 (s, 3H), 3.20-5.10 (m, 5H), 6.64-6.86 (m, 1H), 7.04-7.08 (m, 1H), 7.53-7.60 (m, 1H), 7.83-7.92 (m, 2H), 8.03 (dd, J = 11.10, 1.39 Hz, 1H), 8.14 (t, J = 7.98 Hz, 1H), 8.86-8.89 (m, 1H) | 474 | 472 |
| 63 | 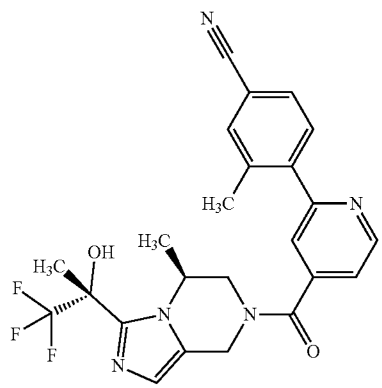 [SMILES: Cc1cc(C#N)ccc1-c1cc(C(=O)N2Cc3cnc([C@@](C)(O)C(F)(F)F)n3[C@@H](C)C2)ccn1] | (400 MHz, DMSO-d₆) δ: 1.28-1.43 (m, 3H), 1.75 (s, 3H), 2.37-2.39 (m, 3H), 3.18-5.10 (m, 5H), 6.67-6.85 (m, 1H), 7.04-7.08 (m, 1H), 7.46-7.53 (m, 1H), 7.61-7.68 (m, 2H), 7.77 (d, J = 7.86 Hz, 1H), 7.83 (s, 1H), 8.80-8.82 (m, 1H) | 470 | 468 |
| 64 | 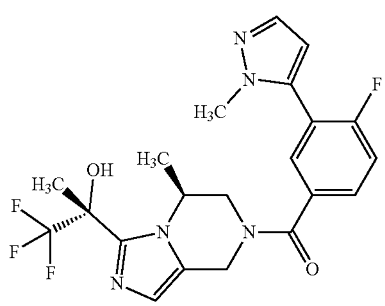 [SMILES: C[C@H]1CN(C(=O)c2ccc(F)c(-c3ccnn3C)c2)Cc2cnc([C@@](C)(O)C(F)(F)F)n21] | (400 MHz, DMSO-d₆) δ: 1.22-1.45 (m, 3H), 1.75 (s, 3H), 3.15-3.27 (m, 0.3H), 3.50-3.61 (m, 0.6H), 3.72-3.82 (m, 0.6H), 3.76 (s, 3H), 4.43-5.09 (m, 3.5H), 6.45 (s, 1H), 6.63-6.87 (m, 1H), 7.05 (s, 1H), 7.45-7.54 (m, 2H), 7.55-7.72 (m, 2H) | 452 | 450 |
| 65 | 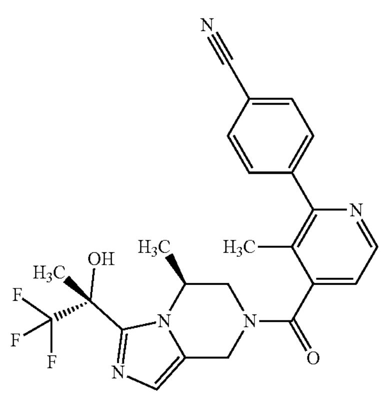 [SMILES: Cc1c(C(=O)N2Cc3cnc([C@@](C)(O)C(F)(F)F)n3[C@@H](C)C2)ccnc1-c1ccc(C#N)cc1] | (400 MHz, DMSO-d₆) δ: 1.33-1.46 (m, 3H), 1.77 (s, 3H), 2.16-2.24 (m, 3H), 3.19-5.13 (m, 5H), 6.69-6.89 (m, 1H), 7.06-7.12 (m, 1H), 7.31-7.42 (m, 1H), 7.78-7.82 (m, 2H), 7.95-7.98 (m, 2H), 8.59-8.64 (m, 1H) | 470 | 514 (M − 1 + 46) |

TABLE 1-12-continued

| Example | Structure | ¹H-NMR | Mass M + 1 | Mass M − 1 |
|---|---|---|---|---|
| 66 | 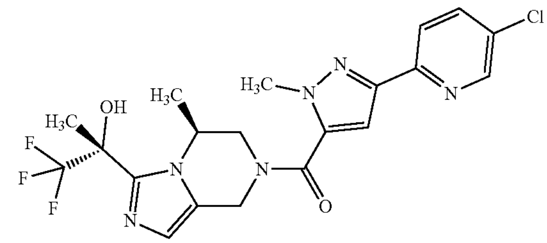 [SMILES: C[C@H]1CN(C(=O)c2cc(-c3ccc(Cl)cn3)nn2C)Cc2cnc([C@@](C)(O)C(F)(F)F)n21] | (400 MHz, CDCl₃) δ: 1.35-1.51 (m, 3H), 1.94 (s, 3H), 3.32-3.72 (m, 2H), 4.08 (s, 3H), 4.17-5.16 (m, 4H), 6.95-6.97 (m, 2H), 7.69-7.95 (m, 2H), 8.54 (s, 1H) | 469 | 464 |

TABLE 1-13

| Example | Structure | ¹H-NMR | Mass M + 1 | Mass M − 1 |
|---|---|---|---|---|
| 67 | 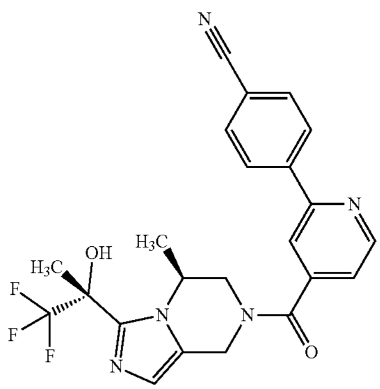 [SMILES: C[C@H]1CN(C(=O)c2ccnc(-c3ccc(C#N)cc3)c2)Cc2cnc([C@@](C)(O)C(F)(F)F)n21] | (400 MHz, DMSO-d₆) δ: 1.28-1.47 (m, 3H), 1.75 (s, 3H), 3.19-5.12 (m, 5H), 6.64-6.87 (m, 1H), 7.04-7.10 (m, 1H), 7.48-7.53 (m, 1H), 7.96-7.99 (m, 2H), 8.16-8.17 (m, 1H), 8.31-8.36 (m, 2H), 8.82-8.84 (m, 1H) | 456 | 454 |
| 68 | 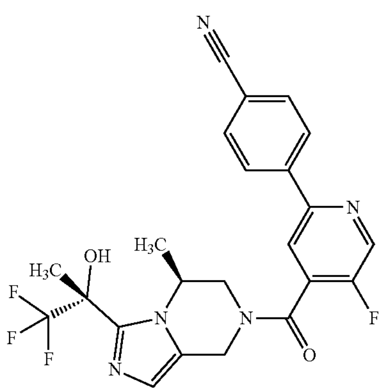 [SMILES: C[C@H]1CN(C(=O)c2cc(-c3ccc(C#N)cc3)ncc2F)Cc2cnc([C@@](C)(O)C(F)(F)F)n21] | (400 MHz, DMSO-d₆) δ: 1.29-1.44 (m, 3H), 1.75 (s, 3H), 3.23-5.12 (m, 5H), 6.64-6.88 (m, 1H), 7.06-7.11 (m, 1H), 7.96-7.99 (m, 2H), 8.25-8.32 (m, 3H), 8.85-8.86 (m, 1H) | 474 | 472 |
| 69 | 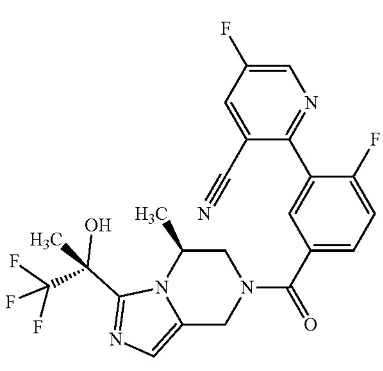 [SMILES: C[C@H]1CN(C(=O)c2ccc(F)c(-c3ncc(F)cc3C#N)c2)Cc2cnc([C@@](C)(O)C(F)(F)F)n21] | (400 MHz, DMSO-d₆) δ: 1.25-1.45 (m, 3H), 1.75 (s, 3H), 3.16-3.27 (m, 0.4H), 3.56-3.64 (m, 0.6H), 3.72-3.81 (m, 0.6H), 4.47-5.09 (m, 3.4H), 6.61-6.87 (m, 1H), 7.05 (s, 1H), 7.54 (t, J = 9.25 Hz, 1H), 7.71-7.83 (m, 2H), 8.63 (dd, J = 8.44, 2.89 Hz, 1H), 9.05 (d, J = 2.77 Hz, 1H) | 492 | 490 |

TABLE 1-13-continued
| Example | Structure | ¹H-NMR | Mass M + 1 | Mass M − 1 |
|---|---|---|---|---|
| 70 | 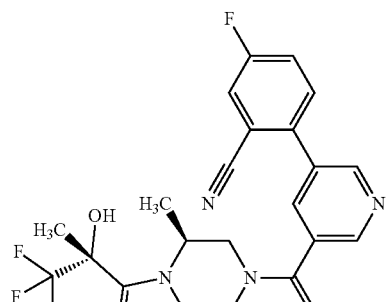 | (400 MHz, DMSO-d₆) δ: 1.24-1.44 (m, 3H), 1.75 (s, 3H), 3.17-3.31 (m, 0.4H), 3.50-3.61 (m, 0.6H), 3.72-3.82 (m, 0.6H), 4.48-5.08 (m, 3.4H), 6.62-6.87 (m, 1H), 7.04 (s, 1H), 7.45 (dd, J = 11.21, 8.44 Hz, 1H), 7.57-7.64 (m, 1H), 7.84-7.94 (m, 2H), 7.99 (dd, J = 7.51, 2.20 Hz, 1H), 8.72 (d, J = 3.01 Hz, 1H) | 467 | 465 |
| 71 | 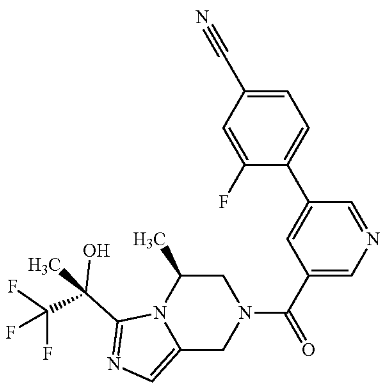 [SMILES: C[C@H]1CN(C(=O)c2cncc(-c3ccc(C#N)cc3F)c2)Cc2cnc([C@@](C)(O)C(F)(F)F)n21] | (400 MHz, DMSO-d₆) δ: 1.28-1.48 (m, 3H), 1.77 (s, 3H), 3.19-3.29 (m, 0.4H), 3.59-3.67 (m, 0.6H), 3.73-3.80 (m, 0.6H), 4.52-4.58 (m, 0.4H), 4.67-4.79 (m, 1.4H), 4.90-5.01 (m, 1.2H), 5.06-5.13 (m, 0.4H), 6.68 (s, 0.4H), 6.87 (s, 0.6H), 7.06-7.11 (m, 1H), 7.85-7.95 (m, 2H), 8.07 (d, J = 9.78 Hz, 1H), 8.14-8.22 (m, 1H), 8.75-8.81 (m, 1H), 8.93 (s, 1H) | 474 | 472 |
TABLE 1-14
| Example | Structure | ¹H-NMR | Mass M + 1 | Mass M − 1 |
|---|---|---|---|---|
| 72 | 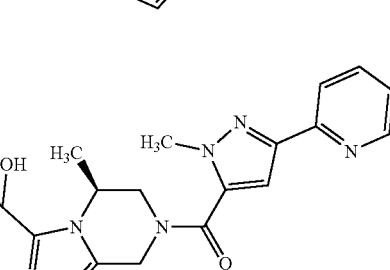 | (400 MHz, DMSO-d₆) δ: 1.28-1.46 (m, 3H), 1.76 (s, 3H), 3.19-3.27 (m, 0.4H), 3.61-3.81 (m, 1.2H), 4.51-4.58 (m, 0.4H), 4.68-5.13 (m, 3H), 6.64 (s, 0.4H), 6.86 (s, 0.6H), 7.06 (s, 1H), 7.75 (td, J = 8.55, 2.85 Hz, 1H), 7.79-7.86 (m, 1H), 8.06 (dd, J = 8.55, 2.54 Hz, 1H), 8.15-8.24 (m, 1H), 8.77-8.82 (m, 1H), 8.87 (s, 1H) | 474 | 472 |
| 73 | 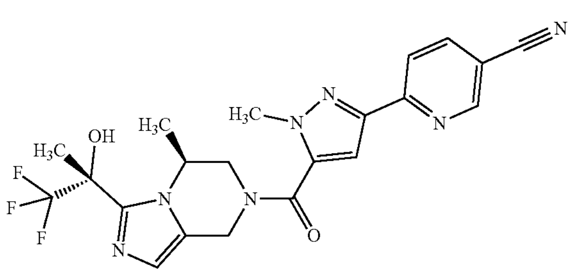 [SMILES: C[C@H]1CN(C(=O)c2cc(-c3ccc(C#N)cn3)nn2C)Cc2cnc([C@@](C)(O)C(F)(F)F)n21] | (400 MHz, DMSO-d₆) δ: 1.32, 1.42 (d, J = 6.47, 3H), 1.76 (s, 3H), 3.21-3.68 (m, 1H), 3.97-5.09 (m, 7H), 6.72-7.36 (m, 3H), 8.09 (d, J = 8.20 Hz, 1H), 8.33 (dd, J = 8.20, 1.85 Hz, 1H), 9.02 (s, 1H) | 460 | 458 |

TABLE 1-14-continued
| Example | Structure | ¹H-NMR | Mass M + 1 | Mass M − 1 |
|---|---|---|---|---|
| 74 | 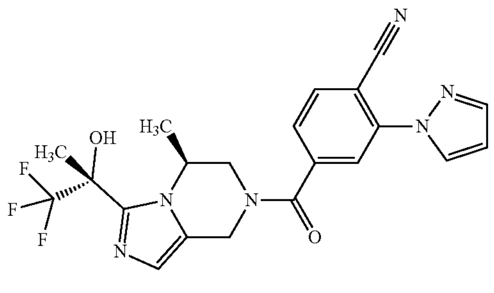 [SMILES: C[C@H]1CN(C(=O)c2ccc(C#N)c(-n3cccn3)c2)Cc2cnc([C@@](C)(O)C(F)(F)F)n21] | (400 MHz, CDCl₃) δ: 1.46-1.50 (m, 3H), 1.96 (s, 3H), 3.36-3.77 (m, 2H), 4.65-5.20 (m, 4H), 6.57 (s, 1H), 6.82-7.02 (m, 1H), 7.47 (d, J = 7.40 Hz, 1H), 7.80 (d, J = 1.39 Hz, 1H), 7.86 (d, J = 8.09 Hz, 1H), 7.92 (s, 1H), 8.23 (d, J = 2.31 Hz, 1H) | 445 | 443 |
| 75 | 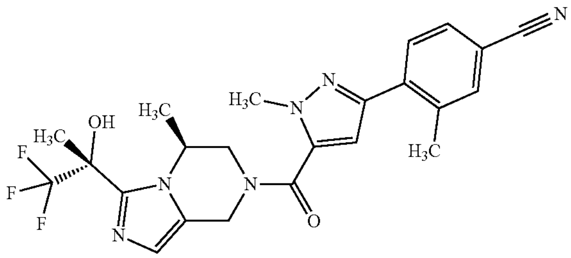 [SMILES: Cc1cc(C#N)ccc1-c1cc(C(=O)N2Cc3cnc([C@@](C)(O)C(F)(F)F)n3[C@@H](C)C2)n(C)n1] | (400 MHz, DMSO-d₆) δ: 1.32-1.48 (m, 3H), 1.78 (s, 3H), 2.52-2.59 (m, 3H), 3.20-3.69 (m, 1H), 3.96 (s, 3H), 4.03-4.56 (m, 1H), 4.66-5.16 (m, 3H), 6.73, 6.87 (s, 1H), 6.95-7.19 (m, 2H), 7.69-7.87 (m, 3H) | 473 | 471 |
| 76 | 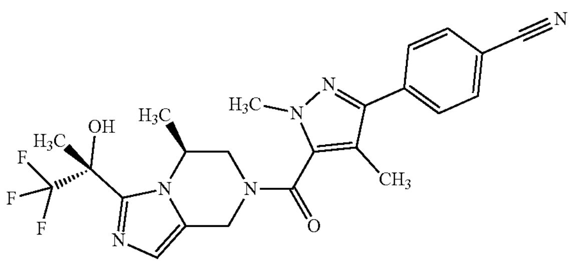 [SMILES: Cc1c(-c2ccc(C#N)cc2)nn(C)c1C(=O)N1Cc2cnc([C@@](C)(O)C(F)(F)F)n2[C@@H](C)C1] | (400 MHz, DMSO-d₆) δ: 1.23-1.47 (m, 3H), 1.72-1.81 (m, 3H), 2.12-2.26 (m, 3H), 3.15-3.89 (m, 5H), 4.56-5.17 (m, 3H), 6.73, 6.88 (s, 1H), 7.08, 7.12 (s, 1H), 7.85-7.94 (m, 4H) | 473 | 471 |
TABLE 1-15
| Example | Structure | ¹H-NMR | Mass M + 1 | Mass M − 1 |
|---|---|---|---|---|
| 77 | 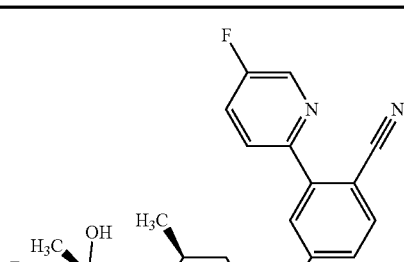 | (400 MHz, DMSO-d₆) δ: 1.29 (d, J = 6.01 Hz, 1.8H), 1.43 (d, J = 6.01 Hz, 1.2H), 1.75 (s, 3H), 3.18-3.26 (m, 0.4H), 3.53-3.59 (m, 0.6H), 3.65-3.71 (m, 0.6H), 4.51-4.56 (m, 0.4H), 4.63-4.69 (m, 1.4H), 4.90-4.97 (m, 1.2H), 5.04-5.10 (m, 0.4H), 6.65 (s, 0.4H), 6.85 (s, 0.6H), 7.02-7.09 (m, 1H), 7.71 (dd, J = 15.49, 8.32 Hz, 1H), 7.93-8.04 (m, 3H), 8.08 (d, J = 7.63 Hz, 1H), 8.76 (d, J = 3.01 Hz, 1H) | 474 | 472 |

TABLE 1-15-continued

| Example | Structure | ¹H-NMR | Mass M + 1 | Mass M − 1 |
|---|---|---|---|---|
| 78 | 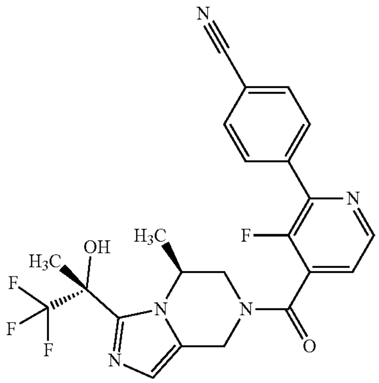 [SMILES: C[C@H]1CN(C(=O)c2ccnc(-c3ccc(C#N)cc3)c2F)Cc2cnc([C@@](C)(O)C(F)(F)F)n21] | (400 MHz, DMSO-d$_6$) δ: 1.30-1.42 (m, 3H), 1.75 (s, 3H), 3.22-5.10 (m, 5H), 6.64-6.87 (m, 1H), 7.05-7.10 (m, 1H), 7.57-7.65 (m, 1H), 7.99-8.02 (m, 2H), 8.09-8.13 (m, 2H), 8.67-8.71 (m, 1H) | 474 | 472 |
| 79 | 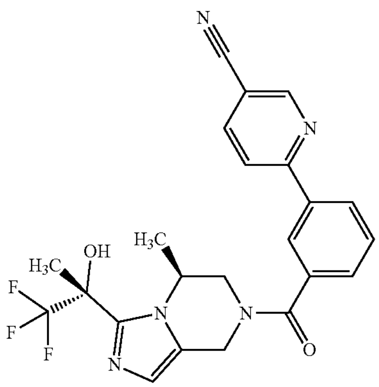 [SMILES: C[C@H]1CN(C(=O)c2cccc(-c3ccc(C#N)cn3)c2)Cc2cnc([C@@](C)(O)C(F)(F)F)n21] | (400 MHz, DMSO-d$_6$) δ: 1.24-1.47 (m, 3H), 1.75 (s, 3H), 3.20-3.32 (m, 0.4H), 3.54-3.62 (m, 0.6H), 3.69-3.77 (m, 0.6H), 4.52-4.70 (m, 1.7H), 4.90-5.11 (m, 1.7H), 6.64 (s, 0.4H), 6.85 (s, 0.6H), 7.01-7.08 (m, 1H), 7.58-7.67 (m, 2H), 8.23-8.25 (m, 1H), 8.26-8.30 (m, 2H), 8.41 (dd, J = 8.44, 2.20 Hz, 1H), 9.11 (dd, J = 2.20, 0.81 Hz, 1H) | 456 | 454 |
| 80 | 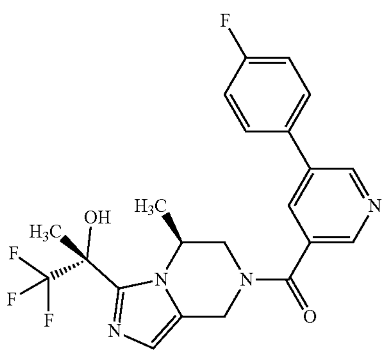 [SMILES: C[C@H]1CN(C(=O)c2cncc(-c3ccc(F)cc3)c2)Cc2cnc([C@@](C)(O)C(F)(F)F)n21] | (400 MHz, DMSO-d$_6$) δ: 1.27-1.48 (m, 3H), 1.76 (s, 3H), 3.18-3.26 (m, 0.4H), 3.60-3.67 (m, 0.6H), 3.73-3.79 (m, 0.6H), 4.50-4.58 (m, 0.4H), 4.66-4.78 (m, 1.4H), 4.88-5.12 (m, 1.6H), 6.66 (s, 0.4H), 6.86 (s, 0.6H), 7.02-7.09 (m, 1H), 7.35 (t, J = 8.79 Hz, 2H), 7.82-7.88 (m, 2H), 8.15-8.20 (m, 1H), 8.63-8.68 (m, 1H), 8.98 (d, J = 2.08 Hz, 1H) | 449 | 447 |
| 81 | 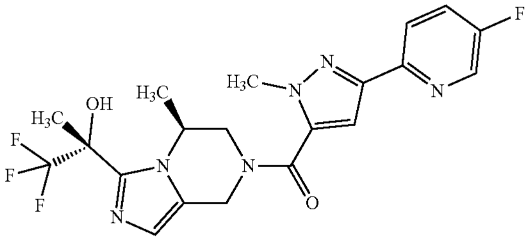 [SMILES: C[C@H]1CN(C(=O)c2cc(-c3ccc(F)cn3)nn2C)Cc2cnc([C@@](C)(O)C(F)(F)F)n21] | (400 MHz, DMSO-d$_6$) δ: 1.33, 1.44 (d, J = 5.98, 3H), 1.78 (s, 3H), 3.22-3.68 (m, 1H), 3.95 (s, 3H), 4.02-5.03 (m, 4H), 6.74-7.22 (m, 3H), 7.80 (td, J = 8.67, 2.09 Hz, 1H), 7.98-8.01 (m, 1H), 8.59 (s, 1H) | 453 | 451 |

TABLE 1-16

| Example | Structure | ¹H-NMR | Mass M + 1 | Mass M − 1 |
|---|---|---|---|---|
| 82 | 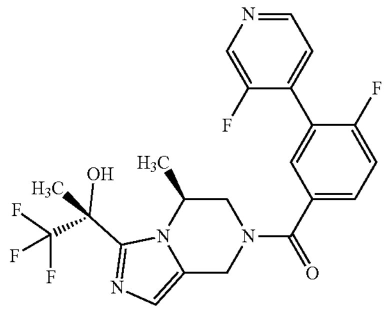 [SMILES: C[C@H]1CN(C(=O)c2ccc(F)c(-c3ccncc3F)c2)Cc2cnc([C@@](C)(O)C(F)(F)F)n21] | (400 MHz, DMSO-d$_6$) δ: 1.22-1.47 (m, 3H), 1.75 (s, 3H), 3.14-3.28 (m, 0.4H), 3.52-3.63 (m, 0.6H), 3.72-3.82 (m, 0.6H), 4.45-5.10 (m, 3.4H), 6.64-6.86 (m, 1H), 7.05 (s, 1H), 7.51 (t, J = 9.25 Hz, 1H), 7.60-7.73 (m, 3H), 8.56 (dd, J = 4.74, 1.04 Hz, 1H), 8.72 (d, J = 2.08 Hz, 1H) | 467 | 465 |
| 83 | 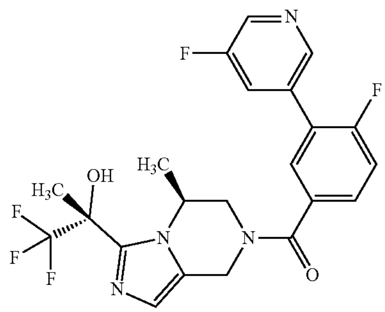 [SMILES: C[C@H]1CN(C(=O)c2ccc(F)c(-c3cncc(F)c3)c2)Cc2cnc([C@@](C)(O)C(F)(F)F)n21] | (400 MHz, DMSO-d$_6$) δ: 1.24-1.47 (m, 3H), 1.75 (s, 3H), 3.15-3.25 (m, 0.4H), 3.56-3.65 (m, 0.6H), 3.74-3.81 (m, 0.6H), 4.46-5.10 (m, 3.4H), 6.65-6.87 (m, 1H), 7.05 (s, 1H), 7.49 (dd, J = 10.63, 8.55 Hz, 1H), 7.59-7.65 (m, 1H), 7.75-7.80 (m, 1H), 7.99-8.06 (m, 1H), 8.64 (d, J = 3.01 Hz, 1H), 8.69 (brs, 1H) | 467 | 465 |
| 84 | 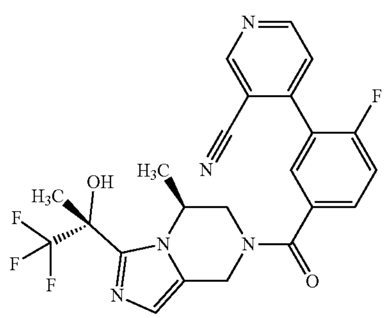 [SMILES: C[C@H]1CN(C(=O)c2ccc(F)c(-c3ccncc3C#N)c2)Cc2cnc([C@@](C)(O)C(F)(F)F)n21] | (400 MHz, DMSO-d$_6$) δ: 1.25-1.45 (m, 3H), 1.75 (s, 3H), 3.16-3.26 (m, 0.4H), 3.57-3.65 (m, 0.6H), 3.74-3.82 (m, 0.6H), 4.47-5.10 (m, 3.4H), 6.63-6.86 (m, 1H), 7.06 (s, 1H), 7.58 (t, J = 9.25 Hz, 1H), 7.71-7.82 (m, 3H), 8.96 (d, J = 5.32 Hz, 1H), 9.17 (d, J = 0.69 Hz, 1H) | 474 | 472 |
| 85 | 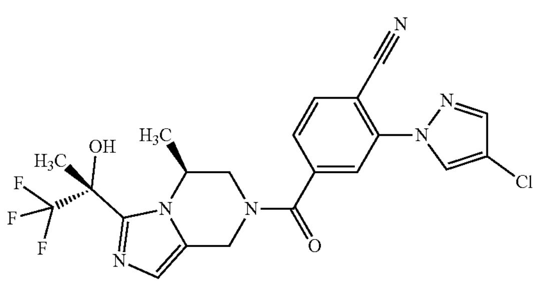 [SMILES: C[C@H]1CN(C(=O)c2ccc(C#N)c(-n3cc(Cl)cn3)c2)Cc2cnc([C@@](C)(O)C(F)(F)F)n21] | (400 MHz, CDCl$_3$) δ: 1.22-1.26 (m, 3H), 1.94 (s, 3H), 2.94-3.66 (m, 2H), 4.61-5.11 (m, 4H), 6.77-6.96 (m, 1H), 7.48-7.50 (m, 1H), 7.73 (s, 1H), 7.86-7.87 (m, 2H), 8.21 (s, 1H) | 479 | 477 |
| 86 | 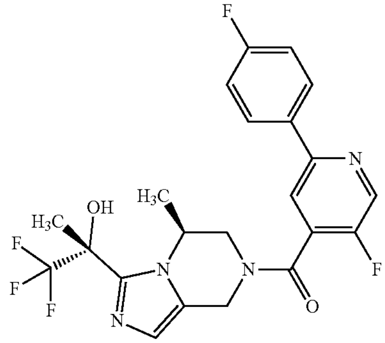 [SMILES: C[C@H]1CN(C(=O)c2cc(-c3ccc(F)cc3)ncc2F)Cc2cnc([C@@](C)(O)C(F)(F)F)n21] | (400 MHz, DMSO-d$_6$) δ: 1.30-1.44 (m, 3H), 1.75 (s, 3H), 3.22-5.11 (m, 5H), 6.65-6.88 (m, 1H), 7.05-7.11 (m, 1H), 7.29-7.35 (m, 2H), 8.11-8.17 (m, 3H), 8.77-8.78 (m, 1H) | 467 | 465 |

TABLE 1-16-continued
| Example | Structure | ¹H-NMR | Mass M + 1 | Mass M − 1 |
|---|---|---|---|---|
| 87 | 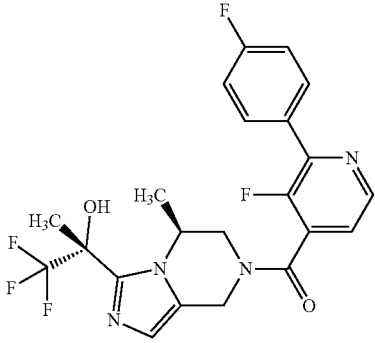 [SMILES: C[C@H]1CN(C(=O)c2ccnc(-c3ccc(F)cc3)c2F)Cc2cnc([C@@](C)(O)C(F)(F)F)n21] | (400 MHz, DMSO-d₆) δ: 1.30-1.42 (m, 3H), 1.75 (s, 3H), 3.23-5.10 (m, 5H), 6.65-6.86 (m, 1H), 7.05-7.10 (m, 1H), 7.34-7.39 (m, 2H), 7.48-7.56 (m, 1H), 7.95-8.02 (m, 2H), 8.61-8.64 (m, 1H) | 467 | 465 |
TABLE 1-17
| Example | Structure | ¹H-NMR | Mass M + 1 | Mass M − 1 |
|---|---|---|---|---|
| 88 | 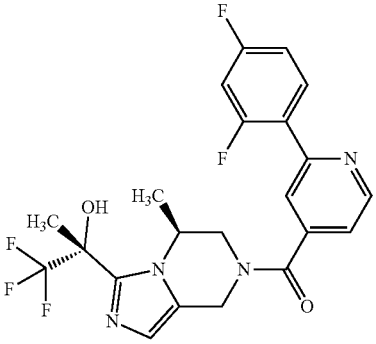 [SMILES: C[C@H]1CN(C(=O)c2ccnc(-c3ccc(F)cc3F)c2)Cc2cnc([C@@](C)(O)C(F)(F)F)n21] | (400 MHz, DMSO-d6) δ: 1.31-1.45 (m, 3H), 1.77 (s, 3H), 3.20-5.11 (m, 5H), 6.66-6.87 (m, 1H), 7.06-7.11 (m, 1H), 7.24-7.29 (m, 1H), 7.39-7.53 (m, 2H), 7.78-7.82 (m, 1H), 8.01-8.07 (m, 1H), 8.82-8.85 (m, 1H) | 467 | 465 |
| 89 | 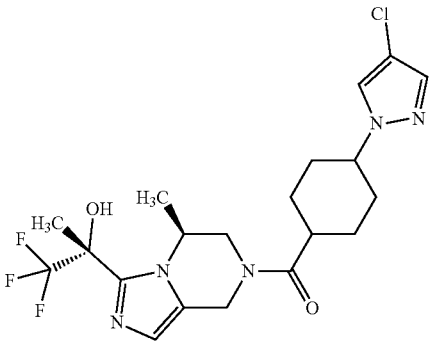 [SMILES: C[C@H]1CN(C(=O)C2CCC(n3cc(Cl)cn3)CC2)Cc2cnc([C@@](C)(O)C(F)(F)F)n21] | (400 MHz, CDCl₃) δ: 1.37-1.44 (m, 3H), 1.68-1.79 (m, 7H), 1.94 (s, 3H), 2.22-2.25 (m, 2H), 2.60 (d, J = 34.22 Hz, 1H), 3.05-3.90 (m, 2H), 4.62-4.92 (m, 3H), 5.07-5.11 (m, 1H), 6.88 (s, 1H), 7.39 (s, 1H), 7.41 (s, 1H) | 460 | 458 |
| 90 | 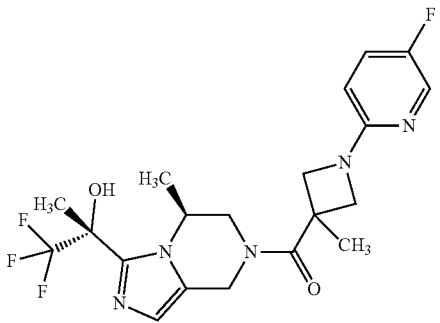 [SMILES: C[C@H]1CN(C(=O)C2(C)CN(c3ccc(F)cn3)C2)Cc2cnc([C@@](C)(O)C(F)(F)F)n21] | (400 MHz, DMSO-d₆) δ: 1.26-1.36 (m, 3H), 1.62 (s, 3H), 1.77 (s, 3H), 3.03-5.08 (m, 9H), 6.47 (dd, J = 9.02, 3.47 Hz, 1H), 6.79 (s, 1H), 7.05-7.10 (brm, 1H), 7.50 (td, J = 8.79, 3.01 Hz, 1H), 8.05 (d, J = 3.01 Hz, 1H) | 442 | 440 |

TABLE 1-17-continued

| Example | Structure | ¹H-NMR | Mass M + 1 | Mass M − 1 |
|---|---|---|---|---|
| 91 | 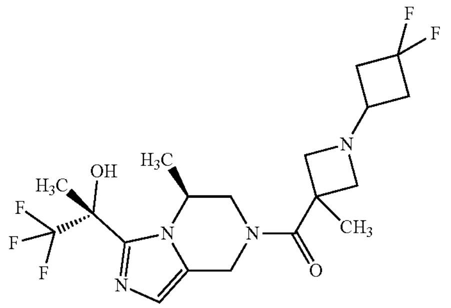 [SMILES: C[C@H]1CN(C(=O)C2(C)CN(C3CC(F)(F)C3)C2)Cc2cnc([C@@](C)(O)C(F)(F)F)n21] | (400 MHz, DMSO-d₆) δ: 1.27-1.34 (m, 3H), 1.51 (s, 3H), 1.77 (s, 3H), 2.29-2.32 (m, 2H), 2.58-2.59 (m, 2H), 2.99-5.04 (m, 10H), 6.75-6.79 (brm, 1H), 7.05-7.10 (brm, 1H) | 437 | 435 |
| 92 | 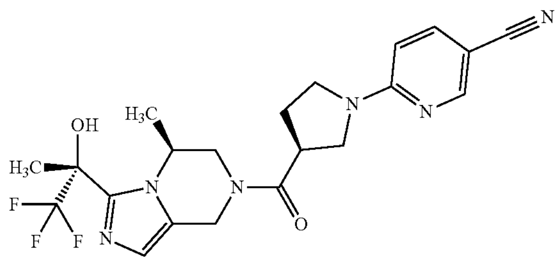 [SMILES: C[C@H]1CN(C(=O)[C@H]2CCN(c3ccc(C#N)cn3)C2)Cc2cnc([C@@](C)(O)C(F)(F)F)n21] | (400 MHz, DMSO-d₆) δ: 1.22-1.41 (m, 3H), 1.76 (s, 3H), 2.05-2.34 (m, 2H), 2.91-3.86 (m, 6H), 4.15-5.12 (m, 4H), 6.54-6.60 (m, 1H), 6.74-6.79 (m, 1H), 7.04-7.10 (m, 1H), 7.80 (dt, J = 8.86, 1.85 Hz, 1H), 8.45 (t, J = 1.85 Hz, 1H) | 449 | 493 (M − 1 + 46) |
| 93 | 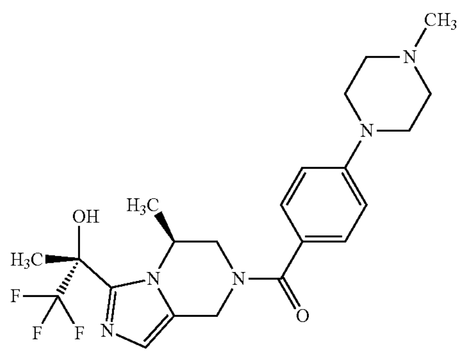 [SMILES: C[C@H]1CN(C(=O)c2ccc(N3CCN(C)CC3)cc2)Cc2cnc([C@@](C)(O)C(F)(F)F)n21] | (400 MHz, DMSO-d₆) δ: 1.28 (s, 3H), 1.75 (s, 3H), 2.21 (s, 3H), 2.43 (t, J = 4.97 Hz, 4H), 3.21 (t, J = 4.97 Hz, 4H), 3.32-3.60 (m, 1H), 3.80-4.20 (m, 1H), 4.50-4.68 (m, 1H), 4.77-4.90 (m, 1H), 4.91-5.02 (m, 1H), 6.76 (s, 1H), 6.95 (d, J = 8.79 Hz, 2H), 7.03 (s, 1H), 7.34 (d, J = 8.79 Hz, 2H) | 452 | 450 |

TABLE 1-18

| Example | Structure | ¹H-NMR | Mass M + 1 | Mass M − 1 |
|---|---|---|---|---|
| 94 | 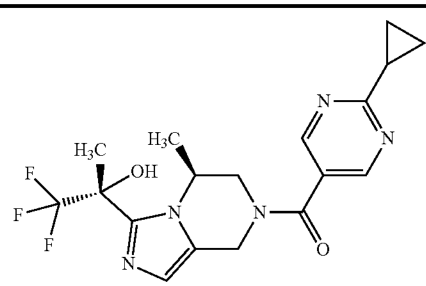 | (400 MHz, CDCl₃) δ: 1.13-1.23 (m, 4H), 1.39-1.44 (m, 3H), 1.94 (s, 3H), 2.27-2.33 (m, 1H), 3.40-3.47 (m, 1H), 3.71 (d, J = 18.26 Hz, 1H), 4.71-5.06 (m, 3H), 6.79-6.95 (m, 1H), 8.66 (s, 2H) | 396 | 394 |
| 95 | 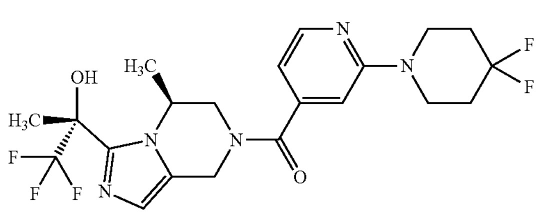 [SMILES: C[C@H]1CN(C(=O)c2ccnc(N3CCC(F)(F)CC3)c2)Cc2cnc([C@@](C)(O)C(F)(F)F)n21] | (400 MHz, DMSO-d₆) δ: 1.24-1.44 (m, 3H), 1.75 (s, 3H), 1.88-2.06 (m, 4H), 3.11-3.78 (m, 6H), 4.45-5.10 (m, 3H), 6.62-6.86 (m, 2H), 6.92-6.97 (m, 1H), 7.01-7.09 (m, 1H), 8.17-8.23 (m, 1H) | 474 | 518 (M − 1 + 46) |

TABLE 1-18-continued

| Example | Structure | ¹H-NMR | Mass M + 1 | Mass M − 1 |
|---|---|---|---|---|
| 96 | 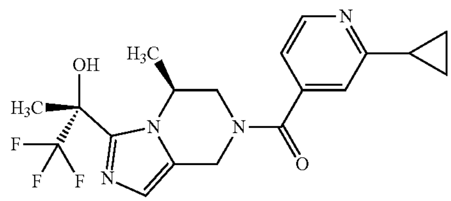 [SMILES: C[C@H]1CN(C(=O)c2ccnc(C3CC3)c2)Cc2cnc([C@@](C)(O)C(F)(F)F)n21] | (400 MHz, DMSO-d₆) δ: 0.88-1.02 (m, 4H), 1.23-1.46 (m, 3H), 1.75 (s, 3H), 2.08-2.20 (m, 1H), 3.14-5.11 (m, 5H), 6.65-6.86 (m, 1H), 7.01-7.09 (m, 1H), 7.11-7.20 (m, 1H), 7.30-7.39 (m, 1H), 8.45-8.52 (m, 1H) | 395 | 393 |
| 97 | 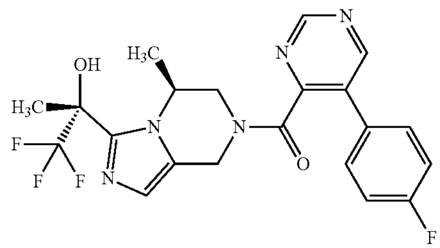 [SMILES: C[C@H]1CN(C(=O)c2ncncc2-c2ccc(F)cc2)Cc2cnc([C@@](C)(O)C(F)(F)F)n21] | (400 MHz, DMSO-d₆) δ: 1.00-1.08 (m, 3H), 1.72 (s, 3H), 3.09-3.17 (m, 1H), 3.50-4.97 (m, 4H), 6.60-6.80 (m, 1H), 7.02 (d, J = 4.39 Hz, 1H), 7.27-7.35 (m, 2H), 7.53-7.56 (m, 2H), 9.03 (d, J = 9.25 Hz, 1H), 9.27 (d, J = 13.41 Hz, 1H) | 450 | 448 |
| 98 | 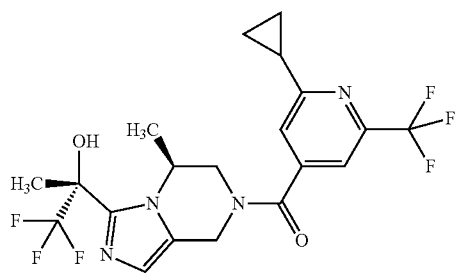 [SMILES: C[C@H]1CN(C(=O)c2cc(C3CC3)nc(C(F)(F)F)c2)Cc2cnc([C@@](C)(O)C(F)(F)F)n21] | (400 MHz, DMSO-d₆) δ: 0.90-1.12 (m, 4H), 1.23-1.48 (m, 3H), 1.76 (s, 3H), 2.21-2.34 (m, 1H), 3.15-3.66 (m, 2H), 4.45-5.15 (m, 3H), 6.65-6.89 (m, 1H), 7.02-7.11 (m, 1H), 7.63-7.74 (m, 2H) | 463 | 461 |
| 99 | 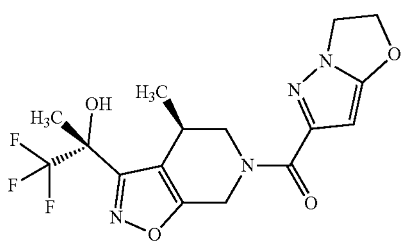 [SMILES: C[C@H]1CN(C(=O)c2cc3n(n2)CCO3)Cc2onc([C@@](C)(O)C(F)(F)F)c21] | (400 MHz, CDCl₃) δ: 1.20-1.29 (m, 3H), 1.86 (s, 3H), 2.79 (s, 1H), 3.02-3.15 (m, 1.6H), 3.35-3.43 (m, 0.4H), 4.22-4.38 (m, 2.6H), 4.60-4.72 (m, 1H), 5.02-5.11 (m, 0.6H), 5.08 (t, J = 7.98 Hz, 2H), 5.42-5.51 (m, 0.4H), 5.84-5.99 (m, 1.4H) | 387 | 385 |

TABLE 1-19

| Example | Structure | ¹H-NMR | Mass M + 1 | Mass M − 1 |
|---|---|---|---|---|
| 100 | 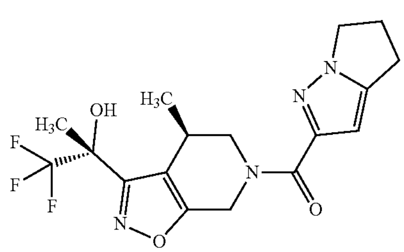 [SMILES: C[C@H]1CN(C(=O)c2cc3n(n2)CCC3)Cc2onc([C@@](C)(O)C(F)(F)F)c21] | (400 MHz, CDCl₃) δ: 1.18-1.30 (m, 3H), 1.85 (s, 3H), 2.59-2.66 (m, 2H), 2.88-2.97 (m, 3H), 3.03-3.15 (m, 1.5H), 3.34-3.44 (m, 0.5H), 4.11-4.20 (m, 2H), 4.21-4.31 (m, 0.5H), 4.59-4.75 (m, 1H), 5.08-5.17 (m, 0.5H), 5.43-5.53 (m, 0.5H), 5.92-6.03 (m, 0.5H), 6.45-6.52 (m, 1H) | 385 | 383 |

TABLE 1-19-continued

| Example | Structure | ¹H-NMR | Mass M + 1 | Mass M − 1 |
|---|---|---|---|---|
| 101 | 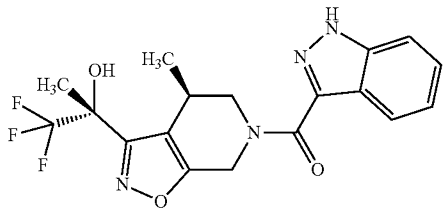 [SMILES: C[C@H]1CN(C(=O)c2n[nH]c3ccccc23)Cc2onc([C@@](C)(O)C(F)(F)F)c21] | (400 MHz, CDCl₃) δ: 1.25-1.34 (m, 3H), 1.86 (s, 3H), 2.93 (s, 1H), 3.08-3.51 (m, 2H), 4.32-5.17 (m, 2H), 5.62-5.97 (m, 1H), 7.26-7.30 (m, 1H), 7.42-7.46 (m, 1H), 7.52 (d, J = 8.55 Hz, 1H), 8.20 (brs, 1H), 10.33 (brs, 1H) | 395 | 393 |
| 102 | 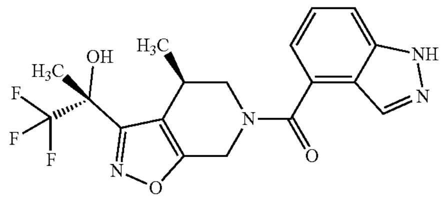 [SMILES: C[C@H]1CN(C(=O)c2cccc3[nH]ncc23)Cc2onc([C@@](C)(O)C(F)(F)F)c21] | (400 MHz, DMSO-d₆) δ: 1.06-1.21 (m, 3H), 1.72 (s, 3H), 2.89-5.49 (m, 5H), 7.14-7.17 (m, 2H), 7.44 (dd, J = 8.32, 6.94 Hz, 1H), 7.66 (d, J = 8.32 Hz, 1H), 7.98 (brs, 1H), 13.33 (s, 1H) | 395 | 393 |
| 103 | 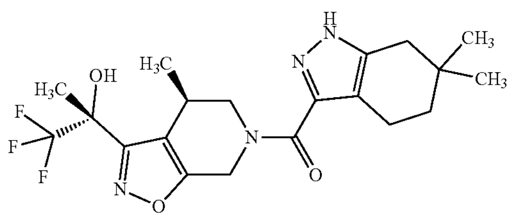 [SMILES: C[C@H]1CN(C(=O)c2n[nH]c3c2CCC(C)(C)C3)Cc2onc([C@@](C)(O)C(F)(F)F)c21] | (400 MHz, DMSO-d₆) δ: 0.96 (s, 6H), 1.11-1.18 (m, 3H), 1.45 (t, J = 6.24 Hz, 2H), 1.72 (s, 3H), 2.38 (s, 2H), 2.45-2.56 (m, 2H), 2.95-3.44 (m, 2H), 4.29-4.55 (m, 1H), 4.64-4.86 (m, 1H), 5.27-5.86 (m, 1H), 7.10-7.12 (brm, 1H), 12.73-12.77 (brm, 1H) | 427 | 425 |
| 104 | 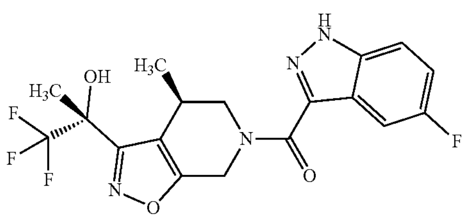 [SMILES: C[C@H]1CN(C(=O)c2n[nH]c3ccc(F)cc23)Cc2onc([C@@](C)(O)C(F)(F)F)c21] | (400 MHz, DMSO-d₆) δ: 1.08-1.29 (m, 3H), 1.72 (s, 3H), 3.00-3.60 (m, 2H), 4.35-6.05 (m, 3H), 7.08-7.14 (m, 1H), 7.33 (td, J = 9.07, 2.47 Hz, 1H), 7.63-7.74 (m, 2H), 13.78 (s, 1H) | 413 | 411 |
| 105 | 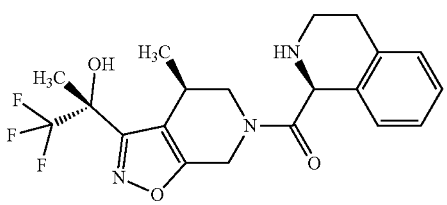 [SMILES: C[C@H]1CN(C(=O)[C@H]2NCCc3ccccc32)Cc2onc([C@@](C)(O)C(F)(F)F)c21] | (400 MHz, CDCl₃) δ: 1.02-1.22 (m, 3H), 1.85 (s, 3H), 2.71-2.87 (m, 2H), 2.97-3.02 (m, 3H), 3.20-3.35 (m, 1H), 3.42-3.77 (m, 1H), 4.17-5.12 (m, 3H), 5.31-5.61 (m, 1H), 6.97 (d, J = 7.40 Hz, 1H), 7.10-7.21 (m, 3H) | 410 | 468 (M − 1 + 60) |

TABLE 1-20

| Example | Structure | ¹H-NMR | Mass M + 1 | Mass M − 1 |
|---|---|---|---|---|
| 106 | 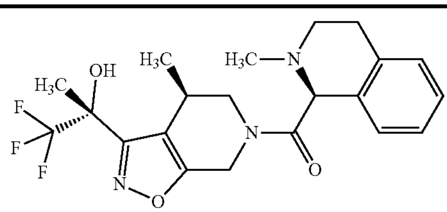 | (400 MHz, CDCl₃) δ: 0.35, 1.23 (d, J = 6.70 Hz, 3H), 1.78, 1.82 (s, 3H), 2.36, 2.44 (s, 3H), 2.46-3.05 (m, 5H), 3.15-3.30 (m, 2H), 4.19-4.66 (m, 2H), 5.10-5.95 (m, 1H), 7.09-7.17 (m, 4H) | 424 | 482 (M − 1 + 60) |

TABLE 1-20-continued

| Example | Structure | ¹H-NMR | Mass M + 1 | Mass M − 1 |
|---|---|---|---|---|
| 107 | 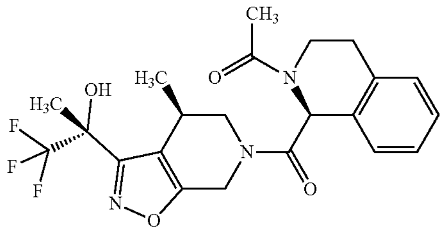 [SMILES: CC(=O)N1CCc2ccccc2[C@H]1C(=O)N1Cc2onc([C@@](C)(O)C(F)(F)F)c2[C@@H](C)C1] | (400 MHz, CDCl$_3$) δ: 1.16-1.26 (m, 3H), 1.85 (s, 3H), 2.19 (s, 3H), 2.83-3.75 (m, 5H), 4.01-4.91 (m, 3H), 5.14-5.42 (m, 1H), 6.25-6.45 (m, 1H), 7.03-7.14 (m, 4H) | 452 | 450 |
| 108 | 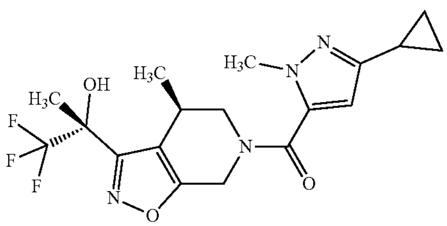 [SMILES: C[C@H]1CN(C(=O)c2cc(C3CC3)nn2C)Cc2onc([C@@](C)(O)C(F)(F)F)c21] | (400 MHz, CDCl$_3$) δ: 0.69-0.75 (m, 2H), 0.88-0.94 (m, 2H), 1.23 (s, 3H), 1.88 (s, 3H), 1.88-1.94 (m, 1H), 3.10-3.34 (m, 3H), 3.87 (s, 3H), 4.02-5.47 (m, 2H), 6.05 (s, 1H) | 399 | 457 (M − 1 + 60) |
| 109 | 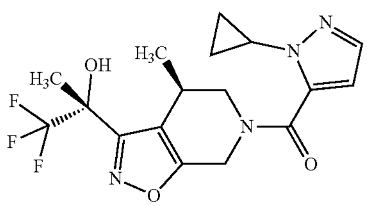 [SMILES: C[C@H]1CN(C(=O)c2ccnn2C2CC2)Cc2onc([C@@](C)(O)C(F)(F)F)c21] | (400 MHz, CDCl$_3$) δ: 0.99 (brs, 2H), 1.23-1.27 (m, 5H), 1.88 (s, 3H), 3.10-3.89 (m, 5H), 4.36-5.53 (m, 2H), 6.35 (s, 1H), 7.44 (s, 1H) | 385 | 443 (M − 1 + 60) |
| 110 | 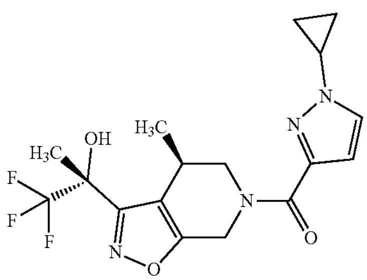 [SMILES: C[C@H]1CN(C(=O)c2ccn(C3CC3)n2)Cc2onc([C@@](C)(O)C(F)(F)F)c21] | (400 MHz, CDCl$_3$) δ: 1.12-1.22 (m, 7H), 1.86-1.88 (m, 3H), 3.09-4.27 (m, 4H), 4.68-4.76 (m, 1H), 5.11-6.01 (m, 2H), 6.71-6.74 (m, 1H), 7.47 (s, 1H) | 385 | 443 (M − 1 + 60) |
| 111 | 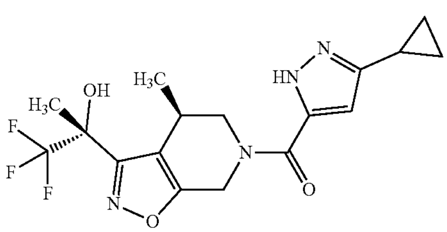 [SMILES: C[C@H]1CN(C(=O)c2cc(C3CC3)n[nH]2)Cc2onc([C@@](C)(O)C(F)(F)F)c21] | (400 MHz, DMSO-d$_6$) δ: 0.68-0.72 (m, 2H), 0.90-0.97 (m, 2H), 1.11-1.17 (m, 3H), 1.71 (s, 3H), 1.88-1.95 (m, 1H), 2.95-3.10 (m, 1.5H), 3.34-3.46 (m, 0.5H), 4.24-3.54 (m, 1H), 4.61-4.97 (m, 1H), 5.18-5.30 (m, 0.5H), 5.76-5.91 (m, 0.5H), 6.22-6.35 (m, 1H), 7.09 (s, 1H), 13.01 (s, 1H) | 385 | 383 |

TABLE 1-21

| Example | Structure | ¹H-NMR | Mass M + 1 | Mass M − 1 |
|---|---|---|---|---|
| 112 | 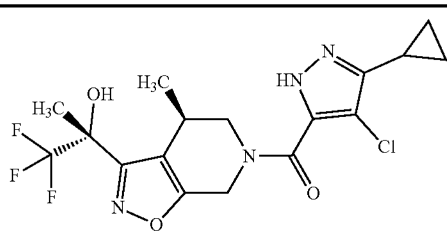 | (400 MHz, DMSO-d$_6$) δ: 0.84-0.90 (m, 2H), 0.94-1.02 (m, 2H), 1.04-1.11 (m, 1.7H), 1.17-1.21 (m, 1.3H), 1.71 (s, 3H), 1.84-1.93 (m, 1H), 2.90-3.13 (m, 1.5H), 3.36-3.46 (m, 0.6H), 3.89-4.05 (m, 0.5H), 4.34-4.52 (m, 1H), 4.57-4.67 (m, 0.4H), 4.89-5.02 (m, 0.4H), 5.33 (d, J = 16.41 Hz, 0.6H), 7.07-7.13 (m, 1H), 13.13 (s, 1H) | 419 | 417 |

TABLE 1-21-continued

| Example | Structure | ¹H-NMR | Mass M + 1 | Mass M − 1 |
|---|---|---|---|---|
| 113 | 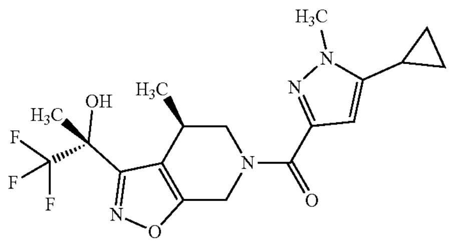 [SMILES: C[C@H]1CN(C(=O)c2cc(C3CC3)n(C)n2)Cc2onc([C@@](C)(O)C(F)(F)F)c21] | (400 MHz, DMSO-d₆) δ: 0.64-0.69 (m, 2H), 0.84-0.89 (m, 2H), 1.06-1.26 (m, 3H), 1.72 (s, 3H), 1.84-1.91 (m, 1H), 2.96-3.14 (m, 1.5H), 3.38-3.51 (m, 0.5H), 3.73 (s, 3H), 3.79-3.91 (m, 0.5H), 4.29-5.38 (m, 2.5H), 6.16-6.38 (m, 1H), 7.14 (s, 1H) | 399 | 397 |
| 114 | 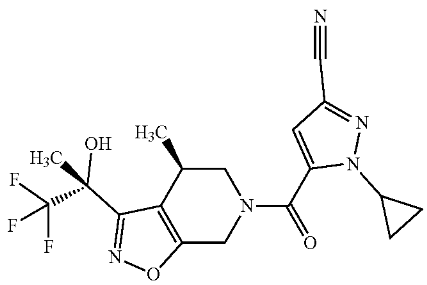 [SMILES: C[C@H]1CN(C(=O)c2cc(C#N)nn2C2CC2)Cc2onc([C@@](C)(O)C(F)(F)F)c21] | (400 MHz, DMSO-d₆) δ: 0.99-1.17 (m, 7H), 1.73 (s, 3H), 3.00-5.36 (m, 6H), 7.15 (s, 1H), 7.28 (m, 1H) | 410 | 408 |
| 115 | 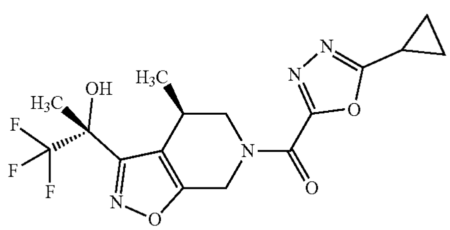 [SMILES: C[C@H]1CN(C(=O)c2nnc(C3CC3)o2)Cc2onc([C@@](C)(O)C(F)(F)F)c21] | (400 MHz, DMSO-d₆) δ: 1.00-1.25 (m, 7H), 1.68-1.75 (m, 3H), 2.30-2.36 (m, 1H), 3.03-3.55 (m, 2H), 4.42-5.63 (m, 3H), 7.15 (s, 1H) | 387 | 445 (M − 1 + 60) and 385 |
| 116 | 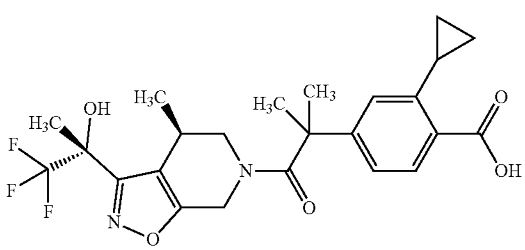 [SMILES: C[C@H]1CN(C(=O)C(C)(C)c2ccc(C(=O)O)c(C3CC3)c2)Cc2onc([C@@](C)(O)C(F)(F)F)c21] | (400 MHz, DMSO-d₆) δ: 0.46-1.68 (m, 16H), 2.33-4.49 (m, 6H), 6.58-7.20 (m, 3H), 7.66-7.75 (m, 1H), 12.81 (brs, 1H) | 481 | 479 |
| 117 | 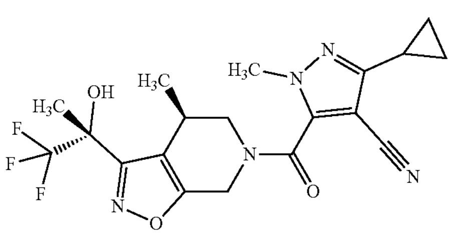 [SMILES: C[C@H]1CN(C(=O)c2c(C#N)c(C3CC3)nn2C)Cc2onc([C@@](C)(O)C(F)(F)F)c21] | (400 MHz, CDCl₃) δ: 1.04-1.06 (m, 4H), 1.10-1.31 (m, 3H), 1.88 (s, 3H), 1.98-2.02 (m, 1H), 2.86-2.91 (m, 1H), 3.12-3.23 (m, 1H), 3.70-3.73 (m, 1H), 3.83 (s, 3H), 4.37-5.72 (m, 2H) | 424 | 422 |

TABLE 1-22

| Example | Structure | ¹H-NMR | Mass M + 1 | Mass M - 1 |
|---|---|---|---|---|
| 118 | 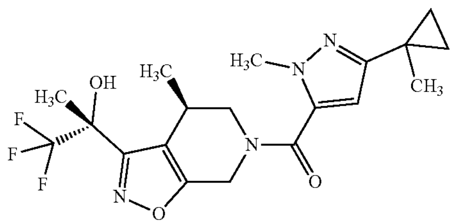 [SMILES: C[C@H]1CN(C(=O)c2cc(C3(C)CC3)nn2C)Cc2onc([C@@](C)(O)C(F)(F)F)c21] | (400 MHz, CDCl$_3$) δ: 0.73-0.77 (m, 2H), 0.94-0.98 (m, 2H), 1.24-1.26 (m, 3H), 1.44 (s, 3H), 1.87 (s, 3H), 3.13-3.49 (m, 2H), 3.85 (s, 3H), 4.15-5.47 (m, 3H), 6.13 (s, 1H) | 413 | 471 (M − 1 + 60) |
| 119 | 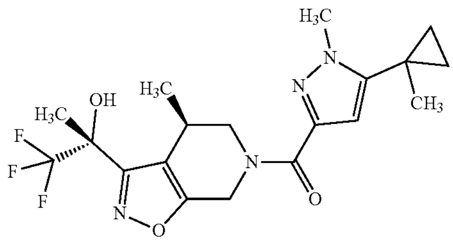 [SMILES: C[C@H]1CN(C(=O)c2cc(C3(C)CC3)n(C)n2)Cc2onc([C@@](C)(O)C(F)(F)F)c21] | (400 MHz, CDCl$_3$) δ: 0.76-0.85 (m, 4H), 1.24-1.29 (m, 3H), 1.33 (s, 3H), 1.86-1.87 (m, 3H), 3.08-3.39 (m, 2H), 3.77-3.84 (m, 1H), 3.93 (s, 3H), 4.22-5.99 (m, 3H), 6.49-6.52 (m, 1H) | 413 | 471 (M − 1 + 60) |
| 120 | 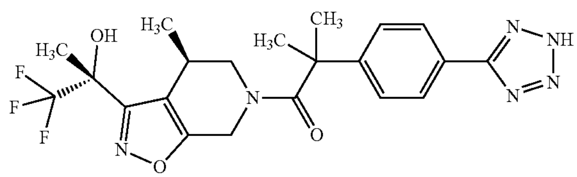 [SMILES: C[C@H]1CN(C(=O)C(C)(C)c2ccc(-c3nn[nH]n3)cc2)Cc2onc([C@@](C)(O)C(F)(F)F)c21] | (400 MHz, DMSO-d$_6$) δ: 0.46-0.64 (m, 3H), 1.48 (s, 3H), 1.56 (s, 3H), 1.66 (s, 3H), 2.77-2.92 (m, 2H), 3.87-4.86 (m, 3H), 7.04 (s, 1H), 7.35 (d, J = 8.40 Hz, 2H), 7.97 (d, J = 8.40 Hz, 2H) | 465 | 463 |
| 121 | 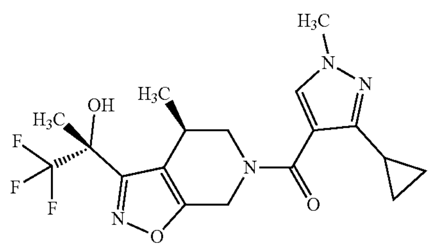 [SMILES: C[C@H]1CN(C(=O)c2cn(C)nc2C2CC2)Cc2onc([C@@](C)(O)C(F)(F)F)c21] | (400 MHz, DMSO-d$_6$) δ: 0.76-0.79 (m, 4H), 1.16 (d, J = 6.94 Hz, 3H), 1.73 (s, 3H), 1.98 (ddd, J = 14.28, 7.34, 4.33 Hz, 1H), 3.01-5.12 (m, 5H), 3.74 (s, 3H), 7.10 (s, 1H), 7.85 (s, 1H) | 399 | 795 (2M − 1) |
| 122 | 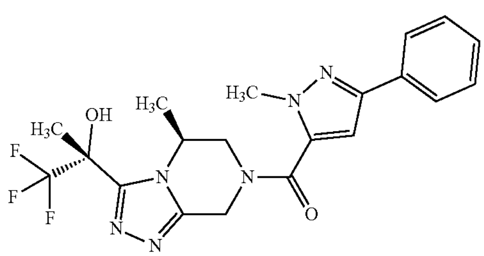 [SMILES: C[C@H]1CN(C(=O)c2cc(-c3ccccc3)nn2C)Cc2nnc([C@@](C)(O)C(F)(F)F)n21] | (400 MHz, DMSO-d$_6$) δ: 1.34-1.46 (m, 3H), 1.83 (s, 3H), 3.26-3.38 (m, 0.5H), 3.64-3.77 (m, 0.5H), 3.91 (s, 3H), 4.10-4.22 (m, 0.5H), 4.60-4.75 (m, 1H), 4.85-5.06 (m, 1.5H), 5.18-5.32 (m, 1H), 6.93-7.02 (m, 0.5H), 7.19-7.27 (m, 0.5H), 7.32 (tt, J = 7.40, 1.46 Hz, 1H), 7.42 (t, J = 7.63 Hz, 2H), 7.48 (s, 1H), 7.80-7.86 (m, 2H) | 435 | 433 |
| 123 | 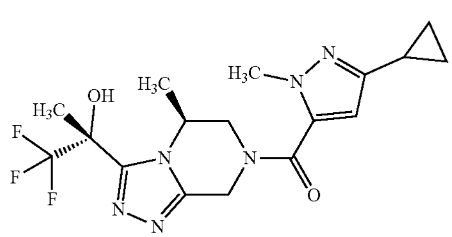 [SMILES: C[C@H]1CN(C(=O)c2cc(C3CC3)nn2C)Cc2nnc([C@@](C)(O)C(F)(F)F)n21] | (400 MHz, DMSO-d$_6$) δ: 0.65-0.71 (m, 2H), 0.84-0.90 (m, 2H), 1.29-1.42 (m, 3H), 1.81-1.93 (m, 1H), 1.84 (s, 3H), 3.24-3.34 (m, 0.6H), 3.57-3.70 (m, 0.5H), 3.76 (s, 3H), 4.00-4.12 (m, 0.4H), 4.55-4.70 (m, 0.9H), 4.83-4.95 (m, 1.6H), 5.05-5.30 (m, 1H), 6.18-6.50 (m, 1H), 7.48 (s, 1H) | 399 | 397 |

Experimental Example 1: Inhibitory Action of PDHK Activity In Vitro

The inhibitory action of PDHK activity was assessed indirectly by measuring the residual PDH activity after PDHK reaction in the presence of a test compound.

(Inhibitory Action of PDHK1 Activity)

In the case of human PDHK1 (hPDHK1, NCBI Reference Database Accession number NM_002610.3), a 1.3 kbp fragment encoding this protein was isolated from human liver cDNA by polymerase chain reaction (PCR). Modified hPDHK1 cDNA wherein FLAG-Tag sequence was added to the N terminus was prepared by PCR and ligated to the NdeI/EcoRI site of pET-17b vector (Merck MGaA, model number 69663-3). The recombinant construct was transformed into *Escherichia coli* DH5a (TOYOBO, model number DNA-903). The recombinant clones were identified, and plasmid DNA was isolated and subjected to the DNA sequence analysis. One clone which had the expected nucleic acid sequence was selected for expression work.

For expression of hPDHK1 activity, *Escherichia coli* strain BL21(DE3) cells (Merck KGaA, model number 69450-4) were transformed with the pET17b vector containing modified hPDHK1 cDNA. The *Escherichia coli* were grown to an optical density 0.6 (600 nmol/L) at 30° C. Protein expression was induced by the addition of 500 µmol/L isopropyl-β-thiogalactopyranoside. The *Escherichia coli* were cultured at 20° C. for 17-18 hr and harvested by centrifugation.

The harvested *Escherichia coli* was resuspended in a suspension buffer (20 mmol/L N-(2-hydroxyethyl)piperazine-N'-2-ethanesulfonic acid-sodium hydroxide (HEPES-NaOH), 500 mmol/L sodium chloride, 1% ethylene glycol, and 0.1% polyoxyethylene-polyoxypropylene block copolymer (Pluronic F-68), complete, EDTA-free (pH 8.0)) and disrupted by a microfluidizer M-110H (MIZUHO INDUSTRIAL CO., LTD.) or ultrasonication. The precipitate was removed by centrifugation and the supernatant was added to DDDDK-tagged Protein PURIFICATION GEL (MBL, model number 3329). DDDDK-tagged Protein PURIFICATION GEL was washed with a washing buffer (20 mmol/L HEPES-NaOH, 500 mmol/L sodium chloride, 1% ethylene glycol, 0.1% pluronic F-68 (pH 8.0)) and the bound protein was eluted with elution buffer 1 (20 mmol/L HEPES-NaOH, 100 µg/mL peptide (amino acid sequence DYKDDDDK) (SEQ ID NO: 1), 500 mmol/L sodium chloride, 1% ethylene glycol, 0.1% pluronic F-68 (pH 8.0)).

The eluted fractions containing FLAG-Tagged protein were pooled, concentrated by an ultrafiltration method, added to a gel filtration column (HiLoad 26/60 Superdex 200 (GE Healthcare, model number 17-1070-01)), and eluted with elution buffer 2 (20 mmol/L HEPES-NaOH, 150 mmol/L sodium chloride, 0.5 mmol/L ethylenediaminetetraacetic acid (EDTA), 1% ethylene glycol, 0.1% pluronic F-68 (pH 8.0)). The eluted fractions were pooled and preserved at −80° C.

0.025 U/mL PDH (porcine heart PDH complex, Sigma P7032) and 0.5 µg/mL hPDHK1 were mixed in an assay buffer (50 mmol/L 3-morpholinopropanesulfonic acid (pH 7.0), 20 mmol/L dipotassium hydrogen phosphate, 60 mmol/L potassium chloride, 2 mmol/L magnesium chloride, 0.4 mmol/L EDTA, 0.2% poloxamer, 2 mmol/L dithiothreitol), and the mixture was incubated at 4° C. overnight to obtain a PDH/hPDHK1 complex solution. In the assay buffer, 0.025 U/mL PDH was mixed and incubated at 4° C. overnight to prepare a PDH solution.

The test compounds were diluted with dimethyl sulfoxide (DMSO). To measure an inhibitory action of the test compound on the PDHK activity in the PDH/hPDHK1 complex solution, PDH/hPDHK1 complex solution (20 µL), test compound (1.5 µL) and 0.353 µmol/L ATP (diluted with assay buffer) (8.5 µL) were added to a 384 well microplate (Greiner Bio-One 781801) and PDHK reaction was performed at room temperature for 45 min (test compound well). DMSO (1.5 µL) was added to control wells instead of test compound. In addition, DMSO (1.5 µL) was added to blank wells instead of the test compound, and PDH solution was added instead of the PDH/hPDHK1 complex solution. To measure an inhibitory action of the test compound on the PDHK activity inherent in the PDH solution, a test compound was added and the PDH solution instead of the PDH/hPDHK1 complex solution was added to a blank+test compound well.

Then, 10 µL of substrates (5 mmol/L sodium pyruvate, 5 mmol/L Coenzyme A, 12 mmol/L NAD, 5 mmol/L thiamine pyrophosphate, diluted with assay buffer) were added. The mixture was incubated at room temperature for 90 min, and the residual PDH activity was measured.

The absorbance of each well at 340 nm was measured using a microplate reader to detect NADH produced by the PDH reaction. The PDH activity of each well was calculated from the changes in the absorbance before and after the PDH reaction. The PDH activity of the test compound-treated sample was calculated from the formula {PDH activity of test compound well−(PDH activity of blank+test compound well−PDH activity of blank well)}. The hPDHK1 inhibition rate (%) of the test compound was calculated from the formula [{(PDH activity of the test compound-treated sample−PDH activity of control well)/PDH activity of blank well−PDH activity of control well)}×100]. $IC_{50}$ value was calculated according to a logistic regression method based on a test compound concentration and hPDHK1 inhibitory rate (%).

(Inhibitory Action of PDHK2 Activity)

In the case of human PDHK2 (hPDHK2, NCBI Reference Database Accession number NM_002611.4), modified hPDHK2 cDNA wherein FLAG-Tag sequence was added to the N terminus of hPDHK2 cDNA clone (pReceiver-M01/PDK2-GeneCopoeia) as the base was prepared by PCR and ligated to the NdeI/EcoRI site of pET-17b vector. The recombinant construct was transformed into *Escherichia coli* DH5a. The recombinant clones were identified, and plasmid DNA was isolated and subjected to the DNA sequence analysis. One clone which had the expected nucleic acid sequence was selected for expression work.

For expression of hPDHK2 activity, *Escherichia coli* strain BL21(DE3) cells were transformed with the pET17b vector containing modified hPDHK2 cDNA. The *Escherichia coli* were grown to an optical density 0.6 (600 nmol/L) at 30° C. Protein expression was induced by the addition of 500 µmol/L isopropyl-β-thiogalactopyranoside. The *Escherichia coli* were cultured at 20° C. for 17-18 hr and harvested by centrifugation. The harvested *Escherichia coli* was resuspended in a suspension buffer (20 mmol/L HEPES-NaOH, 500 mmol/L sodium chloride, 1% ethylene glycol, 0.1% pluronic F-68 (pH 8.0), cOmplete, EDTA-free (pH 8.0)), and disrupted by a microfluidizer. The precipitate was removed by centrifugation and the supernatant was added to DDDDK-tagged Protein PURIFICATION GEL. DDDDK-tagged Protein PURIFICATION GEL was washed with a washing buffer (20 mmol/L HEPES-NaOH, 500 mmol/L sodium chloride, 1% ethylene glycol, 0.1% pluronic F-68 (pH 8.0)) and the bound protein was eluted with elution buffer 1 (20 mmol/L HEPES-NaOH, 100 µg/mL peptide (amino acid sequence DYKDDDDK) (SEQ ID NO: 1), 500 mmol/L sodium chloride, 1% ethylene glycol, 0.1% pluronic F-68 (pH 8.0)). The eluted fractions containing FLAG-Tagged protein were pooled, concentrated by an ultrafiltration method, added to a gel filtration column (HiLoad 26/60 Superdex 200), and eluted with elution buffer 2 (20 mmol/L HEPES-NaOH, 150 mmol/L sodium chloride, 0.5 mmol/L ethylenediaminetetraacetic acid (EDTA), 1% ethylene glycol, 0.1% pluronic F-68 (pH 8.0)). The eluted fractions were pooled and preserved at −80° C.

0.025 U/mL PDH and 0.5 µg/mL hPDHK2 were mixed in an assay buffer (50 mmol/L 3-morpholinopropanesulfonic acid (pH 7.0), 20 mmol/L dipotassium hydrogen phosphate, 60 mmol/L potassium chloride, 2 mmol/L magnesium chloride, 0.4 mmol/L EDTA, 0.2% poloxamer, 2 mmol/L dithiothreitol), and the mixture was incubated at 4° C. overnight to obtain a PDH/hPDHK2 complex solution. In the assay buffer, 0.025 U/mL PDH was mixed and incubated at 4° C. overnight to prepare a PDH solution.

The test compounds were diluted with DMSO. To measure an inhibitory action of the test compound on the PDHK activity in the PDH/hPDHK2 complex solution, PDH/hPDHK2 complex solution (20 µL), test compound (1.5 µL) and 1.06 µmol/L ATP (diluted with assay buffer) (8.5 µL) were added to a 384 well microplate and PDHK reaction was performed at room temperature for 45 min (test compound well). DMSO (1.5 µL) was added to control wells instead of test compound. In addition, DMSO (1.5 µL) was added to blank wells instead of the test compound, and PDH solution was added instead of the PDH/hPDHK2 complex solution. To measure an inhibitory action of the test compound on the PDHK activity inherent in the PDH solution, a test compound was added and the PDH solution instead of the PDH/hPDHK2 complex solution was added to a blank+test compound well.

Then, 10 µL of substrates (5 mmol/L sodium pyruvate, 5 mmol/L Coenzyme A, 12 mmol/L NAD, 5 mmol/L thiamine pyrophosphate, diluted with assay buffer) were added. The mixture was incubated at room temperature for 90 min, and the residual PDH activity was measured.

The absorbance of each well at 340 nm was measured using a microplate reader to detect NADH produced by the PDH reaction. The PDH activity of each well was calculated from the changes in the absorbance before and after the PDH reaction. The PDH activity of the test compound-treated sample was calculated from the formula {PDH activity of test compound well−(PDH activity of blank+test compound well−PDH activity of blank well)}. The hPDHK2 inhibition rate (%) of the test compound was calculated from the formula [{(PDH activity of the test compound-treated sample−PDH activity of control well)/PDH activity of blank well−PDH activity of control well)}×100]. $IC_H$ value was calculated according to a logistic regression method based on a test compound concentration and hPDHK2 inhibitory rate (%).

The results are shown in the following Tables. When $IC_H$ value could not be calculated, the inhibitory rate at the lowest concentration of the test compound in the assay is shown. For example, the compound of Example 5 showed 55% hPDHK1 inhibitory rate at 3 nmol/L.

TABLE 2-1

| Example No. | hPDK1 $IC_{50}$ (nmol/L) | kPDK2 $IC_{50}$ (nmol/L) |
|---|---|---|
| 1 | 6 | 5 |
| 2 | 12 | 15 |
| 3 | 16 | 14 |
| 4 | 4 | 5 |
| 5 | <3 (55%) | 5 |
| 6 | 11 | 11 |
| 7 | 8 | 10 |
| 8 | 49 | 34 |
| 9 | 7 | 11 |
| 10 | 9 | 13 |
| 11 | 14 | 15 |
| 12 | 8 | 10 |
| 13 | 29 | 36 |
| 14 | <3 (68%) | <3 (57%) |
| 15 | 3 | 5 |
| 16 | 6 | 7 |

TABLE 2-1-continued

| Example No. | hPDK1 $IC_{50}$ (nmol/L) | kPDK2 $IC_{50}$ (nmol/L) |
|---|---|---|
| 17 | 8 | 7 |
| 18 | 7 | 7 |
| 19 | 5 | <3 (67%) |
| 20 | 8 | 12 |
| 21 | 13 | 12 |
| 22 | 6 | 8 |
| 23 | 6 | 12 |
| 24 | 42 | 36 |
| 25 | 7 | 14 |
| 26 | 9 | 14 |
| 27 | 9 | 8 |
| 28 | 12 | 10 |
| 29 | 7 | 7 |
| 30 | 20 | 13 |

TABLE 2-2

| Example No. | hPDK1 $IC_{50}$ (nmol/L) | kPDK2 $IC_{50}$ (nmol/L) |
|---|---|---|
| 31 | 9 | 11 |
| 32 | 13 | 10 |
| 33 | 12 | 16 |
| 34 | 10 | 13 |
| 35 | 3 | 4 |
| 36 | 4 | 5 |
| 37 | 3 | 8 |
| 38 | <3 (73%) | 4 |
| 39 | 46 | 18 |
| 40 | 5 | 6 |
| 41 | 6 | 6 |
| 42 | 4 | 5 |
| 43 | <3 (52%) | 5 |
| 44 | 5 | 7 |
| 45 | 9 | 8 |
| 46 | 5 | 5 |
| 47 | <3 (53%) | 4 |
| 48 | <3 (88%) | <3 (81%) |
| 49 | 3 | 3 |
| 50 | 4 | 5 |
| 51 | 4 | 6 |
| 52 | 4 | 6 |
| 53 | 4 | 8 |
| 54 | <3 (53%) | 5 |
| 55 | <3 (54%) | 4 |
| 56 | 10 | 10 |
| 57 | 11 | 10 |
| 58 | 3 | 4 |
| 59 | 4 | 3 |
| 60 | 14 | 9 |

TABLE 2-3

| Example No. | hPDK1 $IC_{50}$ (nmol/L) | kPDK2 $IC_{50}$ (nmol/L) |
|---|---|---|
| 61 | 3 | 5 |
| 62 | 3 | 4 |
| 63 | 5 | 7 |
| 64 | 5 | 7 |
| 65 | 4 | 5 |
| 66 | 4 | 6 |
| 67 | 5 | 7 |
| 68 | 4 | 6 |
| 69 | 5 | 8 |
| 70 | 3 | 6 |
| 71 | 4 | 7 |
| 72 | 7 | 9 |
| 73 | 6 | 7 |
| 74 | 6 | 11 |
| 75 | 6 | 11 |
| 76 | 6 | 9 |

TABLE 2-3-continued

| Example No. | hPDK1 IC$_{50}$ (nmol/L) | kPDK2 IC$_{50}$ (nmol/L) |
|---|---|---|
| 77 | 6 | 9 |
| 78 | 4 | 7 |
| 79 | 5 | 8 |
| 80 | 3 | 6 |
| 81 | 5 | 7 |
| 82 | 5 | 7 |
| 83 | 5 | 11 |
| 84 | 5 | 11 |
| 85 | <3 (49%) | 6 |
| 86 | <3 (52%) | 4 |
| 87 | <3 (66%) | <3 (53%) |
| 88 | 3 | 4 |
| 89 | 20 | 19 |
| 90 | 66 | 45 |

TABLE 2-4

| Example No. | hPDK1 IC$_{50}$ (nmol/L) | kPDK2 IC$_{50}$ (nmol/L) |
|---|---|---|
| 91 | 49 | 28 |
| 92 | 27 | 23 |
| 93 | 8 | 11 |
| 94 | 40 | 24 |
| 95 | 6 | 15 |
| 96 | 8 | 8 |
| 97 | 63 | 26 |
| 98 | 6 | 6 |
| 99 | 8 | 12 |
| 100 | 4 | 5 |
| 101 | <3 (69%) | 4 |
| 102 | 4 | 4 |
| 103 | <3 (67%) | <3 (66%) |
| 104 | 4 | 6 |
| 105 | 9 | 8 |
| 106 | <3 (61%) | 4 |
| 107 | 5 | 6 |
| 108 | 5 | 6 |
| 109 | <3 (53%) | 5 |
| 110 | 7 | 13 |
| 111 | 3 | 6 |
| 112 | 3 | 5 |
| 113 | 4 | 5 |
| 114 | 5 | 7 |
| 115 | 6 | 8 |
| 116 | 17 | 32 |
| 117 | 6 | 8 |
| 118 | 4 | 4 |
| 119 | 4 | 5 |
| 120 | 5 | 9 |
| 121 | 5 | 5 |
| 122 | 5 | 7 |
| 123 | 6 | 12 |

As a Formulation Example of the present invention, the following preparation can be mentioned. However, the present invention is not limited by these Formulation Examples.

Formulation Example 1: Production of Capsule

| | |
|---|---|
| 1) compound of Example 1 | 30 mg |
| 2) microcrystalline cellulose | 10 mg |
| 3) lactose | 19 mg |
| 4) magnesium stearate | 1 mg |

1), 2), 3) and 4) are mixed and filled in a gelatin capsule.

Formulation Example 2: Production of Tablet

| | |
|---|---|
| 1) compound of Example 1 | 10 g |
| 2) lactose | 50 g |
| 3) cornstarch | 15 g |
| 4) carmellose calcium | 44 g |
| 5) magnesium stearate | 1 g |

The total amount of 1), 2), 3) and 30 g of 4) are kneaded with water, vacuum dried, and sieved. The sieved powder is mixed with 14 g of 4) and 1 g of 5), and the mixture is punched by a tableting machine. In this way, 1000 tablets each containing 10 mg of the compound of Example 1 per tablet are obtained.

Formulation Example 3: Production of Injection

| | |
|---|---|
| 1) compound of Example 1 | 5 mg |
| 2) D-mannitol | 5 g |
| 3) distilled water | 100 mL |

1) and 2) are dissolved in 3) and the solution is filled in a container for injection, sealed and sterilized.

INDUSTRIAL APPLICABILITY

Since the compound of the formula [I-a] or the formula [II] or a pharmaceutically acceptable salt thereof has a PDHK inhibitory activity, it is useful as an active ingredient of a medicament for the treatment or prophylaxis of diabetes (type 1 diabetes, type 2 diabetes etc.), insulin resistance syndrome, metabolic syndrome, hyperglycemia, hyperlactacidemia, diabetic complications (diabetic neuropathy, diabetic retinopathy, diabetic nephropathy, cataract etc.), cardiac failure (acute cardiac failure, chronic cardiac failure), cardiomyopathy, myocardial ischemia, myocardial infarction, angina pectoris, dyslipidemia, atherosclerosis, peripheral arterial disease, intermittent claudication, chronic obstructive pulmonary disease, brain ischemia, cerebral apoplexy, mitochondrial disease, mitochondrial encephalomyopathy, cancer, pulmonary hypertension or Alzheimer disease.

The invention claimed is:
1. A compound of the formula [I-a] or the formula [II], or a pharmaceutically acceptable salt thereof:

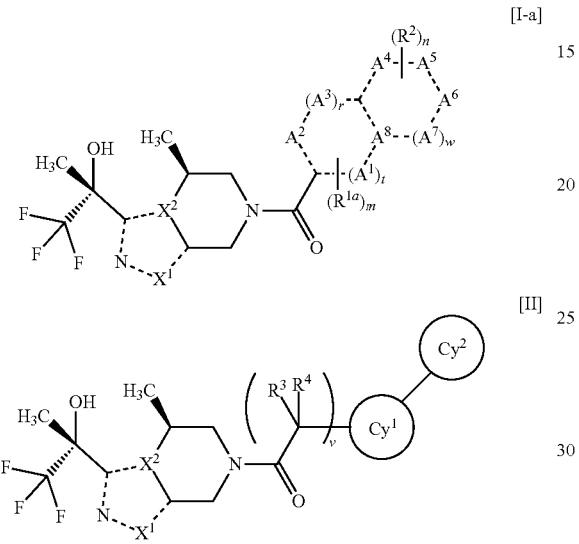

wherein
a bond in a dotted line is a single bond or a double bond,
$X^1$ is a carbon atom, a nitrogen atom or an oxygen atom,
$X^2$ is a carbon atom or a nitrogen atom,
$R^{1a}$ is $C_{1-4}$ alkyl or $C_{1-4}$ alkylcarbonyl,
$R^2$ is halogen, cyano or $C_{1-4}$ alkyl,
m is 0 or 1,
n is 0, 1 or 2, when n is 2, each $R^2$ is the same or different,
$A^1$, $A^2$, $A^3$, $A^4$, $A^5$, $A^6$ and $A^7$ are each independently selected from a carbon atom, a nitrogen atom and an oxygen atom, $A^8$ is selected from a carbon atom and a nitrogen atom, and a total number of nitrogen and oxygen atoms contained in a partial structural formula:

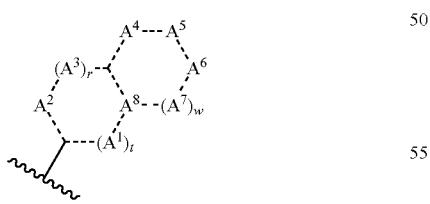

is 0, 1, 2 or 3,
t is 0 or 1,
r is 0, 1 or 2, and a total of t and r is 1 or 2,
w is 0 or 1,
$R^3$ and $R^4$ are each independently hydrogen or $C_{1-4}$ alkyl,
$Cy^1$ is
(1) (i) $C_{4-6}$ cycloalkyl or (ii) 4- to 6-membered saturated or partially saturated heterocyclyl having one nitrogen atom, the $C_{4-6}$ cycloalkyl and the saturated or partially saturated heterocyclyl is optionally substituted by one substituent independently selected from the group consisting of $C_{1-4}$ alkyl and oxo, or
(2) (i) phenyl or (ii) 5- or 6-membered heteroaryl having 1, 2 or 3 hetero atoms independently selected from the group consisting of a nitrogen atom and an oxygen atom, the phenyl and the heteroaryl are optionally substituted by 1 or 2 substituents independently selected from the group consisting of halogen, cyano, carboxy, $C_{1-4}$ alkyl, halo$C_{1-4}$ alkyl and $C_{3-6}$ cycloalkyl,
$Cy^2$ is
(1) (i) $C_{3-6}$ cycloalkyl or (ii) 4- to 6-membered saturated heterocyclyl having 1 or 2 hetero atoms independently selected from the group consisting of a nitrogen atom and an oxygen atom, and the $C_{3-6}$ cycloalkyl and the saturated heterocyclyl are optionally substituted by 1 or 2 substituents independently selected from the group consisting of halogen, hydroxy and $C_{1-4}$ alkyl, or
(2) (i) phenyl or (ii) 5- or 6-membered heteroaryl having 1, 2, 3 or 4 nitrogen atoms, and the phenyl and the heteroaryl are optionally substituted by 1 or 2 substituents independently selected from the group consisting of halogen, cyano, $C_{1-4}$ alkyl, $C_{1-4}$ alkoxy and $C_{1-4}$ alkylsulfonyl, and
v is 0 or 1.

2. The compound according to claim 1, wherein $X^1$ is a carbon atom, and $X^2$ is a nitrogen atom, or a pharmaceutically acceptable salt thereof.

3. The compound according to claim 1, wherein, in the formula [I-a], the total number of nitrogen and oxygen atoms contained in the partial structural formula:

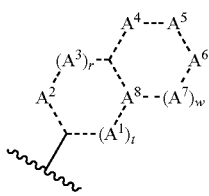

is 2, or a pharmaceutically acceptable salt thereof.

4. The compound according to claim 1, which is a compound of formula [I-b]:

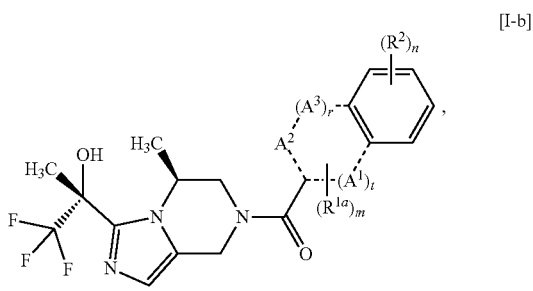

or a pharmaceutically acceptable salt thereof.

5. The compound according to claim 1, wherein v is 0, or a pharmaceutically acceptable salt thereof.

6. The compound according to claim 1, wherein $Cy^1$ is 5- or 6-membered heteroaryl having 1, 2 or 3 hetero atoms independently selected from the group consisting of a nitrogen atom and an oxygen atom, and the heteroaryl is optionally substituted by 1 or 2 substituents independently selected from the group consisting of halogen, cyano, $C_{1-4}$ alkyl, halo$C_{1-4}$ alkyl and $C_{3-6}$ cycloalkyl, or a pharmaceutically acceptable salt thereof.

7. The compound according to claim 1, wherein $Cy^2$ is:
(1) $C_{3-6}$ cycloalkyl optionally substituted by 1 or 2 substituents independently selected from the group consisting of halogen, hydroxy and $C_{1-4}$ alkyl, or
(2) phenyl optionally substituted by 1 or 2 substituents independently selected from the group consisting of halogen, cyano, $C_{1-4}$ alkyl, $C_{1-4}$ alkoxy and $C_{1-4}$ alkylsulfonyl, or a pharmaceutically acceptable salt thereof.

8. A pharmaceutical composition comprising the compound according to claim 1, or the pharmaceutically acceptable salt thereof, and a pharmaceutically acceptable carrier.

9. A method for treating a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension, the method comprising administering a therapeutically effective amount of the compound according to claim 1, or the pharmaceutically acceptable salt thereof to a mammal.

10. The method according to claim 9, wherein the diabetes is type 1 diabetes or type 2 diabetes.

11. The method according to claim 9, wherein the diabetic complication is selected from the group consisting of diabetic neuropathy, diabetic retinopathy, diabetic nephropathy and cataract.

12. The method according to claim 9, wherein the cardiac failure is acute cardiac failure or chronic cardiac failure.

13. The method according to claim 9, wherein the pulmonary hypertension is pulmonary arterial hypertension.

14. A compound represented by formula:

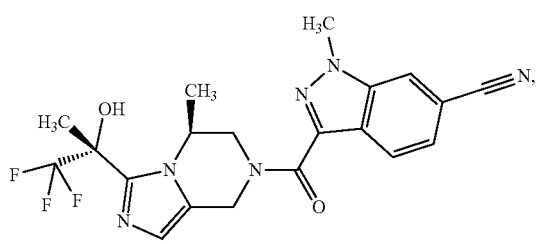 [SMILES: C[C@H]1CN(C(=O)c2nn(C)c3cc(C#N)ccc23)Cc2cnc([C@@](C)(O)C(F)(F)F)n21]

or a pharmaceutically acceptable salt thereof.

15. A compound represented by formula:

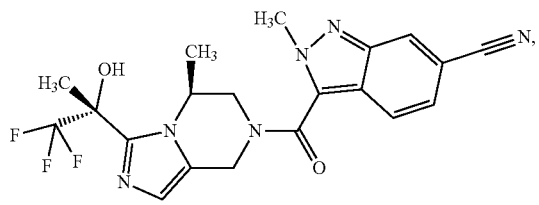 [SMILES: C[C@H]1CN(C(=O)c2c3ccc(C#N)cc3nn2C)Cc2cnc([C@@](C)(O)C(F)(F)F)n21]

or a pharmaceutically acceptable salt thereof.

16. A compound represented by formula:

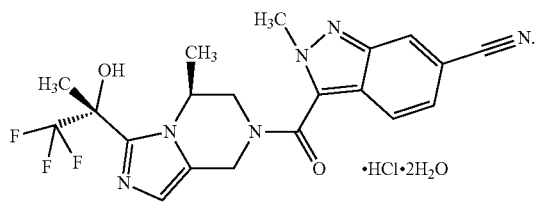 [SMILES: C[C@H]1CN(C(=O)c2c3ccc(C#N)cc3nn2C)Cc2cnc([C@@](C)(O)C(F)(F)F)n21]

17. A compound represented by formula:

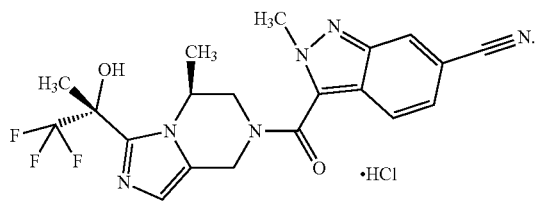 [SMILES: C[C@H]1CN(C(=O)c2c3ccc(C#N)cc3nn2C)Cc2cnc([C@@](C)(O)C(F)(F)F)n21 ; Cl]

18. A compound represented by formula:

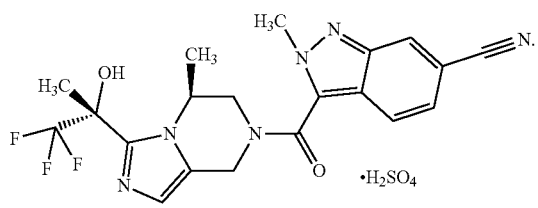

19. A compound represented by formula:

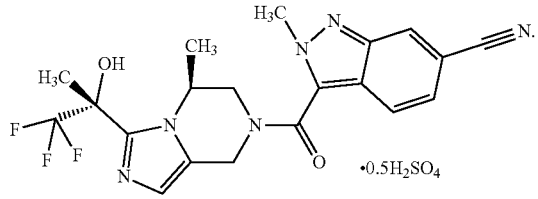

20. A compound represented by formula:

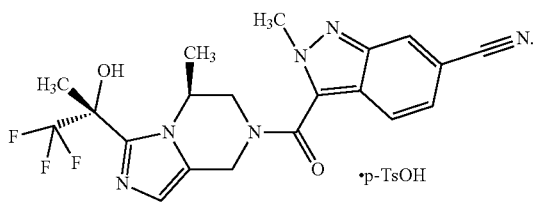

21. A compound represented by formula:

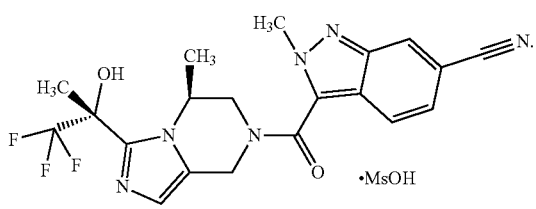 [SMILES: "·MsOH" ; C[C@H]1CN(C(=O)c2c3ccc(C#N)cc3nn2C)Cc2cnc([C@@](C)(O)C(F)(F)F)n21]

22. A compound represented by formula:

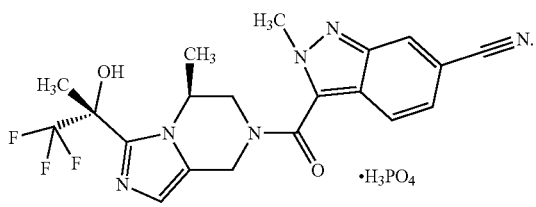

23. A compound represented by formula:

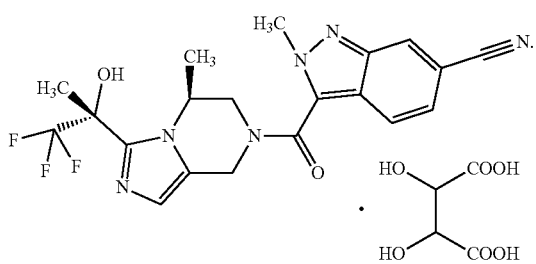

24. A compound represented by formula:

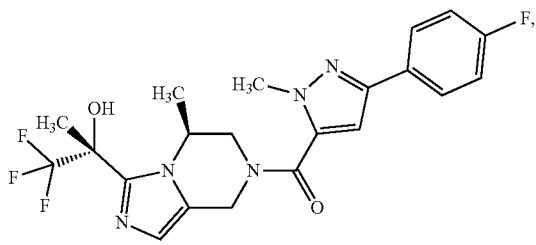 [SMILES: C[C@H]1CN(C(=O)c2cc(-c3ccc(F)cc3)nn2C)Cc2cnc([C@@](C)(O)C(F)(F)F)n21]

or a pharmaceutically acceptable salt thereof.

25. A compound represented by formula:

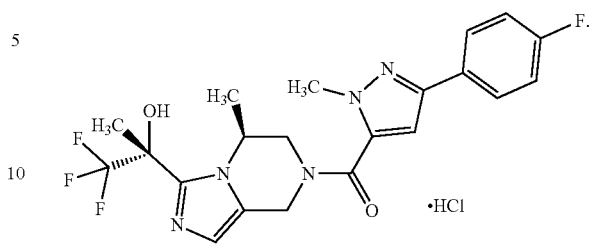

26. A compound represented by formula:

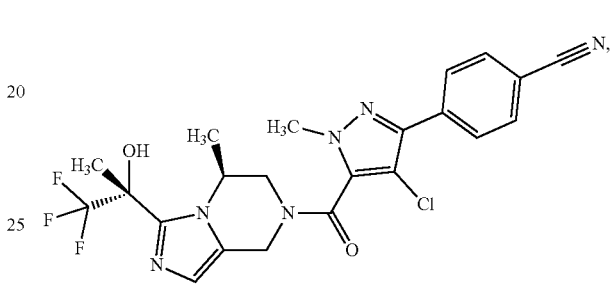

or a pharmaceutically acceptable salt thereof.

27. A compound represented by formula:

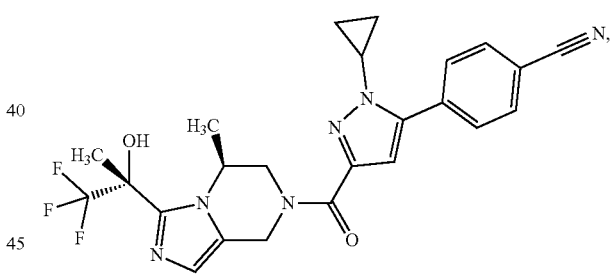

or a pharmaceutically acceptable salt thereof.

28. A compound represented by formula:

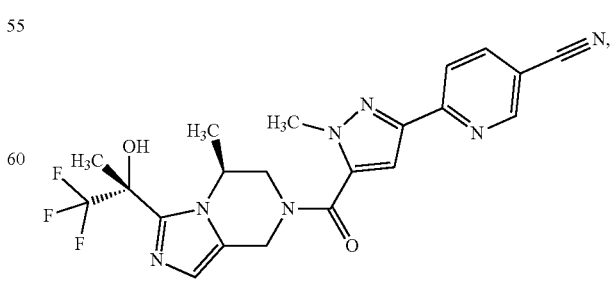

or a pharmaceutically acceptable salt thereof.

29. A compound represented by formula:

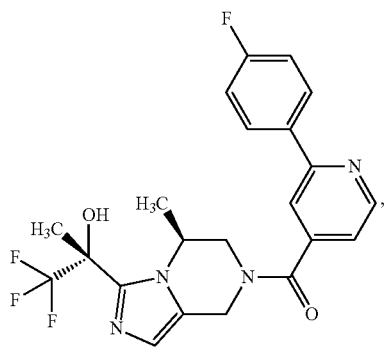 [SMILES: C[C@H]1CN(C(=O)c2ccnc(-c3ccc(F)cc3)c2)Cc2cnc([C@@](C)(O)C(F)(F)F)n21]

or a pharmaceutically acceptable salt thereof.

30. A compound represented by formula:

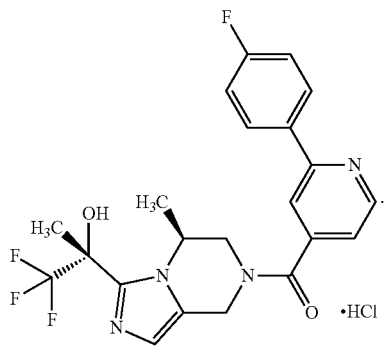 [SMILES: C[C@H]1CN(C(=O)c2ccnc(-c3ccc(F)cc3)c2)Cc2cnc([C@@](C)(O)C(F)(F)F)n21 ; Cl]

31. A compound represented by formula:

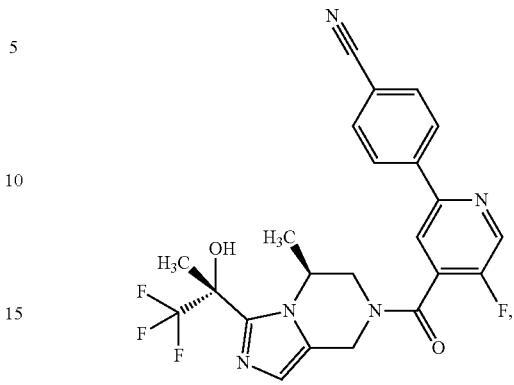

or a pharmaceutically acceptable salt thereof.

32. A pharmaceutical composition comprising the compound according to any one of claims 14 to 31 and a pharmaceutically acceptable carrier.

33. A method for treating a disease selected from the group consisting of diabetes, insulin resistance syndrome, metabolic syndrome, hyperglycemia, hyperlactacidemia, diabetic complication, cardiac failure, cardiomyopathy, myocardial ischemia, myocardial infarction, angina pectoris, dyslipidemia, atherosclerosis, peripheral arterial disease, intermittent claudication, chronic obstructive pulmonary diseases, brain ischemia, cerebral apoplexy, mitochondrial disease, mitochondrial encephalomyopathy, cancer and pulmonary hypertension, the method comprising administering a therapeutically effective amount of the compound according to any one of claims 14 to 31 to a mammal.

34. The method according to claim 33, wherein the diabetes is type 1 diabetes or type 2 diabetes.

35. The method according to claim 33, wherein the diabetic complication is selected from the group consisting of diabetic neuropathy, diabetic retinopathy, diabetic nephropathy and cataract.

36. The method according to claim 33, wherein the cardiac failure is acute cardiac failure or chronic cardiac failure.

37. The method according to claim 33, wherein the pulmonary hypertension is pulmonary arterial hypertension.

\* \* \* \* \*

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: FLAG-Tag

```
<400> SEQUENCE: 1

Asp Tyr Lys Asp Asp Asp Asp Lys
1               5
```